(12) United States Patent
Wickline et al.

(10) Patent No.: US 9,987,371 B2
(45) Date of Patent: Jun. 5, 2018

(54) COMPOSITIONS AND METHODS FOR POLYNUCLEOTIDE TRANSFECTION

(71) Applicant: Washington University, St. Louis, MO (US)

(72) Inventors: Samuel A. Wickline, St. Louis, MO (US); Kirk Hou, St. Louis, MO (US)

(73) Assignee: WASHINGTON UNIVERSITY, Saint Louis, MO (US)

( * ) Notice: Subject to any disclaimer, the term of this patent is extended or adjusted under 35 U.S.C. 154(b) by 0 days. days.

(21) Appl. No.: 14/790,408

(22) Filed: Jul. 2, 2015

(65) Prior Publication Data

US 2015/0314013 A1    Nov. 5, 2015

Related U.S. Application Data

(63) Continuation-in-part of application No. PCT/US2014/010212, filed on Jan. 3, 2014.

(60) Provisional application No. 61/748,615, filed on Jan. 3, 2013, provisional application No. 61/869,634, filed on Aug. 23, 2013, provisional application No. 61/873,187, filed on Sep. 3, 2013.

(51) Int. Cl.
| | |
|---|---|
| *C07K 19/00* | (2006.01) |
| *A61K 47/48* | (2006.01) |
| *A61K 31/713* | (2006.01) |
| *A61K 47/42* | (2017.01) |
| *C12N 15/11* | (2006.01) |
| *C12N 15/113* | (2010.01) |
| *C12N 15/87* | (2006.01) |
| *A61K 47/64* | (2017.01) |
| *A61K 38/00* | (2006.01) |

(52) U.S. Cl.
CPC ...... *A61K 47/48323* (2013.01); *A61K 31/713* (2013.01); *A61K 47/42* (2013.01); *A61K 47/6455* (2017.08); *C07K 19/00* (2013.01); *C12N 15/111* (2013.01); *C12N 15/113* (2013.01); *C12N 15/87* (2013.01); *A61K 38/00* (2013.01); *C12N 2310/14* (2013.01); *C12N 2310/3513* (2013.01); *C12N 2320/32* (2013.01); *Y10T 428/2982* (2015.01)

(58) Field of Classification Search
CPC ... C07K 14/00; A61K 47/48315; A61K 38/16
USPC ........................................................ 530/326
See application file for complete search history.

(56) References Cited

U.S. PATENT DOCUMENTS

| | | | |
|---|---|---|---|
| 7,098,032 B2 | 8/2006 | Trubetskoy et al. | |
| 7,446,099 B2* | 11/2008 | Van | C08L 59/00 424/93.2 |
| 7,795,380 B2 | 9/2010 | Rice et al. | |
| 8,501,930 B2 | 8/2013 | Rozema et al. | |
| 8,617,516 B2 | 12/2013 | Wickline et al. | |
| 2005/0191746 A1* | 9/2005 | Van | C08L 59/00 435/455 |
| 2007/0275923 A1 | 11/2007 | Chen et al. | |
| 2011/0123438 A1 | 5/2011 | Wickline et al. | |

FOREIGN PATENT DOCUMENTS

| | | |
|---|---|---|
| WO | 2005/085458 A2 | 9/2005 |
| WO | 2007069090 A2 | 6/2007 |
| WO | 2011020188 A1 | 2/2011 |
| WO | 2014107596 A1 | 7/2014 |
| WO | 2017004512 A1 | 1/2017 |

OTHER PUBLICATIONS

Wu et al., 2012, Recent progress in copolymer-mediated siRNA delivery, Journal of Drug Targeting, 20(7): 551-560.*
Noguchi et al., 2006, Protein Transduction Technology: A Novel Therapeutic Perspective, 60(1): 1-11.*
Examination Report for related CA application 2,896,834 dated Aug. 23, 2016, 5 pages.
Partial Supplementary European Search Report dated Aug. 9, 2016 from related EP Application No. 14735277.7, 10 pages.
International Search Report and Written Opinion dated Oct. 4, 2016 from International Patent Application No. PCT/US2016/040678; 10 pgs.
Salomone F. et al., "In Vitro Efficient Transfection by CM18-Tat11 Hybrid Peptide: A New Tool for Gene-Delivery Applications," PLoS ONE, Jul. 29, 2013, pp. 1-11, vol. 8, No. 7, e70108.
Hou, et al., "A novel mellitin-derived peptide nanoparticle delivery system for STAT3 siRNA mediated killing of B16 melanoma cells," The FASEB Journal, 2012, vol. 26, No. 1.
Hou, et al., "Mellitin Derived Peptides for Nanoparticle Based siRNA Transfection," Biomaterials, Apr. 2013, pp. 3110-3119, vol. 34, No. 12.
Hou, et al., "Mechanisms of Nanoparticle Mediated siRNA Transfection by Melittin-Derived Peptides," ACS Nano, Oct. 2013, pp. 8605-8615, vol. 7, No. 10.
Hou, et al., "Peptide-siRNA nanocomplexes targeting NF-κb subunit p65 suppress nascent experimental arthritis," The Journal of Clinical Investigation, pp. 4363-4374, vol. 124, No. 10.
Lochmann, et al., "Albumin-protamine-oligonucleotide nanoparticles as a new antisense delivery system. Part 1: Physiochemical characterization," European Journal of Pharmaceutics and Biopharmaceutics, 2005, pp. 419-429, vol. 59.
Hou et al., "A role for peptides in overcoming endosomal entrapment in siRNA delivery—a focus on mellitin," Biotechnology Advances, 2015, pp. 931-940, vol. 33.
Office Action dated Jul. 19, 2017 from related Australian Patent Application No. 2014204012; 5 pgs.

(Continued)

*Primary Examiner* — Amber D Steele
(74) *Attorney, Agent, or Firm* — Polsinelli PC

(57) ABSTRACT

A pharmaceutical composition comprising a peptide-polynucleotide complex, and methods of use thereof.

15 Claims, 91 Drawing Sheets
(38 of 91 Drawing Sheet(s) Filed in Color)

(56) References Cited

OTHER PUBLICATIONS

Extended European Search Report dated Dec. 7, 2016 from related European Patent Application No. 14735277.7; 21 pgs.
Lee, U. et al., "Dual knockdown of p65 and p50 subunits of NF-kappaB by siRNA inhibits the induction of inflammatory cytokines and significantly enhance apoptosis in human primary synoviocytes treated with tumor necrosis factor-alpha," Mol. Biol. Rep., 2008, pp. 291-298, vol. 35, No. 3.
Takabe, W. et al., "Oscillatory Shear Stress Induces Mitochondrial Superoxide Production: Implication of NADPH Oxidase and c-Jun NH2-Terminal Kinase Signaling," Antioxidants & Redox Signaling, Jan. 1, 2011, pp. 1379-1388, vol. 15, No. 5.
Tian, F. et al., "A small interfering RNA targeting NF-B p65 alone or combined with 5-FU inhibits growth of esophageal squamous cell carcinoma in nude mice," Pathology—Research and Practice, Oct. 30, 2011, pp. 32-38, vol. 208, No. 1.
Xu, Y. et al., "Targeting Stat3 suppresses growth of U251 cell-derived tumours in nude mice," J. Clinical Neuroscience, Mar. 1, 2012, pp. 443-446, vol. 19, No. 3.
Office Action dated Sep. 5, 2017 from related Japanese Patent Application No. 2015-551782, 5 pgs., with English translation.
Office Action dated Sep. 25, 2017 from related Canadian Patent Application No. 2,896,834; 3 pgs.
Ohtsuki, T. et al., "Intracellular introduction of RNA by carrier peptide," J. Japanese Biochem. Soc., 2009, pp. 110-112, vol. 81, No. 2, with English translation.

* cited by examiner

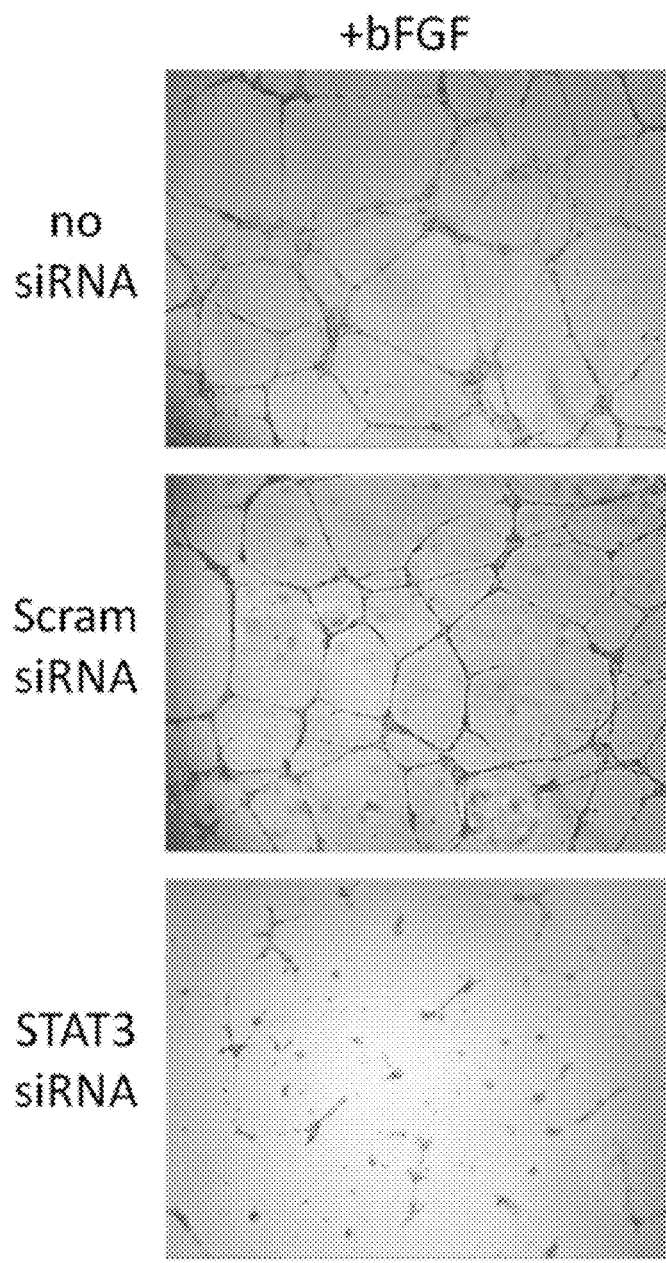

FIG. 17H FIG. 17I pH 7.5-6.5 pH 5.5 pH 4.5

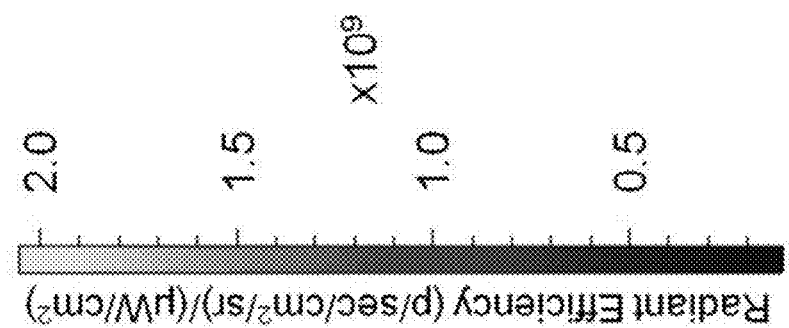
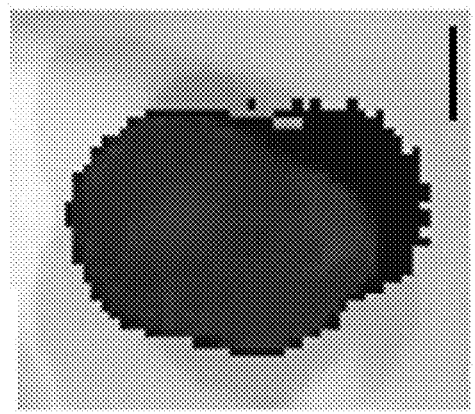
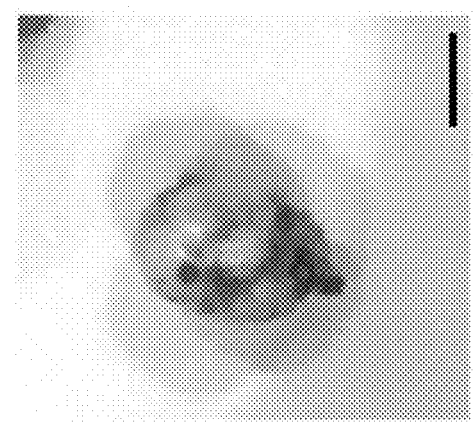
FIG. 24E
FIG. 24D

COMPOSITIONS AND METHODS FOR POLYNUCLEOTIDE TRANSFECTION

CROSS REFERENCE TO RELATED APPLICATIONS

This application claims the priority of PCT application number PCT/US2014/10212, filed Jan. 3, 2014, which claims priority to U.S. provisional application No. 61/873,187, filed Sep. 3, 2013, U.S. provisional application No. 61/869,634, filed Aug. 23, 2013, and U.S. provisional application No. 61/748,615, filed Jan. 3, 2013, each of which is hereby incorporated by reference in its entirety.

GOVERNMENTAL RIGHTS

This invention was made with government support under Grant Nos. U01 CA141541 and R01 HL073646-08 awarded by the National Institutes of Health (NIH). The government has certain rights in the invention.

FIELD OF THE INVENTION

The invention provides a peptide-polynucleotide complex that can be formulated as a pharmaceutical composition, and methods of use thereof.

BACKGROUND OF THE INVENTION

RNA interference (RNAi) with the use of small interfering RNA (siRNA) has been proposed as a highly effective therapy for myriad diseases including cancer and inflammatory diseases. However, despite nearly two decades of intense research, siRNA therapeutics have demonstrated limited success in translation to clinical applications due to poor cellular uptake and instability of free siRNA in serum. Cationic lipids and polymers have been successfully employed for siRNA transfection, but can exhibit unacceptable cytotoxicity and cause generation of reactive oxygen species (ROS) and $Ca^{+2}$ leakage. In addition, cell penetrating peptide (CPP) based siRNA transfection agents, although showing promise with respect to reducing cytotoxicity, have not achieved the high efficiency of traditional lipidic transfection agents due to lysosomal trapping.

Therefore, there is a need in the art for new classes of therapeutic siRNA compositions and siRNA transfection agents capable of efficient cellular uptake and delivery into the cytoplasm for treating diseases.

SUMMARY OF THE INVENTION

The present invention encompasses a pharmaceutical composition comprising a peptide-polynucleotide complex. The peptide-polynucleotide complex comprises a ratio of peptide:polynucleotide that is more than about 50:1 and less than about 200:1. The peptide is (a) non-lytic and capable of affecting the release of a polynucleotide from an endosome of a cell, and (b) comprises an amino acid sequence with at least 80% identity to an amino acid sequence chosen from SEQ ID NO: 1, SEQ ID NO: 57 or SEQ ID NO: 63. The polynucleotide is an RNA sequence or a DNA sequence. In an aspect, the peptide comprises at least one cationic region and at least one histidine residue located adjacent to at least one cationic region of the peptide. In another aspect, the polynucleotide is a non-coding RNA capable of regulating or inhibiting the expression of a nucleic acid sequence.

The present invention also encompasses a method of delivering a polynucleotide to the cytoplasm of a cell. The method comprises contacting a cell with a peptide-polynucleotide complex, the peptide-polynucleotide complex comprising a ratio of peptide:polynucleotide that is more than about 50:1 and less than about 200:1, wherein the peptide is (a) non-lytic and capable of affecting the release of a polynucleotide from an endosome of a cell, and (b) comprises an amino acid sequence with at least 80% identity to an amino acid sequence chosen from SEQ ID NO: 1, SEQ ID NO: 57 or SEQ ID NO: 63. In an aspect, the peptide comprises at least one cationic region and at least one histidine residue located adjacent to or within at least one cationic region of the peptide. In another aspect, the polynucleotide is a non-coding RNA capable of regulating or inhibiting the expression of a nucleic acid sequence.

The present invention also encompasses a method of delivering a polynucleotide to the cytoplasm of a cell in a subject in need thereof. The method comprises administering to the subject a therapeutically effective amount of a pharmaceutical composition comprising a peptide-polynucleotide complex, the peptide-polynucleotide complex comprising a ratio of peptide:polynucleotide that is more than about 50:1 and less than about 200:1, wherein the peptide is (a) non-lytic and capable of affecting the release of a polynucleotide from an endosome of a cell, and (b) comprises an amino acid sequence with at least 80% identity to an amino acid sequence chosen from SEQ ID NO: 1, SEQ ID NO: 57 or SEQ ID NO: 63. In an aspect, the peptide comprises at least one cationic region and at least one histidine residue located adjacent to or within at least one cationic region of the peptide. In another aspect, the polynucleotide is a non-coding RNA capable of regulating or inhibiting the expression of a nucleic acid sequence.

The present invention also encompasses an amino acid sequence that has at least 80% identity to an amino acid sequence chosen from SEQ ID NO: 1, SEQ ID NO: 57 or SEQ ID NO: 63, and encodes a peptide that is non-lytic and capable of affecting the release of a polynucleotide from an endosome of a cell.

The present invention also encompasses a peptide comprising an amino acid sequence that has at least 80% identity to an amino acid sequence chosen from SEQ ID NO: 1, SEQ ID NO: 57 or SEQ ID NO: 63, wherein the peptide is non-lytic and capable of affecting the release of a polynucleotide from an endosome of a cell.

Other aspects and iterations of the invention are described more thoroughly below.

BRIEF DESCRIPTION OF THE FIGURES

The application file contains at least one photograph executed in color. Copies of this patent application publication with color photographs will be provided by the Office upon request and payment of the necessary fee.

FIG. 7A-I depicts graphs and images of p5RHH mediated transfection. (A) Western blotting depicts a dose dependent decrease in STAT3 protein levels in HUVECs treated with STAT3 specific siRNA. (B) RT-PCR data illustrate a p5RHH-dependent 60% knockdown in STAT3 mRNA at concentrations as high as 200 nM. (C) p5RHH has no cytotoxicity towards HUVEC cells when transfecting siRNA. (D) HUVECs treated with STAT3 siRNA show decreased a 60% tube formation on matrigel when compared to controls (E, F) as quantified in (G). A decrease in tube formation is accompanied by a 40% decrease in HUVEC migration in response to bFGF in transwell migration assays as determined by microscopy (H) and Alamar Blue assays (I).

FIG. 17A-J depicts graphs and microscopy images showing uptake and colocalization of p5RHH/siRNA nanoparticles. (A-D) 40 minute uptake of p5RHH/Alexa488-siRNA nanoparticles shows that 60% of the treated cells take up (A) p5RHH/siRNA nanoparticles. The presence of endocytosis inhibitors indicates that (B) 100 µg/mL filipin (caveolae inhibitor) and (C) 10 µM PAO (clathrin mediated endocytosis inhibitor) do not inhibit p5RHH/siRNA nanoparticle uptake. Alternatively, treatment with (D) macropinocytosis inhibitor (EIPA, 80 µM) nearly abolishes nanoparticle uptake. (E-J) Colocalization as determined by confocal microscopy shows that p5RHH/Cy-3 siRNA nanoparticles are taken up with FITC-70 kDa dextran (J) but not FITC-transferrin (I). Scale bar 10 µm.

FIG. 24A-G depicts Western blots, a graph, and microscopy images (A, B) Western blotting demonstrates a dose-dependent decrease in p100/p52 or p65 expression that is not seen when treating F8 cells with scrambled siRNA. (C) Alamar blue assays 48 hours post transfection reveals that scrambled siRNA (■) does not affect F8 cell viability. Knockdown of the canonical NFκB pathway with p65 siRNA (▲) has an $IC_{50}$ of nearly 200 nM. Targeting the non-canonical NFκB pathway with p100/p52 siRNA (●) yields an $IC_{50}$ of 100 nM. However, simultaneous blockade of both canonical and non-canonical NFκB pathways (♦) improves the $IC_{50}$ to 50 nM. IVIS imaging (scale bar 5 mm) reveals tumor localization of Cy5.5 labeled siRNA to the tumor of treated mice (E), and is confirmed by confocal microscopy (G) (scale bar 50 µm). Non treated controls shown for comparison (D, F).

FIG. 32A-F depicts images and graphs showing p65-siRNA nanotherapy in collagen antibody-induced arthritis (CAIA) is effective. Arthritis was induced with i.p. injection of 1.5 mg of 5-clone antibody cocktail on day 0 followed by the injection of 50 ug of LPS on day 3. On day 4 when early arthritis was established, mice were randomly divided into 3 groups for treatment (Tx) with saline, scrambled sequence nanoparticle, and p65-siRNA nanoparticle given i.v. on days 4, 5, and 6. Paws were photographed on day 10 (A-C). Change in ankle thickness (D), arthritis score (E), and % weight loss (F) were chronicled daily. Values are presented as mean±SEM, n=6-8 mice per treatment group. *P<0.05, P<0.01, *P<0.001

DETAILED DESCRIPTION OF THE INVENTION

Figure 1A:
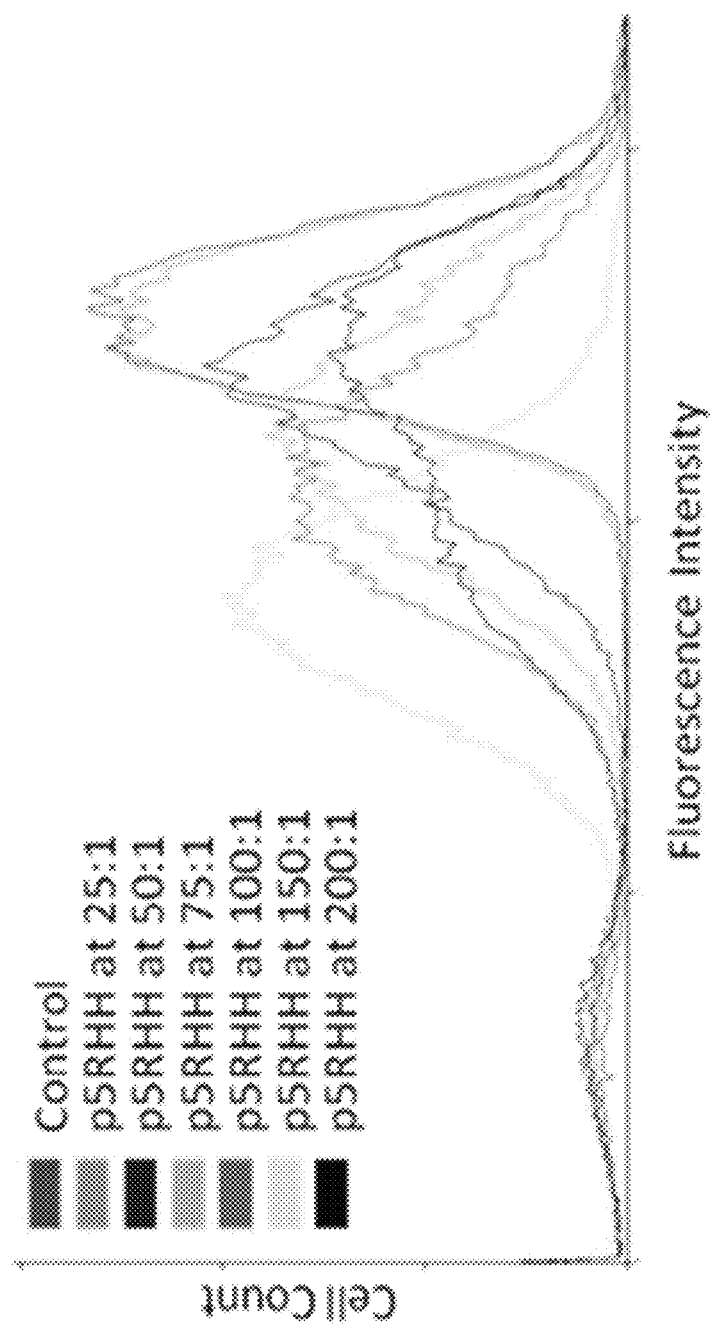
FIGS. 1A and B depicts two plots showing (A) optimization of p5RHH/siRNA ratios reveal an increasing transfection efficiency with increasing amounts of p5RHH until a maximum at 150:1 p5RHH:siRNA, and (B) Alamar blue assays indicate no cytotoxicity at p5RHH:siRNA ratios up to 200:1 when transfecting 50 nM siRNA.

The present invention provides a peptide-polynucleotide complex capable of efficient transfection of the polynucleotide into the cytoplasm of a cell with reduced cytotoxicity, as compared to other methods of polynucleotide transfection known in the art. Advantageously, a peptide-polynucleotide complex of the invention is stable in the presence of serum and, therefore, is capable of efficiently delivering a polynucleotide to the cytoplasm of a cell in vivo. Accordingly, the present invention encompasses, a pharmaceutical composition comprising a peptide-polynucleotide complex of the invention, a method of preparing a peptide-polynucleotide complex of the invention, a method of using a peptide-polynucleotide complex of the invention to transfect the polynucleotide into the cytoplasm of a cell, and a kit for preparing a peptide-polynucleotide complex of the invention.

I. Peptide-Polynucleotide Complex

One aspect of the present invention encompasses a peptide-polynucleotide complex. A peptide-polynucleotide complex of the invention is capable of efficient transfection of a polynucleotide associated with the peptide into the cytoplasm of a cell. The peptide, the polynucleotide, the peptide-polynucleotide complex, and the cell are described below.

(a) Peptide

In an aspect, a peptide-polynucleotide complex of the invention comprises a peptide. In general, and as described in the examples, a peptide of the invention is derived from melittin and modified to attenuate its cytotoxicity while maintaining its propensity for interacting with membrane bilayers. Furthermore, the peptide is substantially non-lytic and non-cytotoxic to cells. Preferably, a peptide-polynucleotide complex of the invention comprises a peptide that (1) has a function substantially similar to a peptide with an amino acid sequence of SEQ ID NO: 1, and (2) has an amino acid sequence with similarity or identity to the amino acid sequence of SEQ ID NO: 1.

As used herein, the phrase "functions substantially similar to a peptide comprising SEQ ID NO: 1" refers to a substantially non-lytic and/or non-cytotoxic peptide that is capable of affecting the release of a polynucleotide from an endosome. In some embodiments a peptide of the invention is non-lytic. The term "non-lytic" means that the lipid bilayer of a cell typically is not compromised upon contact with the peptide. The integrity of the lipid bilayer may be assessed by the improper entry or exit of cellular or extracellular components into a cell. For example, cellular proteins and/or organelles may leak out of a cell with a compromised lipid bilayer. Alternatively, extracellular components (i.e., those that normally do not enter via gap junctions, for example) may enter a cell with a compromised lipid bilayer. It should be noted, however, that the peptide may penetrate the lipid bilayer of a cell and enter the interior of the cell, but in doing so the integrity of the lipid bilayer is not affected. In other embodiments, a peptide of the invention is substantially non-cytotoxic. The term "non-cytotoxic" indicates that the cell typically is not killed upon contact with the peptide. Typically, a peptide of the invention decreases cell viability by no more than about 10%, more preferably no more than about 7%, more preferably no more than about 5%, or more preferably no more than about 3%. In certain embodiments, a peptide of the invention is non-lytic and non-cytotoxic.

As described in Section I(b) and (c) below, a peptide of the invention is capable of associating with a polynucleotide. Thus, in one aspect, a peptide of the invention comprises at least one cationic region that interacts with a polynucleotide. Typically, a cationic region has 2 or more contiguous, basic amino acids. Importantly, a peptide of the invention also possesses an endosomolytic capacity, which allows it to affect the release of a polynucleotide from an endosome and into the cytoplasm of a cell. The term "endosomolytic" can be used to describe substances that initiate or facilitate the lysis of endosomes. As described in the Examples, protonation of histidine residues of a peptide of the invention promotes disassembly of the peptide-polynucleotide complex, which releases the peptide to permeabilize the endosomal membrane for polynucleotide release. Thus, in another aspect, a peptide of the invention comprises one or more histidine residues located adjacent to or within at least one cationic region of the peptide. By way of non-limiting example, if a peptide of the invention comprises three cationic regions, the peptide may have at least one histidine adjacent to or within the first cationic region of the peptide, at least one histidine adjacent to or within the second cationic region of the peptide, at least one histidine adjacent to or within the third cationic region of the peptide, at least one histidine adjacent to or within each of the first and second cationic region of the peptide, at least one histidine adjacent to or within each of the first and third cationic region of the peptide, at least one histidine adjacent to or within each of the second and third cationic region of the peptide, or at least one histidine adjacent to or within each of the first, second and third cationic region of the peptide. A histidine residue adjacent to a cationic region may be positioned before or after the cationic region. In some embodiments, a histidine residue adjacent to a cationic region is immediately adjacent to the region. In other embodiments, a histidine residue adjacent to a cationic region is not immediately adjacent to the region. For example, the histidine residue may be within about 2, 3, 4 or 5 positions from the cationic region. In other embodiments, a histidine residue is within a cationic region. The endosomolytic capacity of a peptide of the invention obviates the need for additional endosomolytic agents, such as chloroquine, fusogenic peptides, inactivated adenoviruses and polyethyleneimine, for releasing transfected polynucleotides from endosomes for delivery into the cytoplasm of a cell. Such known endosomolytic agents have negative effects on cells, and may increase cytotoxicity during transfection.

In some embodiments, a peptide of the invention comprises SEQ ID NO: 1. In other embodiments, a peptide of the inventions consists of SEQ ID NO: 1. In certain embodiments, a peptide of the invention is a variant of SEQ ID NO: 1, wherein the variant comprises at least 10 contiguous amino acids of SEQ ID NO: 1 and functions substantially similar to a peptide comprising SEQ ID NO: 1. For instance, a peptide of the invention may encompass at least 10, 11, 12, 13, 14, 15, 16, 17, 18, 19, or 20 contiguous amino acids of SEQ ID NO: 1. In some embodiments, a peptide of the invention may be selected from Table A. In other embodiments, a peptide of the invention may be selected from Table B.

TABLE A

| SEQ ID NO. | Sequence |
|---|---|
| 1 | VLTTGLPALISWIRRRHRRHC |
| 2 | VLTTGLPALISWIRRRH |
| 3 | VLTTGLPALISWIRRRHR |
| 4 | VLTTGLPALISWIRRRHRR |
| 5 | VLTTGLPALISWIRRRHRRH |
| 6 | LTTGLPALISWIRRRH |
| 7 | LTTGLPALISWIRRRHR |
| 8 | LTTGLPALISWIRRRHRR |
| 9 | LTTGLPALISWIRRRHRRH |
| 10 | LTTGLPALISWIRRRHRRHC |
| 11 | TTGLPALISWIRRRH |
| 12 | TTGLPALISWIRRRHR |
| 13 | TTGLPALISWIRRRHRR |
| 14 | TTGLPALISWIRRRHRRH |
| 15 | TTGLPALISWIRRRHRRHC |
| 16 | TGLPALISWIRRRH |
| 17 | TGLPALISWIRRRHR |
| 18 | TGLPALISWIRRRHRR |
| 19 | TGLPALISWIRRRHRRH |
| 20 | TGLPALISWIRRRHRRHC |
| 21 | GLPALISWIRRRH |
| 22 | GLPALISWIRRRHR |
| 23 | GLPALISWIRRRHRR |
| 24 | GLPALISWIRRRHRRH |
| 25 | GLPALISWIRRRHRRHC |
| 26 | LPALISWIRRRH |
| 27 | LPALISWIRRRHR |
| 28 | LPALISWIRRRHRR |
| 29 | LPALISWIRRRHRRH |
| 30 | LPALISWIRRRHRRHC |
| 31 | PALISWIRRRH |
| 32 | PALISWIRRRHR |
| 33 | PALISWIRRRHRR |
| 34 | PALISWIRRRHRRH |
| 35 | PALISWIRRRHRRHC |
| 36 | ALISWIRRRH |
| 37 | ALISWIRRRHR |
| 38 | ALISWIRRRHRR |
| 39 | ALISWIRRRHRRH |

TABLE A-continued

| SEQ ID NO. | Sequence |
|---|---|
| 40 | ALISWIRRRHRRHC |
| 41 | LISWIRRRHR |
| 42 | LISWIRRRHRR |
| 43 | LISWIRRRHRRH |
| 44 | LISWIRRRHRRHC |
| 45 | ISWIRRRHRR |
| 46 | ISWIRRRHRRH |
| 47 | ISWIRRRHRRHC |
| 48 | SWIRRRHRRH |
| 49 | SWIRRRHRRHC |
| 50 | WIRRRHRRHC |

TABLE B

| SEQ ID NO | SEQUENCE |
|---|---|
| 57 | VLTTGLPALISWIRRRHRRC |
| 58 | VLTTGLPALISWIRR |
| 59 | VLTTGLPALISWIRRR |
| 60 | VLTTGLPALISWIRRRH |
| 61 | VLTTGLPALISWIRRRHR |
| 62 | VLTTGLPALISWIRRRHRR |
| 63 | VLKVLTTLAPALISWIRRRHRRC |
| 64 | VLKVLTTLAPALISWIRR |
| 65 | VLKVLTTLAPALISWIRRR |
| 66 | VLKVLTTLAPALISWIRRRH |
| 67 | VLKVLTTLAPALISWIRRRHR |
| 68 | VLKVLTTLAPALISWIRRRHRR |

In a preferred embodiment, a peptide of the invention comprises an amino acid sequence that has at least 80% identity to SEQ ID NO: 1, wherein the peptide is non-lytic and is capable of affecting the release of a polynucleotide from an endosome of a cell. The peptide comprising an amino acid sequence that has at least 80% identity to SEQ ID NO: 1, can have about 80%, preferably about 85%, more preferably about 90%, more preferably about 95% identity to the amino acid sequence of SEQ ID NO: 1. A peptide of the invention comprising an amino acid sequence that has at least 80% identity to SEQ ID NO: 1 may comprise one or more amino acids that have been conservatively substituted. For instance, one, two, three, four, five, six, seven, eight, nine, or more than nine amino acids may be conservatively substituted as long as the resulting peptide functions substantially similar to a peptide comprising SEQ ID NO: 1.

In another preferred embodiment, a peptide of the invention comprises an amino acid sequence that has at least 80% identity to SEQ ID NO: 57, wherein the peptide is non-lytic and is capable of affecting the release of a polynucleotide from an endosome of a cell. The peptide comprising an amino acid sequence that has at least 80% identity to SEQ ID NO: 57, can have about 80%, preferably about 85%, more preferably about 90%, more preferably about 95% identity to the amino acid sequence of SEQ ID NO: 57. A peptide of the invention comprising an amino acid sequence that has at least 80% identity to SEQ ID NO: 57 may comprise one or more amino acids that have been conservatively substituted. For instance, one, two, three, four, five, six, seven, eight, nine, or more than nine amino acids may be conservatively substituted as long as the resulting peptide functions substantially similar to a peptide comprising SEQ ID NO: 57.

In a preferred embodiment, a peptide of the invention comprises an amino acid sequence that has at least 80% identity to SEQ ID NO: 63, wherein the peptide is non-lytic and is capable of affecting the release of a polynucleotide from an endosome of a cell. The peptide comprising an amino acid sequence that has at least 80% identity to SEQ ID NO: 63, can have about 80%, preferably about 85%, more preferably about 90%, more preferably about 95% identity to the amino acid sequence of SEQ ID NO: 63. A peptide of the invention comprising an amino acid sequence that has at least 80% identity to SEQ ID NO: 63 may comprise one or more amino acids that have been conservatively substituted. For instance, one, two, three, four, five, six, seven, eight, nine, or more than nine amino acids may be conservatively substituted as long as the resulting peptide functions substantially similar to a peptide comprising SEQ ID NO: 63.

In another aspect, the present invention provides an amino acid sequence that has at least 80% identity to SEQ ID NO: 1 and encodes a peptide that is non-lytic and capable of affecting the release of a polynucleotide from an endosome of a cell. In some embodiments, the amino acid sequence has at least 80% identity, at least 85% identity, at least 90% identity, or at least 95% identity to an amino acid sequence chosen from SEQ ID NO: 1, SEQ ID NO: 57 or SEQ ID NO: 63. In other embodiments, the amino acid sequence is SEQ ID NO: 1, SEQ ID NO: 57 or SEQ ID NO: 63.

A peptide of the invention may be produced using a variety of techniques known in the art. The peptides may be isolated using standard techniques, may be synthesized using standard techniques, or may be purchased or obtained from a depository.

When a peptide of the invention contains a C-terminal thiol in the form of a cysteine residue, a peptide of the invention may be able to form a disulfide bond with another free thiol group, for example, with a free thiol group from the same or different peptide. A skilled artisan can readily determine whether dimer formation does or does not improve the delivery of plasmid DNA. Without wishing to be bound by theory, dimer formation may improve the delivery of plasmid DNA for certain peptides of the invention due to improved DNA condensation. Dimerization may be induced by incubation of free peptide in 20% DMSO for 24-72 hours, or by other methods known in other art. As a non-limiting example, free thiols may be quantified by colorimetric assays using Ellman's Reagent.

A peptide of the invention may be labeled. Non-limiting examples of suitable labels include fluorescent labels, chemiluminescent labels, radioactive labels, colorimetric labels, and resonance labels. Methods of labeling peptides are well known in the art.

A peptide may be bound to a cargo complex. As used herein, the term "cargo complex" may refer to any molecule or agent that may be carried by or bound to the peptide other than a polynucleotide of the invention. Stated another way, a peptide of the invention may be bound to a cargo complex in addition to a polynucleotide of the invention. For instance, a cargo complex may be an imaging cargo, a therapeutic cargo, a cytotoxic cargo, or a targeting cargo.

Non-limiting examples of imaging cargo molecules and agents may include any molecule, agent, or material having a detectable physical or chemical property. Such imaging cargos have been well-developed in the field of fluorescent imaging, magnetic resonance imaging, positron emission tomography, Raman imaging, optical coherence tomography, photoacoustic imaging, Fourier transform infrared imaging, or immunoassays and, in general, most any label useful in such methods may be applied to the present invention. For a review of various labeling or signal producing systems that may be used, see U.S. Pat. No. 4,391,904, incorporated herein by reference in its entirety.

Non-limiting examples of therapeutic cargo may include any substance that has a biological activity, such as pharmacological agents. Such therapeutic cargo may include analgesics, antipyretics, antiasthmatics, antibiotics, antidepressants, antidiabetics, antifungal agents, antihypertensive agents, anti-inflammatories including non-steroidal and steroidal, antineoplastics, antianxiety agents, immunosuppressive agents, anti migraine agents, sedatives, hypnotics, antianginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines, anti-restenosis agents, antipruritics, agents useful for calcium regulation, antibacterial agents, antiviral agents, antimicrobials, anti-infectives, bronchodilators, steroidal compounds and hormones, and combinations thereof. Alternatively, a cargo complex may be in the form of components of molecular complexes or pharmacologically acceptable salts.

Cytotoxic cargo refers to a molecule or agent that is detrimental to (e.g., kills or damages) a cell. Examples may include anti-microtubule drugs such as the taxols (paclitaxel, docetaxel) and vinca alkaloids (vincristine, vinblastine). For instance, examples may include taxol, cytochalasin B, gramicidin D, ethidium bromide, emetine, mitomycin, etoposide, tenoposide, vincristine, vinblastine, colchicin, doxorubicin, daunorubicin, dihydroxy anthracin didne, mitoxantrone, mithramycin, actinomycin D, 1-dehydrotestosterone, glucocorticoids, procaine, tetracaine, lidocaine, propranolol, and puromycin and analogs or homologs thereof.

A targeting cargo may be any molecule or agent that directs a peptide-polynucleotide complex of the invention to a cell. A targeting cargo may be directed to a eukaryotic target cell or a prokaryotic target cell. Non-limiting examples of targeting agents may include an antibody or an antibody fragment, a receptor ligand, a small molecule, a peptide, a polypeptide, a lipid, a carbohydrate, a nucleic acid, a siRNA, a shRNA, an antisense RNA, a dendrimer, a microbubble, or an aptamer.

The means by which a cargo complex is bound to a peptide of the invention can and will vary depending on the embodiment. A cargo complex may be bound to a peptide of the invention by any means known in the art, including covalently or non-covalently.

(b) Polynucleotide

In another aspect, a peptide-polynucleotide complex of the invention comprises a polynucleotide. A polynucleotide may be single stranded, double stranded, or a combination thereof. In some embodiments, a polynucleotide is double stranded. In other embodiments, a polynucleotide is single stranded. In yet other embodiments, a polynucleotide is a combination of single stranded and double stranded.

A polynucleotide of the invention may comprise a ribonucleic acid (RNA), a deoxyribonucleic acid (DNA), or a combination of RNA and DNA. Additionally, a polynucleotide may comprise modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). Alternatively, a polynucleotide may be a nucleotide mimic. Examples of nucleotide mimics include locked nucleic acids (LNA), peptide nucleic acids (PNA), and phosphorodiamidate morpholino oligomers (PMO).

In some embodiments, a polynucleotide of the invention is a combination of RNA and DNA. In other embodiments, a polynucleotide comprises DNA. When a polynucleotide is DNA, the polynucleotide may comprise an expression cassette. As used herein, an "expression cassette" is a nucleic acid construct comprising a nucleic acid sequence encoding a protein or peptide operably linked to a promoter. In certain embodiments, a nucleic acid construct further comprises additional regulatory sequences. A non-limiting example of an additional regulatory sequence includes a transcription termination sequence. Other additional regulatory sequences are known in the art. As used herein, the term promoter may mean a synthetic or naturally-derived molecule capable of conferring or activating expression of a target nucleic acid sequence in a cell. A promoter may be the promoter normally associated with a DNA polynucleotide of the invention, or may be a heterologous promoter. A heterologous promoter may be derived from such sources as viruses, bacteria, fungi, plants, insects, and animals. A promoter may regulate the expression of a DNA sequence constitutively or differentially with respect to the cell, the tissue or organ in which expression occurs. Or, a promoter may regulate expression with respect to developmental stage, or in response to external stimuli such as physiological stresses, pathogens, metal ions, or inducing agents or activators (i.e. an inducible promoter). Non-limiting representative examples of promoters may include the bacteriophage T7 promoter, bacteriophage T3 promoter, SP6 promoter, HSP70 basal promoter, lac operator-promoter, tac promoter, SV40 late promoter, SV40 early promoter, RSV-LTR promoter, CMV IE promoter, a promoter comprising the tetracycline response element (TRE) nucleic acid sequence, and the CMV IE promoter. In some alternatives of these embodiments, a DNA polynucleotide of the invention is incorporated into a vector. One of skill in the art would be able to construct a vector through standard recombinant techniques (see, for example, Sambrook et al., 2001 and Ausubel et al., 1996, both incorporated herein by reference). Vectors include but are not limited to plasmids, cosmids, transposable elements, viruses (bacteriophage, animal viruses, and plant viruses), and artificial chromosomes (e.g., YACs), such as retroviral vectors (e.g., derived from Moloney murine leukemia virus vectors (MoMLV), MSCV, SFFV, MPSV, SNV etc.), lentiviral vectors (e.g., derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, and Rous sarcoma virus vectors.

In yet other embodiments, a polynucleotide comprises RNA. Non-limiting examples of RNA sequences may include mRNA capable of encoding a protein, and non-coding RNA such as tRNA, rRNA, snoRNAs, microRNAs, siRNAs, piRNAs and the long noncoding RNA (lncRNA). For instance, a nucleic acid may comprise mRNA. In preferred embodiments, when a nucleic acid comprises mRNA, the mRNA molecule may be 5' capped, polyadenylated, or capped and polyadenylated. Alternatively, a mRNA molecule may comprise an internal ribosomal entry sites (IRES) for translation of an internal open reading frame of the mRNA.

In certain embodiments, a polynucleotide comprises non-coding RNA capable of regulating or inhibiting the expression of a nucleic acid sequence expressed in a cell. Non-limiting examples of non-coding RNA capable of regulating or inhibiting the expression of a nucleic acid sequence expressed in a cell include microRNAs (also known as miRNAs), siRNAs, piRNAs and lncRNAs. In general, transfection of a cell with a non-coding RNA capable of regulating or inhibiting the expression of a nucleic acid sequence may lead to cleavage of the nucleic acid sequence, may enhance, prevent, or disrupt translation of the nucleic acid sequence into a protein, or may regulate the transcription of a nucleic acid sequence.

In preferred embodiments, a polynucleotide of the invention comprises a non-coding RNA capable of disrupting expression of a nucleic acid sequence expressed in a cell. As used herein, "disrupting expression of a nucleic acid sequence" may be used to describe any decrease in the expression level of a nucleic acid sequence, or a protein translated from the nucleic acid sequence, when compared to a level of expression of the nucleic acid sequence in a cell that was not treated with a peptide-polynucleotide complex of the invention. In some alternatives of the embodiments, a polynucleotide comprises a short interfering RNA (siRNA).

In a preferred embodiment, a polynucleotide of the invention comprises a non-coding RNA capable of disrupting the expression of a nucleic acid sequence encoding STAT3. In another preferred embodiment, a polynucleotide of the invention comprises a non-coding RNA capable of disrupting the expression of a nucleic acid sequence encoding JNK2. In certain preferred embodiments, the non-coding RNA is an siRNA. In other preferred embodiments, the non-coding RNA is a miRNA. In still other preferred embodiments, the non-coding RNA is a shRNA.

In yet another preferred embodiment, a polynucleotide of the invention comprises a non-coding RNA capable of disrupting the expression of a nucleic acid sequence normally associated with a NFκB signaling pathway. Non-limiting examples of a NFκB pathway may include the canonical NFκB pathway and the non-canonical NFκB pathway. In certain preferred embodiments, the non-coding RNA is an siRNA. In other preferred embodiments, the non-coding RNA is a miRNA. In still other preferred embodiments, the non-coding RNA is a shRNA.

Non-limiting examples of a nucleic acid sequence normally associated with the canonical NFκB signaling pathway may include a nucleic acid encoding the transcription factor p65 subunit of the canonical NFκB signaling pathway and a nucleic acid encoding the transcription factor p105/p50 subunit of the canonical NFκB signaling pathway. In one alternative of the embodiments, a polynucleotide of the invention comprises a non-coding RNA capable of disrupting the expression of a nucleic acid sequence encoding the p105/p50 subunit of the canonical NFκB signaling pathway. In another alternative of the embodiments, a polynucleotide of the invention comprises a non-coding RNA capable of disrupting the expression of a nucleic acid sequence encoding the p65 subunit of the canonical NFκB signaling pathway. In an exemplary embodiment, a polynucleotide of the invention comprises a siRNA with a nucleic acid sequence of SEQ ID NO: 51 (GGAGUACCCUGAAGCUAUA).

Non-limiting examples of a nucleic acid sequence normally associated with the canonical NFκB signaling pathway may include a nucleic acid encoding the p100/p52 subunit of the non-canonical NFκB signaling pathway and a nucleic acid encoding the RelB subunit of the non-canonical NFκB signaling pathway. In one alternative of the embodiments, a polynucleotide of the invention comprises a non-coding RNA capable of disrupting the expression of a nucleic acid sequence encoding the RelB subunit of the non-canonical NFκB signaling pathway. In another alternative of the embodiments, a polynucleotide of the invention comprises a non-coding RNA capable of disrupting the expression of a nucleic acid sequence encoding the p100/p52 subunit of the non-canonical NFκB signaling pathway. In an exemplary embodiment, a polynucleotide of the invention comprises a siRNA with a nucleic acid sequence of SEQ ID NO: 52 (GAAAGAAGACAGAGCCUAU).

In some embodiments, a polynucleotide of the invention comprises more than one non-coding RNA capable of disrupting the expression of a nucleic acid sequence normally associated with a NFκB signaling pathway. In preferred embodiments, a polynucleotide of the invention comprises a non-coding RNA capable of disrupting the expression of a nucleic acid sequence normally associated with the canonical NFκB signaling pathway, and a non-coding RNA capable of disrupting the expression of a nucleic acid sequence normally associated with the non-canonical NFκB signaling pathway. In an exemplary embodiment, a polynucleotide of the invention comprises a non-coding RNA capable of disrupting the expression of a nucleic acid sequence encoding the p65 subunit of the canonical NFκB signaling pathway, and a non-coding RNA capable of disrupting the expression of a nucleic acid sequence encoding the p100/p52 subunit of the canonical NFκB signaling pathway.

In general, a siRNA comprises a double-stranded RNA molecule that ranges from about 15 to about 29 nucleotides in length. In some embodiments, the siRNA may be 16, 17, 18, 19, 20, 21, 22, 23, 24, 25, 26, 27, 28 or 29 nucleotides in length. In other embodiments, the siRNA may be about 16 to about 18, about 17 to about 19, about 21 to about 23, about 24 to about 27, or about 27 to about 29 nucleotides in length. In a preferred embodiment, the siRNA may be about 21 nucleotides in length. A siRNA may optionally further comprise one or two single-stranded overhangs, e.g., a 5' overhang on one or both ends, a 3' overhang on one or both ends, or a combination thereof. The siRNA may be formed from two RNA molecules that hybridize together or, alternatively, may be generated from a short hairpin RNA (shRNA) (see below). In some embodiments, the two strands of the siRNA may be completely complementary, such that no mismatches or bulges exist in the duplex formed between the two sequences. In other embodiments, the two strands of the siRNA may be substantially complementary, such that one or more mismatches and/or bulges may exist in the duplex formed between the two sequences. In certain embodiments, one or both of the 5' ends of the siRNA may have a phosphate group, while in other embodiments one or both of the 5' ends lack a phosphate group. In other embodiments, one or both of the 3' ends of the siRNA may have a hydroxyl group, while in other embodiments one or both of the 5' ends lack a hydroxyl group.

One strand of the siRNA, which is referred to as the "antisense strand" or "guide strand," includes a portion that hybridizes with a target transcript. A target transcript refers to a nucleic acid sequence expressed by a cell for which it is desired expression be disrupted. In the context of a therapeutic composition of the invention, disrupting expression of a target transcript may produce a beneficial effect. In preferred embodiments, the antisense strand of the siRNA may be completely complementary with a region of the target transcript, i.e., it hybridizes to the target transcript without a single mismatch or bulge over a target region between about 15 and about 29 nucleotides in length, preferably at least 16 nucleotides in length, and more preferably about 18-20 nucleotides in length. In other embodiments, the antisense strand may be substantially complementary to the target region, i.e., one or more mismatches and/or bulges may exist in the duplex formed by the antisense strand and the target transcript. Typically, siRNAs are targeted to exonic sequences of the target transcript. Those of skill in the art are familiar with programs, algorithms, and/or commercial services that design siRNAs for target transcripts. An exemplary example is the Rosetta siRNA Design Algorithm (Rosetta Inpharmatics, North Seattle, Wash.), MISSION® siRNA (Sigma-Aldrich, St. Louis, Mo.) and siGENOME siRNA (Thermo Scientific). The siRNA may be enzymatically synthesized in vitro using methods well known to those of skill in the art. Alternatively, the siRNA may be chemically synthesized using oligonucleotide synthesis techniques that are well known in the art.

In other embodiments, the non-coding RNA may be a short hairpin RNA (shRNA). In general, a shRNA is an RNA molecule comprising at least two complementary portions that are hybridized or are capable of hybridizing to form a double-stranded structure sufficiently long to mediate RNA interference (as described above), and at least one single-stranded portion that forms a loop connecting the regions of the shRNA that form the duplex. The structure may also be called a stem-loop structure, with the stem being the duplex portion. In some embodiments, the duplex portion of the structure may be completely complementary, such that no mismatches or bulges exist in the duplex region of the shRNA. In other embodiments, the duplex portion of the structure may be substantially complementary, such that one or more mismatches and/or bulges may exist in the duplex portion of the shRNA. The loop of the structure may be from about 1 to about 20 nucleotides in length, preferably from about 4 to about 10 about nucleotides in length, and more preferably from about 6 to about 9 nucleotides in length. The loop may be located at either the 5' or 3' end of the region that is complementary to the target transcript (i.e., the antisense portion of the shRNA).

The shRNA may further comprise an overhang on the 5' or 3' end. The optional overhang may be from about 1 to about 20 nucleotides in length, and more preferably from about 2 to about 15 nucleotides in length. In some embodiments, the overhang may comprise one or more U residues, e.g., between about 1 and about 5 U residues. In some embodiments, the 5' end of the shRNA may have a phosphate group, while in other embodiments it may not. In other embodiments, the 3' end of the shRNA may have a hydroxyl group, while in other embodiments it may not. In general, shRNAs are processed into siRNAs by the conserved cellular RNAi machinery. Thus, shRNAs are precursors of siRNAs and are similarly capable of inhibiting expression of a target transcript that is complementary of a portion of the shRNA (i.e., the antisense portion of the shRNA). Those of skill in the art are familiar with the available resources (as detailed above) for the design and synthesis of shRNAs. An exemplary example is MISSION® shRNAs (Sigma-Aldrich).

In still other embodiments, the non-coding RNA may be an RNA interference (RNAi) RNAi expression vector. Typically, an RNAi expression vector may be used for intracellular (in vivo) synthesis of RNAi agents, such as miRNAs, siRNAs or shRNAs. In one embodiment, two separate, complementary siRNA strands may be transcribed using a single vector containing two promoters, each of which directs transcription of a single siRNA strand (i.e., each promoter is operably linked to a template for the siRNA so that transcription may occur). The two promoters may be in the same orientation, in which case each is operably linked to a template for one of the complementary siRNA strands. Alternatively, the two promoters may be in opposite orientations, flanking a single template so that transcription for the promoters results in synthesis of two complementary siRNA strands. In another embodiment, the RNAi expression vector may contain a promoter that drives transcription of a single RNA molecule comprising two complementary regions, such that the transcript forms a shRNA.

Generally speaking, the promoters utilized to direct in vivo expression of the one or more siRNA or shRNA transcription units may be promoters for RNA polymerase III (Pol III). Certain Pol III promoters, such as U6 or H1 promoters, do not require cis-acting regulatory elements within the transcribed region, and thus, are preferred in certain embodiments. In other embodiments, promoters for Pol II may be used to drive expression of the one or more siRNA or shRNA transcription units. In some embodiments, tissue-specific, cell-specific, or inducible Pol II promoters may be used.

A construct that provides a template for the synthesis of siRNA or shRNA may be produced using standard recombinant DNA methods and inserted into any of a wide variety of different vectors suitable for expression in eukaryotic cells. Guidance may be found in Current Protocols in Molecular Biology (Ausubel et al., John Wiley & Sons, New York, 2003) or Molecular Cloning: A Laboratory Manual (Sambrook & Russell, Cold Spring Harbor Press, Cold Spring Harbor, N.Y., 3rd edition, 2001). Those of skill in the art also appreciate that vectors may comprise additional regulatory sequences (e.g., termination sequence, translational control sequence, etc.), as well as selectable marker sequences. DNA plasmids are known in the art, including those based on pBR322, PUC, and so forth. Since many expression vectors already contain a suitable promoter or promoters, it may only be necessary to insert the nucleic acid sequence that encodes the RNAi agent of interest at an appropriate location with respect to the promoter(s). Viral vectors may also be used to provide intracellular expression of RNAi agents. Suitable viral vectors include retroviral vectors, lentiviral vectors, adenoviral vectors, adeno-associated virus vectors, herpes virus vectors, and so forth. In preferred embodiments, the RNAi expression vector is a shRNA lentiviral-based vector or lentiviral particle, such as that provided in MISSION® TRC shRNA products (Sigma-Aldrich).

Nucleic acid sequences of the invention may be obtained using a variety of different techniques known in the art. The nucleotide sequences, as well as homologous sequences, may be isolated using standard techniques, purchased or obtained from a depository. Once the nucleotide sequence is obtained, it may be amplified for use in a variety of applications, using methods known in the art.

(c) Polypeptide-Polynucleotide Complex

In another aspect of the invention, a polypeptide and a polynucleotide of the invention associate to form a complex. As used herein, the term "associate" may refer to the interaction of a peptide and a polynucleotide through non-covalent bonds, or to the covalent bonding of a peptide and a polynucleotide. In preferred embodiments, a polypeptide and a polynucleotide of the invention associate through non-covalent bonds such as a hydrogen bond, an ionic bond, a bond based on Van der Waals, a hydrophobic bond, or electrostatic interactions. For instance, a peptide of the invention may have an overall net positive charge, which may allow the peptide to associate with a polynucleotide of the invention through electrostatic interactions to form a complex of the invention. Methods for forming a polypeptide-polynucleotide complex of the invention are known in the art and further described in Section V and in the Examples.

The molar ratio of peptide to polynucleotide at which a peptide of the invention associates with a polynucleotide of the invention can and will vary depending on the peptide, the polynucleotide composition, or the size of the polynucleotide, and may be determined experimentally. In essence, a suitable molar ratio of a peptide of the invention to a polynucleotide of the invention may be a molar ratio wherein the peptide completely complexes the polynucleotide, while minimizing exposure of a subject to the peptide.

For instance, a peptide of the invention may associate with a polynucleotide in a peptide to polynucleotide molar ratio of about 1:1, 10:1, 20:1, 30:1, 40:1, 50:1, 60:1, 70:1, 80:1, 90:1, 100:1, 110:1, 120:1, 130:1, 140:1, 150:1, 160:1, 170:1, 180:1, 190:1, 200:1, 210:1, 220:1, 230:1, 240:1, 250:1, 260:1, 270:1, 280:1, 290:1, or about 300:1 or more. In some embodiments, a peptide and a polynucleotide of the invention associate in a peptide to polynucleotide molar ratio of about 1:1, 5:1, 10:1, 15:1, 20:1, 25:1, 30:1, 35:1, 40:1, 45:1, or about 50:1. In other embodiments, a peptide and a polynucleotide of the invention associate in a peptide to polynucleotide molar ratio of about 50:1, 55:1, 60:1, 65:1, 70:1, 75:1, 80:1, 85:1, 90:1, 95:1, or about 100:1. In yet other embodiments, a peptide and a polynucleotide of the invention associate in a peptide to polynucleotide molar ratio of about 100:1, 105:1, 110:1, 115:1, 120:1, 125:1, 130:1, 135:1, 140:1, 145:1, or about 150:1. In other embodiments, a peptide and a polynucleotide of the invention associate in a peptide to polynucleotide molar ratio of about 150:1, 155:1, 160:1, 165:1, 170:1, 175:1, 180:1, 185:1, 190:1, 195:1, or about 200:1. In additional embodiments, a peptide and a polynucleotide of the invention associate in a peptide to polynucleotide molar ratio of about 200:1, 205:1, 210:1, 215:1, 220:1, 225:1, 230:1, 235:1, 240:1, 245:1, or about 250:1. In still other embodiments, a peptide and a polynucleotide of the invention associate in a peptide to polynucleotide molar ratio of about 250:1, 255:1, 260:1, 265:1, 270:1, 275:1, 280:1, 285:1, 290:1, 295:1, or about 300:1 or more. In alternative embodiments, a peptide and a polynucleotide of the invention associate in a peptide to polynucleotide molar ratio of at least about 25:1. In different embodiments, a peptide and a polynucleotide of the invention associate in a peptide to polynucleotide molar ratio of at least about 50:1. In further embodiments, a peptide and a polynucleotide of the invention associate in a peptide to polynucleotide molar ratio of at least about 75:1. In still further embodiments, a peptide and a polynucleotide of the invention associate in a peptide to polynucleotide molar ratio of at least about 100:1.

When a polynucleotide of the invention is siRNA, a suitable molar ratio of a peptide of the invention to a polynucleotide of the invention capable of completely complexing the siRNA polynucleotide may be more than about 50:1, but less than about 200:1 to minimize exposure of a subject to the peptide. Stated another way, in some embodiments, a molar ratio of a peptide and a siRNA polynucleotide of the invention may be between about 50:1 to about 200:1. In other embodiments, a molar ratio of a peptide and a siRNA polynucleotide of the invention may be about 45:1, about 46:1, about 47:1, about 48:1, about 49:1, about 50:1, about 51:1, about 52:1, about 53:1, about 54:1, or about 55:1. In other embodiments, a molar ratio of a peptide and a siRNA polynucleotide of the invention may be about 70:1, about 71:1, about 72:1, about 73:1, about 74:1, about 75:1, about 76:1, about 77:1, about 78:1, about 79:1, or about 80:1. In yet other embodiments, a molar ratio of a peptide and a siRNA polynucleotide of the invention may be about 95:1, about 96:1, about 97:1, about 98:1, about 99:1, about 100:1, about 101:1, about 102:1, about 103:1, about 104:1, or about 105:1. In still other embodiments, a molar ratio of a peptide and a siRNA polynucleotide of the invention may be about 145:1, about 146:1, about 147:1, about 148:1, about 149:1, about 150:1, 151:1, about 152:1, about 153:1, about 154:1, or about 155:1. In other embodiments, a molar ratio of a peptide and a siRNA polynucleotide of the invention may be about 195:1, about 196:1, about 197:1, about 198:1, about 199:1, about 200:1, about 201:1, about 202:1, about 203:1, about 204:1, or about 205:1. In a preferred embodiment, a molar ratio of a peptide and a siRNA polynucleotide of the invention may be about 150:1. In another preferred embodiment, a molar ratio of a peptide and a siRNA polynucleotide of the invention may be about 100:1. In another preferred embodiment, a molar ratio of a peptide and a siRNA polynucleotide of the invention may be between about 50:1. In another preferred embodiment, a molar ratio of a peptide and a siRNA polynucleotide of the invention may be between about 50:1 to about 100:1. In another preferred embodiment, a molar ratio of a peptide and a siRNA polynucleotide of the invention may be between about 75:1 to about 150:1.

Methods of determining a molar ratio wherein the peptide is capable of completely complexing the polynucleotide are known in the art, and may include gel retardation assays as described in the examples. Methods of determining a molar ratio wherein exposure of a subject to the peptide is minimized are known in the art, and may include cytotoxicity measurements using increasing doses of the polypeptide.

A peptide-polynucleotide complex of the invention may be about 50 nm to about 999 nm in diameter, more preferably about 50 nm to about 500 nm in diameter, more preferably about 50 nm to about 250 nm in diameter. As such, a peptide-polynucleotide complex of the invention may be referred to as a "nanoparticle". In some embodiments, a nanoparticle of the invention is about 50, 55, 60, 65, 70, 75, 80, 85, 90, 95, 100, 105, 110, 115, or about 120 nm in diameter. In other embodiments, a nanoparticle of the invention is about 125, 130, 135, 140, 145, 150, 155, 160, 165, 170, 175, 180, 185, 190, 195, 200, 205, 210, 215, or 220 nm in diameter. In other embodiments, a nanoparticle of the invention is about 225, 230, 235, 240, 245, 250, 255, 260, 265, or 270 nm in diameter. In other embodiments, a nanoparticle of the invention is about 280, 285, 290, 295, 300, 310, 315, 320, 325, 330, 335, 340, or 345 nm in diameter. In other embodiments, a nanoparticle of the invention is about 350, 355, 360, 370, 375, 380, 385, 390, 395, 400, 405, 410, or 415 nm in diameter. In other embodiments, a nanoparticle of the invention is about 420, 425, 430, 435, 440, 445, 450, 455, 460, 465, 470, 475, 480, 485, 490, 495, or 500 nm in diameter. In other embodiments, a nanoparticle of the invention is about 570, 575, 580, 585, 590, 595, 600, 605, 610, 615, 620, 625, or 630 nm in diameter.

In a preferred embodiment, a nanoparticle of the invention is about 50 to about 250 nm in diameter. For example, a nanoparticle of the invention may be about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, about 160, about 161, about 162, about 163, about 164, about 165, about 166, about 167, about 168, about 169, about 170, about 171, about 172, about 173, about 174, about 175, about 176, about 177, about 178, about 179, about 180, about 181, about 182, about 183, about 184, about 185, about 186, about 187, about 188, about 189, about 190, about 191, about 192, about 193, about 194, about 195, about 196, about 197, about 198, about 199, about 200, about 201, about 202, about 203, about 204, about 205, about 206, about 207, about 208, about 209, about 210, about 211, about 212, about 213, about 214, about 215, about 216, about 217, about 218, about 219, about 220, about 221, about 222, about 223, about 224, about 225, about 226, about 227, about 228, about 229, about 230, about 231, about 232, about 233, about 234, about 235, about 236, about 237, about 238, about 239, about 240, about 241, about 242, about 243, about 244, about 245, about 246, about 247, about 248, about 249, or about 250 nm in diameter. In another preferred embodiment, a nanoparticle of the invention is about 50 to about 200 nm in diameter. In another preferred embodiment, a nanoparticle of the invention is about 50 to about 150 nm in diameter. In another preferred embodiment, a nanoparticle of the invention is about 50 to about 100 nm in diameter. In another preferred embodiment, a nanoparticle of the invention is about 75 to about 125 nm in diameter. In another preferred embodiment, a nanoparticle of the invention is about 100 to about 150 nm in diameter. In another preferred embodiment, a nanoparticle of the invention is about 125 to about 175 nm in diameter. In another preferred embodiment, a nanoparticle of the invention is about 150 to about 200 nm in diameter. In another preferred embodiment, a nanoparticle of the invention is about 175 to about 225 nm in diameter. In another preferred embodiment, a nanoparticle of the invention is about 200 to about 250 nm in diameter. In another preferred embodiment, a nanoparticle of the invention is about 180 to about 200 nm in diameter.

In certain embodiments, a nanoparticle comprising a peptide-polynucleotide complex of the invention may comprise an aggregate of smaller particles of about 5 to about 30 nm in diameter. As such, a nanoparticle of the invention may comprise an aggregate of smaller particles of about 5, 6, 7, 8, 9, 10, 11, 12, 13, 14, 15, 16, 17, 18, 19, 20, 21, 22, 23, 24, 25, 26, 27, 28, 29, or about 30 nm in diameter. In some embodiments, a nanoparticle comprising a peptide-polynucleotide complex of the invention comprises an aggregate of smaller particles of about 5, 6, 7, 8, 9, 10, 11, 12, 13, 14, or about 15 nm in diameter. In other embodiments, a nanoparticle comprising a peptide-polynucleotide complex of the invention comprises an aggregate of smaller particles of about 10, 11, 12, 13, 14, 15, 16, 17, 18, 19, or about 20 nm in diameter. In yet other embodiments, a nanoparticle comprising a peptide-polynucleotide complex of the invention comprises an aggregate of smaller particles of about 15, 16, 17, 18, 19, 20, 21, 22, 23, 24, or about 25 nm in diameter. In other embodiments, a nanoparticle comprising a peptide-polynucleotide complex of the invention comprises an aggregate of smaller particles of about 20, 21, 22, 23, 24, 25, 26, 27, 28, 29, or about 30 nm in diameter.

A nanoparticle of the invention may be further modified to enhance stability of the nanoparticle. For instance, a nanoparticle of the invention may be coated with albumin to enhance stability. A nanoparticle of the invention coated with albumin may be about 5 to about 90 nm or more in diameter. As such, a nanoparticle of the invention may comprise particles of about 5, about 10, about 15, about 20, about 25, about 30, about 35, about 40, about 45, about 50, about 55, about 60, about 65, about 70, about 75, about 80, about 85, about or about 90 nm in diameter. In some embodiments, a nanoparticle of the invention comprises particles of about 5, about 10, about 15, about 20, about 25, or about 30 nm in diameter. In other embodiments, a nanoparticle of the invention comprises particles of about 30, about 35, about 40, about 45, about 50, or about 55 nm in diameter. In yet other embodiments, a nanoparticle of the invention comprises particles of about 55, about 60, about 65, about 70, about 75, or about 80 nm in diameter. In other embodiments, a nanoparticle of the invention comprises particles of about 80, about 85, or about 90 nm or more in diameter. In preferred embodiments, a nanoparticle of the invention comprises particles of about 35, about 40, about 45, about 50, about 55, about 60, about 65, about 70, or about 75 nm in diameter.

Particle size may be assessed using methods known in the art. Non-limiting examples of methods of measuring the size of a particle may include dynamic light scattering, laser diffraction, electrozone (electric sensing zone), light obscuration—also referred to as photozone and single particle optical sensing (SPOS), sieve analysis, aerodynamic measurements, air permeability diameter, sedimentation, measuring the zeta potential of the particle, or combinations thereof. In a preferred embodiment, particle size is assessed by dynamic light scattering. In another preferred embodiment, particle size is assessed by measuring the zeta potential of the particle. In yet another preferred embodiment, particle size is assessed by dynamic light scattering or by measuring the zeta potential of the particle.

A nanoparticle of the invention may have a zeta potential of about −15 to about 20 mV, preferably about 0 mV or more. For instance, a nanoparticle may have a zeta potential of about 1, about 2, about 3, about 4, about 5, about 6, about 7, about 8, about 9, about 10, about 11, about 12, about 13, about 14, about 15, about 16, about 17, about 18, about 19 or about 20 mV or more. In some embodiments, a nanoparticle has a zeta potential of about 1, about 2, about 3, about 4, or about 5 mV. In other embodiments, a nanoparticle has a zeta potential of about 10, 11, 12, 13, or about 14 mV. In yet other embodiments, a nanoparticle has a zeta potential of about 11, about 12, about 13, about 14, or about 15 mV. In an exemplary embodiment, a nanoparticle has a zeta potential of about 1, about 2, about 3, about 4, or about 5 mV. In other embodiments, a nanoparticle has a zeta potential of about 10, about 11, 12, about 13, or about 14 mV. In an exemplary embodiment, a nanoparticle has a zeta potential of about 3.72 mV. In another exemplary embodiment, a nanoparticle has a zeta potential of about 12 mV. In yet another exemplary embodiment, a nanoparticle has a zeta potential of about 13.1 mV.

A nanoparticle comprising a peptide-polynucleotide complex of the invention may have a positive to negative charge ratio of about 1:1 to about 30:1, preferably about 5:1 to about 25:1. In some embodiments, a nanoparticle has a positive to negative charge ratio of about 4:1, about 5:1, about 6:1, about 7:1, or about 8:1. In other embodiments, a nanoparticle has a positive to negative charge ratio of about 10:1, about 11:1, about 12:1, about 13:1, or about 14:1. In yet other embodiments, a nanoparticle has a positive to negative charge ratio of about 22:1, about 23:1, about 24:1, about 25:1, or about 26:1.

As described in Section I(a), a peptide-polynucleotide complex is capable of efficient release of the polynucleotide into the cytoplasm of a cell. A peptide-polynucleotide complex may also be capable of protecting the polynucleotide from degradation upon administration in a subject. As such, a peptide-polynucleotide nanoparticle of the invention may remain stable in the presence of serum. A nanoparticle may remain stable in the presence of serum for about 10, 20, 30, 40, 50, 60 minutes, about 1, 2, 3, 4, 5, 6, 7, 8, 9, 10, 11, 12, 13, 14, 15, 16, 17, 18, 19 hours, about 1, 2, 3, 4, 5, 6, 7 days or longer. A nanoparticle may remain stable in the presence of about 50, 100, 150, 200, or about 300 µg/ml or more human serum albumin. Stability of a nanoparticle may be determined by measuring the ability of a nanoparticle to maintain the activity of a polynucleotide of the peptide-polynucleotide complex of the nanoparticle, or by measuring changes in the size of a nanoparticle over time. Methods of measuring the size of a nanoparticle may be as described in this Section.

Methods of preparing a peptide-polynucleotide complex of the invention generally comprise contacting a peptide of the invention with a polynucleotide of the invention to form a peptide-polynucleotide complex. Typically, a peptide and a polynucleotide are contacted by incubating under conditions suitable for a peptide-polynucleotide complex to form. Conditions suitable for a peptide-polynucleotide complex to form may be as described in the examples. Typically, such conditions may comprise a temperature of about 30° C. to about 40° C., and incubation times of between about 20 sec to about 60 min or more. Suitable temperatures may also be lower than about 30° C. For example, incubation may occur on ice. One skilled in the art will appreciate that the length and temperature of incubation can and will vary depending on the peptide and the polynucleotide, and may be determined experimentally.

A nanoparticle comprising a peptide-polynucleotide complex of the invention may be further modified to enhance stability of the nanoparticle. For instance, a peptide-polynucleotide complex of the invention may be crosslinked to enhance the stability of nanoparticles. One of ordinary skill in the art would recognize that a suitable cross-linker can and will vary depending on the composition of the nanoparticle and the antibody or antibody fragment. In some aspects, a peptide-polynucleotide complex of the invention may be chemically crosslinked using chemical crosslinkers such as glutaraldehyde, bis-carboxylic acid spacers, bis-carboxylic acid-active esters, using a bis-linker amine/acid by carbodiimide coupling protocol, or using a click chemistry protocol, carbodiimde-coupling chemistry, acylation, active ester coupling, or alkylation.

Alternatively, a peptide-polynucleotide complex of the invention may be coated with a compound capable of enhancing the stability of nanoparticles. Methods of modifying a nanoparticle to enhance stability are known in the art, and may be as described in Nicolas et al., 2013 Acta Biomater. 9:4754-4762, the disclosure of which is incorporated herein by reference in its entirety.

As used herein, the term "coating" may refer to the interaction of a peptide-polynucleotide complex with a compound through non-covalent bonds, or to the covalent bonding of a peptide-polynucleotide complex and a compound. In preferred embodiments, a peptide-polynucleotide complex of the invention and a coating compound associate through non-covalent bonds such as a hydrogen bond, an ionic bond, a bond based on Van der Waals, a hydrophobic bond, or electrostatic interactions. For instance, a peptide-polynucleotide complex of the invention may have an overall net positive charge, and a coating compound may have an overall negative charge which may allow the peptide-polynucleotide complex and compound to associate through electrostatic interactions to form a complex of the invention.

Non-limiting examples of compounds that may be used to coat a nanoparticle to enhance stability of the nanoparticle include albumin, fatty acids such as oleic acid, polyethylene glycol, polysaccharides such as chitosan, heparin or heparans and other glycosaminoglycans, or other published coating materials known to those skilled in the art. In some embodiments, stability of a peptide-polynucleotide complex of the invention may be enhanced by coating nanoparticles with a fatty acid. In other embodiments, stability of a peptide-polynucleotide complex of the invention may be enhanced by coating nanoparticles with a polysaccharide.

In preferred embodiments, stability of a nanoparticle comprising a peptide-polynucleotide complex of the invention may be enhanced by coating nanoparticles with albumin. Albumins are negatively charged globular proteins commonly found in blood serum. While not wishing to be bound by theory, it is believed that coating nanoparticles of the invention with albumin may enhance stability of nanoparticles by preventing flocculation. Preferably, albumins that may be used to coat a nanoparticle comprising a peptide-polynucleotide complex of the invention are serum albumins, and may include bovine serum albumin and human serum albumin. In exemplary embodiments, stability of a nanoparticle comprising a peptide-polynucleotide complex of the invention may be enhanced by coating nanoparticles with human serum albumin.

In essence, a nanoparticle is coated with albumin by incubating the nanoparticle with a solution comprising albumin. Nanoparticles may be incubated in a solution comprising about 0.1, 0.2, 0.3, 0.4, 0.5, 0.6, 0.7, 0.8, 0.9, or about 1 mg/ml or more albumin. In some embodiments, nanoparticles comprising a peptide-polynucleotide complex of the invention may be incubated in a solution comprising about 0.1, 0.15, 0.2, 0.25, or about 0.3 mg/ml albumin. In other embodiments, nanoparticles comprising a peptide-polynucleotide complex of the invention may be incubated in a solution comprising about 0.3, 0.35, 0.4, 0.45, or about 0.5 mg/ml albumin. In yet other embodiments, nanoparticles comprising a peptide-polynucleotide complex of the invention may be incubated in a solution comprising about 0.5, 0.55, 0.6, 0.65, or about 0.7 mg/ml albumin. In other embodiments, nanoparticles comprising a peptide-polynucleotide complex of the invention may be incubated in a solution comprising about 0.7, 0.75, 0.8, 0.85, or about 0.9 mg/ml albumin. In additional embodiments, nanoparticles comprising a peptide-polynucleotide complex of the invention may be incubated in a solution comprising about 0.9, 0.95, 1, or about 1.5 mg/ml albumin. In preferred embodiments, nanoparticles comprising a peptide-polynucleotide complex of the invention may be incubated in a solution comprising about 0.4, 0.45, 0.5, 0.55, or about 0.6 mg/ml albumin.

A peptide-polynucleotide complex may be incubated with albumin for about 5, 10, 15, 20, 25, 30, 35, 40, 45, 50, 55, or about 60 minutes or more to coat the peptide-polynucleotide complex. In some embodiments, a particle comprising a peptide-polynucleotide complex of the invention is incubated with albumin for about 5, 10, 15, or about 20 minutes. In other embodiments, a particle comprising a peptide-polynucleotide complex of the invention is incubated with albumin for about 20, 25, 30, or about 35 minutes. In yet other embodiments, a particle comprising a peptide-polynucleotide complex of the invention is incubated with albumin for about 35, 40, 45, or about 50 minutes. In other embodiments, a particle comprising a peptide-polynucleotide complex of the invention is incubated with albumin for about 50, 55, or about 60 minutes or more. In preferred embodiments, a particle comprising a peptide-polynucleotide complex of the invention is incubated with albumin for about 25, 30, or about 35 minutes.

(d) Cell

In another aspect of the invention, a peptide-polynucleotide complex of the invention is capable transfecting the polynucleotide into the cytoplasm of a cell. In some embodiments, a cell is a prokaryotic cell. In preferred embodiments, a cell is a eukaryotic cell. A cell may be in vitro, in vivo, in situ, or ex vivo. A cell may be a single cell, or may comprise a tissue or an organ. The term "cell" also refers to a cell in a subject.

A peptide-polynucleotide complex of the invention may be administered to a cell in vitro by incubating a cell in the presence of a peptide-polynucleotide complex of the invention under conditions suitable for transfection of a polynucleotide of a peptide-polynucleotide complex. Conditions suitable for transfection of a polynucleotide in a peptide-polynucleotide complex may be as described in the examples. One skilled in the art will appreciate that the length of incubation can and will vary depending on the peptide-polynucleotide complex, and the cells. Typically, such conditions may comprise incubation times of between about ten minutes and 24 hours. More preferably, transfection conditions may comprise incubation times of between about 15 minutes and 3 hours.

A peptide-polynucleotide complex of the invention may be administered to a cell in vivo (i.e. in a subject) by administering to a subject a composition comprising a peptide-polynucleotide complex of the invention. Suitable compositions are described in further detail in Section II below.

II. Pharmaceutical Composition

In another aspect of the invention, a peptide-polynucleotide complex of the invention may be incorporated into pharmaceutical compositions suitable for administration. A pharmaceutical composition of the invention may be used to disrupt the expression of one or more than one nucleic acid sequence normally expressed in a cell. For instance, a pharmaceutical composition of the invention may be used to disrupt the expression of 1, 2, 3, 4, 5, 6, 7, 8, 9, 10 or more nucleic acid sequences normally expressed in a cell. A skilled artisan will appreciate that pharmaceutical compositions may be administered to treat a disease, to prevent a disease, or to promote good health. As such, a pharmaceutical composition of the invention may be used to disrupt expression of any nucleic acid sequence normally expressed in a cell, such that disrupted expression leads to measurable and beneficial effects for the subject administered the composition (i.e. significant efficacy)

In some embodiments, a pharmaceutical composition of the invention is used to disrupt the expression of one nucleic acid sequence normally expressed in a cell. In a preferred embodiment, a pharmaceutical composition of the invention is used to disrupt the expression of a nucleic acid sequence encoding STAT3. In another preferred embodiment, a pharmaceutical composition of the invention is used to disrupt the expression of a nucleic acid sequence encoding JNK2. In yet another preferred embodiment, a pharmaceutical composition of the invention is used to disrupt the expression of a nucleic acid sequence encoding the p65 subunit of the canonical NFκB signaling pathway. In another preferred embodiment, a pharmaceutical composition of the invention is used to disrupt the expression of a nucleic acid sequence encoding the p100/p52 subunit of the canonical NFκB signaling pathway.

In other embodiments, a pharmaceutical composition of the invention is used to disrupt the expression of two nucleic acid sequences normally expressed in a cell. In a preferred embodiment, a pharmaceutical composition of the invention is used to disrupt the expression of a nucleic acid sequence encoding the p65 subunit of the canonical NFκB signaling pathway, and a nucleic acid sequence encoding the p100/p52 subunit of the canonical NFκB signaling pathway.

When a pharmaceutical composition of the invention is used to disrupt the expression of more than one nucleic acid sequence normally expressed in a cell, a pharmaceutical composition may be formulated using a mixture of more than one peptide-polynucleotide complex, wherein each complex comprises a polynucleotide capable of disrupting the expression of a different nucleic acid sequence normally expressed in a cell. Alternatively, more than one polynucleotide may be used for generating a mixture of peptide-polynucleotide complexes, wherein each polynucleotide is capable of disrupting the expression of a different nucleic acid sequence normally expressed in a cell.

A pharmaceutical composition of the invention may also comprise one or more nontoxic pharmaceutically acceptable carriers, adjuvants, excipients, and vehicles as desired. As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with nanoparticles of the invention, use thereof in the compositions is contemplated. Supplementary active compounds may also be incorporated into the compositions.

A pharmaceutical composition of the invention may be formulated to be compatible with its intended route of administration. Suitable routes of administration include parenteral, oral, pulmonary, transdermal, transmucosal, and rectal administration. The term parenteral, as used herein, includes subcutaneous, intravenous, intramuscular, intrathecal, or intrasternal injection, or infusion techniques.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH may be adjusted with acids or bases, such as hydrochloric acid or sodium hydroxide. The parenteral preparation may be enclosed in ampoules, disposable syringes or multiple dose vials made of glass or plastic.

Oral compositions generally may include an inert diluent or an edible carrier. Oral compositions may be enclosed in gelatin capsules or compressed into tablets. For the purpose of oral therapeutic administration, the active compound may be incorporated with excipients and used in the form of tablets, troches, or capsules. Oral compositions may also be prepared using a fluid carrier for use as a mouthwash, wherein the compound in the fluid carrier is applied orally and swished and expectorated or swallowed. Pharmaceutically compatible binding agents and/or adjuvant materials may be included as part of the composition. The tablets, pills, capsules, troches, and the like, may contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressured container or dispenser which contains a suitable propellant, e.g., a gas such as carbon dioxide, or a nebulizer.

In preferred embodiments, a pharmaceutical composition of the invention is formulated to be compatible with parenteral administration. For instance, pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.), or phosphate buffered saline (PBS). In exemplary embodiments, a pharmaceutical composition of the invention is formulated with phosphate buffered saline (PBS).

In all cases, a composition may be sterile and may be fluid to the extent that easy syringeability exists. A composition may be stable under the conditions of manufacture and storage, and may be preserved against the contaminating action of microorganisms such as bacteria and fungi. The carrier may be a solvent or dispersion medium containing, for example, water, ethanol, polyol (for example, glycerol, propylene glycol, and liquid polyetheylene glycol, and the like), and suitable mixtures thereof. The proper fluidity may be maintained, for example, by the use of a coating such as lecithin, by the maintenance of the required particle size in the case of dispersion, and by the use of surfactants. Prevention of the action of microorganisms may be achieved by various antibacterial and antifungal agents, for example, parabens, chlorobutanol, phenol, ascorbic acid, thimerosal, and the like. In many cases, it may be preferable to include isotonic agents, for example, sugars, polyalcohols such as mannitol, sorbitol, or sodium chloride, in the composition. Prolonged absorption of the injectable compositions may be brought about by including in the composition an agent which delays absorption, for example, aluminum monostearate and gelatin.

Sterile injectable solutions may be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Systemic administration may also be by transmucosal or transdermal means. For transmucosal or transdermal administration, penetrants appropriate to the barrier to be permeated are used in the formulation. Such penetrants are generally known in the art, and may include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds may also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid. Methods for preparation of such formulations will be apparent to those skilled in the art. These may be prepared according to methods known to those skilled in the art, for example, as described in U.S. Pat. No. 4,522,811.

Additional formulations of pharmaceutical compositions may be in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980). Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

One of skill in the art will recognize that the concentration of a peptide-polynucleotide complex of the invention in a pharmaceutical composition can and will vary depending in part on the route of administration, the subject, and the reason for the administration, and may be determined experimentally. Methods of experimentally determining the concentration of an active agent such as nanoparticles of the invention in a pharmaceutical composition are known in the art. In general, a pharmaceutical composition may be formulated to comprise about 0.1 nM to about 50 µM of a polynucleotide in a peptide-polynucleotide complex of the invention. For example, a pharmaceutical composition may be formulated to comprise about 0.1 nm, 0.2 nm, 0.3 nm, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm, 90 nm, 91 nm, 92 nm, 93 nm, 94 nm, 95 nm, 96 nm, 97 nm, 98 nm, 99 nm, 100 nm, 101 nm, 102 nm, 103 nm, 104 nm, 105 nm, 106 nm, 107 nm, 108 nm, 109 nm, 110 nm, 111 nm, 112 nm, 113 nm, 114 nm, 115 nm, 116 nm, 117 nm, 118 nm, 119 nm, 120 nm, 121 nm, 122 nm, 123 nm, 124 nm, 125 nm, 126 nm, 127 nm, 128 nm, 129 nm, 130 nm, 131 nm, 132 nm, 133 nm, 134 nm, 135 nm, 136 nm, 137 nm, 138 nm, 139 nm, 140 nm, 141 nm, 142 nm, 143 nm, 144 nm, 145 nm, 146 nm, 147 nm, 148 nm, 149 nm, 150 nm, 151 nm, 152 nm, 153 nm, 154 nm, 155 nm, 156 nm, 157 nm, 158 nm, 159 nm, 160 nm, 161 nm, 162 nm, 163 nm, 164 nm, 165 nm, 166 nm, 167 nm, 168 nm, 169 nm, 170 nm, 171 nm, 172 nm, 173 nm, 174 nm, 175 nm, 176 nm, 177 nm, 178 nm, 179 nm, 180 nm, 181 nm, 182 nm, 183 nm, 184 nm, 185 nm, 186 nm, 187 nm, 188 nm, 189 nm, 190 nm, 191 nm, 192 nm, 193 nm, 194 nm, 195 nm, 196 nm, 197 nm, 198 nm, 199 nm, 200 nm, 201 nm, 202 nm, 203 nm, 204 nm, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, 220 nm, 221 nm, 222 nm, 223 nm, 224 nm, 225 nm, 226 nm, 227 nm, 228 nm, 229 nm, 230 nm, 231 nm, 232 nm, 233 nm, 234 nm, 235 nm, 236 nm, 237 nm, 238 nm, 239 nm, 241 nm, 242 nm, 243 nm, 244 nm, 245 nm, 246 nm, 247 nm, 248 nm, 249 nm, 251 nm, 252 nm, 253 nm, 254 nm, 255 nm, 256 nm, 257 nm, 258 nm, 259 nm, 261 nm, 262 nm, 263 nm, 264 nm, 265 nm, 266 nm, 267 nm, 268 nm, 269 nm, 271 nm, 272 nm, 273 nm, 274 nm, 275 nm, 276 nm, 277 nm, 278 nm, 279 nm, 281 nm, 282 nm, 283 nm, 284 nm, 285 nm, 286 nm, 287 nm, 288 nm, 289 nm, 291 nm, 292 nm, 293 nm, 294 nm, 295 nm, 296 nm, 297 nm, 298 nm, 299 nm, 300 nm, 301 nm, 302 nm, 303 nm, 304 nm, 305 nm, 306 nm, 307 nm, 308 nm, 309 nm, 310 nm, 311 nm, 312 nm, 313 nm, 314 nm, 315 nm, 316 nm, 317 nm, 318 nm, 319 nm, 320 nm, 321 nm, 322 nm, 323 nm, 324 nm, 325 nm, 326 nm, 327 nm, 328 nm, 329 nm, 330 nm, 331 nm, 332 nm, 333 nm, 334 nm, 335 nm, 336 nm, 337 nm, 338 nm, 339 nm, 340 nm, 341 nm, 342 nm, 343 nm, 344 nm, 345 nm, 346 nm, 347 nm, 348 nm, 349 nm, 350 nm, 351 nm, 352 nm, 353 nm, 354 nm, 355 nm, 356 nm, 357 nm, 358 nm, 359 nm, 360 nm, 361 nm, 362 nm, 363 nm, 364 nm, 365 nm, 366 nm, 367 nm, 368 nm, 369 nm, 370 nm, 371 nm, 372 nm, 373 nm, 374 nm, 375 nm, 376 nm, 377 nm, 378 nm, 379 nm, 380 nm, 381 nm, 382 nm, 383 nm, 384 nm, 385 nm, 386 nm, 387 nm, 388 nm, 389 nm, 390 nm, 391 nm, 392 nm, 393 nm, 394 nm, 395 nm, 396 nm, 397 nm, 398 nm, 399 nm, 400 nm, 401 nm, 402 nm, 403 nm, 404 nm, 405 nm, 406 nm, 407 nm, 408 nm, 409 nm, 410 nm, 411 nm, 412 nm, 413 nm, 414 nm, 415 nm, 416 nm, 417 nm, 418 nm, 419 nm, 420 nm, 421 nm, 422 nm, 423 nm, 424 nm, 425 nm, 426 nm, 427 nm, 428 nm, 429 nm, 430 nm, 431 nm, 432 nm, 433 nm, 434 nm, 435 nm, 436 nm, 437 nm, 438 nm, 439 nm, 440 nm, 441 nm, 442 nm, 443 nm, 444 nm, 445 nm, 446 nm, 447 nm, 448 nm, 449 nm, 450 nm, 451 nm, 452 nm, 453 nm, 454 nm, 455 nm, 456 nm, 457 nm, 458 nm, 459 nm, 460 nm, 461 nm, 462 nm, 463 nm, 464 nm, 465 nm, 466 nm, 467 nm, 468 nm, 469 nm, 470 nm, 471 nm, 472 nm, 473 nm, 474 nm, 475 nm, 476 nm, 477 nm, 478 nm, 479 nm, 480 nm, 481 nm, 482 nm, 483 nm, 484 nm, 485 nm, 486 nm, 487 nm, 488 nm, 489 nm, 490 nm, 491 nm, 492 nm, 493 nm, 494 nm, 495 nm, 496 nm, 497 nm, 498 nm, 499 nm, 500 nm, 501 nm, 502 nm, 503 nm, 504 nm, 505 nm, 506 nm, 507 nm, 508 nm, 509 nm, 510 nm, 511 nm, 512 nm, 513 nm, 514 nm, 515 nm, 516 nm, 517 nm, 518 nm, 519 nm, 520 nm, 521 nm, 522 nm, 523 nm, 524 nm, 525 nm, 526 nm, 527 nm, 528 nm, 529 nm, 530 nm, 531 nm, 532 nm, 533 nm, 534 nm, 535 nm, 536 nm, 537 nm, 538 nm, 539 nm, 540 nm, 541 nm, 542 nm, 543 nm, 544 nm, 545 nm, 546 nm, 547 nm, 548 nm, 549 nm, 550 nm, 551 nm, 552 nm, 553 nm, 554 nm, 555 nm, 556 nm, 557 nm, 558 nm, 559 nm, 560 nm, 561 nm, 562 nm, 563 nm, 564 nm, 565 nm, 566 nm, 567 nm, 568 nm, 569 nm, 570 nm, 571 nm, 572 nm, 573 nm, 574 nm, 575 nm, 576 nm, 577 nm, 578 nm, 579 nm, 580 nm, 581 nm, 582 nm, 583 nm, 584 nm, 585 nm, 586 nm, 587 nm, 588 nm, 589 nm, 590 nm, 591 nm, 592 nm, 593 nm, 594 nm, 595 nm, 596 nm, 597 nm, 598 nm, 599 nm, 600 nm, 601 nm, 602 nm, 603 nm, 604 nm, 605 nm, 606 nm, 607 nm, 608 nm, 609 nm, 610 nm, 611 nm, 612 nm, 613 nm, 614 nm, 615 nm, 616 nm, 617 nm, 618 nm, 619 nm, 620 nm, 621 nm, 622 nm, 623 nm, 624 nm, 625 nm, 626 nm, 627 nm, 628 nm, 629 nm, 630 nm, 631 nm, 632 nm, 633 nm, 634 nm, 635 nm, 636 nm, 637 nm, 638 nm, 639 nm, 640 nm, 641 nm, 642 nm, 643 nm, 644 nm, 645 nm, 646 nm, 647 nm, 648 nm, 649 nm, 650 nm, 651 nm, 652 nm, 653 nm, 654 nm, 655 nm, 656 nm, 657 nm, 658 nm, 659 nm, 660 nm, 661 nm, 662 nm, 663 nm, 664 nm, 665 nm, 666 nm, 667 nm, 668 nm, 669 nm, 670 nm, 671 nm, 672 nm, 673 nm, 674 nm, 675 nm, 676 nm, 677 nm, 678 nm, 679 nm, 680 nm, 681 nm, 682 nm, 683 nm, 684 nm, 685 nm, 686 nm, 687 nm, 688 nm, 689 nm, 690 nm, 691 nm, 692 nm, 693 nm, 694 nm, 695 nm, 696 nm, 697 nm, 698 nm, 699 nm, 700 nm, 701 nm, 702 nm, 703 nm, 704 nm, 705 nm, 706 nm, 707 nm, 708 nm, 709 nm, 710 nm, 711 nm, 712 nm, 713 nm, 714 nm, 715 nm, 716 nm, 717 nm, 718 nm, 719 nm, 720 nm, 721 nm, 722 nm, 723 nm, 724 nm, 725 nm, 726 nm, 727 nm, 728 nm, 729 nm, 730 nm, 731 nm, 732 nm, 733 nm, 734 nm, 735 nm, 736 nm, 737 nm, 738 nm, 739 nm, 740 nm, 741 nm, 742 nm, 743 nm, 744 nm, 745 nm, 746 nm, 747 nm, 748 nm, 749 nm, 750 nm, 751 nm, 752 nm, 753 nm, 754 nm, 755 nm, 756 nm, 757 nm, 758 nm, 759 nm, 760 nm, 761 nm, 762 nm, 763 nm, 764 nm, 765 nm, 766 nm, 767 nm, 768 nm, 769 nm, 770 nm, 771 nm, 772 nm, 773 nm, 774 nm, 775 nm, 776 nm, 777 nm, 778 nm, 779 nm, 780 nm, 781 nm, 782 nm, 783 nm, 784 nm, 785 nm, 786 nm, 787 nm, 788 nm, 789 nm, 790 nm, 791 nm, 792 nm, 793 nm, 794 nm, 795 nm, 796 nm, 797 nm, 798 nm, 799 nm, 800 nm, 801 nm, 802 nm, 803 nm, 804 nm, 805 nm, 806 nm, 807 nm, 808 nm, 809 nm, 810 nm, 811 nm, 812 nm, 813 nm, 814 nm, 815 nm, 816 nm, 817 nm, 818 nm, 819 nm, 820 nm, 821 nm, 822 nm, 823 nm, 824 nm, 825 nm, 826 nm, 827 nm, 828 nm, 829 nm, 830 nm, 831 nm, 832 nm, 833 nm, 834 nm, 835 nm, 836 nm, 837 nm, 838 nm, 839 nm, 840 nm, 841 nm, 842 nm, 843 nm, 844 nm, 845 nm, 846 nm, 847 nm, 848 nm, 849 nm, 850 nm, 851 nm, 852 nm, 853 nm, 854 nm, 855 nm, 856 nm, 857 nm, 858 nm, 859 nm, 860 nm, 861 nm, 862 nm, 863 nm, 864 nm, 865 nm, 866 nm, 867 nm, 868 nm, 869 nm, 870 nm, 871 nm, 872 nm, 873 nm, 874 nm, 875 nm, 876 nm, 877 nm, 878 nm, 879 nm, 880 nm, 881 nm, 882 nm, 883 nm, 884 nm, 885 nm, 886 nm, 887 nm, 888 nm, 889 nm, 890 nm, 891 nm, 892 nm, 893 nm, 894 nm, 895 nm, 896 nm, 897 nm, 898 nm, 899 nm, 900 nm, 901 nm, 902 nm, 903 nm, 904 nm, 905 nm, 906 nm, 907 nm, 908 nm, 909 nm, 910 nm, 911 nm, 912 nm, 913 nm, 914 nm, 915 nm, 916 nm, 917 nm, 918 nm, 919 nm, 920 nm, 921 nm, 922 nm, 923 nm, 924 nm, 925 nm, 926 nm, 927 nm, 928 nm, 929 nm, 930 nm, 931 nm, 932 nm, 933 nm, 934 nm, 935 nm, 936 nm, 937 nm, 938 nm, 939 nm, 940 nm, 941 nm, 942 nm, 943 nm, 944 nm, 945 nm, 946 nm, 947 nm, 948 nm, 949 nm, 950 nm, 951 nm, 952 nm, 953 nm, 954 nm, 955 nm, 956 nm, 957 nm, 958 nm, 959 nm, 960 nm, 961 nm, 962 nm, 963 nm, 964 nm, 965 nm, 966 nm, 967 nm, 968 nm, 969 nm, 970 nm, 971 nm, 972 nm, 973 nm, 974 nm, 975 nm, 976 nm, 977 nm, 978 nm, 979 nm, 980 nm, 981 nm, 982 nm, 983 nm, 984 nm, 985 nm, 986 nm, 987 nm, 988 nm, 989 nm, 990 nm, 991 nm, 992 nm, 993 nm, 994 nm, 995 nm, 996 nm, 997 nm, 998 nm, 999 nm, 1 µm, 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 36 µm, 37 µm, 38 µm, 39 µm, 40 µm, 41 µm, 42 µm, 43 µm, 44 µm, 45 µm, 46 µm, 47 µm, 48 µm, 49 µm, or about 50 µm of a polynucleotide in a peptide-polynucleotide complex of the invention. In some embodiments, a pharmaceutical composition may be formulated to comprise about 0.1 nM to about 1.0 nM of a polynucleotide in a peptide-polynucleotide complex of the invention. In other embodiments, a pharmaceutical composition may be formulated to comprise about 1 nM to about 10 nM of a polynucleotide in a peptide-polynucleotide complex of the invention. In other embodiments, a pharmaceutical composition may be formulated to comprise about 1 nM to about 100 nM of a polynucleotide in a peptide-polynucleotide complex of the invention. In other embodiments, a pharmaceutical composition may be formulated to comprise about 1 nM to about 200 nM of a polynucleotide in a peptide-polynucleotide complex of the invention. In other embodiments, a pharmaceutical composition may be formulated to comprise about 1 nM to about 50 nM of a polynucleotide in a peptide-polynucleotide complex of the invention. In other embodiments, a pharmaceutical composition may be formulated to comprise about 10 nM to about 100 nM of a polynucleotide in a peptide-polynucleotide complex of the invention. In other embodiments, a pharmaceutical composition may be formulated to comprise about 10 nM to about 200 nM of a polynucleotide in a peptide-polynucleotide complex of the invention. In other embodiments, a pharmaceutical composition may be formulated to comprise about 50 nM to about 100 nM of a polynucleotide in a peptide-polynucleotide complex of the invention. In other embodiments, a pharmaceutical composition may be formulated to comprise about 50 nM to about 200 nM of a polynucleotide in a peptide-polynucleotide complex of the invention. In other embodiments, a pharmaceutical composition may be formulated to comprise about 100 nM to about 200 nM of a polynucleotide in a peptide-polynucleotide complex of the invention. In other embodiments, a pharmaceutical composition may be formulated to comprise about 150 nM to about 200 nM of a polynucleotide in a peptide-polynucleotide complex of the invention. In other embodiments, a pharmaceutical composition may be formulated to comprise about 200 nM to about 100 nM of a polynucleotide in a peptide-polynucleotide complex of the invention. In other embodiments, a pharmaceutical composition may be formulated to comprise about 500 nM to about 1000 nM of a polynucleotide in a peptide-polynucleotide complex of the invention. In other embodiments, a pharmaceutical composition may be formulated to comprise about 1 µM to about 50 µM of a polynucleotide in a peptide-polynucleotide complex of the invention. A concentration of peptide in a peptide-polynucleotide complex of the invention may be calculated based on the desired concentration of polynucleotide and the ratio of peptide to polynucleotide in the peptide-polynucleotide complex of the invention.

A pharmaceutical composition may also be formulated to comprise about 30, 40, 50, 60, 70, 80, 90, 100, 150, 200, 250, 300, 350, 400, 450, 500, 550, 600, 650, or about 700 µg/ml or more of a peptide-polynucleotide complex of the invention. In some embodiments, a pharmaceutical composition is formulated to comprise 30, 35, 40, 45, 50, 55, 60, 65, 70, 75, 80, 85, 90, 95, or about 100 µg/ml of a peptide-polynucleotide complex of the invention. In other embodiments, a pharmaceutical composition is formulated to comprise 100, 110, 120, 130, 140, 150, 160, 170, 180, 190, 200, 210, 220, 230, 240, 250, 260, 270, 280, 290, or about 300 µg/ml of a peptide-polynucleotide complex of the invention. In yet other embodiments, a pharmaceutical composition is formulated to comprise 300, 310, 320, 330, 340, 350, 360, 370, 380, 390, 400, 410, 420, 430, 440, 450, 460, 470, 480, 490, or about 500 µg/ml of a peptide-polynucleotide complex of the invention. In yet other embodiments, a pharmaceutical composition is formulated to comprise 500, 510, 520, 530, 540, 550, 560, 570, 580, 590, 600, 610, 620, 630, 640, 650, 660, 670, 680, 690, or about 700 µg/ml or more of a peptide-polynucleotide complex of the invention.

III. Method of Use

In another aspect, the invention encompasses a method for using a peptide-polynucleotide complex of the invention to transfect the polynucleotide into the cytoplasm of a cell. In some embodiments, the cell is in vitro. In other embodiments, the cell is in vivo. Thus, the present invention also provides a method for using a peptide-polynucleotide complex of the invention to transfect the polynucleotide into the cytoplasm of a cell in a subject in need thereof. Generally speaking, a method of the invention comprises contacting a cell with a peptide-polynucleotide complex of the invention under conditions suitable for transfection of a polynucleotide. Suitable cells and conditions are described above in Section I. In embodiments where the cell is in vivo, a method of the invention typically comprises administering a pharmaceutical composition comprising a peptide-polynucleotide complex of the invention to a subject in need thereof. Suitable pharmaceutical compositions are described in Section II.

In another aspect, the invention encompasses a method for treating a condition in a subject. The method comprises administering to a subject in need thereof a therapeutically effective amount of a pharmaceutical composition comprising a peptide-polynucleotide complex. A peptide-polynucleotide complex of the invention is capable of efficiently transfecting, or delivering, the polynucleotide of the peptide-polynucleotide complex into a cell of the subject.

In some embodiments, a polynucleotide of the invention comprises non-coding RNA capable of regulating or inhibiting expression of a nucleic acid sequence expressed in a cell. By efficiently transfecting a polynucleotide capable of regulating or inhibiting expression of a nucleic acid sequence expressed in a cell, a method of the invention may be used to treat any condition that can be treated by regulating or inhibiting the expression of a nucleic acid sequence normally expressed in a cell. In some preferred embodiments, the invention encompasses a method of administering a peptide-polynucleotide complex of the invention to a subject to treat an NFκB-mediated condition in the subject. In other preferred embodiments, the invention encompasses a method of administering to a subject a peptide-polynucleotide complex of the invention to treat a condition associated with STAT3 dysregulation in the subject. In other preferred embodiments, the invention encompasses a method of administering to a subject a peptide-polynucleotide complex of the invention to treat a condition associated with JNK2 dysregulation in the subject. Specific diseases?

In other embodiments, a polynucleotide of the invention comprises DNA encoding a protein that is deficient or absent in the subject. Non-limiting examples of diseases characterized by deficient or absent protein in a subject include lower motor neuron diseases, Pompe disease, lysosomal storage disorders, and glioblastoma multiforme. In a preferred embodiment, a polynucleotide of the invention comprises DNA encoding a protein that is deficient or absent in a subject with a lysosomal storage disease. Enzyme replacement therapy is particularly well suited for lysosomal storage diseases, and a peptide-polynucleotide complex of the invention may be used to transfect an expression cassette or vector encoding a protein that is deficient or absent in a subject with a lysosomal storage disease into the cytoplasm of the subject. Lysosomal storage disorders include, but are not limited to, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease (Type I, Type II, Type III), GM1 gangliosidosis (Infantile, Late infantile/Juvenile, Adult/Chronic), I-Cell disease/Mucolipidosis II, Infantile Free Sialic Acid Storage Disease/ISSD, Juvenile Hexosaminidase A Deficiency, Krabbe disease (Infantile Onset, Late Onset), Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease (Type A, Type B, Type C), Neuronal Ceroid Lipofuscinoses (CLN6 disease (Atypical Late Infantile, Late Onset variant, Early Juvenile), Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis, Pompe disease/Glycogen storage disease type II, Pycnodysostosis, Sandhoff Disease/Adult Onset/GM2 Gangliosidosis, Sandhoff Disease/GM2 gangliosidosis—Infantile, Sandhoff Disease/GM2 gangliosidosis—Juvenile, Schindler disease, Salla disease/Sialic Acid Storage Disease, Tay-Sachs/GM2 gangliosidosis, Wolman disease. In exemplary embodiments, the subject requires treatment for a disease selected from the group consisting of Gaucher disease, Fabry disease, MPS I, MPS II] MPS VI and Glycogen storage disease type II.

The peptide, the polynucleotide and peptide-polynucleotide complex may be as described in Section I. Pharmaceutical compositions comprising a peptide-polynucleotide complex of the invention may be as described in Section II. Methods of administering a peptide-polynucleotide complex of the invention, and methods of treating a condition are described below.

(a) Administration to a Subject in Need Thereof

In an aspect, the present invention encompasses administering a therapeutically effective amount of a pharmaceutical composition to a subject in need thereof. As used herein, the phrase "a subject in need thereof" refers to a subject in need of preventative or therapeutic treatment. A subject may be a rodent, a human, a livestock animal, a companion animal, or a zoological animal. In one embodiment, a subject may be a rodent, e.g., a mouse, a rat, a guinea pig, etc. In another embodiment, a subject may be a livestock animal. Non-limiting examples of suitable livestock animals may include pigs, cows, horses, goats, sheep, llamas and alpacas. In still another embodiment, a subject may be a companion animal. Non-limiting examples of companion animals may include pets such as dogs, cats, rabbits, and birds. In yet another embodiment, a subject may be a zoological animal. As used herein, a "zoological animal" refers to an animal that may be found in a zoo. Such animals may include non-human primates, large cats, wolves, and bears. In a preferred embodiment, a subject is a mouse. In another preferred embodiment, a subject is a human.

As described in Section II, a pharmaceutical composition of the invention is formulated to be compatible with its intended route of administration. Suitable routes of administration include parenteral, oral, pulmonary, transdermal, transmucosal, and rectal administration. In preferred embodiments, a pharmaceutical composition of the invention is administered by injection.

One of skill in the art will recognize that the amount and concentration of the composition administered to a subject will depend in part on the subject and the reason for the administration. Methods for determining optimal amounts are known in the art. In general, the concentration of a peptide-polynucleotide complex of the invention in a pharmaceutical composition may be as described in Section II.

Compositions of the invention are typically administered to a subject in need thereof in an amount sufficient to provide a benefit to the subject. This amount is defined as a "therapeutically effective amount." A therapeutically effective amount may be determined by the efficacy or potency of the particular composition, the disorder being treated, the duration or frequency of administration, the method of administration, and the size and condition of the subject, including that subject's particular treatment response. A therapeutically effective amount may be determined using methods known in the art, and may be determined experimentally, derived from therapeutically effective amounts determined in model animals such as the mouse, or a combination thereof. Additionally, the route of administration may be considered when determining the therapeutically effective amount. In determining therapeutically effective amounts, one skilled in the art may also consider the existence, nature, and extent of any adverse effects that accompany the administration of a particular compound in a particular subject.

When a pharmaceutical composition of the invention is administered to a subject by injection, a composition may be administered to the subject in a bolus in an amount of about 0.1, 0.2, 0.3, 0.4, 0.5, 1, 1.5, 2, 2.5, 3, 3.5, 4, 4.5, 5, 5.5, 6.5, 7, 7.5, 8, 8.5, 9, 9.5, 10, 10.5, 11, 11.5, 12, 12.5, 13, 13.5, 14, 14.5, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or about 100 mg/kg or more. In some embodiments, a pharmaceutical composition of the invention is administered to a subject in an amount of about 0.1, 0.2, 0.3, 0.4, 0.5, 1, 1.5, 2, 2.5, 3, 3.5, 4, 4.5, or about 5 mg/kg. In other embodiments, a pharmaceutical composition of the invention is administered to a subject in an amount of about 5, 5.5, 6.5, 7, 7.5, 8, 8.5, 9, 9.5, 10, 10.5, 11, 11.5, 12, 12.5, 13, 13.5, 14, 14.5, or about 15 mg/kg. In yet other embodiments, a pharmaceutical composition of the invention is administered to a subject in an amount of about 15, 16, 17, 18, 19, 20, 21, 22, 23, 24, 25, 26, 27, 28, 29, or about 30 mg/kg. In other embodiments, a pharmaceutical composition of the invention is administered to a subject in an amount of about 30, 31, 32, 33, 34, 35, 36, 37, 38, 39, 40, 41, 42, 43, 44, or about 45 mg/kg. In additional embodiments, a pharmaceutical composition of the invention is administered to a subject in an amount of about 45, 46, 47, 48, 49, 50, 60, 70, 80, 90, or about 100 mg/kg or more. In preferred embodiments, a composition is administered to the subject in a bolus in an amount of about 0.5, 0.6, 0.7, 0.8, 0.9, 1, 1.1, 1.2, 1.3, 1.4, or about 1.5 mg/kg.

A composition may also be administered by injecting more than one bolus into the subject over a period of time. For instance, a composition may be administered by injecting 1, 2, 3, 4, 5, 6, 7, 8, 9, 10 or more boluses into the subject. In some embodiments, a composition is administered by injecting 1, 2, 3, 4, or 5 boluses into the subject. In other embodiments, a composition is administered by injecting 5, 6, 7, 8, 9, 10 or more boluses into the subject. In preferred embodiments, a composition is administered by injecting 2, 3, or 4 boluses into the subject. The boluses may be injected about every 1, 2, 3, 4, 5, 6, 7, 8, 9, 10, 11, or about every 12 hours, or they may be injected about every 1, 2, 3, 4, 5, 6, or about every 7 days. In preferred embodiments, boluses may be injected about every day.

(b) Treating a NFκB-Mediated Condition

As described above, a method of the invention may be used to treat a NFκB-mediated condition in a subject. A method of the invention may be used to treat a NFκB-mediated condition in a subject by disrupting the expression of a nucleic acid sequence normally associated with a NFκB signaling pathway. A method of the invention may be used to treat a NFκB-mediated condition in a subject by disrupting the expression of a nucleic acid sequence normally associated with the canonical NFκB signaling pathway, the non-canonical NFκB signaling pathway, or both the canonical and non-canonical NFκB signaling pathway. As described in the examples, the applicants surprisingly discovered that disrupting the expression of a nucleic acid sequence normally associated with the canonical NFκB signaling pathway and the non-canonical NFκB signaling pathway is synergistic. The term "synergistic" refers to an effect in which two or more agents work in synergy to produce an effect that is more than additive of the effects of each agent independently. One measure of synergism can be shown by the Chou-Talalay Combination Index Method. The Chou-Talalay Index method is based on the median-effect equation, and derived from the mass-action law principle, which is the theory that links single entity and multiple entities, and first order and higher order dynamics, encompassing the Michaelis-Menten, Hill, Henderson-Hasselbalch, and Scatchard equations. The Chou-Talalay Combination Index Method gives a combination index (CI) where an additive effect gives a CI=1, synergism gives a CI<1, and antagonism gives a CI>1. See Ting-Chao Chou, 2008, Preclinical versus clinical drug combination studies, Leukemia & Lymphoma, 49:2059-2080.

In some embodiments, a method of the invention is used to treat a NFκB-mediated condition in a subject by disrupting the expression of a nucleic acid sequence normally associated with the canonical NFκB signaling pathway. In an exemplary alternative of the embodiments, a NFκB-mediated condition in a subject is treated by disrupting the expression of a nucleic acid sequence encoding the transcription factor p65 subunit of the canonical NFκB signaling pathway.

In other embodiments, a method of the invention is used to treat a NFκB-mediated condition in a subject by disrupting the expression of a nucleic acid sequence normally associated with the non-canonical NFκB signaling pathway. In an exemplary alternative of the embodiments, a NFκB-mediated condition in a subject is treated by disrupting the expression of a nucleic acid sequence encoding the p100/p52 subunit of the canonical NFκB signaling pathway.

In preferred embodiments, a method of the invention is used to treat a NFκB-mediated condition in a subject by disrupting the expression of a nucleic acid sequence normally associated with the canonical NFκB signaling pathway, and a nucleic acid sequence normally associated with the non-canonical NFκB signaling pathway. In an exemplary alternative of the embodiments, a NFκB-mediated condition in a subject is treated by disrupting the expression of a nucleic acid sequence encoding the transcription factor p65 subunit of the canonical NFκB signaling pathway and disrupting the expression of a nucleic acid sequence encoding the p100/p52 subunit of the canonical NFκB signaling pathway.

The term "NFκB-mediated condition" may be used to describe any condition that may be caused by dysregulation of signaling in a NFκB signaling pathway. Non-limiting examples of NFκB-mediated conditions may include an inflammation disorder, an autoimmune disease, transplant rejection, osteoporosis, cancer, arthritis, Alzheimer's disease, arthritis, atherosclerosis, a viral infection, or ataxia telangiectasia. In some embodiments, a method of the invention is used to treat an inflammation disorder. In other embodiments, a method of the invention is used to treat an autoimmune disease. In yet other embodiments, a method of the invention is used to treat transplant rejection. In other embodiments, a method of the invention is used to treat osteoporosis. In additional embodiments, a method of the invention is used to treat Alzheimer's disease. In other embodiments, a method of the invention is used to treat atherosclerosis. In yet other embodiments, a method of the invention is used to treat a viral infection. In still other embodiments, a method of the invention is used to treat ataxia telangiectasia.

i. Treating Cancer

In preferred embodiments, a method of the invention is used to treat a neoplasm or cancer. The neoplasm may be malignant or benign, the cancer may be primary or metastatic; the neoplasm or cancer may be early stage or late stage. A cancer or a neoplasm may be treated by delivering a nucleic acid sequence to a cancer tumor in a subject. The cancer or neoplasm may be treated by slowing cancer cell growth or killing cancer cells.

In some embodiments, a polynucleotide of a peptide-polynucleotide complex of the invention may treat a cancer or a neoplasm by delivering a polynucleotide of the nanoparticle to a cancer cell in a subject in vivo. Non-limiting examples of neoplasms or cancers that may be treated with a method of the invention may include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-cell lymphoma (cutaneous), T-cell leukemia and lymphoma, testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In a preferred embodiment, a method of the invention is used to treat T-cell leukemia and lymphoma. In an exemplary embodiment, a method of the invention is used to treat Human T-Lymphotropic Virus-1 (HTLV-1) induced adult T-cell leukemia/lymphoma (ATLL).

In other embodiments, a polynucleotide of a peptide-polynucleotide complex of the invention may be delivered to a cancer cell in vitro. For instance, a polynucleotide of a peptide-polynucleotide complex of the invention may be delivered to a cancer cell line in vitro. A cancer cell may be a cancer cell line cultured in vitro. In some alternatives of the embodiments, a cancer cell line may be a primary cell line that is not yet described. Methods of preparing a primary cancer cell line utilize standard techniques known to individuals skilled in the art. In other alternatives, a cancer cell line may be an established cancer cell line. A cancer cell line may be adherent or non-adherent, or a cell line may be grown under conditions that encourage adherent, non-adherent or organotypic growth using standard techniques known to individuals skilled in the art. A cancer cell line may be contact inhibited or non-contact inhibited.

In some embodiments, the cancer cell line may be an established human cell line derived from a tumor. Non-limiting examples of cancer cell lines derived from a tumor may include the osteosarcoma cell lines 143B, CAL-72, G-292, HOS, KHOS, MG-63, Saos-2, and U-2 OS; the prostate cancer cell lines DU145, PC3 and Lncap; the breast cancer cell lines MCF-7, MDA-MB-438 and T47D; the myeloid leukemia cell line THP-1, the glioblastoma cell line U87; the neuroblastoma cell line SHSY5Y; the bone cancer cell line Saos-2; the colon cancer cell lines WiDr, COLO 320DM, HT29, DLD-1, COLO 205, COLO 201, HCT-15, SW620, LoVo, SW403, SW403, SW1116, SW1463, SW837, SW948, SW1417, GPC-16, HCT-8HCT 116, NCI-H716, NCI-H747, NCI-HSO8, NCI-H498, COLO 320HSR, SNU-C2A, LS 180, LS 174T, MOLT-4, LS513, LS1034, LS411N, Hs 675.T, CO 88BV59-1, Co88BV59H21-2, Co88BV59H21-2V67-66, 1116-NS-19-9, TA 99, AS 33, TS 106, Caco-2, HT-29, SK-CO-1, SNU-C2B and SW480; B16-F10, RAW264.7, the F8 cell line, and the pancreatic carcinoma cell line Panc1. In an exemplary embodiment, a peptide-polynucleotide complex of the invention may be administered to a F8 cell line. In another exemplary embodiment, a peptide-polynucleotide complex of the invention may be administered to a B16-F10 cell line.

ii. Treating an Arthritic Condition

In other preferred embodiments, a method of the invention is used to treat an arthritic condition. Non-limiting examples of arthritic conditions include osteoarthritis, rheumatoid arthritis, gout and pseudo-gout, septic arthritis, ankylosing spondylitis, juvenile idiopathic arthritis, still's disease, lupus, or arthritis caused by an infection or treatment. In some embodiments, a method of the invention is used to treat osteoarthritis. In other embodiments, a method of the invention is used to treat rheumatoid arthritis. In yet other embodiments, a method of the invention is used to treat gout. In other embodiments, a method of the invention is used to treat pseudo-gout. In additional embodiments, a method of the invention is used to treat septic arthritis. In other embodiments, a method of the invention is used to treat ankylosing spondylitis. In still other embodiments, a method of the invention is used to treat juvenile idiopathic arthritis. In other embodiments, a method of the invention is used to treat still's disease. In additional embodiments, a method of the invention is used to treat lupus. In yet other embodiments, a method of the invention is used to treat arthritis caused by an infection or treatment. For instance, a method of the invention may be used to treat arthritis caused by collagen antibody induced arthritis.

As used herein, the term "treating an arthritic condition" may be used to describe relieving arthritic symptoms. Non-limiting examples of arthritic symptoms, regardless of the type of arthritis, include varied levels of pain, swelling, joint stiffness, inability to use the hand or walk, malaise and a feeling of tiredness, weight loss, poor sleep, muscle aches and pains, tenderness, and difficulty moving the joint. Methods of measuring arthritic symptoms are well known in the art, and may include measuring the thickness of an arthritic joint such as the ankle, using an arthritic score, or using image-based measurements.

In some embodiments, arthritic symptoms are measured by the thickness of the ankle. As such, treating an arthritic condition using a method of the invention may prevent an increase in ankle thickness in a subject treated with a pharmaceutical composition of the invention when compared to a subject that was not treated with the pharmaceutical composition.

In other embodiments, arthritic symptoms are measured using an arthritic score. Methods of measuring an arthritic score are known in the art and may include the American college of rheumatology (ACR) score, the rheumatoid arthritis severity scale (RASS), or the ACR/EULAR Rheumatoid Arthritis Classification Criteria. As such, treating an arthritic condition using a method of the invention may prevent an increase in arthritic score in a subject treated with a pharmaceutical composition of the invention when compared to a subject that was not treated with the pharmaceutical composition. For instance, treating an arthritic condition using a method of the invention may prevent an increase in arthritic score above about 1, 2, 3, 4, 5, 6, 7, 8, or 9 using the ACR/EULAR Rheumatoid Arthritis Classification Criteria. In preferred embodiments, treating an arthritic condition using a method of the invention may prevent an increase in arthritic score above about 1, 2, or about 3.

In yet other embodiments, arthritic symptoms are measured using image-based measurements. Methods of measuring arthritic symptoms using image-based measurements are known in the art and may include using ultrasonic molecular imaging as described in Hughes et al., 2011 J Acoust Soc Am. 129:3756; Hughes 2011 IEEE Trans Ultrason Ferroelectr Freq Control. 58:2361-2369; Hughes et al., 2007 Ultrasound Med Biol. 33:1236-1243; Hughes et al., 2007 Journal of the Acoustical Society of America. 121: 3542-3557; Hughes et al., 2013 J Acoust Soc Am. 133:283-300; Hughes et al., 2009 Journal of the Acoustical Society of America. 126:2350-2358, the disclosures of which are incorporated herein in their entirety.

(c) Treating Conditions Associated with STAT3 Dysregulation

In some embodiments, the invention encompasses a method of administering to a subject a peptide-polynucleotide complex of the invention to treat a condition associated with STAT3 dysregulation in the subject. In some preferred embodiments, the invention is used to treat a condition associated with STAT3 dysregulation in a subject by disrupting the expression of a nucleic acid sequence encoding STAT3 in the subject. For instance, a method of the invention may be used to treat cancer by disrupting the expression of a nucleic acid sequence encoding STAT3. A cancer or neoplasm may be as described in Section III(c)i. The cancer or neoplasm may be treated by slowing cancer cell growth, or by preventing angiogenesis. In some embodiments, the cancer or neoplasm is treated by slowing cancer cell growth. In other embodiments, the cancer or neoplasm is treated by preventing angiogenesis. The term "angiogenesis" means the formation of new blood vessels in a tissue, the stimulation of endothelial cells to proliferate, or the promotion of survival of proliferating endothelial cells. In a preferred embodiment, the invention is used to treat cancer in a subject by disrupting the expression of a nucleic acid sequence encoding STAT3 in the subject. In an exemplary embodiment, the invention is used to treat cancer in a subject by disrupting the expression of a nucleic acid sequence encoding STAT3 in the subject by slowing cancer cell growth. In another exemplary embodiment, the invention is used to treat cancer in a subject by disrupting the expression of a nucleic acid sequence encoding STAT3 in the subject by preventing angiogenesis.

Disrupting the expression of a nucleic acid sequence encoding STAT3 may reduce the expression level of STAT3 protein. Disrupting the expression of a nucleic acid sequence encoding STAT3 may also reduce the level of a mRNA encoding STAT3. For instance, disrupting the expression of a nucleic acid sequence encoding STAT3 may reduce the level of a mRNA encoding STAT3 by about 1, 2, 3, 4, 5, 6, 7, 8, 9, or about 10 fold or more. In some embodiments disrupting the expression of a nucleic acid sequence encoding STAT3 reduces the level of a mRNA encoding STAT3 by about 1, 2, 3, 4, or about 5 fold. In other embodiments disrupting the expression of a nucleic acid sequence encoding STAT3 reduces the level of a mRNA encoding STAT3 by about 5, 6, 7, 8, 9, or about 10 fold or more.

In general, titration curves measuring the ability of a pharmaceutical composition of the invention to disrupt the expression of a nucleic acid sequence normally expressed in a cell may be performed to determine the $IC_{50}$. For instance, the $IC_{50}$ of a pharmaceutical composition comprising a peptide-polynucleotide complex capable of disrupting the expression of STAT3 in a cell may be about 10, 15, 20, 25, 30, 35, 40, 45, 50, 55, 60, 65, 70, 75, 80, 85, 90, 9, or about 100 nM or more. In some embodiments, the $IC_{50}$ of a pharmaceutical composition comprising a peptide-polynucleotide complex capable of disrupting the expression of STAT3 in a cell is about 10, 15, 20, 25, or about 30 nM. In other embodiments, the $IC_{50}$ of a pharmaceutical composition comprising a peptide-polynucleotide complex capable of disrupting the expression of STAT3 in a cell is about 30, 35, 40, 45, 50, 55, or about 60 nM. In yet other embodiments, the $IC_{50}$ of a pharmaceutical composition comprising a peptide-polynucleotide complex capable of disrupting the expression of STAT3 in a cell is about 60, 65, 70, 75, 80, 85, 90, 9, or about 100 nM or more. In preferred embodiments, the $IC_{50}$ of a pharmaceutical composition comprising a peptide-polynucleotide complex capable of disrupting the expression of STAT3 in a cell is about 40, 45, 50, 55, or about 70 nM.

Disrupting the expression of a nucleic acid sequence encoding STAT3 may prevent angiogenesis. Methods of measuring angiogenesis are known in the art and may be as described in the examples and may include matrigel tube formation assays and transwell cell migration assays. Disrupting the expression of a nucleic acid sequence encoding STAT3 may reduce matrigel tube formation by about 30, 35, 40, 45, 50, 55, 60, 65, 70, 75, 80, 85, 90, or about 95% or more. In some embodiments, disrupting the expression of a nucleic acid sequence encoding STAT3 reduces matrigel tube formation by about 30, 35, 40, 45, or about 50%. In other embodiments, disrupting the expression of a nucleic acid sequence encoding STAT3 reduces matrigel tube formation by about 50, 55, 60, 65, 70, 75, 80, 85, 90, or about 95% or more. In preferred embodiments, disrupting the expression of a nucleic acid sequence encoding STAT3 reduces matrigel tube formation by about 50, 55, 60, 65, or about 70%.

(d) Treating Conditions Associated with JNK2 Dysregulation

In other embodiments, the invention encompasses a method of administering to a subject a peptide-polynucleotide complex of the invention to treat a condition associated with JNK2 dysregulation in the subject. In an exemplary embodiment, the invention is used to treat a condition associated with JNK2 dysregulation in a subject by disrupting the expression of a nucleic acid sequence encoding JNK2 in the subject. For instance, a method of the invention may be used to treat atherosclerosis by disrupting the expression of a nucleic acid sequence encoding JNK2. In some preferred embodiments, atherosclerosis is treated by blocking foam cell formation. Foam cell formation is the hallmark of atherosclerotic plaques, and can become a problem when they accumulate at particular foci thus creating a necrotic center of atherosclerosis. In an exemplary embodiment, a peptide-polynucleotide complex wherein the polynucleotide of the complex is an anti-JNK2 siRNA is used to block foam cell formation.

IV. Kit

Another aspect of the invention encompasses a kit. The kit comprises a first composition comprising a peptide of the invention, and optionally a second composition comprising a polynucleotide. Alternatively, a polynucleotide of interest may be provided by a user of the kit. By following directions provided by the kit, a user of the kit may mix the composition comprising a peptide of the invention and a composition comprising a polynucleotide to form a peptide-polynucleotide complex. The directions of the kit may include instructions to mix the peptide and polynucleotide at a suitable ratio. Suitable ratios are described above in Section I. The kit may also include suitable buffers, water, cross-linking reagents or albumin.

DEFINITIONS

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The terms "homologous," "identical," or percent "identity" in relation to two or more peptides, refers to two or more sequences or subsequences that have a specified percentage of amino acid residues that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/ or the like). The definition also includes sequences that have deletions and/or additions, as well as those that have substitutions, as well as naturally occurring, e.g., polymorphic or allelic variants, and man-made variants. As described below, the preferred algorithms can account for gaps and the like.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

EXAMPLES

The following examples are included to demonstrate preferred embodiments of the disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Introduction for Examples 1-8

RNA interference (RNAi) with the use of small interfering RNA (siRNA) has been proposed as a highly effective therapy for myriad diseases including cancer and atherosclerosis. However, despite nearly two decades of intense research, siRNA therapeutics have demonstrated limited success in translation to clinical applications. The major barriers preventing successful siRNA based therapeutics comprise poor cellular uptake and instability of free siRNA in serum. It's large molecular weight (~14 kDa) and high surface charge prevent siRNA from passing through the cellular membrane to reach the cytoplasmic compartment where siRNA is active, thus blocking successful induction of RNAi. These traits, combined with a serum half-life of only ~10 minutes, necessitate the packaging of siRNA into transfection agents. These agents can protect siRNA from serum endonucleases, and promote siRNA uptake through endocytosis. Unfortunately, these endocytic pathways present another barrier, as siRNA must avoid remaining trapped in the endosomal/lysosomal compartment where it is degraded by an increasingly acidic environment.

Despite these challenges, cationic lipids and polymers have been successfully employed for siRNA transfection. Unfortunately these types of transfection agents can exhibit unacceptable cytotoxicity. The incorporation of cationic lipids into membrane bilayers within the cells promotes siRNA release into the cytoplasm, but also causes generation of reactive oxygen species (ROS) and Ca+2 leakage, a side effect shared by high molecular weight polyetheyleneimine cationic polymers. Despite continued development of these siRNA carriers to reduce cytotoxicity, these agents have experienced difficulties when given systemically in vivo due to aggregation with serum proteins and complement activation. If the problem of systemic siRNA delivery is to be solved, new classes of siRNA transfection agents will have to be developed.

Cell penetrating peptide (CPP) based siRNA transfection agents have shown promise with respect to reducing cytotoxicity. Although CPP based siRNA transfection appears nearly free of cytotoxicity, peptide based transfection agents have not achieved the high efficiency of traditional lipidic transfection agents. Insights have been provided by the studies of Veldhoen et al. (2006, Nucleic Acids Res. 34:6561-73), which suggest that peptide based transfection is limited by lysosomal trapping. Despite early work suggesting that CPP mediates siRNA uptake in an energy independent manner, it appears that nanoparticles produced by the assembly of CPP and siRNA are endocytosed and must escape the endosomal-lysosomal pathway to gain access to the cytosolic compartment. With this barrier in mind, existing CPP technology has achieved a new level of sophistication through the chemical conjugation of CPPs to membrane active lipids or endosomolytic agents, although these still require further peptide processing and purification.

The Examples presented below propose an alternative strategy for efficient peptide based siRNA transfection based on modifications of the cytolytic peptide, melittin, which is the pore forming component of honey bee venom. Melittin's ability to form pores in membrane bilayers suggests that it can serve as a basis for the development of simple peptides which can improve endosomal escape, thereby setting the stage for more efficient siRNA delivery into the cytosolic compartment for improved RNAi, and overcoming the lower efficiency associated with traditional CPP based strategies. Previous work performed by the inventors has shown that melittin can be modified to attenuate its cytotoxicity while maintaining its propensity for interacting with membrane bilayers. As is demonstrated in the present Examples, incorporating these changes along with modifications to enhance peptide/siRNA interactions, melittin derived peptides can safely deliver siRNA to the cytoplasmic compartment owing to their inherent membrane active properties.

Example 1

Screening for siRNA Knockdown

Knockdown of B16 cells stably expressing GFP-PEST allowed quick screening for effective siRNA knockdown of GFP expression because the PEST sequence shortens GFP half-life from 26 to 10 hours. Melittin derivatives were chosen based on modifications designed to decrease cytotoxicity as well as improve interactions with oligonucleotides. These peptides were screened for their ability to deliver GFP siRNA for the knockdown of GFP in B16 GFP cells (Table 1, FIG. 1). While mellitin itself was too toxic in this concentration range, three derivatives, p5RHH, p5RH and p5RH-LL, were able to transfect when used at a ratio of peptide:polynucleotide that is between 50:1 and 200:1 and exhibited GFP knockdown. p5RHH exhibited especially efficient siRNA transfection and was chosen for further characterization and optimization of formulation.

TABLE 1

Melittin along with four derivatives were tested for GFP knockdown at 50 nM.

| | Particle composition (peptide/ siRNA) | Charge ratio (+/−) | Able to transfect? |
|---|---|---|---|
| Melittin | 62:1 | 6:1 | No |
| (SEQ ID NO: 53) GIGAV | 124:1 | 12:1 | Toxic |
| LKVLTTGLPALISWIKRKRQQ | 248:1 | 24:1 | Toxic |
| Peptide 5C | 62:1 | 6:1 | No |
| (SEQ ID NO: 54) | 124:1 | 12:1 | No |
| VLTTGLPALISWIKRKRQQC | 248:1 | 24:1 | No |
| Peptide 5RWR | 28:1 | 6:1 | No |
| (SEQ ID NO: 55) VLTTG | 56:1 | 12:1 | No |
| LPALISWIKRKRQQRWRRRR | 112:1 | 24:1 | No |
| Peptide 5RHH | 50:1 | 6:1 | Yes |
| (SEQ ID NO: 1) | 100:1 | 12:1 | Yes |
| VLTTGLPALISWIRRRHRRHC | 200:1 | 24:1 | Yes |
| Peptide 5RH | 50:1 | 6:1 | No |
| (SEQ ID NO: 57) | 100:1 | 12:1 | Yes |
| | 200:1 | 24:1 | No |
| Peptide 5RH-LL | 50:1 | 6:1 | No |
| (SEQ ID NO: 63) | 100:1 | 12:1 | Yes |
| | 200:1 | 24:1 | No |

Figure 1B:
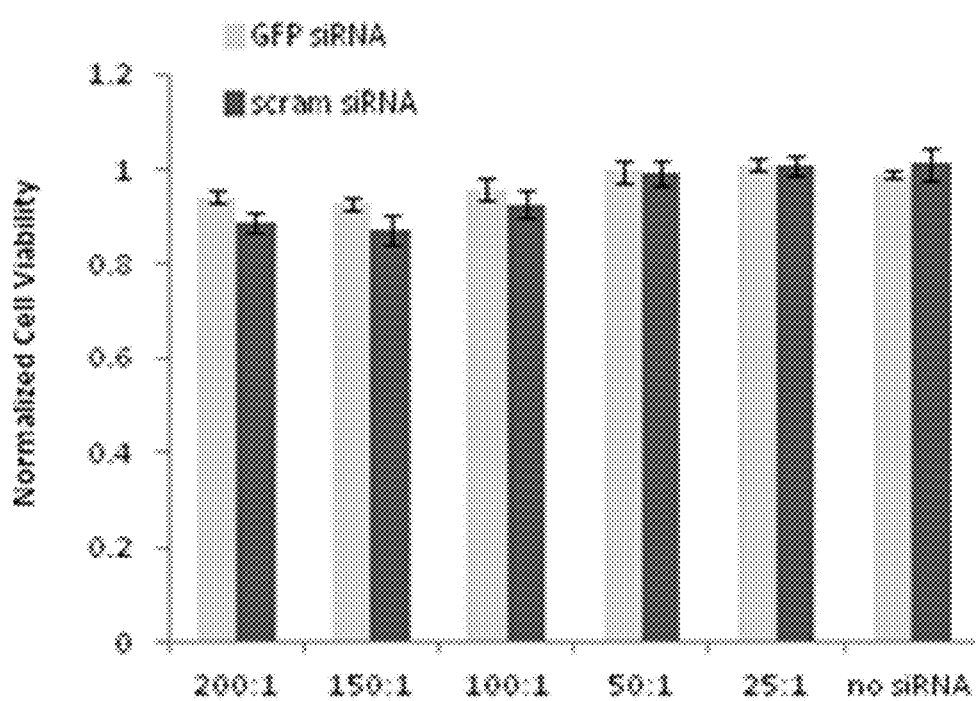

Flow cytometry was performed to determine the optimum p5RHH:siRNA ratio for transfection, where transfection efficiency improved with increasing p5RHH content until maximal at a p5RHH:siRNA ratio of 150:1 (FIG. 1A). In contrast, scrambled siRNA had no effect on GFP expression levels under the same conditions. Although there was no sign of cytotoxicity associated with the peptide at ratios up to 200:1 (FIG. 1B), a p5RHH:siRNA ratio of 100:1 was selected for the remaining experiments to minimize exposure to the p5RHH.

Example 2

Nanoparticle Formation and Characterization

Figure 2A:
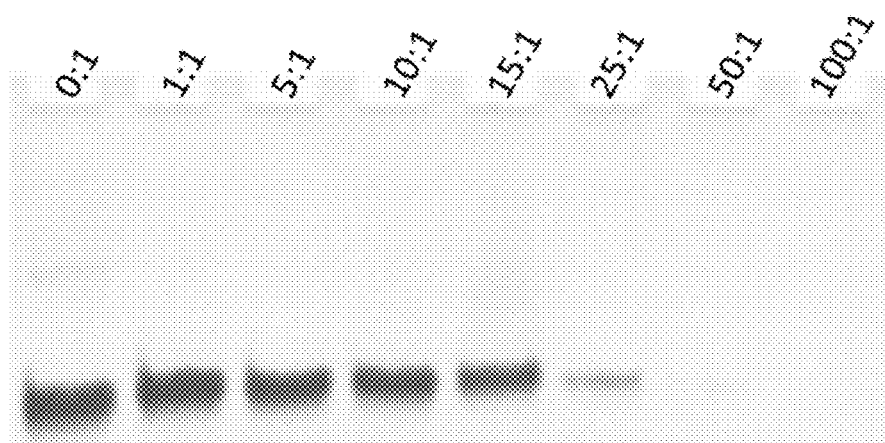
FIGS. 2A and B depicts an electrophoresis gel and an SEM micrograph, respectively, showing (A) a gel retardation assay showing that a p5RHH:siRNA ration of 50:1 is required to completely complex siRNA, and (B) SEM analysis of particle size confirms the dynamic light scattering data revealing small complexes of 100-200 nm in diameter. (scale bar 100 nm)

Based on the overall net positive charge of the melittin derivative, p5RHH, it was anticipated that it would interact electrostatically with the negatively charged siRNA. These interactions were monitored at varying peptide:siRNA ratios using gel retardation assays, in which only free unbound siRNA could migrate into the polyacrylamide gel under the presence of an electric field. In these assays, a set amount of siRNA was mixed with increasing amounts of p5RHH in PBS for 40 minutes before loading on the gel (FIG. 2A). It is apparent that a peptide:siRNA ratio of at least 50:1 is required to completely compact the siRNA, which confirmed the lack of siRNA transfection noted by FACS at p5RHH:siRNA ratios below 50:1 (FIG. 1A).

Figure 2B:
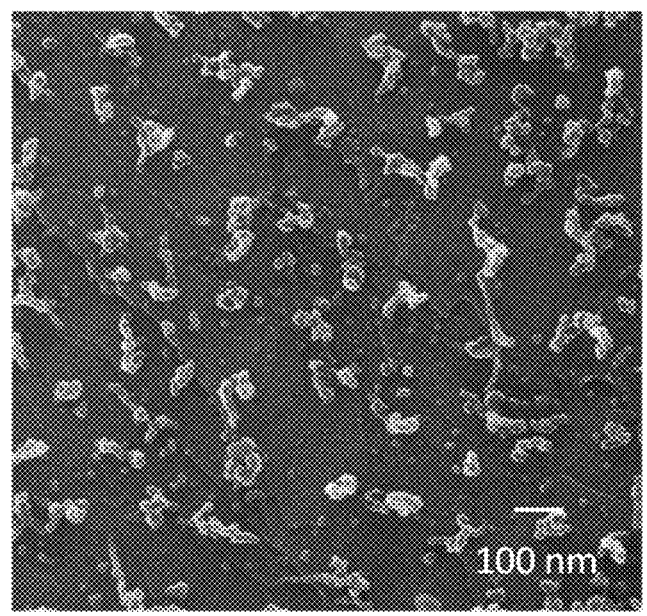

Dynamic light scattering (DLS) and zeta potential measurements (Table 2) revealed that particle size is tied closely to the effective surface charge. Particles carrying a surface charge near 0 mV exhibit the largest diameter, while particles with a zeta potential of greater magnitude have smaller diameters. The smallest particle size of 190 nm was found to be produced with a peptide:siRNA molar ratio of 100:1 or a charge ratio around 12:1 (+/−). It is important to note that increasing p5RHH:siRNA ratio to 200:1 (doubling the +/− ratio to 24:1) does not increase the zeta potential, but does result in an increased particle size. This phenomenon has been previously reported with other peptide transfection agents, although the cause has not yet been established. Freeze fracture SEM (FIG. 2B) shows the presence of distinct nanoparticles with an overall diameter near 150 nm. Interestingly, these particles appear to consist of aggregates of smaller, 10-20 nm particles that have coalesced to form a stable particle of larger diameter. When size is assessed by atomic force microscopy (AFM), particle size after 72 hours is <100 nm, typically around 50-100 nm. Overall, it appears that when particle size is assessed by DLS, particle size may appear larger because aggregates are included in the answer. The size of the active particles, as more accurately measured by SEM or AFM, is around 50 to 100 nm.

TABLE 2

Nanoparticle (NP) characteristics at various peptide:siRNA ratios. Analysis of p5RHH:siRNA nanoparticles by dynamic light scattering and zeta potential analysis suggest that effective surface charge determines particle size. Nanoparticles with a surface charge of larger magnitude exhibit smaller diameters suggesting the importance of electrostatic interactions in stabilizing p5RHH:siRNA nanoparticles. A p5RHH:siRNA ratio of 100:1 generates the smallest particle size of 190 nm.

| Particle composition (siRNA/peptide) | Charge ratio (+/−) | Particle size (nm) | Zeta potential (mV) |
|---|---|---|---|
| 10:1 | 1.2:1 | 299.6 | −13 |
| 25:1 | 3:1 | 830.6 | −2.28 |
| 50:1 | 6:1 | 603.6 | 3.72 |
| 100:1 | 12:1 | 187.9 | 12 |
| 200:1 | 24:1 | 315.5 | 13.1 |

Example 3

Comparison with LF2000

Figure 3A:
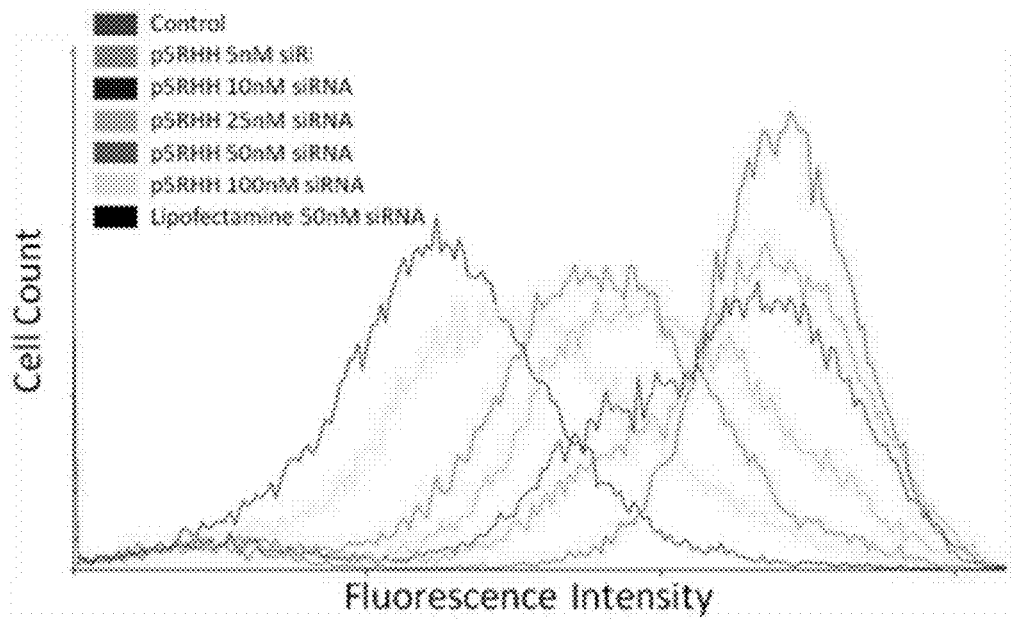
FIG. 3A-F depicts plots and images of data following p5RHH mediated transfection. (A) Dose response by flow cytometry shows that p5RHH mediated transfection is less efficient than Lipofectamine2000, but also shows high siRNA transfection efficiency with visible knockdown at concentrations as low as 5 nM. (B) Alamar blue assays indicate that p5RHH exhibits minimal toxicity at siRNA concentrations up to 200 nM. Western blotting (C) and RT-PCR (D) analysis of GFP mRNA confirms the ability of p5RHH to decrease mRNA levels in a sequence specific manner with and IC50 of ~50 nM. Lipofectamine 2000 has a higher transfection efficiency with an IC50 of between 10-25 nM as determined by western blotting (E) and RT-PCR (F).
Figure 3B:
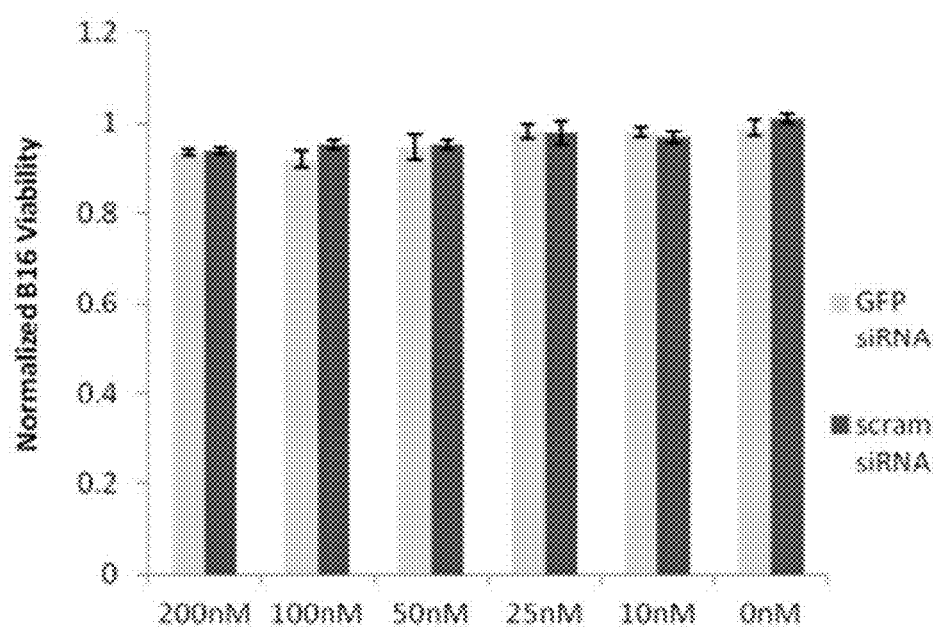
Figure 3C:
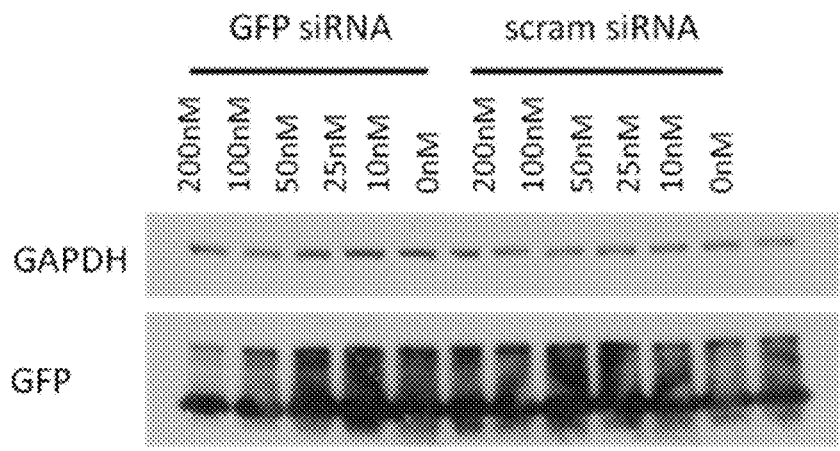
Figure 3D:
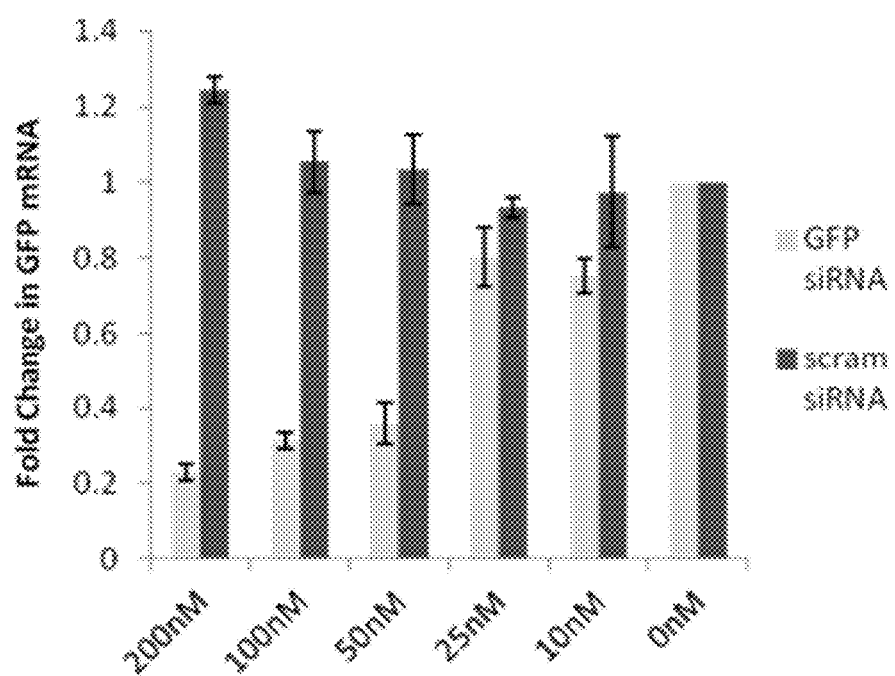
Figure 3E:
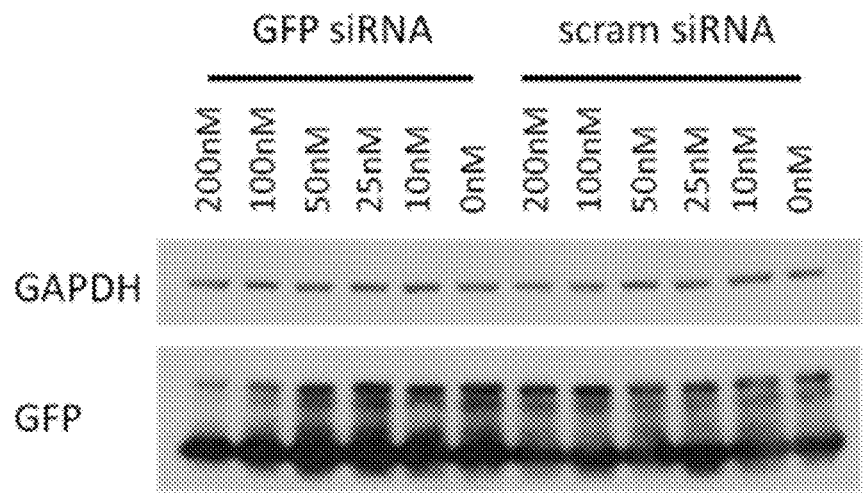
Figure 3F:
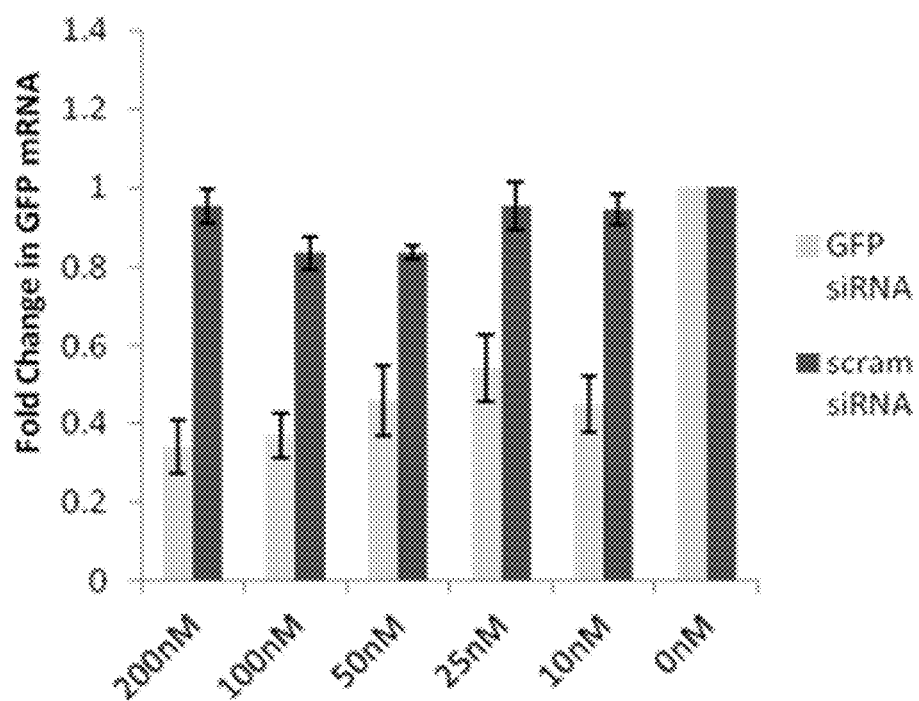
Figure 44A:
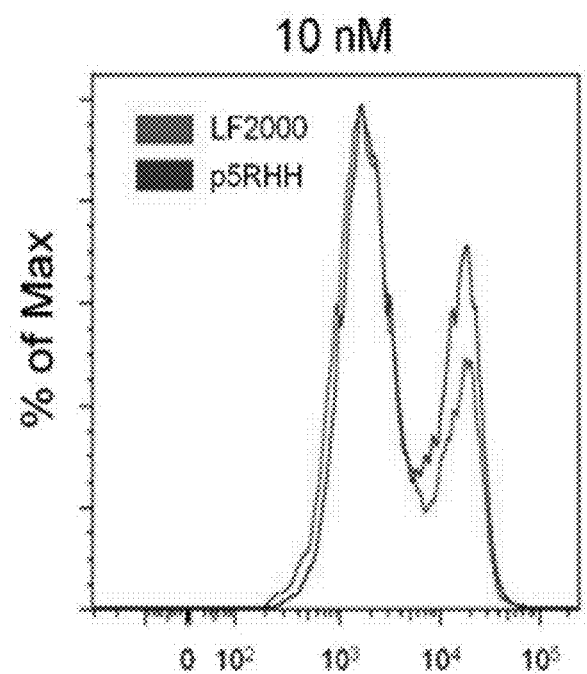
FIG. 44A-C depicts graphs comparing p5RHH mediated transfection to Lipofectamine 2000 at three doses. Comparison of GFP knockdown by p5RHH and Lipofectamine 2000 (red) at 10 mM (A), 50 nM (B), and 200 nM (C), reveals that p5RHH is slightly less effective than lipidic transfection at low concentration and high concentration.
Figure 44B:
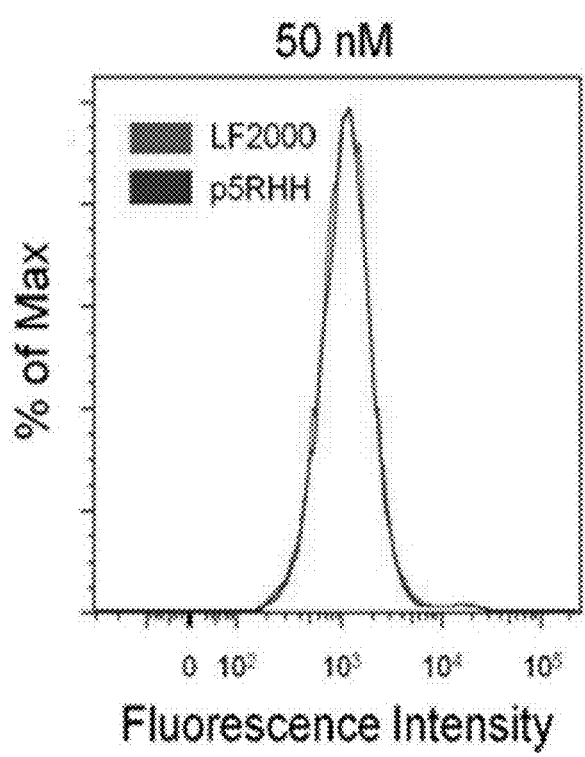
Figure 44C:
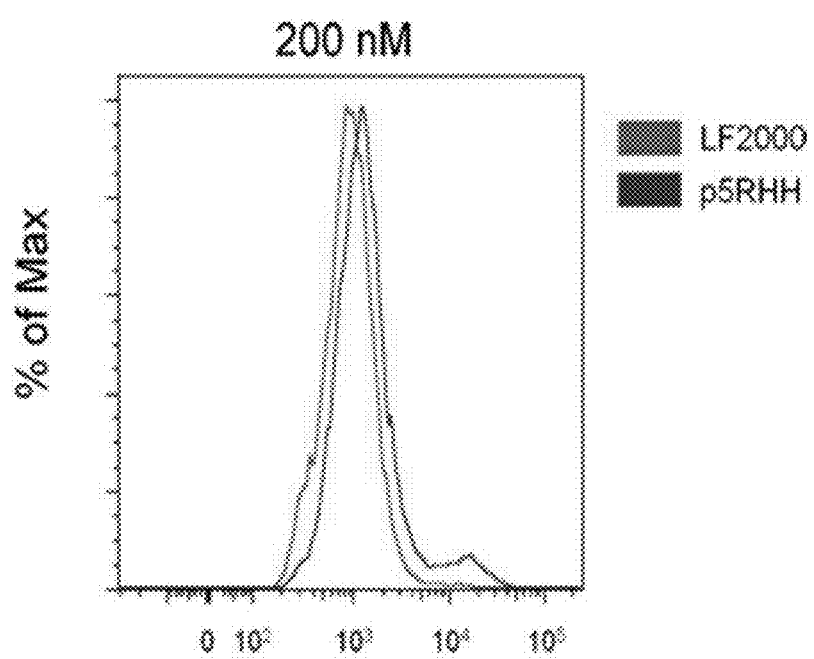

Dose response analysis using flow cytometry reveal that GFP knockdown by GFP siRNA transfected with p5RHH is highly efficient, with an ability to decrease GFP expression in ~15% of cells at concentrations as low as 5 nM (FIG. 3A) and the ability to decrease GFP expression in ~70% of cells at concentrations as low as 10 nM (FIG. 44). Scrambled siRNA had no effect on GFP protein levels when transfected under the same conditions (FIG. 3C, D). However, in comparison to Lipofectamine 2000, p5RHH is less efficient at transfecting siRNA, with an $IC_{50}$ at 50 nM based on RT-PCR as compared to the reported $IC_{50}$ of Lipofectamine 2000 of 10 nM (FIG. 3E, F). Additionally, the ability of p5RHH to transfect siRNA at low concentrations as noted by flow cytometry is not apparent via western blotting or RT-PCR, likely due to the low percentage of cells (~15%) showing knockdown by FACS. However, it is readily apparent that p5RHH dramatically improves the cytotoxicity profile over lipofectamine 2000, which is apparent from the minimal decrease (~3%) in cell viability, even at the highest concentrations tested (FIG. 3B).

Example 4

Efficient siRNA Release into the Cytoplasm

Figure 4A:
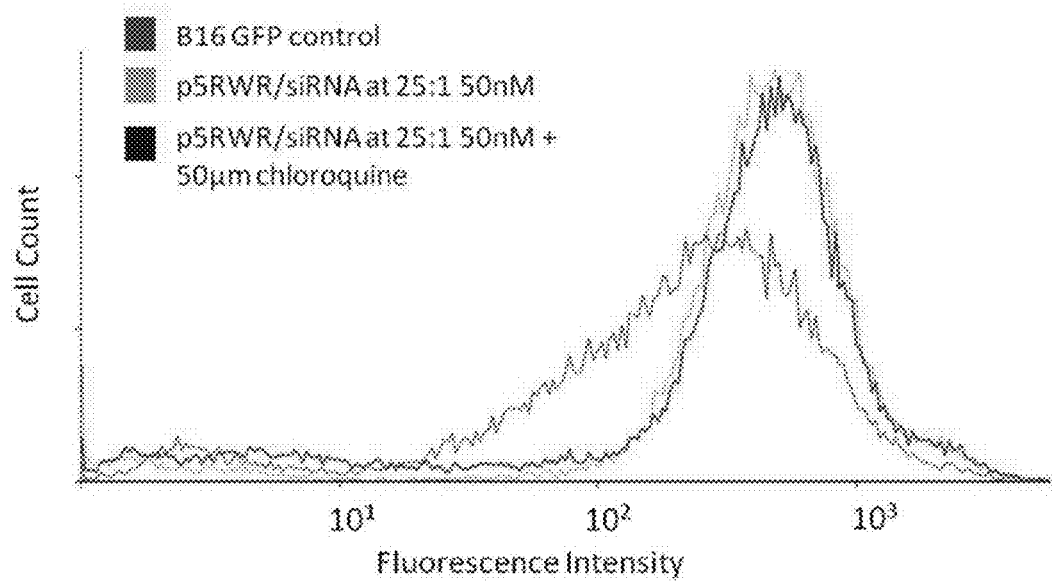
FIG. 4A-E depicts plots and images of data following p5RWR mediated transfection. (A) The nonfunctioning melittin derivative, p5RWR, exhibits no siRNA transfection ability when screened for knockdown of GFP in B16GFP cells via flow cytometry. siRNA is being delivered, but does not reach cytoplasm until incubated with 50 µM chloroquine. (B, C) Confocal microscopy confirms the flow cytometry data, indicating that p5RWR does not manifest appreciable oligonucleotide release into the cytoplasm unless incubated with 50 µM chloroquine. (D, E) In comparison, p5RHH shows efficient oligo release into the cytoplasm similar to oligonucleotide delivery via Lipofectamine 2000.
Figure 4B:
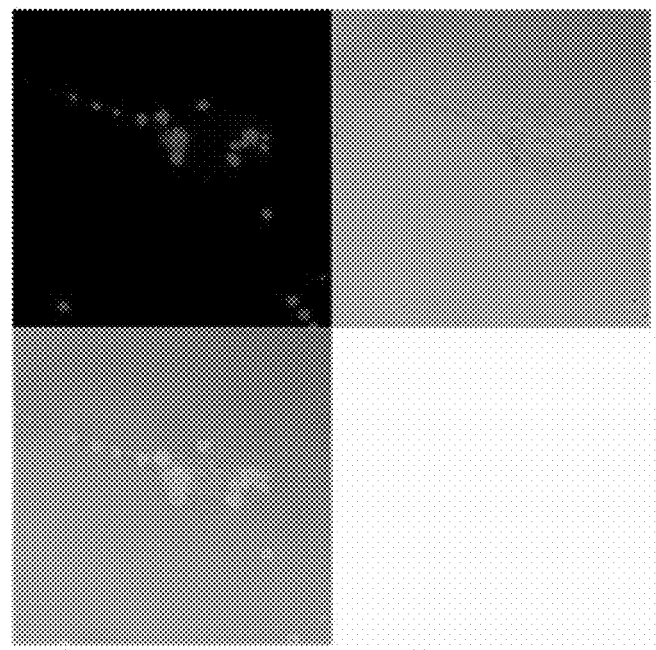
Figure 4C:
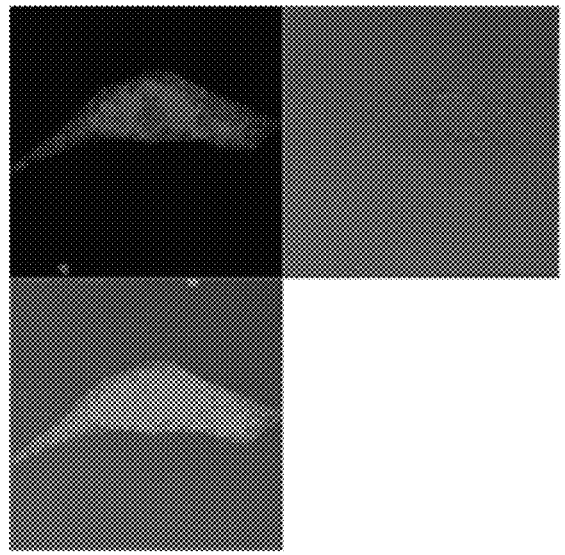
Figure 4D:
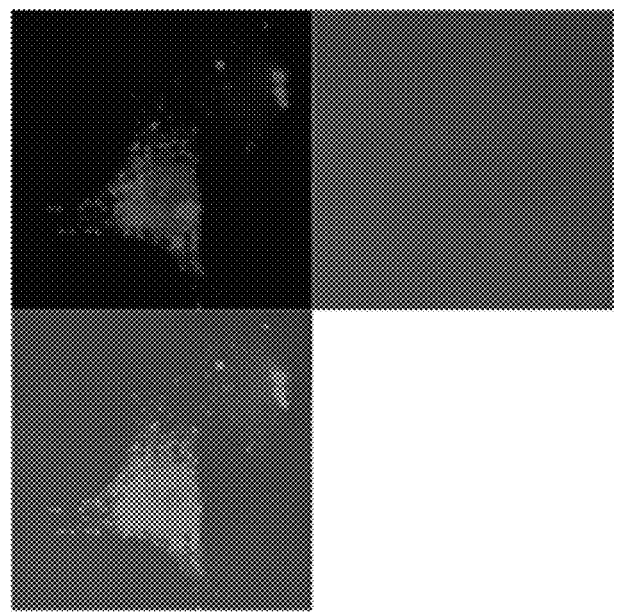
Figure 4E:
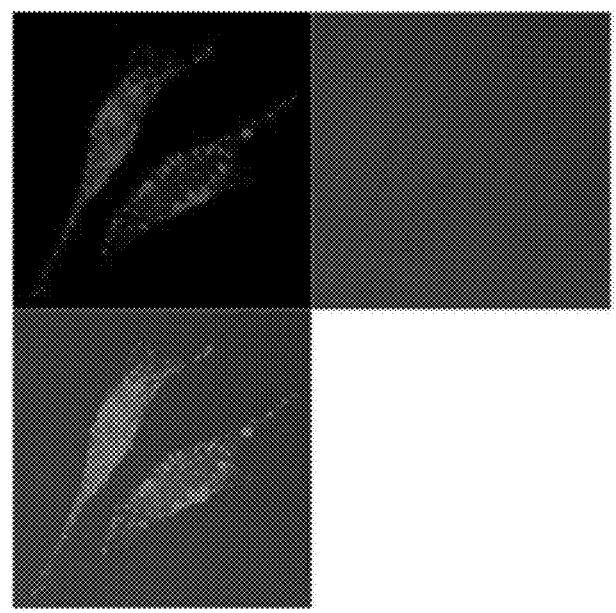

Analysis of a melittin derivative known to be inactive for siRNA transfection (p5RWR: VLTTGLPAL-ISWIKRKRQQRWRRRR (SEQ ID NO:55), Table 1, FIG. 1) by confocal microscopy reveals that oligonucleotides packaged with p5RWR do not reach the cytoplasm without co-incubation in the presence of 50 μM chloroquine, which is a known endosomolytic agent (FIG. 4B, C). FACS analysis for GFP knockdown confirms that siRNA transfected by p5RWR is unable to initiate GFP knockdown without the aid of chloroquine (FIG. 4A). These data suggest that p5RWR/siRNA nanoparticles remain trapped in the endosomal compartment and cannot initiate RNAi. In comparison, p5RHH alone is able to deliver oligonucleotides to the cytoplasm when analyzed 24 hours post transfection (FIG. 4D, E), suggesting that p5RHH possesses innate endosomolytic capacity.

Example 5 siRNA Delivery to Slow Cancer Growth

Figure 5A:
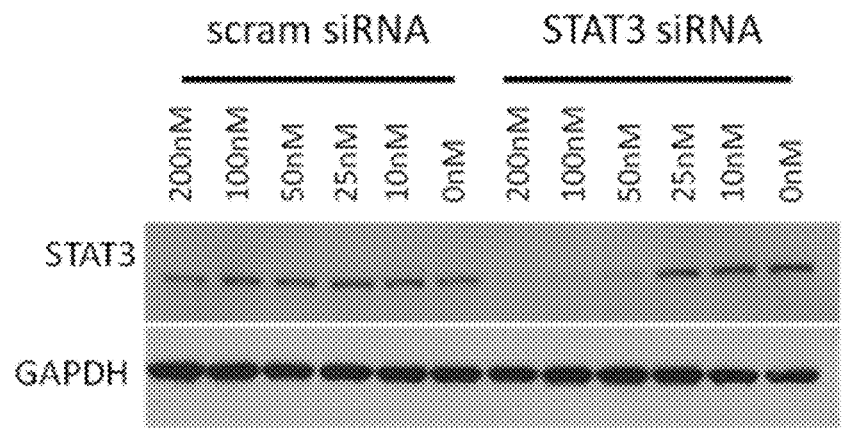
FIG. 5A-F depicts images and graphs comparing p5RHH mediated transfection to Lipofectamine 2000 trasnfection. Western blotting data indicate that p5RHH (A) is approximately 5-fold less efficient than Lipofectamine 2000 (B) at initiating a decrease in STAT3 protein levels in B16 cells. RT-PCR data show that p5RHH (C) loses activity at concentrations below 50 nM while Lipofectamine 2000 (D) exhibits activity at doses as low as 10 nM. B16 viability analysis via Alamar Blue demonstrates that p5RHH (E) transfection leads a decrease in B16 viability by silencing oncogene expression in a sequence specific manner whereas Lipofectamine2000 (F) causes nonspecific dose dependent cytotoxicity.
Figure 5B:
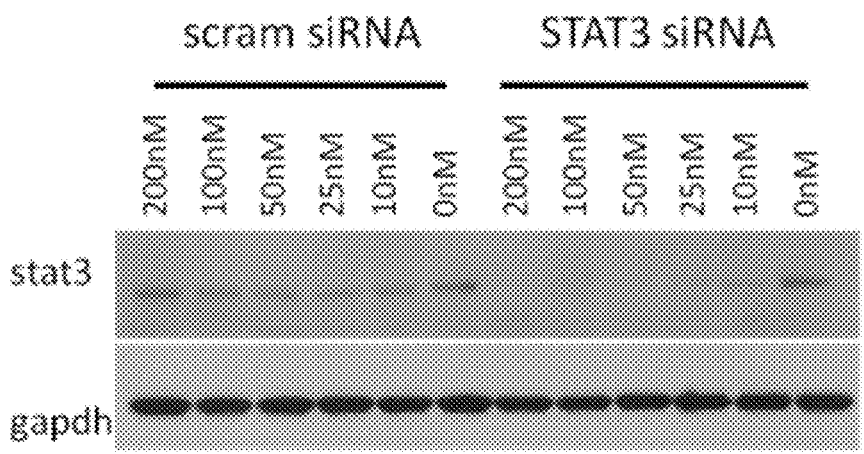
Figure 5C:
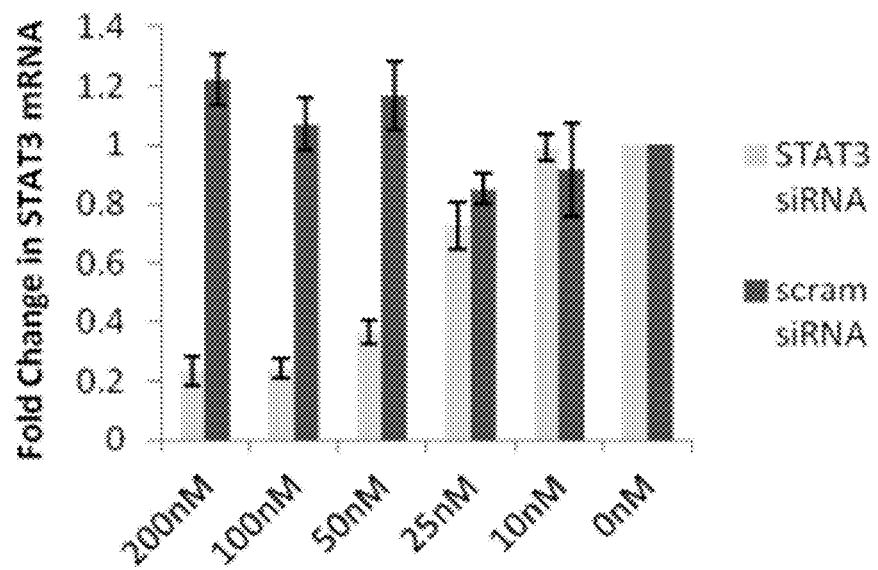
Figure 5D:
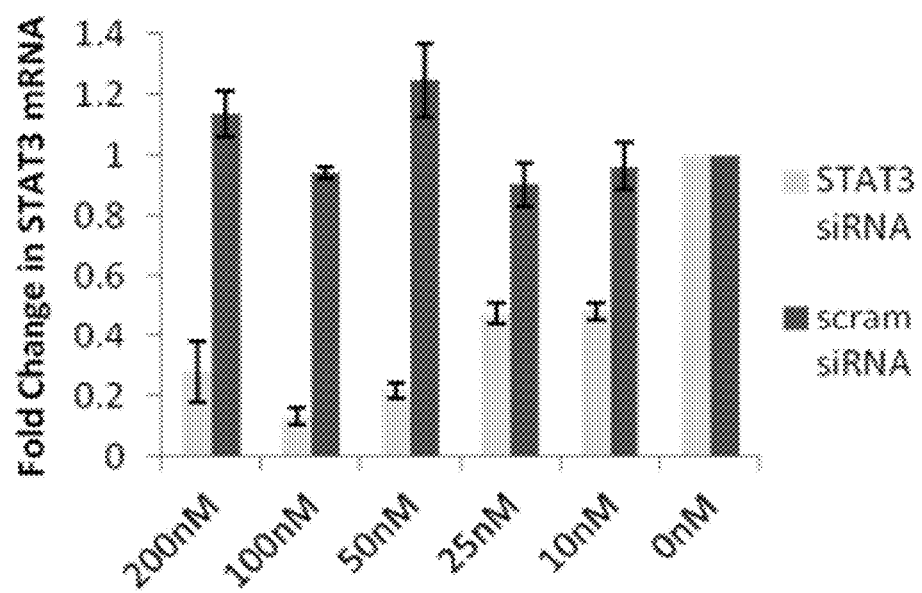
Figure 5E:
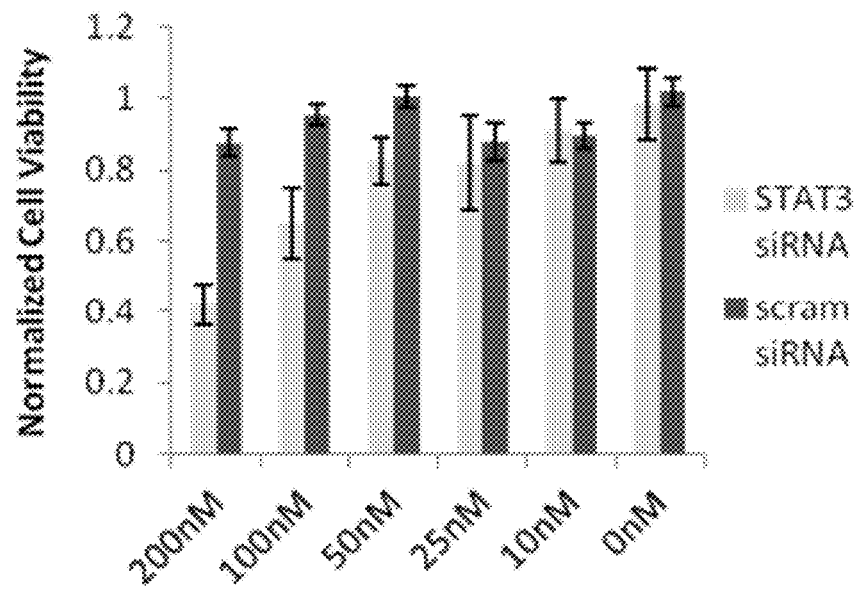
Figure 5F:
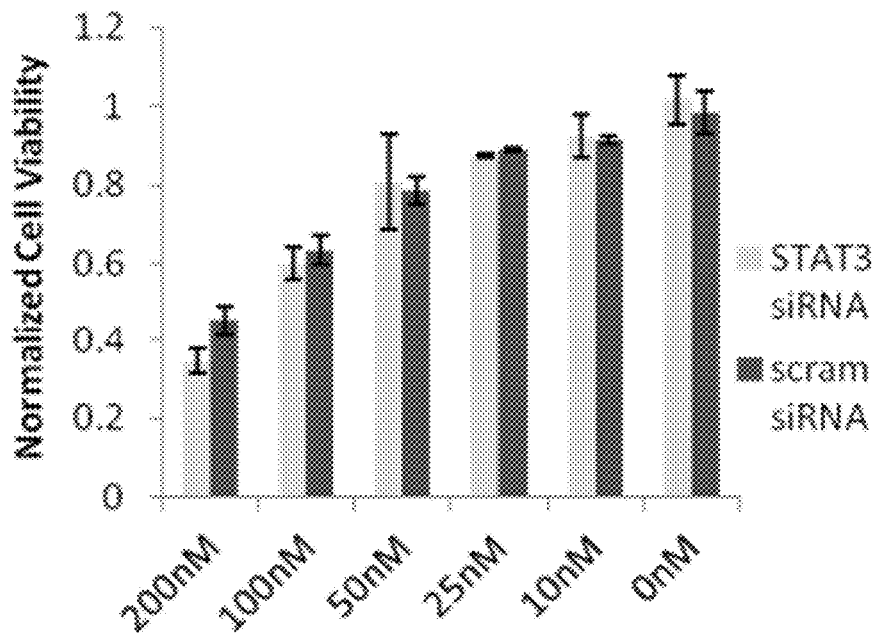
Figure 6A:
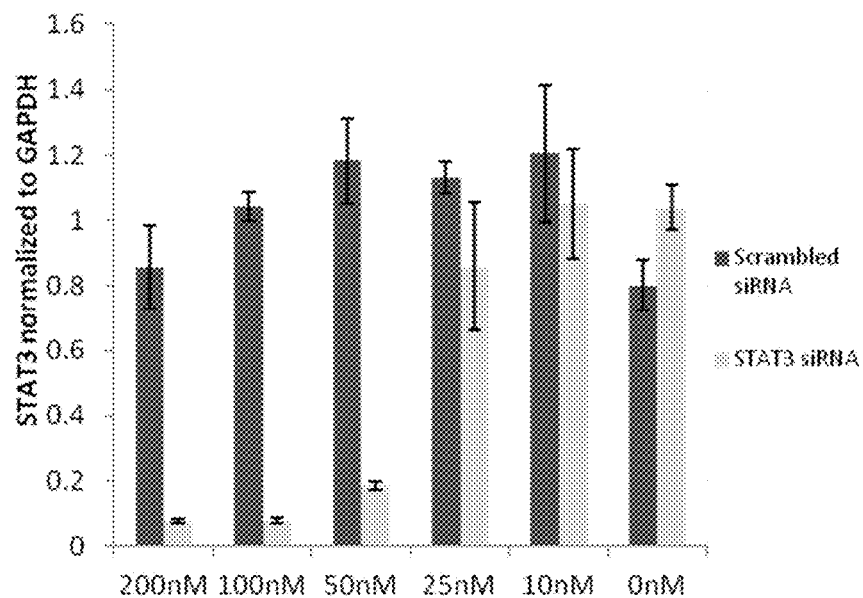
FIG. 6A-B depicts graphs comparing p5RHH mediated transfection to Lipofectamine 2000 trasnfection. Quantification of STAT3 protein levels in B16 cells when delivering scrambled or STAT3 specific siRNA by p5RHH (A) or Lipofectamine 2000 (B). Data are presented as the average of 3 independent experiments.
Figure 6B:
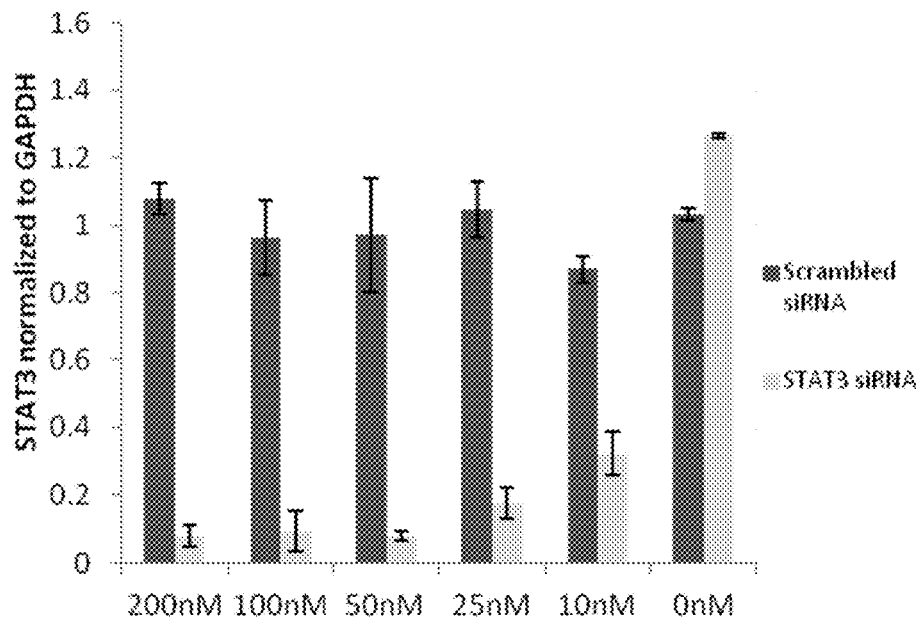

Signal Transducer and Activator of Transcription 3 (STAT3) is a well-known oncogene believed to play a critical role a wide variety of human malignancies. To test the ability of p5RHH to downregulate constitutively activated oncogenes, STAT3 expression was targeted in B16-F10 cells which are known to be STAT3 dependent. Delivery of a STAT3 specific siRNA led to degradation of STAT3 mRNA with a subsequent decrease in STAT3 protein expression (p5RHH $IC_{50}$: ~50 nM, Lipofectamine 2000 $IC_{50}$: ~10 nM) (FIG. 5A-D, FIG. 6). P5RHH mediated STAT3 siRNA transfection led to decreased B16-F10 viability (60% at 200 nM) 72 hours following transfection as determined by Alamar Blue assays (FIG. 5E). Importantly, scrambled siRNA showed no effect on B16 viability illustrating the safety of p5RHH in comparison to Lipofectamine 2000 (FIG. 5F), which produced an equivalent decrease in cell viability (up to 60% at 200 nM) when delivering either STAT3 specific or scrambled siRNAs.

Example 6 siRNA Delivery to Prevent Angiogenesis

Figure 7A:
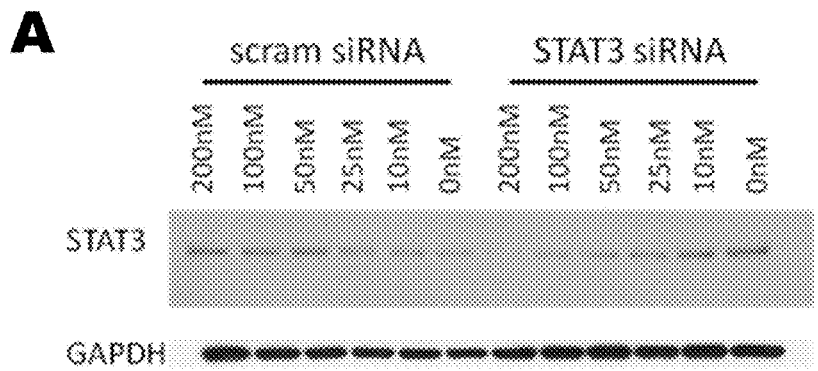
Figure 7B:
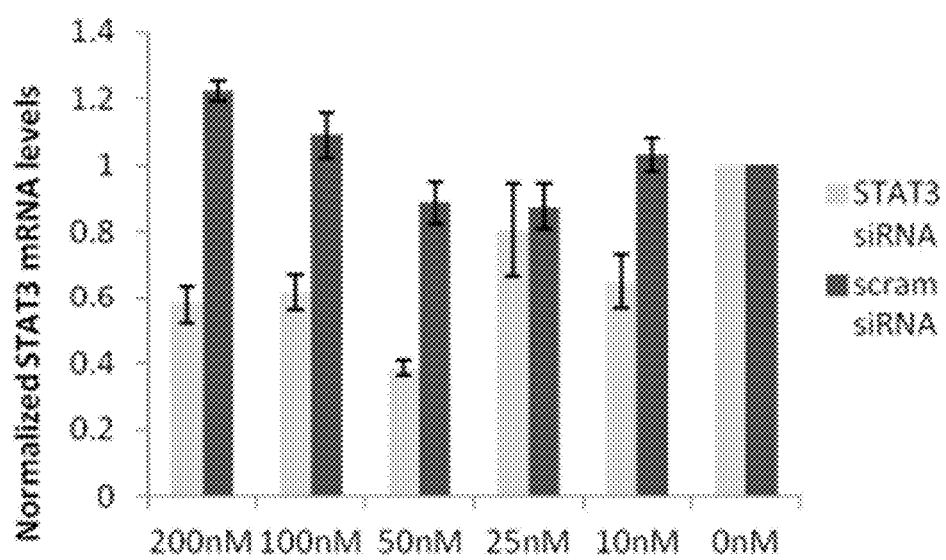
Figure 7C:
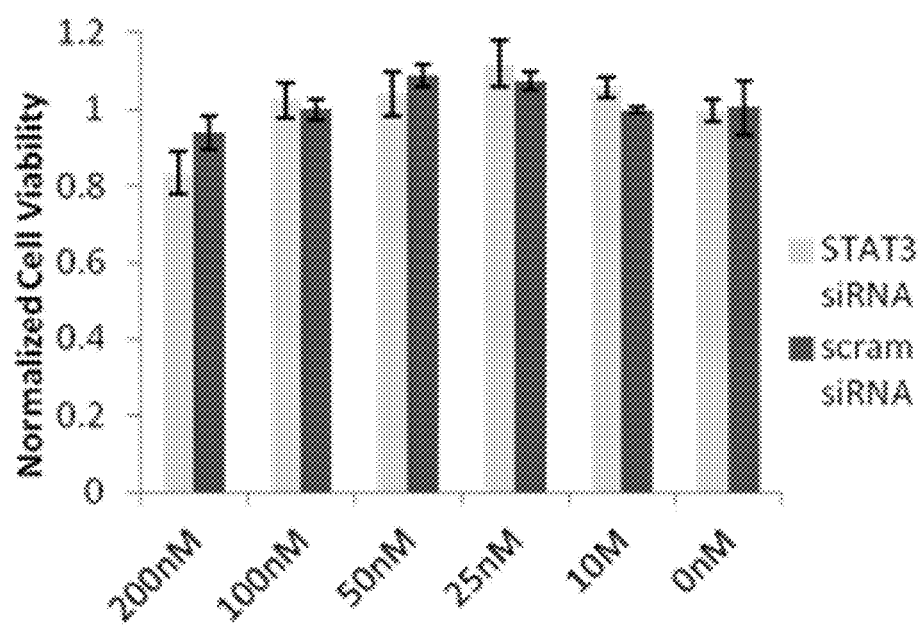
Figure 7G:
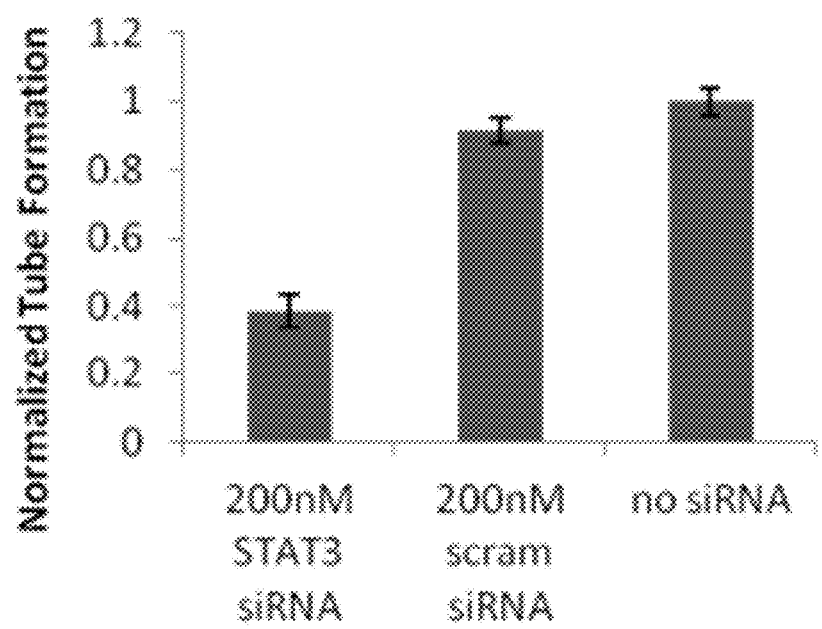
Figure 8:
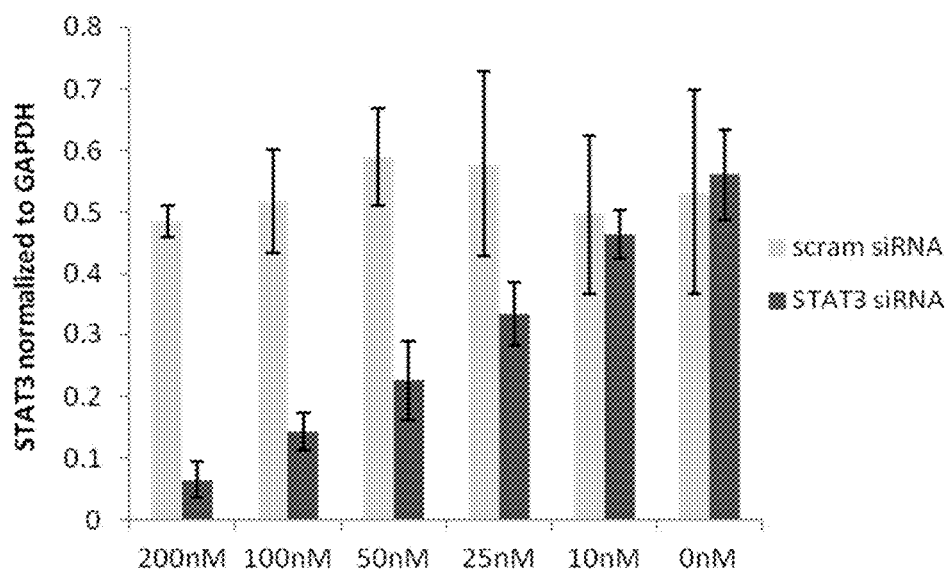
FIG. 8 depicts quantification of STAT3 protein levels from HUVECs transfected with p5RHH demonstrates an IC50 of ~50 nM. Average of 3 independent experiments.
Figure 9A:
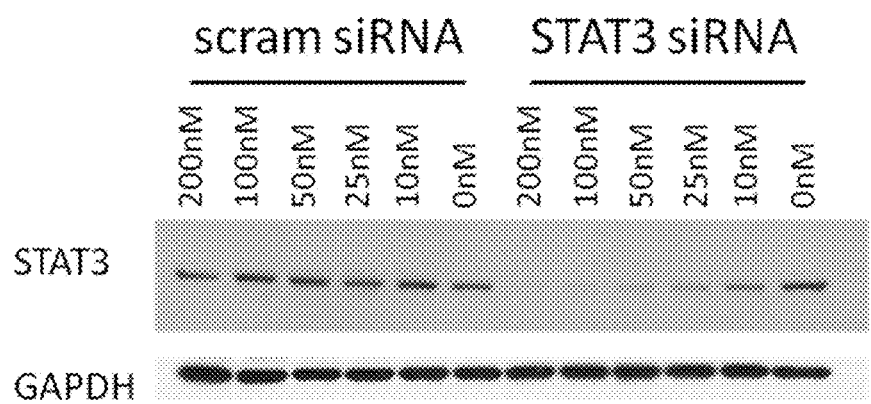
FIG. 9A-D depicts graphs of Lipofectamien 2000 transfection. Representative western blot (A) showing knockdown of STAT3 using Lipofectamine 2000 shows an IC50 less than 10 nM with quantification (B). RT-PCR verifies a strong knockdown at 10 nM (C). Despite high siRNA delivery efficiency, Lipofectamine 2000 causes extensive cytotoxicity, with a >50% decrease in cell viability at only 50 nM siRNA.
Figure 9B:
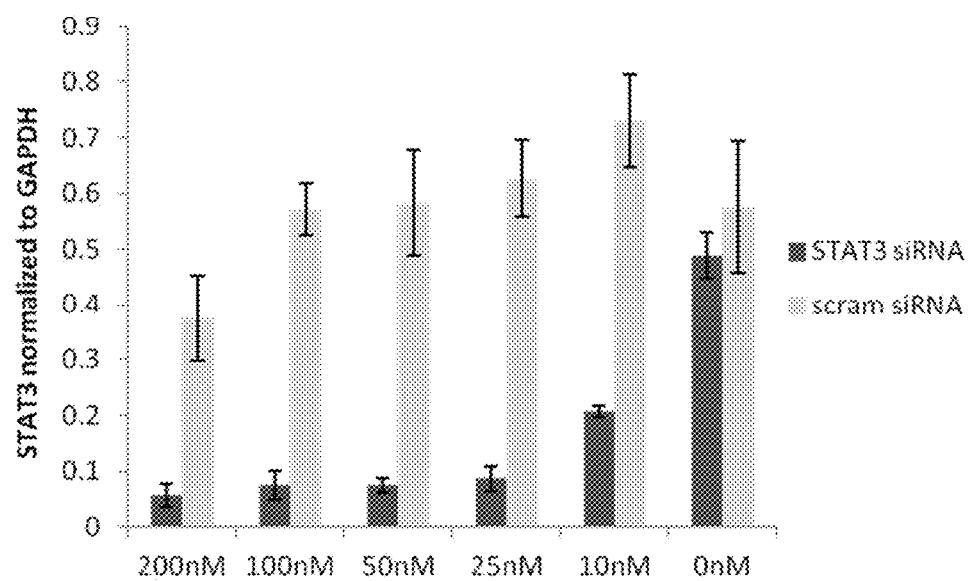
Figure 9C:
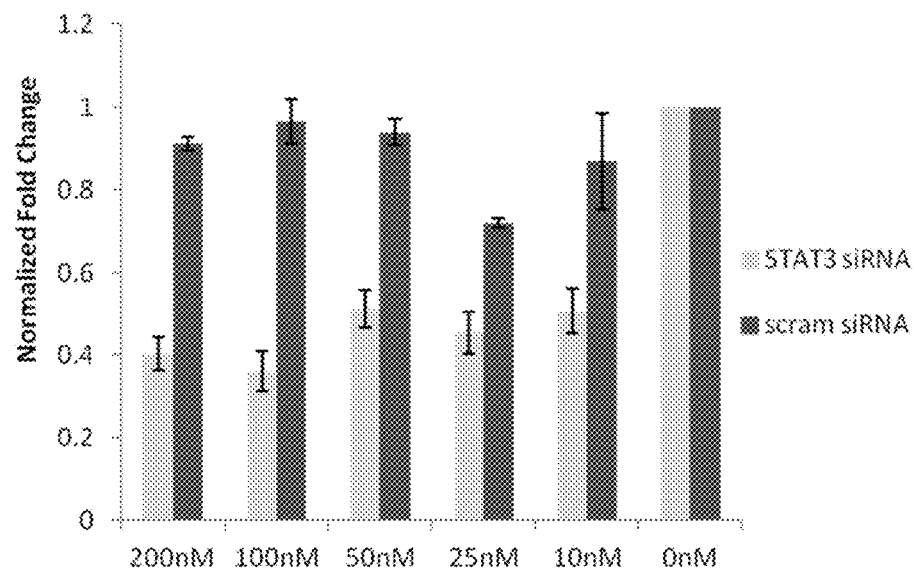
Figure 9D:
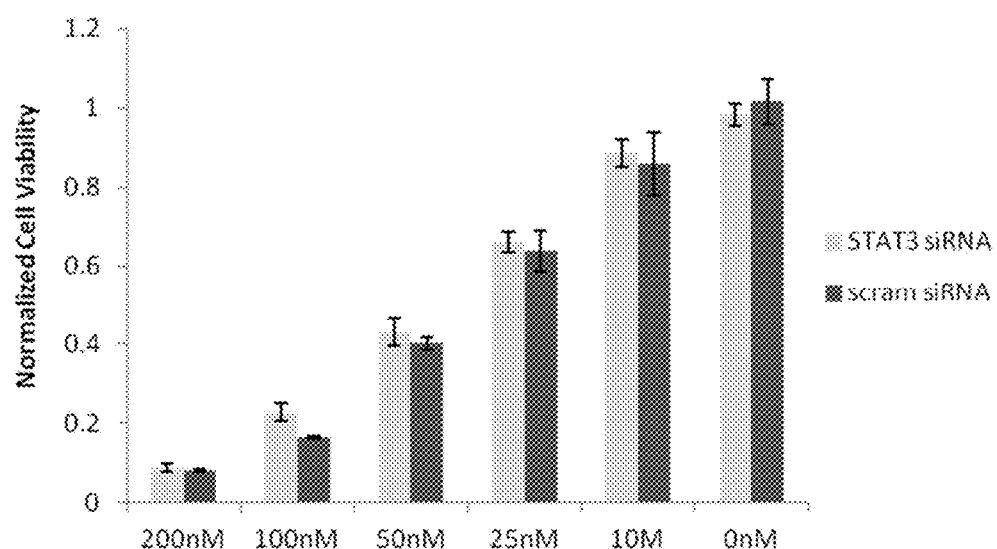

Pathological angiogenesis is a hallmark of many disease states, including cancer, atherosclerosis, and inflammation. STAT3 has previously been shown to be a key mediator in the migration and maturation of endothelial cells during angiogenesis. Therefore, the ability of p5RHH to deliver STAT3 siRNA to HUVEC cells for the blockade of angiogenesis was delineated with the use of matrigel tube formation assays and transwell cell migration assays. HUVECs transfected with p5RHH/STAT3 siRNA nanoparticles exhibited a decrease in STAT3 mRNA and protein levels with an $IC_{50}$ of ~50 nM (FIG. 7A, B, FIG. 8) without any accompanying decrease in HUVEC viability (FIG. 7C). As with transfection of B16-F10 cells, Lipofectamine 2000 mediated transfection exhibits an $IC_{50}$ of ~10 nM, but strong cytotoxicity, with a 40% decrease in cell viability at siRNA doses as low as 25 nM (FIG. 9).

Figure 7H:
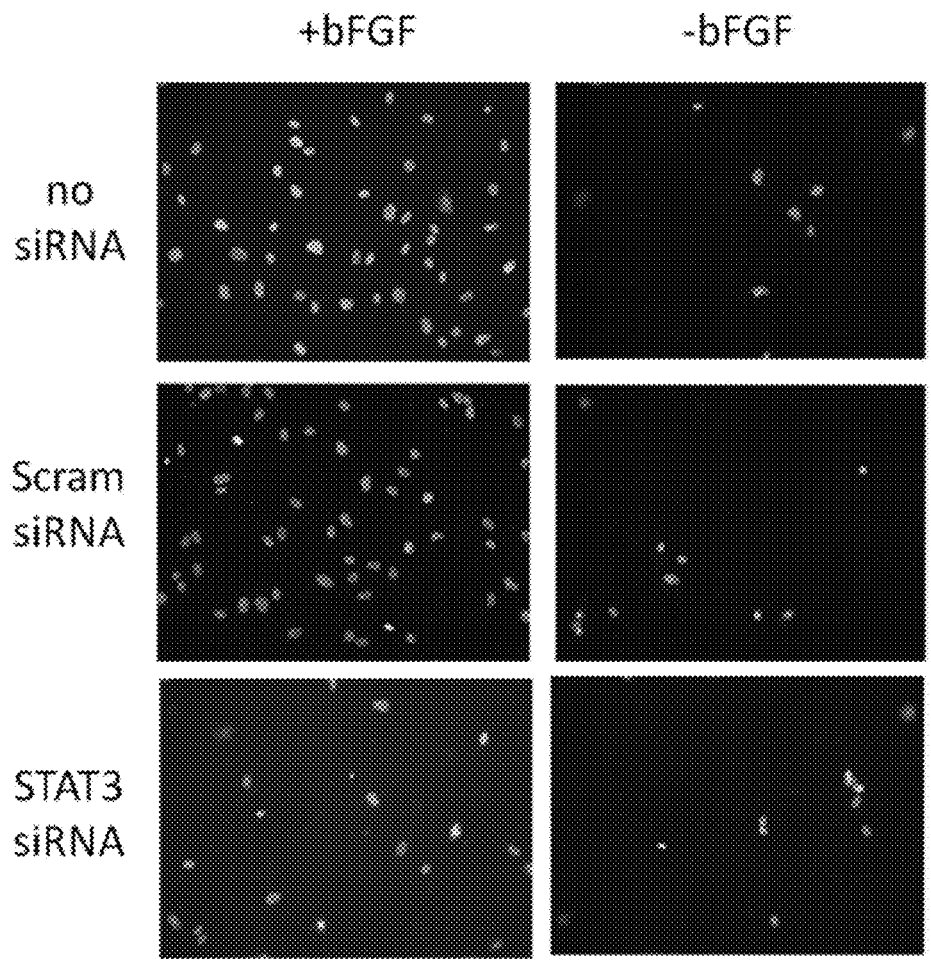
Figure 7I:
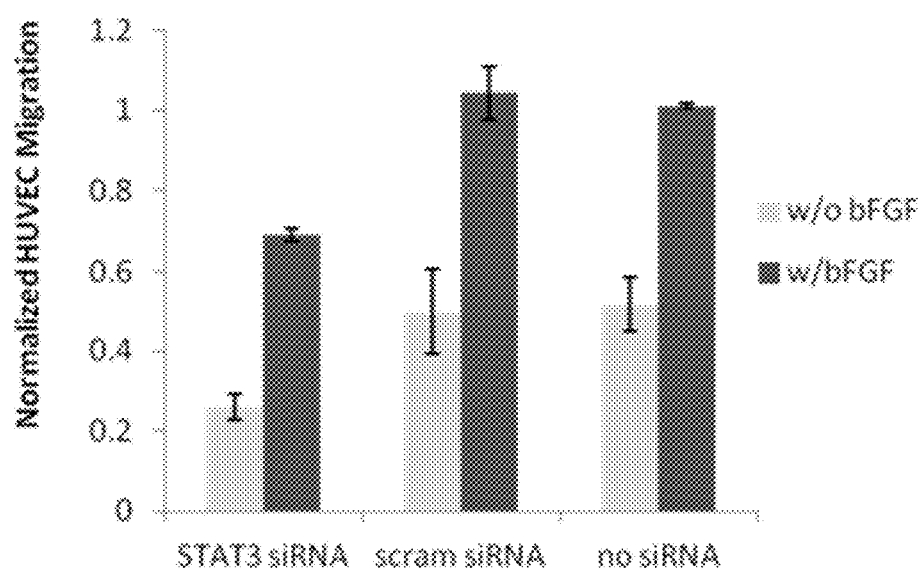
Figure 10:
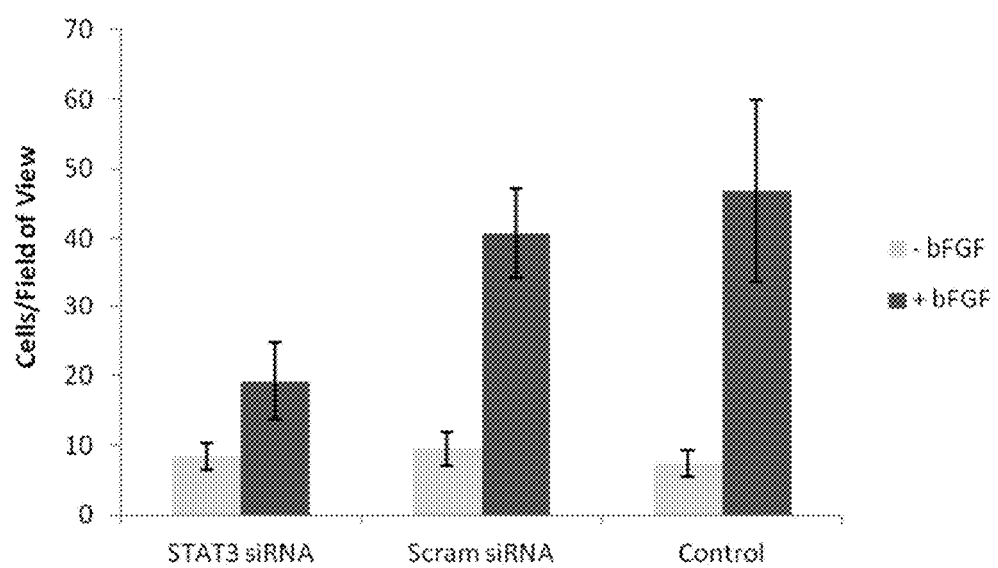
FIG. 10 depicts Quantification of HUVEC transmigration in response to a bFGF gradient by fluorescence microscopy shows that STAT3 siRNA decreases HUVEC transmigration by >50% compared to samples treated with scrambled siRNA.

Although p5RHH mediated STAT3 siRNA transfection did not impact cell viability, p5RHH/STAT3 siRNA nanoparticles used to treat HUVECs manifested a ~60% decrease in tube formation as compared to scrambled siRNA for treatment of HUVECs (FIG. 7D-F). In addition, migration of HUVECs transfected by p5RHH was reduced by 50% as quantified by Alamar Blue (FIG. 7I) and fluorescence microscopy (FIG. 7H, FIG. 10). These data demonstrate the high efficiency with which p5RHH is able to safely transfect primary human endothelial cells for the prevention of pathological angiogenesis.

Example 7 siRNA Delivery to Decrease Foam Cell Formation

Figure 11A:
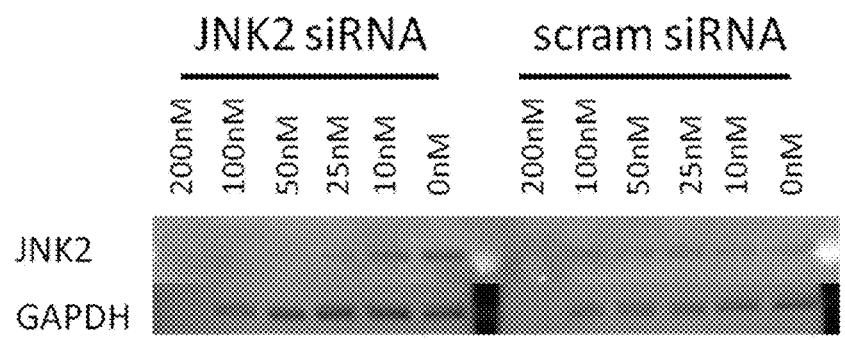
FIG. 11A-E depicts graphs and images of p5RHH mediated transfection. (A) Western blot analysis illustrate knockdown of JNK2 in RAW264.7 cells by p5RHH with IC50<25 nM. (B) Importantly, p5RHH causes only a ~5% decrease in cell viability when transfecting scrambled siRNA at 100 nM. (C-E) Knockdown of JNK2 at 50 nM siRNA shows a strong decrease in lipid droplet accumulation in RAW264.7 cells when incubated with 50 µg/mL Ac-LDL overnight when compared to Cells treated with Scrambled siRNA and untreated controls.
Figure 11B:
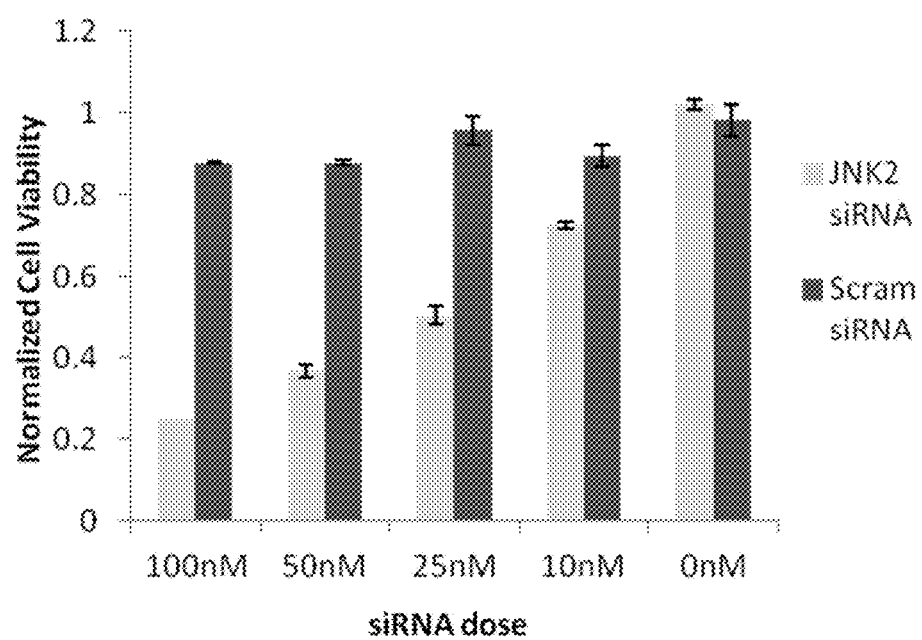
Figures 11C, 11D, 11E:
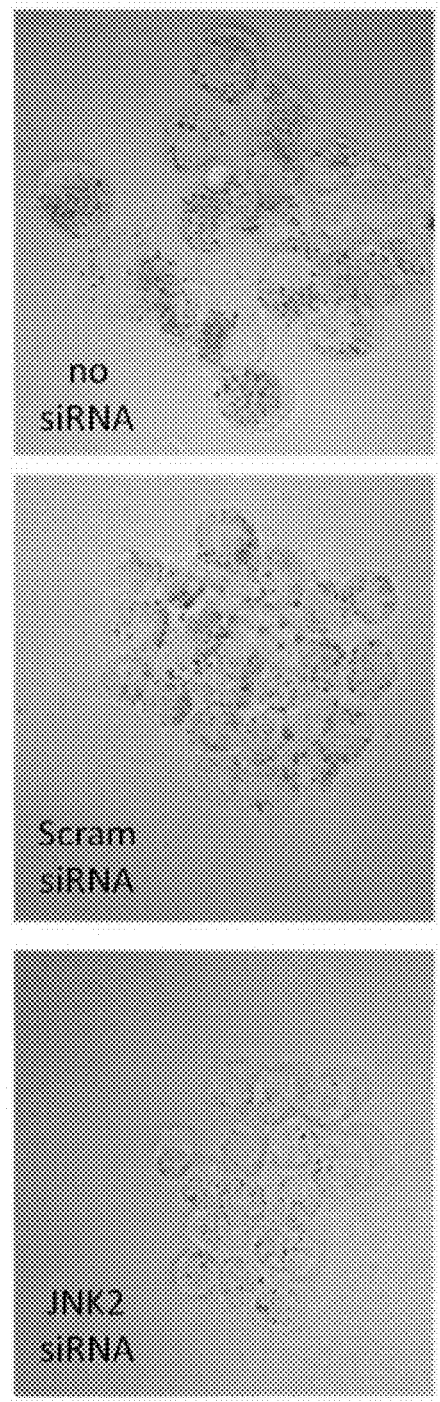
Figure 12A:
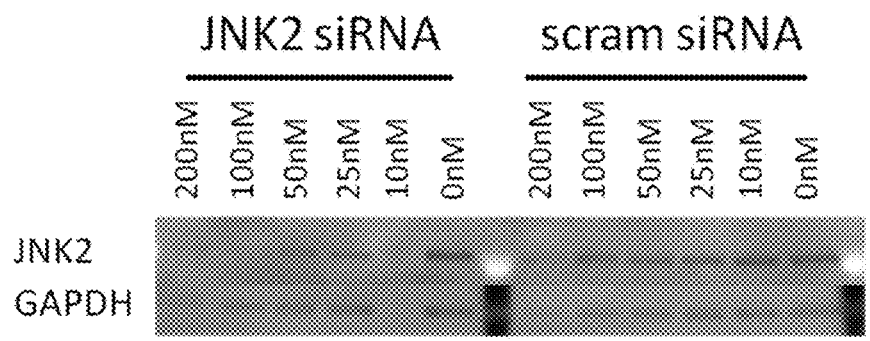
FIG. 12A-B depicts a graph and image of Lipofectamine 2000 transfection. Lipofectamine 2000 knocks down JNK2 in RAW264.7 cells with an IC50<25 nM (A), but induces extensive cytotoxicity at concentrations as low as 10 nM (B).
Figure 12B:
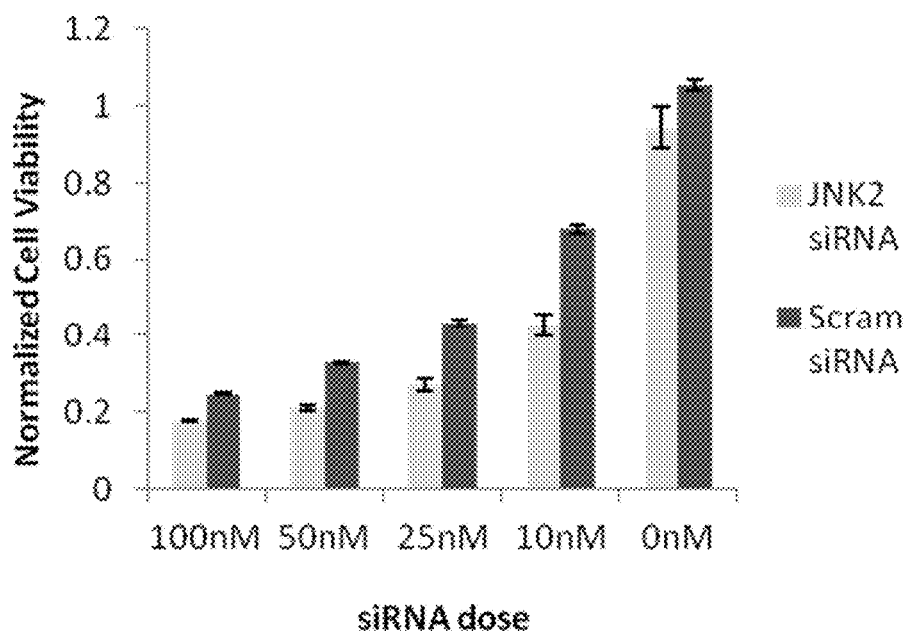

The disrupted endothelial barriers that characterize atherosclerotic plaques make atherosclerosis a prime target for nanoparticle-based therapies. To ensure that foam cell formation, the hallmark of atherosclerotic plaques, could be blocked with p5RHH/siRNA nanoparticles, JNK2 siRNA was delivered to RAW264.7 (mouse monocyte/macrophage cell line). JNK2 is a known mediator of foam cell formation and has been implicated in the uptake of both Ac-LDL by scavenger receptor A as well as oxLDL by CD36. p5RHH was able to deliver JNK2 siRNA to RAW264.6 cells without cytotoxicity (FIG. 11A, B), leading to a strong decrease in JNK2 protein levels at concentrations as low as 25 nM. In comparison, Lipofectamine 2000 has a similar $IC_{50}$ as determined by western blotting, but also exhibits extensive cytotoxicity (FIG. 12). Decreased JNK2 protein levels suppressed foam cell formation in RAW264.7 cells that have been incubated in the presence of 50 µg/ml Ac-LDL for 12 hours as determined by light microscopy following Oil-Red 0 staining (FIG. 11C-E). These images show extensive lipid droplet accumulation in non-treated controls and scrambled siRNA treated cells, but no lipid droplet accumulation in RAW264.7 cells treated with a JNK2 specific siRNA.

Example 8

Performance of p5RHH in the Presence of Serum

Figure 13A:
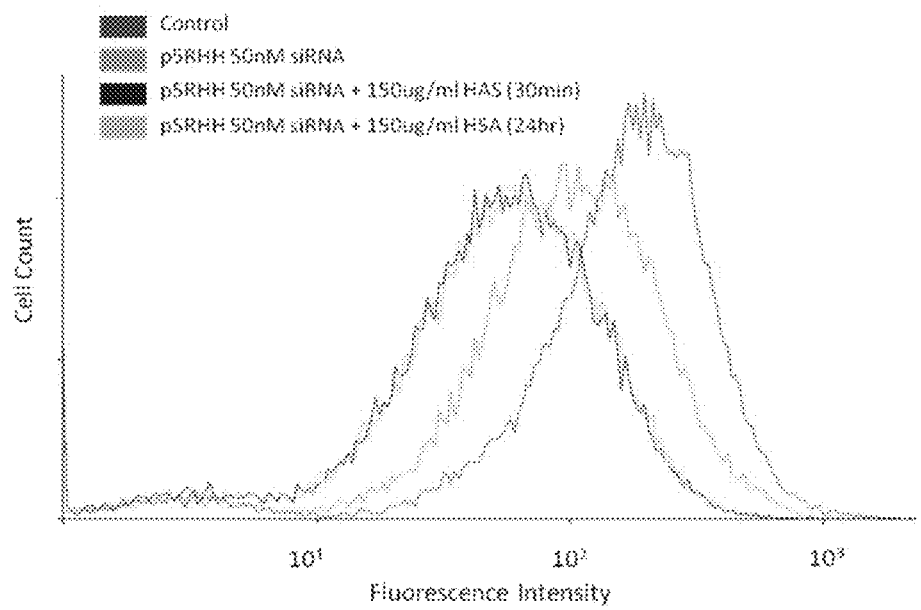
FIG. 13A-B depicts graphs and images of p5RHH mediated transfection. (A) Incubation of p5RHH:siRNA nanoparticles with 50 µg/mL HSA for 30 minutes or overnight are characterized by improved GFP knockdown when compared to freshly prepared p5RHH:siRNA nanoparticles. (B) Confocal microscopy of B16 cells transfected in normal cell culture media supplemented with 10% FBS shows efficient oligonucleotide release into the cytoplasm.
Figure 13B:
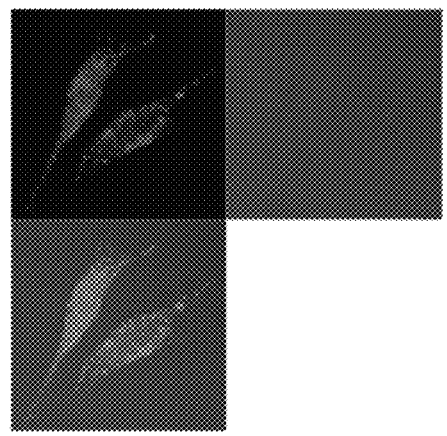

To ensure that particles used in the experiments are stable in the presence of serum, p5RHH/siRNA nanoparticles were incubated in 150 µg/ml human serum albumin (HSA) for 12 hours or overnight. Dynamic light scattering revealed that the size did not change when compared with freshly prepared particles (Table 3). Moreover, the zeta potential of nanoparticles incubated with HSA became less positive, which could be due to coating of the nanoparticles with negatively charged albumin. When the activity of these particles was tested, their ability to knockdown GFP expression was fortuitously enhanced as compared to fresh nanoparticles (FIG. 13A, B). These experiments demonstrate the serum stability of p5RHH/siRNA nanoparticles, their maturation to even more potent transfection agents over time under certain conditions, which suggests potential applicability to in vivo settings.

TABLE 3

Particle size analysis of p5RHH:siRNA incubated in the presence of serum albumin (average population of a formulation).

| | Particle size (nm) | Polydispersity Index | Zeta Potential (mV) |
|---|---|---|---|
| Peptide 5RHH/siRNA − HSA (30 min) | 190 | 0.120 | 12.0 ± 0.7 |
| Peptide 5RHH/siRNA − HSA (12 hours) | >5,000 | — | — |
| Peptide 5RHH/siRNA + HSA (30 min) | 190 | 0.194 | −7.0 ± 1.0 |
| Peptide 5RHH/siRNA + HSA (12 hours) | 220 | 0.191 | −5.5 ± 1.5 |

Discussion for Examples 1-8

The applicants have previously explored highly efficient siRNA delivery methods based on cationic lipids in a novel perfluorocarbon nanoemulsion formulation. Despite the high efficiency of transfection achieved in vitro, difficulties with transfection at high nanoparticle concentrations reflected the challenges that accompany traditional cationic lipid transfection agents. In the present examples, melittin peptides were modified to realize a high efficiency siRNA transfection agent based on the hypothesis that melittin's membrane inserting and pore forming capacity would provide a novel means of endosomal escape, which is a key drawback to previously reported CPP based siRNA transfection agents.

Indeed the experiments presented herein demonstrate that p5RHH is able to facilitate release of siRNA into the cytoplasm. Analysis of an inactive melittin derivative (p5RWR) suggests that, as with traditional CPP based siRNA delivery, p5RWR/siRNA particles are also taken up into endosomes and require endosomolytic agents to gain access to the cytoplasm. P5RHH/siRNA nanoparticles have a positive surface charge as determined by zeta potential measurements, which is a characteristic that has been shown to play an important role in nanoparticle association with the cell membranes, and subsequent endocytosis. Based on similarity of surface charge, it is likely that p5RHH/siRNA nanoparticles are handled via the same endocytotic machinery as are inactive p5RWR/siRNA complexes, which suggests that p5RHH can promote the release of siRNA from the endosomal/lysosomal pathway in an efficient manner. Although the exact uptake pathway responsible for p5RHH/siRNA nanoparticle internalization remains to be determined, the analysis of the inactive p5RWR complexes provides insight into the potential mechanisms of p5RHH/siRNA nanoparticle processing by the cell.

While the exact properties responsible for efficient endosomal escape are not yet clarified, work on histidylated peptides used for oligonucleotide transfection provides some intuition regarding the function of p5RHH. Histidylated peptides and polymers were designed originally to aid plasmid release based on protonation of histidine's imidazole group (pKa~6.0) during lysosomal acidification (pH ~4.5). These polymers incorporate high histidine content (80-90% histidine) to drive endosomal lysis via the proton sponge effect. p5RHH possesses only two histidine residues and thus is unlikely able to buffer enough protons to lyse endosomes. However, protonation of histidine residues likely promotes p5RHH/siRNA nanoparticle disassembly and release of p5RHH to permeabilize the endosomal membrane for siRNA release. Detailed studies of p5RHH/siRNA disassembly and lytic capacity at low pH are currently underway.

The ability of p5RHH to deliver siRNA to the cytoplasm yields a quantifiable decrease in GFP expression at concentrations as low as 5 nM. However, p5RHH is still unable to attain the level of transfection efficiency provided by Lipofectamine 2000 in B16-F10 cells or HUVECs. p5RHH seems to exhibit improved efficiency when transfecting RAW264.7 cells, with an $IC_{50}$ that is approximately equal to that of Lipofectamine 2000. Not surprisingly, different cell types favor different endocytic mechanisms which could explain the differences between transfection efficiencies in different cell types. Nevertheless, p5RHH exhibits a substantial improvement over traditional cationic lipid based transfection in regards to cytotoxicity, exhibiting minimal decrease in cell viability against a variety of mouse and human cell lines at all tested concentrations. Moreover, it appears that the efficiency of p5RHH-mediated transfection can be further optimized as suggested by the observation of an increased transfection efficiency when particles are first incubated with serum albumin that is used to test for serum stability. Zeta potential measurements suggest that albumin coats the p5RHH/siRNA nanoparticles, but it is unclear how this enhances transfection. Existing studies have shown that albumin can aid fusion of lipid bilayers at low pH and this activity may play a role in endosomal escape. The observed improvement in siRNA transfection efficiency should establish an interesting avenue for improved formulation methods to maximize the efficiency of p5RHH-mediated transfection.

The ability of p5RHH to transfect siRNA into cancer cells, endothelial cells, and even macrophages points to a broad spectrum of transfection activity while maintaining favorable cytotoxicity characteristics. Given the size of the nanoparticles (~190 nm), disease processes that do not require vascular extravasation through intact endothelial barriers were targeted. Cancer, angiogenesis, and atherosclerosis are all characterized by a discontinuous endothelial barrier with enhanced leakage of nanoparticles into the surrounding tissues. In cancer, this effect is widely known as "enhanced permeability and retention", and similar effects have been previously reported for states of severe atherosclerosis. Moreover, the size of the nanoparticles in the instant examples should provide favorable pharmacokinetics and serum half-life by avoiding both kidney filtration as well as uptake by the reticulendothelial system. p5RHH/siRNA nanoparticles also exhibit size stability and retain siRNA transfection capacity when incubated in the presence of human serum albumin for 24 hours before transfection, an issue which has been acknowledged to diminish the activity of some CPP transfection agents. Although detailed siRNA protection and long-term stability analysis remains to be performed, these data suggest that p5RHH/siRNA nanoparticles might provide therapeutic benefits when utilized for transfection in in vivo settings.

As such, the novel melittin derivative p5RHH exhibits the ability to interact with siRNA electrostatically and form stable nanoparticles which show efficient delivery into the cytoplasm with subsequent sequence specific degradation of mRNA and decreased protein expression in a variety of cell types. Our studies did not reveal any signs of cytotoxicity, suggesting the potential utility of p5RHH/siRNA nanoparticles in clinical settings. The stability of these particles in the presence of serum proteins suggests that p5RHH/siRNA nanoparticles would be good test candidates for delivering siRNA in vivo to intravascular targets or to diseased tissue characterized by endothelial barrier dysfunction.

Methods for Examples 1-8

Preparation of Peptide/siRNA Nanoassemblies and Analysis

The melittin derivatives were formulated by Genscript (Piscataway, N.J.), dissolved at 10 mM in RNAse/DNAse free water (Sigma, St. Louis, Mo.) and stored in 4 µl aliquots at −80° C. before use. P5RHH/siRNA transfection complexes were prepared by diluting p5RHH 1:200 in phosphate buffered saline (PBS, Sigma), vortexed for 30 seconds, followed by addition of the appropriate amount of siRNA (stock concentration of 10 µM in 1×siRNA buffer (Thermo)) and incubated for 40 minutes at 37° C. with shaking in an Eppendorf Thermomixer R. Resulting nanoparticles were analyzed for siRNA incorporation by resolution on a 12% polyacrylamide gel followed by ethidium bromide staining. Dynamic light scattering (DLS) and zeta potential measurements were performed on a Zeta Plus particle sizer (Brookhaven Instruments, Newton, Mass.). Serum stability analysis was performed by incubating freshly formed peptide/siRNA nanoparticles in 10 mg/ml Human Serum Albumin (HSA, Sigma) overnight followed by DLS and zeta potential measurements.

Cell Culture

B16F10 and RAW264.7 (ATCC, Manassas, Va.) cell lines were maintained under standard cell culture conditions (37° C. and 5% $CO_2$ in a humidified incubator) in DMEM (Gibco, Carlsbad, Calif.) supplemented with 10% fetal bovine serum (Gibco). B16F10 cells stably expressing GFP were produced as follows. B16F10 were transfected (Lipofectamine 2000, Invitrogen) with a fusion of EGFP (pEGFP-N1, Clontech) and the PEST sequence from mouse ornithine decarboxylase (S421-V461) in pEF6V5HisTOPO (Invitrogen). Cells were selected for four rounds with cell sorting by flow cytometry without antibiotic selection. An aliquot of cells was maintained in continuous culture for a month without a noticeable change in EGFP expression level. Human umbilical vein endothelial cells (HUVECs) were purchased from Lifeline Technologies (Frederick, Md.) and cultured in VascuLife Basal Medium (Lifeline Technologies) supplemented with 5 ng/mL EGF, 5 ng/ml bFGF, 15 ng/mL IGF-1, 50 µg/mL ascorbic acid, 1 µg/mL hydrocortisone hemisuccinate, 0.75 U/mL Heparin Sulfate, 10 mM L-glutamine, 2% fetal bovine serum in accordance with manufacturer instructions. For all experiments, HUVECs were used at passage 3.

siRNA Transfection

Cells were plated in 6 well plates 12 hours before transfection and cultured under standard cell culture conditions. P5RHH/siRNA nanoparticles were prepared and incubated with cells for 4 hours in a final volume of 1 mL OptimemI (Gibco) or appropriate media supplemented with 10% FBS. Transfections were scaled accordingly for cells plated in 12 well plates based on cell culture surface area. After transfection, cells were washed twice with PBS and incubated with standard cell culture medium for another 24-72 hours before analysis. Lipofectamine 2000 was used in accordance with the manufacturer's protocol. Briefly, Lipofectamine 2000 was diluted in OptimemI to a final concentration of 8.4 µg/ml and incubated at room temperature for 15 minutes. siRNA was then added to the diluted lipid and incubated for another 40 minutes before dilution to 1 mL total volume with OptimemI for transfection. eGFP siRNA (Sense: 5'-GACGUAAACGGCCACAAGUUC-3'; SEQ ID NO: 56) was purchased from Sigma. siGENOME mouse MAPK9 siRNA1, siGENOME mouse STAT3 siRNA2, and siGENOME human STAT3 siRNA2 gene specific siRNAs were purchased from Dharmacon (Lafayette, Colo.). Scrambled siRNA was purchased from Qiagen (Valencia, Calif.).

Western Blotting 24 or 48 hours after transfection, 100-200 µl RIPA buffer (10 mM Tris-HCl (pH 7.5), 150 mM NaCl, 1.0% IgepalCA-630, 0.5% sodium deoxycholate, 0.1% sodium dodecyl sulfate, 1 mM EDTA, 5% glycerol) with 1 mM PMSF and Complete Protease Inhibitor Cocktail (Roche) was added to each well of a 6 well plate and incubated on ice for 1 hour. Cell lysates were then centrifuged at 4° C. for 5 minutes and supernatants stored at −20° C. Lysates were resolved on Nupage Bis-Tris gels (Life Technologies) and transferred to 0.22 µm nitrocellulose before blocking in 5% bovine serum albumin (Sigma) in TBS-T. Primary antibodies used were: rabbit anti-GAPDH (1:1500, Santa Cruz Biotechnology, Santa Cruz, Calif.), mouse anti-β-actin (1:1000, Sigma), mouse anti-STAT3 (1:1000, Cell Signaling, Danvers, Mass.), rabbit anti-JNK2 (1:1000, Cell Signaling). Secondary antibodies used were: anti-Rabbit HRP (1:5000, Santa Cruz Biotechnology) and anti-mouse HRP (1:5000, Santa Cruz Biotechnology). Blots were developed using ECL Western Blotting Substrate (Pierce, Rockford, Ill.). Knockdown was quantified using densitometry in ImageJ (NIH, Bethesda, Md.) and normalized to an untreated control. All data are presented as average of 3 separate experiments.

Real time PCR 24 hours post transfection, cDNA was produced using the FastLane Cell cDNA kit (Qiagen). cDNA was stored at −20° C. until use. mRNA levels were quantified using SYBR green detection on a Applied Biosystems 7300 System (Applied Biosystems, Carlsbad, Calif.) using iTaq SYBR green with ROX (Bio-Rad, Hercules, Calif.). Quantitect Primer Assay (Qiagen) provided gene specific primers for each gene. Genes of interest were normalized to species-appropriate B-actin. Results are reported as the average "fold change" relative to untreated controls for 3 separate experiments.

Confocal Microscopy

B16F10 cells were cultured on glass coverslips and transfected with Cy5.5 labeled anti-GFP siRNA (Sigma) according to standard transfection procedure. 12 hours post transfection, cells were washed 3× in PBS and fixed in 4% PFA before mounting on glass slides (Vectashield Mounting Medium with DAPI, Vector Labs, Burlingame, Calif.). Cells were imaged by confocal microscopy on a Zeiss Meta 510 (Thornwood, N.Y.).

Flow Cytometry 24 hours after B16-GFP cells were transfected with p5RHH/siRNA nanoparticles containing GFP specific or scrambled siRNA, cells were trypsinized and resuspended in FACS buffer (0.2% FBS and 0.5 mM EDTA) for analysis of GFP fluorescence.

Cell Viability Assays

Cell viability was determined 72 hours post transfection using Alamar Blue (Life technologies). Briefly, Alamar Blue was diluted 1:10 into phenol red free medium and incubated with cells for 2-4 hours. Fluorescence was measured on a fluorescent plate reader with excitation at 570 nm and emission at 585 nm (Varian Cary Eclipse, Agilent Technologies, Santa Clara, Calif.).

Tube Formation Assays

Matrigel (BD Biosciences, San Jose, Calif.) was thawed overnight at 4° C. in an ice bath and subsequently allowed to gel in 24 well plates for 1 hour at 37° C. 24 hours after transfection with STAT3 specific or control siRNA, HUVECs were trypsinized and plated on matrigel at a cell density of 30,000 cells/well. Tube formation was allowed to proceed for 24 hours before visualization on an inverted microscope. A tube formation score was determined based on total tube length per field of view normalized to untreated controls as measured in ImageJ (NIH).

HUVEC Migration Assays

The bottoms of 12 well transwell inserts with 1.0 µm pore size (Corning, Tewksbury, Mass.) were coated with 0.1% porcine gelatin (Sigma) at room temperature for 1 hour. HUVECs transfected with STAT3 specific or control siRNA 24 hours in advance were then trypsinized and resuspended in growth factor free media and added to the apical transwell chamber at a density of 30,000-50,000 cells/well. The bottom chamber contained growth factor free VascuLife basal media ±5 ng/ml bFGF. Cells were allowed to migrate through the polymer insert for 12 hours. Unmigrated cells were removed from the apical chamber with a sterile cotton swab, and migrated cell numbers were determined via Alamar Blue. Data are presented as the average normalized migration from 3 separate experiments. For visualization, inserts were cut out and mounted on glass slides. Cell nuclei were visualized with DAPI staining on an Olympus BX610 (Tokyo, Japan) and reported as average cell number per field of view.

Foam Cell Formation Assay/Oil Red 0 Staining 48 hours after transfection with JNK2-specific or control siRNA, RAW264.7 cells were incubated ±50 ug/ml Ac-LDL (Intracel, Frederick, Md.) for an additional 24 hours. Cells were then stained with Oil-Red O to visualize foam cell formation. Briefly, Oil-Red O was dissolved in neat methanol at (0.5 g/100 mL) overnight before filtration through a 0.22 µm filter. The Oil-Red O stock was then diluted 3:5 in distilled water to make-up Oil-Red O working solution and filtered a second time through a 0.22 µm filter. Cells were fixed in 4% PFA for 10 minutes at room temperature and washed with 60% methanol before staining in the Oil-Red O working solution for 15 minutes. After staining, cells were washed once with 60% methanol and once with distilled water before mounting on glass slides.

Introduction for Examples 9-14

Post-transcriptional degradation of mRNA via RNA interference (RNAi) provides a targeted approach for silencing gene expression that may prove beneficial in the treatment of many clinically relevant diseases. RNAi can be induced by delivery of small-interfering RNA (siRNA) into the cytoplasm of a mammalian cell, after which incorporation of the siRNA into RNA-induced silencing complexes (RISC) leads to sequence-specific cleavage of complementary mRNA. Given siRNA's activity in the cytoplasm, siRNA must bypass impermeable cellular membranes to reach the cytoplasmic compartment. Unfortunately, due to siRNA's large molecular weight (~21 kDa) and negative charge, naked siRNA cannot diffuse freely through cell membranes, necessitating an effective delivery system to aid cellular uptake and subsequent endosomal escape.

Common siRNA delivery systems include cationic lipids and polymers, which are efficient, yet hampered by potential toxicity. Recent work has focused on poly-basic peptides or peptide transduction domains (PTD) for siRNA transfection owing to their lack of toxic side effects. Unfortunately, many studies have reported only modest success at achieving highly efficient siRNA delivery when complexed with peptides as a consequence of excessive endosomal entrapment. Acknowledging endosomal entrapment as the primary barrier hindering the progress of peptide-based siRNA vectors emphasizes that new strategies must be developed to improve peptide-mediated transfection. Accordingly, it is proposed by the inventors that membrane-disrupting peptides carrying a net positive charge may provide an unexplored alternative for efficient siRNA transfection due to their dual functionality to both complex siRNA and disrupt endosomal compartments.

Unfortunately, it is difficult to predict the utility of melittin derivatives in siRNA transfection because the mechanisms that allow successful peptide-mediated transfection have not yet been fully clarified. For example, recent work by van Asbeck et al. (2013; ACS Nano 7:3797-3807) concludes that sensitivity to decomplexation by polyanionic macromolecules contributes to improved transfection, but the role decomplexation plays in siRNA delivery to the cytoplasm was not established. Furthermore, pH-responsive fusogenic peptides from the influenza virus have previously been leveraged to augment peptide-mediated transfection, but their ability to improve siRNA transfection may be attributable to increased siRNA packaging or uptake, and not endosomal escape. While CPP/siRNA nanoparticles have been well characterized from a physico-chemical perspective, the mechanisms involved in peptide/siRNA nanocomplex transfection that contribute to successful bypass of endosomal entrapment and subsequent induction of RNAi have yet to be elucidated. Additional studies regarding the intracellular processing of peptide/siRNA nanocomplexes and the mechanism of siRNA release to the cytoplasm are required to further develop peptides for siRNA transfection.

The inventors have previously reported that melittin derivative, p5RHH, is capable of siRNA transfection with an $IC_{50}$ as low as 25 nM without significant cytotoxicity at all tested doses (Hou et al., 2013; 34:3110-3119). In the examples herein, this peptide is employed for the delivery of p65 and p100/52 siRNA for simultaneous knockdown of both canonical and non-canonical NFκB signaling pathways in a murine model of Human T-Lymphotropic Virus-1 (HTLV-1) induced adult T-cell leukemia/lymphoma (ATLL). For enhanced stability, it is shown herein that an albumin-coated formulation of p5RHH exhibits remarkable transfection efficiency attributable to pH triggered nanoparticle disassembly. Detailed studies regarding the mechanism of action reveal that exposure to endosomal pH triggers both nanoparticle disassembly and endosomal escape. Moreover, it is clear from comparisons with nonfunctioning melittin derivatives that endosomal disruption alone does not result in successful induction of RNAi, but requires concurrent siRNA release from the vector.

Results presented herein offer general parameters that yield efficient siRNA delivery into the cytoplasm by peptide vectors, which may aid in the development of noncovalent peptide/siRNA nanocomplexes for siRNA therapeutics.

Example 9

Formulation of Albumin-Stabilized p5RHH/siRNA Nanoparticles

Figure 14A:
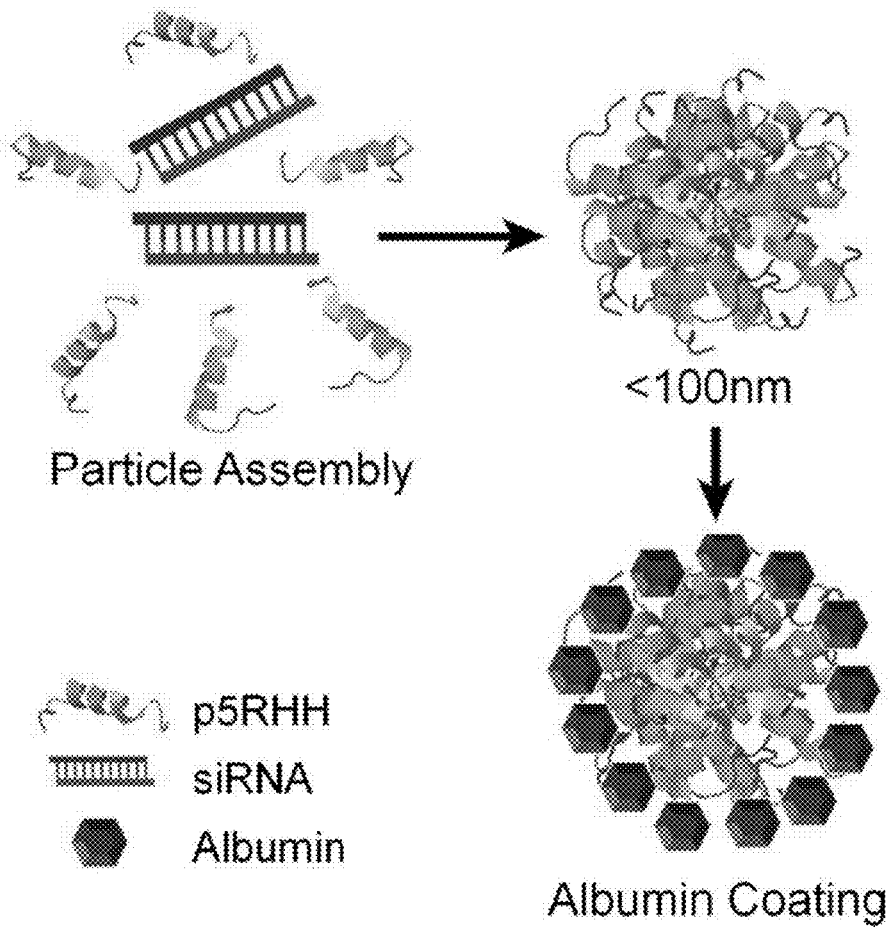
FIG. 14A-B depicts a schematic and an atomic force microscopy image showing assembly of p5RHH/siRNA nanoparticles. (A) Scheme for formulation of albumin-stabilized p5RHH/siRNA nanoparticles. (B) Wet-mode AFM imaging of p5RHH/siRNA nanoparticles reveals an average particle size of ~55 nM±18.
Figure 15A:
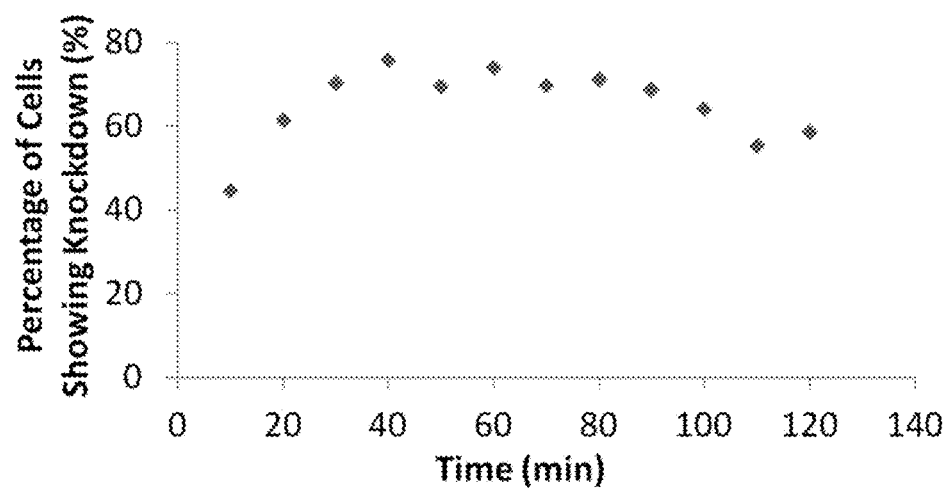
FIG. 15A-B depicts a graph and an electron micrograph showing siRNA particles and transfection efficiency of particles. (A) Transfection efficiency of complexes incubated for the indicated duration as measured by percentage of cells exhibiting GFP knockdown at 50 nM final GFP siRNA concentration when packaged with p5RHH. This data indicates that p5RHH/siRNA incubation of 40 minutes provides the optimal incubation duration for maximal transfection. (B) Particles incubated for the indicated duration shows that p5RHH/siRNA particles have a size of <100 nm.
Figure 15B:
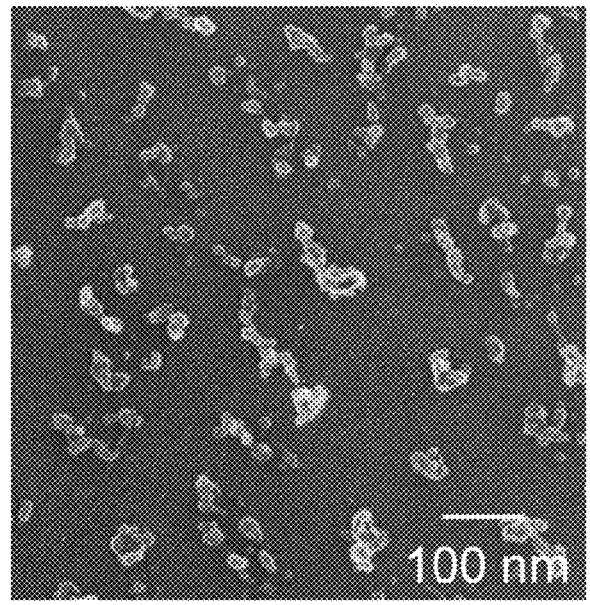

To formulate p5RHH/siRNA nanoparticles, p5RHH (10 mM stock in DI H$_2$O) is dissolved 1:200 in Dulbecco's Phosphate Buffered Saline, vortexed for 30 seconds followed by addition of the appropriate amount of siRNA (100 µM stock in 1×siRNA) and incubated at 37° C. for 40 minutes (FIG. 14A). 40 minute incubations were chosen based on the particle size as tracked by Deep-Etch Electron Microscopy. Electron micrographs (FIG. 15A) indicate that particles formed at this time-point have not begun to exhibit further aggregation, allowing a platform for kinetic stabilization via albumin surface coating. Notably, 40 minute incubations also exhibit maximal transfection efficiency based on knockdown of green fluorescent protein (GFP) expression in B16-F10 melanoma cells (ATCC, Manassas, Va.)(FIG. 15B).

Figure 14B:
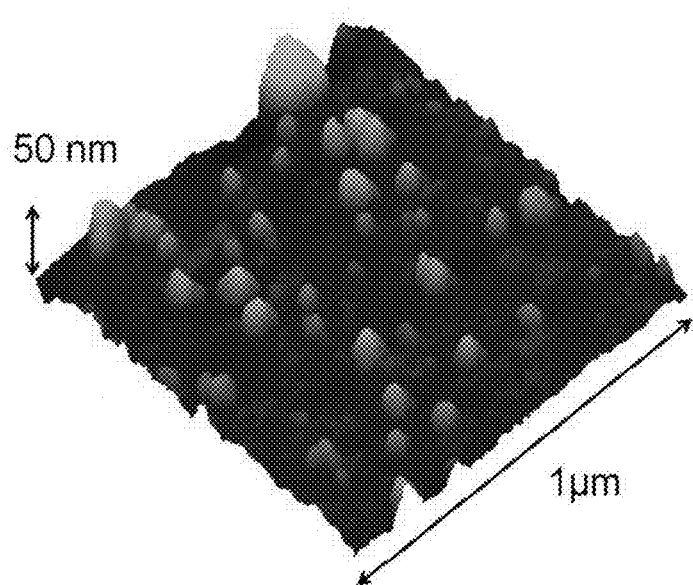

Albumin is known to provide enhanced nanoparticle stability by coating nanoparticles to prevent flocculation. Albumin-stabilized formulations include a subsequent 30 minute incubation in the presence of 0.5 mg/ml human serum albumin (50 mg/ml stock in DI H$_2$O) prior to use. The size of albumin stabilized p5RHH/siRNA nanoparticles 72 hours post formulation was measured to be ~55 nm±18 by wet mode atomic force microscopy (FIG. 14B), indicating that albumin prevents flocculation of p5RHH/siRNA nanoparticles.

Example 10

Mechanism of Cellular Entry of Peptide/siRNA Nanoparticles

Figure 16A:
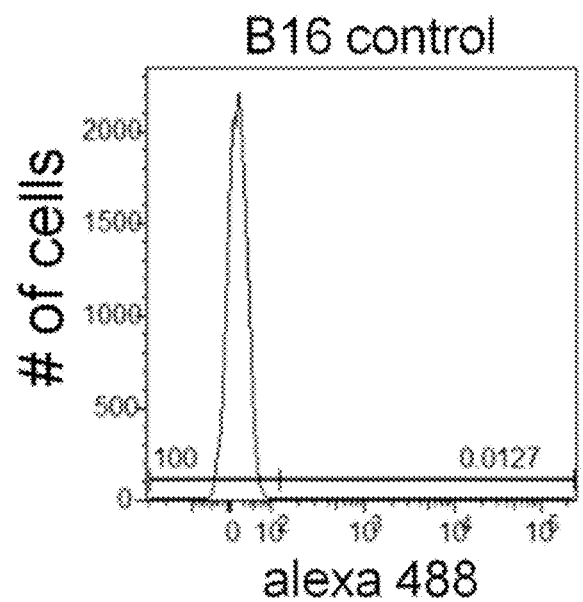
FIG. 16A-C depicts graphs showing p5RHH mediated transfection at two different temperatures. Uptake of p5RHH/Alexa488-siRNA nanoparticles at 4° C. (C) is dramatically reduced compared to uptake at 37° C. (B). Untreated cells are shown for comparison (A).
Figure 16B:
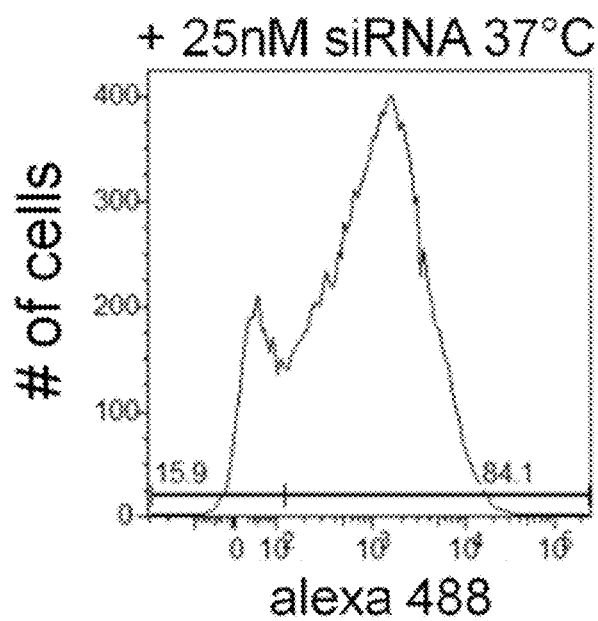
Figure 16C:
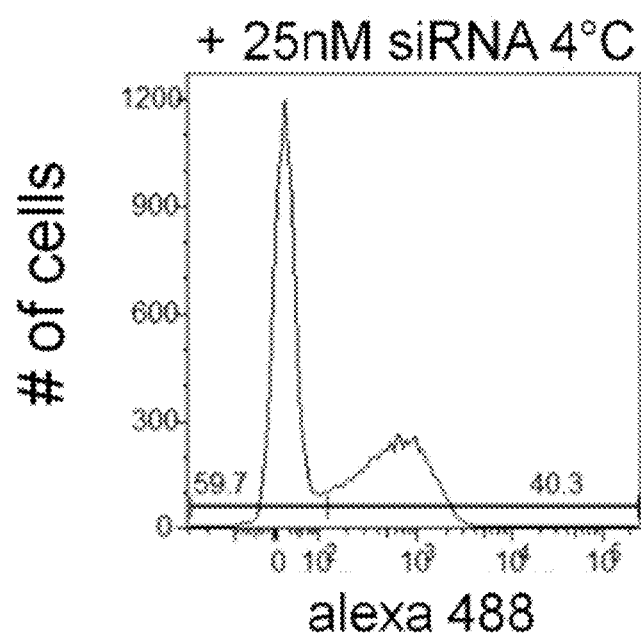

Considering the uncertainty surrounding the cellular entry of peptide/siRNA nanoparticles, uptake assays were performed to provide insight into the mechanism by which p5RHH achieves cytoplasmic delivery of siRNA. Flow cytometry assays depicting the uptake of Alexa488-labeled scrambled siRNA packaged with p5RHH provide a convenient experimental tool to determine the role of select endocytotic pathways in p5RHH/siRNA nanoparticle uptake. Incubation of cells at 4° C. causes near complete inhibition of p5RHH/siRNA uptake, thus rejecting the hypothesis that p5RHH mediates direct membrane translocation for cytoplasmic release of siRNA (FIG. 16). Instead, studies of p5RHH/siRNA uptake in the presence of endocytosis inhibitors indicate that macropinocytosis is the major pathway responsible for p5RHH/siRNA uptake (FIG. 17A-D). The macropinocytosis inhibitor EIPA dramatically reduces p5RHH/siRNA uptake, whereas caveolae inhibitor, filipin, and clathrin mediated endocytosis (CME) inhibitor, PAO, have no effect on p5RHH/siRNA uptake.

The use of endosomal inhibitors for evaluating uptake mechanisms has been shown to be nonspecific and also cell-type dependent. Consequently, uptake inhibition assays were performed for only 40 minutes at inhibitor concentrations that were determined to be specific to the expected pathway (FIG. 18), as demonstrated by inhibition of standard endosomal markers transferrin (CME) and 70 kDa Dextran (macropinocytosis). B16 cells are known not to express caveolin-1, and not surprisingly, uptake of caveolae marker Cholera Toxin B is not measurable in this cell type (unpublished observation).

Figure 17A:
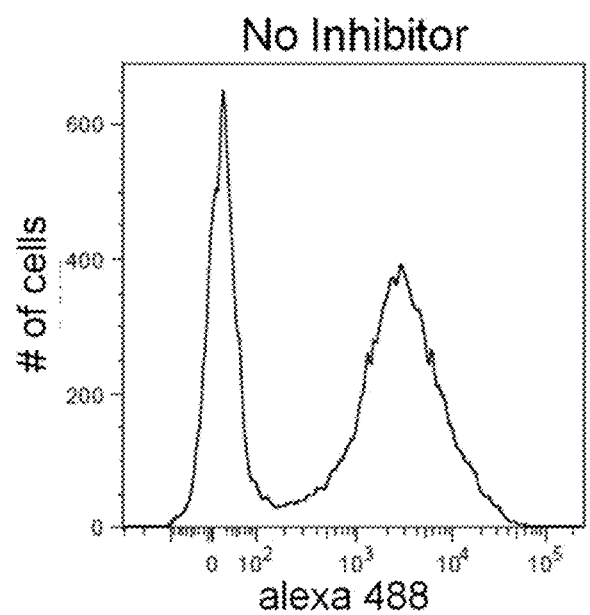
Figure 17B:
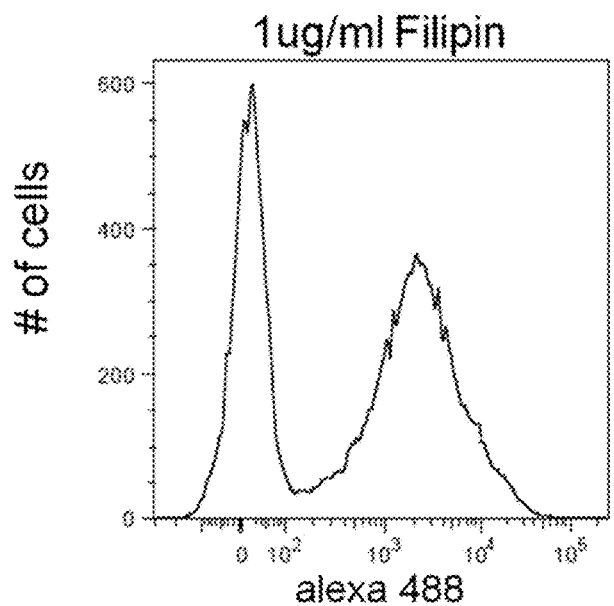
Figure 17C:
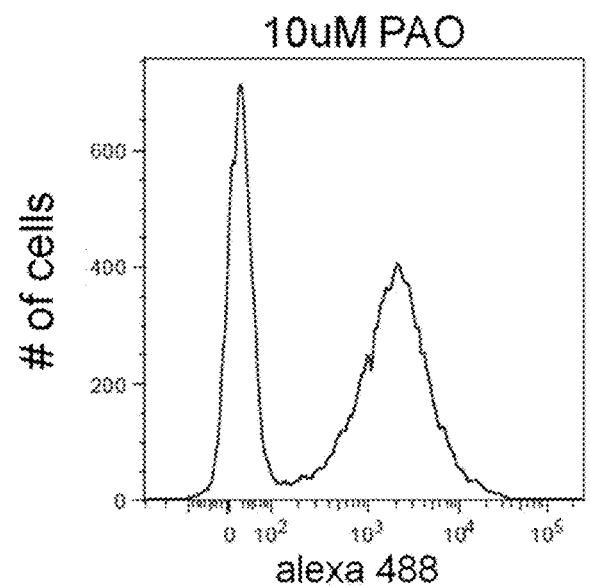
Figure 17D:
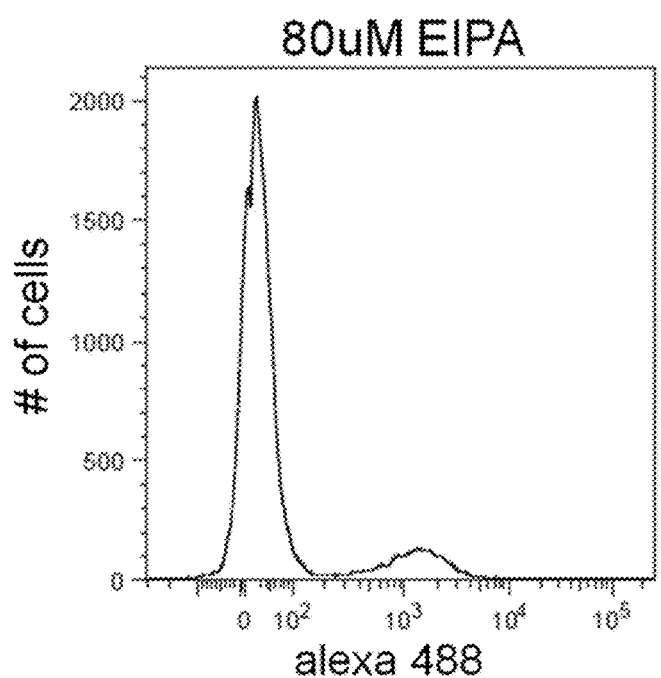
Figures 17E, 17F:
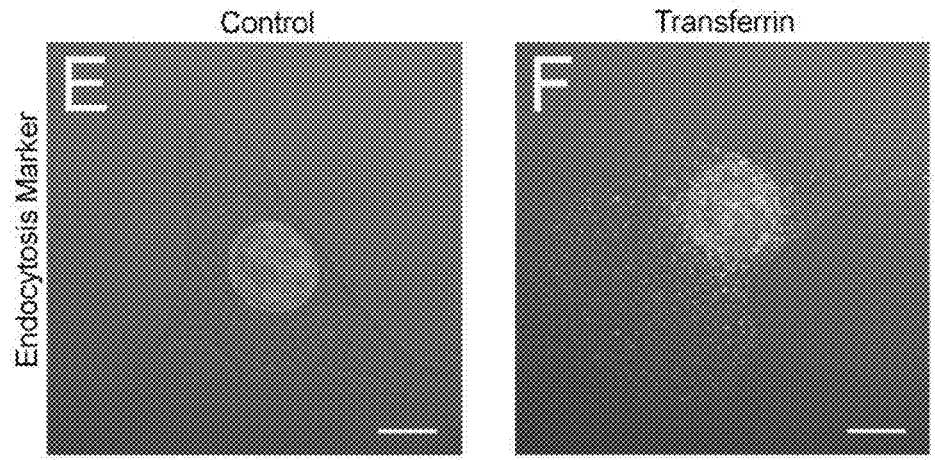
Figure 17G:
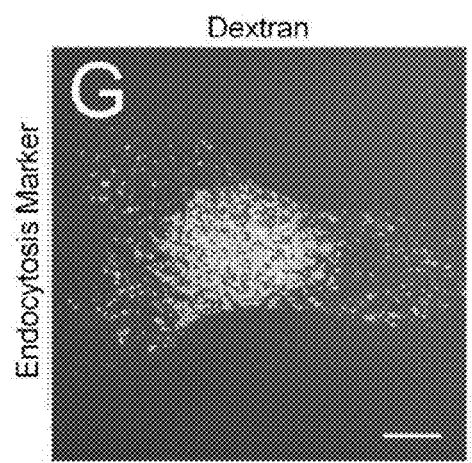
Figure 17J:
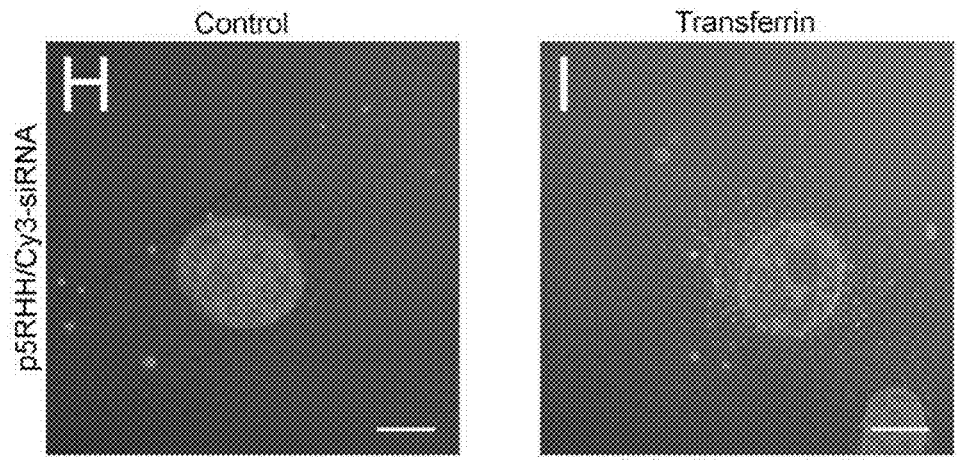
Figure 17J:
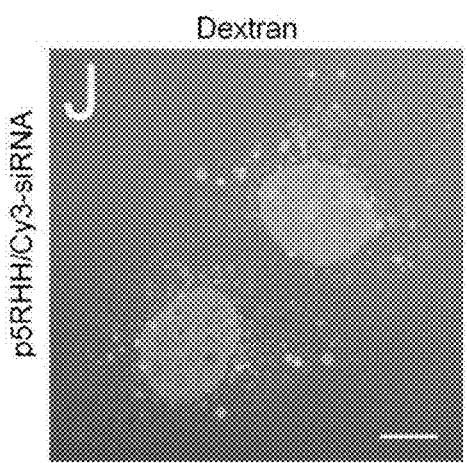
Figure 18A:
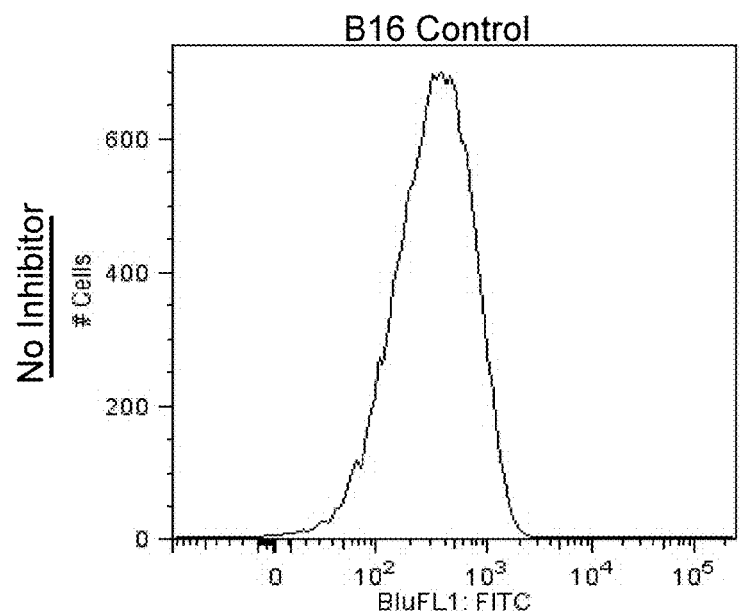
FIG. 18A-I depicts graphs showing that endocytosis inhibitors only inhibit uptake of markers specific for the indicated pathway. Uptake inhibition assays were performed for only 40 minutes at inhibitor concentrations that were determined to be specific to the expected pathway, as demonstrated by inhibition of standard endosomal markers transferrin (B, D, F, H) and 70 kDa Dextran (C, E, G, I). In (B and C), no inhibitor was used. In (D and E), 1 µg/ml filipin was used. In (F and G), 10 µg/ml PAO was used. In (H and I), 80 µg/ml EIPA was used. B12, a control, is shown in (A).
Figure 18B:
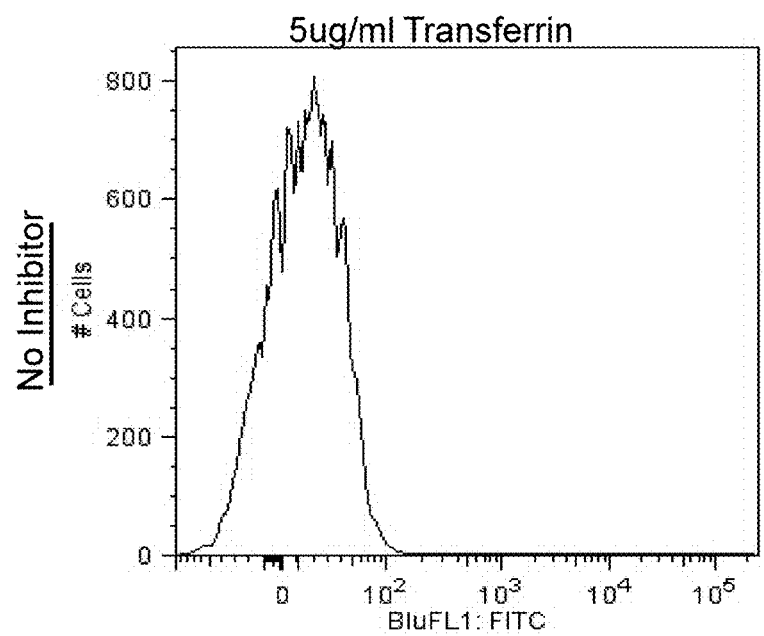
Figure 18C:
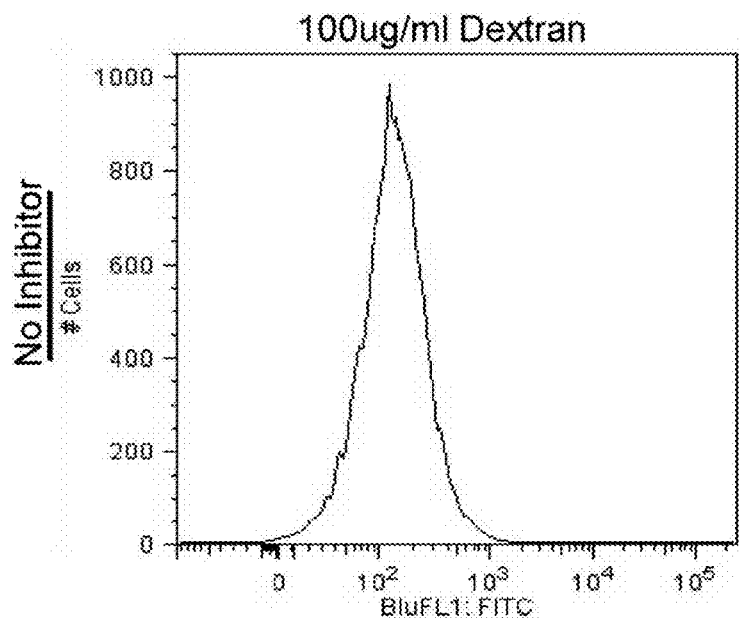
Figure 18D:
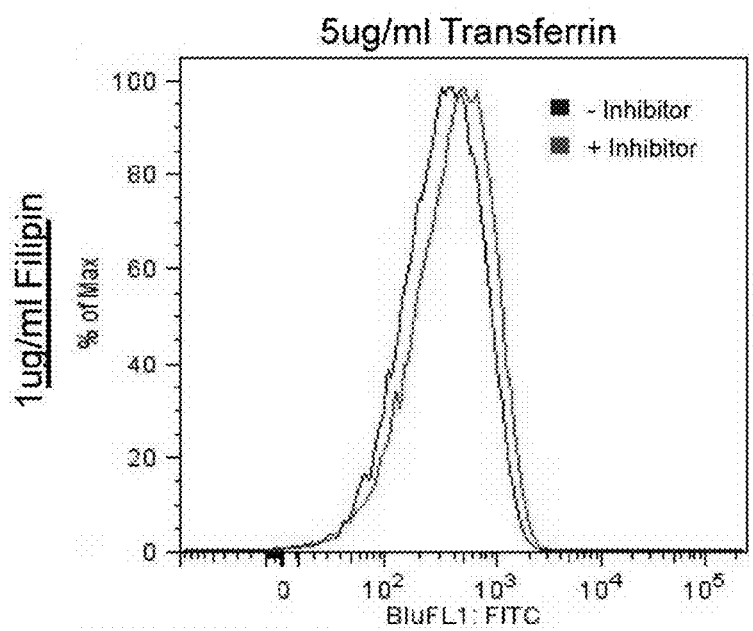
Figure 18E:
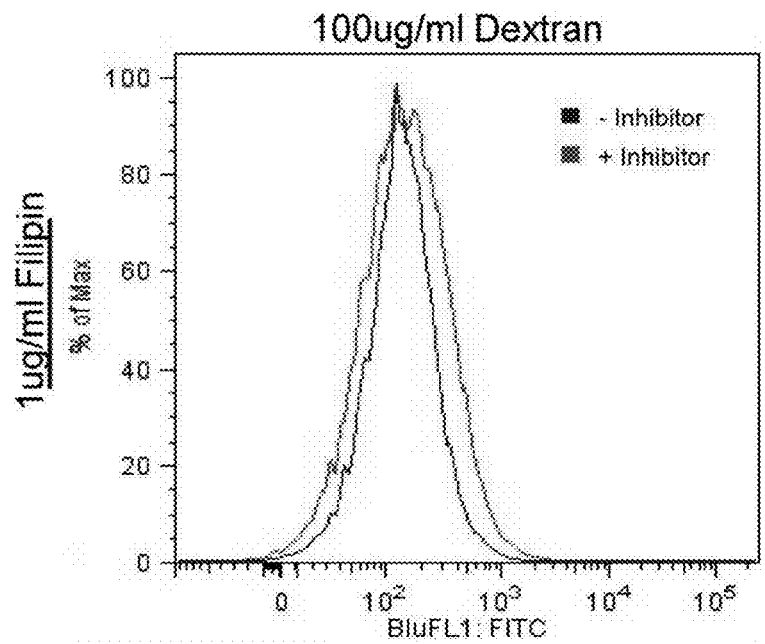
Figure 18F:
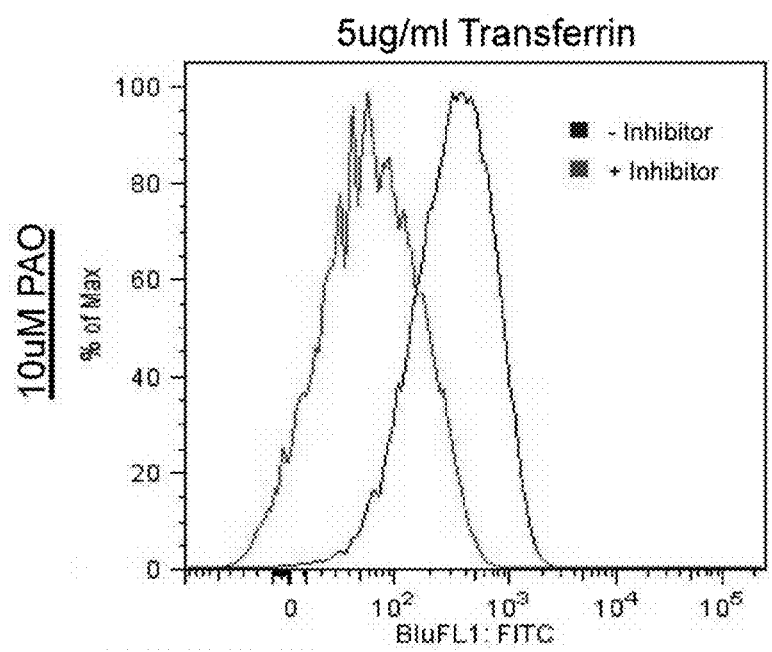
Figure 18G:
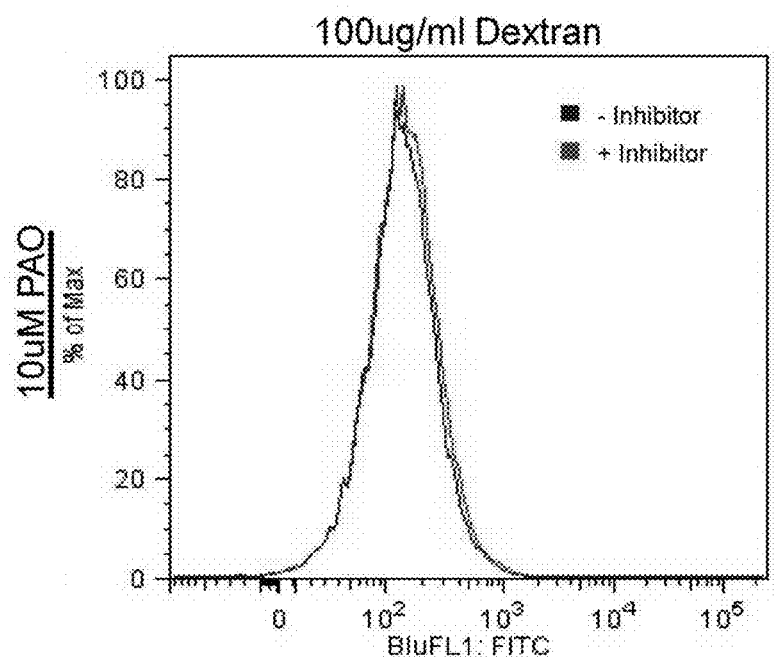
Figure 18H:
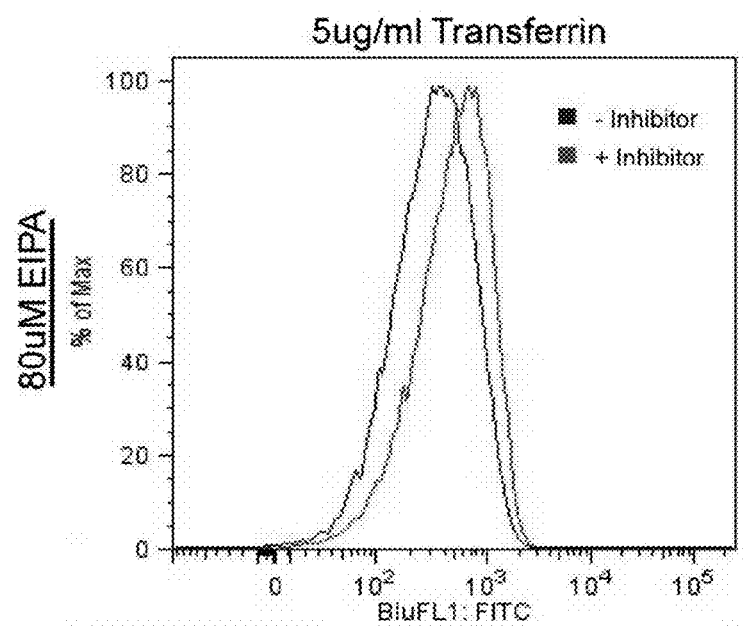
Figure 18I:
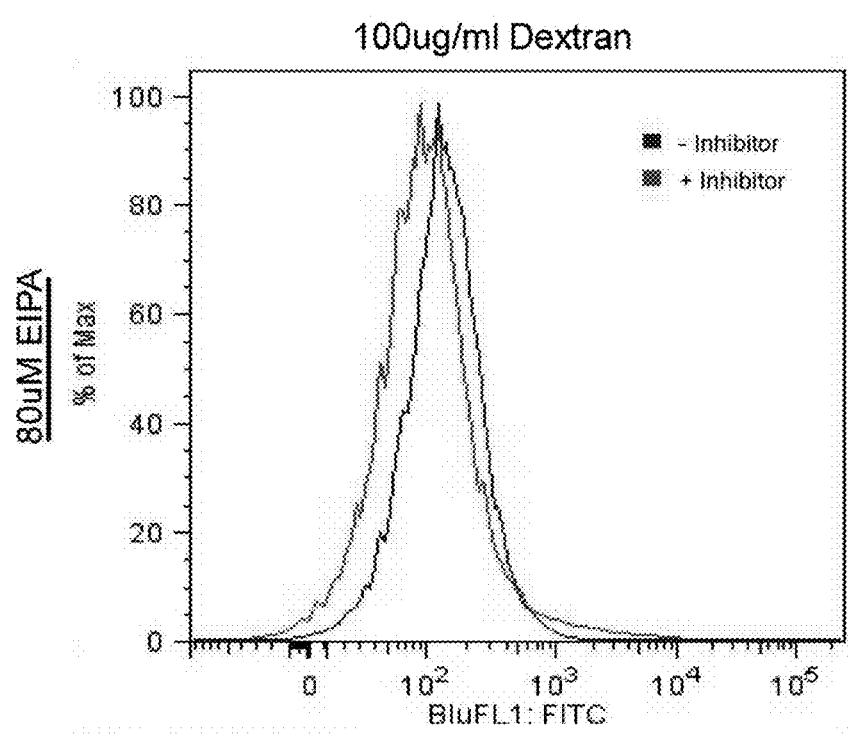
Figure 19:
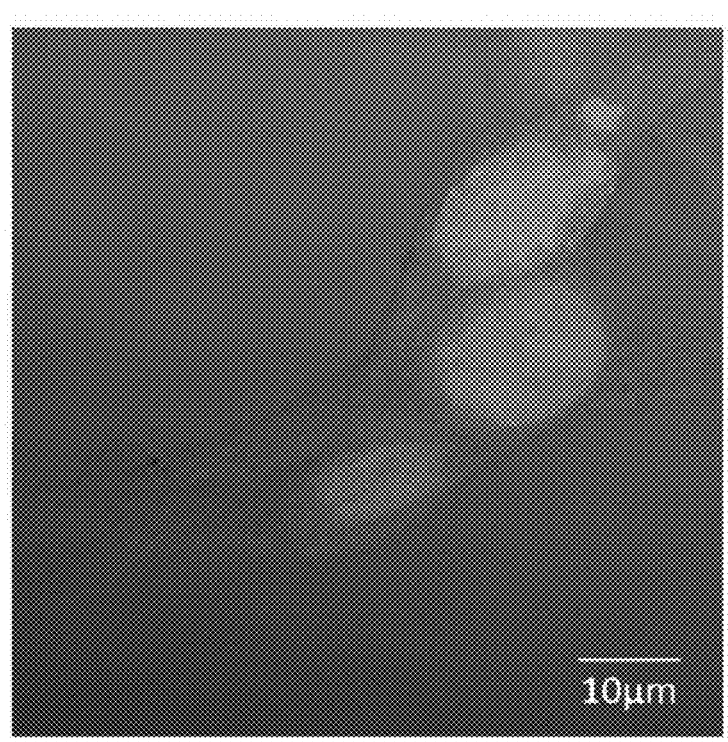
FIG. 19 depicts a microscopy image showing cytoplasmic release of Cy-3-siRNA within 1 hour.

Confocal microscopy confirms the flow cytometry data, illustrating strong colocalization of p5RHH/Cy3-siRNA with FITC-70 kDa dextran (FIG. 17J), but not with FITC-Transferrin (FIG. 17I). Cells were incubated with uptake markers for only 40 minutes to minimize release of Cy-3 labeled siRNA into the cytoplasm, which could yield cytoplasmic or nuclear fluorescence that otherwise might confound the analysis, and thus cells exhibiting cytoplasmic release were not imaged to avoid these issues. Interestingly, the rapid (<1 hour uptake and release) of Cy-3 labeled siRNA confirms the rapid endosomal escape induced by p5RHH/siRNA nanoparticles (FIG. 19).

These results are in accordance with general rules regulating the cellular uptake of many positively-charged peptides containing basic residues. Specifically, arginine residues can form bidentate ionic interactions with cell surface proteoglycans, which results in close association with the plasma membrane. Moreover, these nonspecific binding interactions can stimulate actin rearrangements that are required for fluid phase uptake by macropinocytosis. The robust uptake of positively-charged peptides indicates that electrostatic association with the plasma membrane and subsequent fluid phase uptake is sufficient to achieve substantial peptide/siRNA uptake.

Example 11 siRNA Trafficking Subsequent to Endocytosis

Figure 20A:
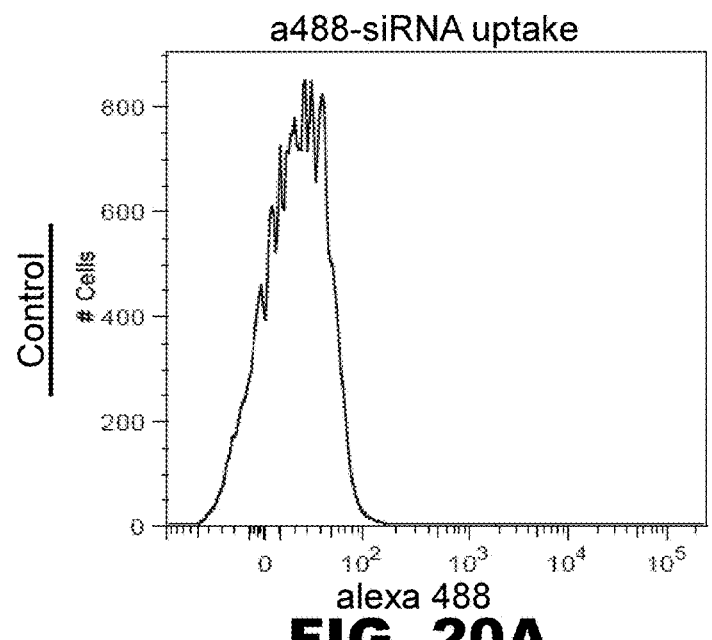
FIG. 20A-F depicts graphs showing p5RHH mediated transfection. (A-C) Bafilomycin A1 does not inhibit uptake of p5RHH/Alexa488-siRNA nanoparticles (C) compared to transfection in the absence of bafilomycin A1 (B). (D-F) On the other hand, bafilomycin A1 blocks knockdown of GFP (F) compared to transfection in the absence of bafilomycin A1 (E) indicating that endosomal acidification is crucial for p5RHH mediated siRNA transfection. Controls cells are shown for comparison in (A) and (D).
Figure 20B:
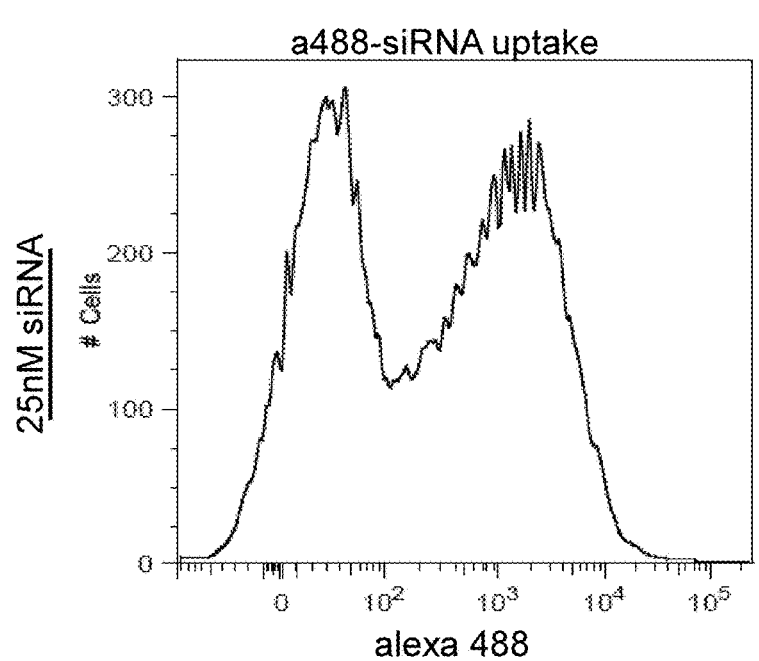
Figure 20C:
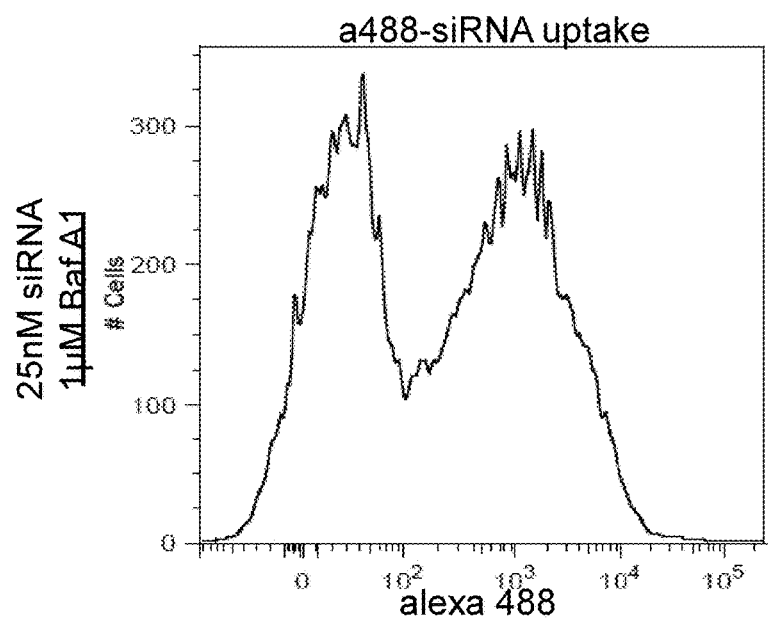
Figure 20D:
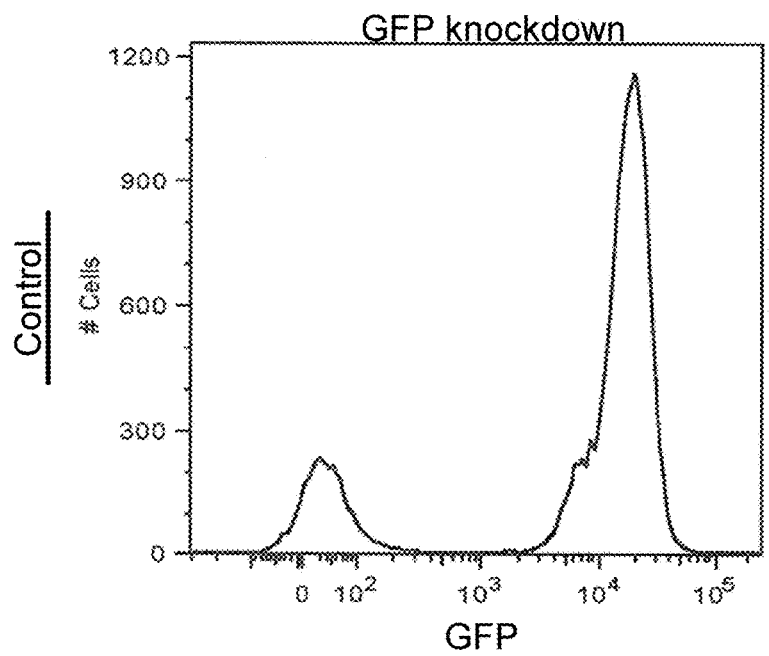
Figure 20E:
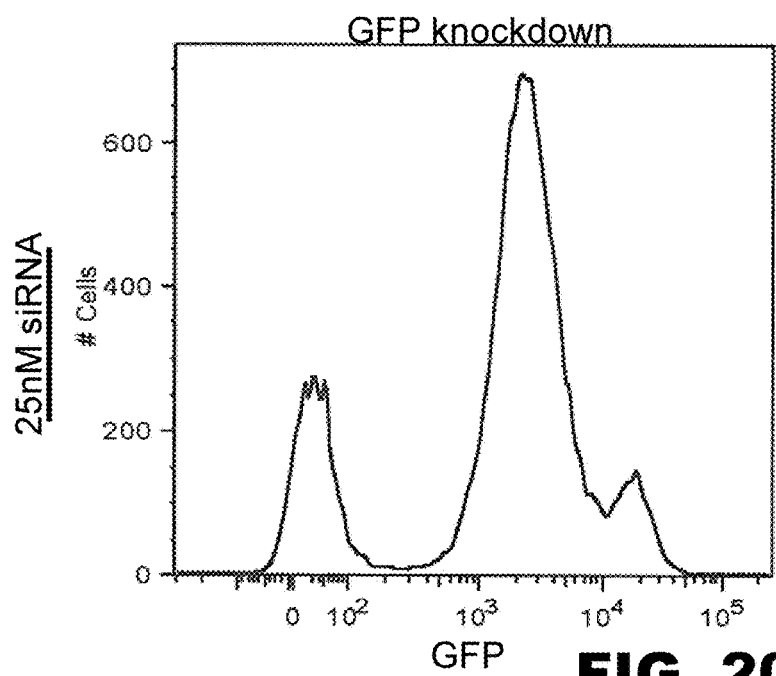
Figure 20F:
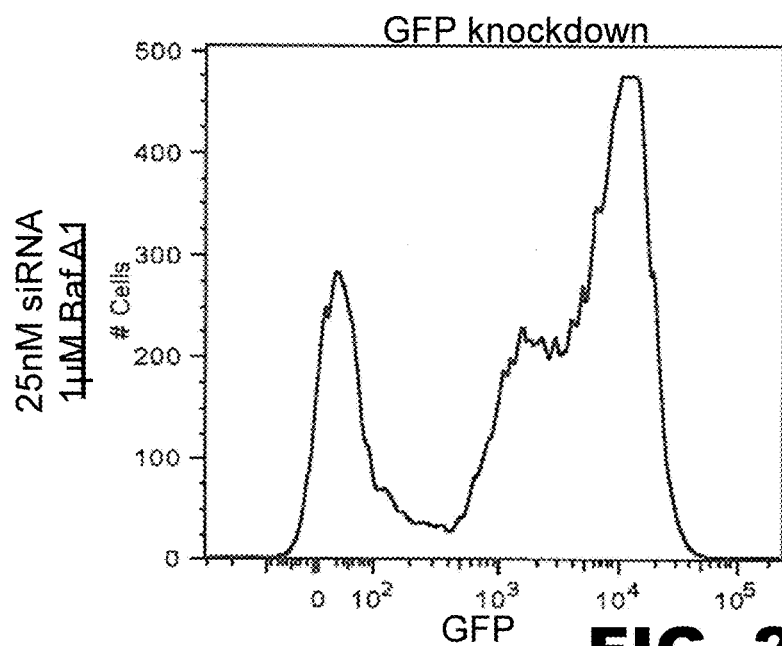

Proper siRNA trafficking subsequent to the initial endocytic event is also vitally important for successful siRNA transfection. In particular, the pH of endosomes and lysosomes is tightly controlled by acidification via membrane-bound vacuolar ATPases and can provide a trigger for environmentally-sensitive siRNA release from p5RHH/siRNA nanoparticles. To determine if the low pH generated by these vacuolar ATPases is involved in siRNA release from endosomes, cells were incubated in the presence of bafilomycin A1 during the transfection. Compared to control cells transfected without bafilomycin A1 (FIG. 20E), bafilomycin A1-treated cells (FIG. 20F) led to a near complete loss of GFP knockdown as determined by flow cytometry. Since bafilomycin A1 could be slowing p5RHH/siRNA uptake, flow cytometric evaluation of the uptake of fluorescently-labeled siRNA in B16 cells was utilized to ensure that the concentration of bafilomycin A1 used in these assays did not impair p5RHH/siRNA uptake (FIG. 20A-C). These data confirm the importance of endosomal acidification in the cytoplasmic release of siRNA when delivered to cells via p5RHH.

Example 12

Nanoparticle Integrity at Acidic pH

Figure 21A:
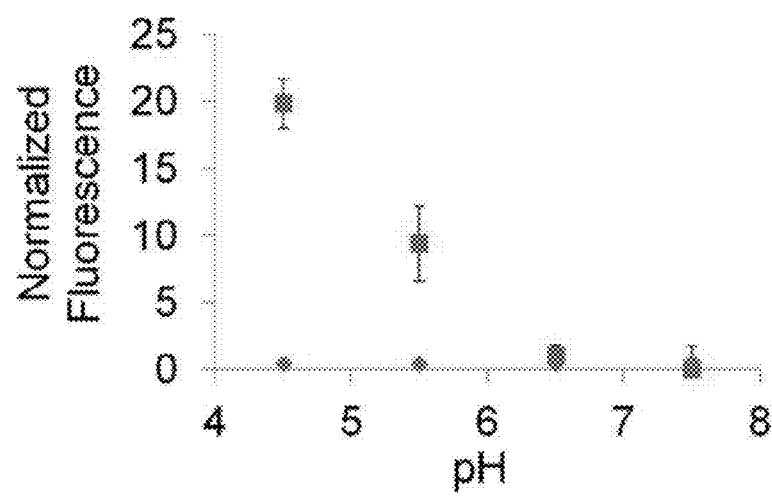
FIG. 21A-K depicts graphs and microscopy images of p5RHH mediated transfection. (A) Fluorescence from TOPRO3 binding to siRNA increases dramatically at pH ≤5.5 when packaged via p5RHH (■), but not the non-functioning peptide p5RWR (♦). (B) Polyacrylamide gel electrophoresis confirms that p5RHH releases siRNA at pH 4.5 but p5RWR shows no pH-dependent release. (C) p5RHH is also released at low pH with an increase in p5RHH release at pH ≤5.5. (D) Freed p5RHH is capable of hemolysis, leading to increased hemoglobin release at pH ≤5.5. (E-H) Acridine orange release assays show that p5RHH/siRNA nanoparticles are able to disrupt endosomes (H) when tested in tissue culture, as exhibited by dye release similar to that of 100 µM chloroquine (F), whereas p5RWR cannot (G). (I-K) schematic showing disassembly of peptide-polynucleotide complex at various pH values. Scale bar 50 µm.
Figure 21B:
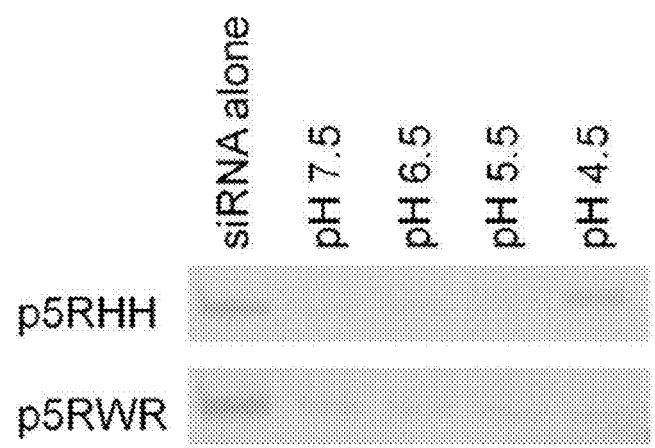

Because endosomal acidification is crucial to the ability of p5RHH to deliver siRNA to the cytoplasm, p5RHH/siRNA nanoparticles were incubated at low pH to ascertain how an increasingly acidic environment affects nanoparticle integrity. Dye-binding assays using the nucleic acid stain TOPRO3 reveal that siRNA becomes increasingly accessible at pH ≤5.5 as manifested by increased TOPRO3 fluorescence intensity (FIG. 21A). To determine if increased dye accessibility was correlated with increased siRNA release, additional samples were run on a 20% polyacrylamide gel to resolve free siRNA (FIG. 21B). Based on these data, it is apparent that siRNA does not become free to migrate into the gel until a pH of 4.5 is achieved. Taken together, these assays imply a pH-dependent mechanism for particle disassembly and siRNA release, with a lower pH (4.5) required for siRNA to be completely released than that required to initiate particle disassembly (pH 5.5). In contrast to p5RHH, p5RWR is unable to respond to pH as demonstrated by a lack of TOPRO3 fluorescence at pH ≤5.5 (FIG. 21A), and a lack of siRNA release as measured by gel mobility (FIG. 21B).

Figure 21C:
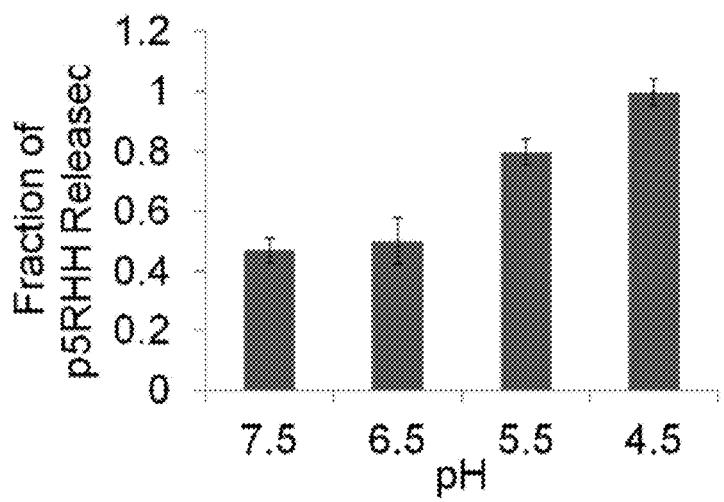
Figure 21D:
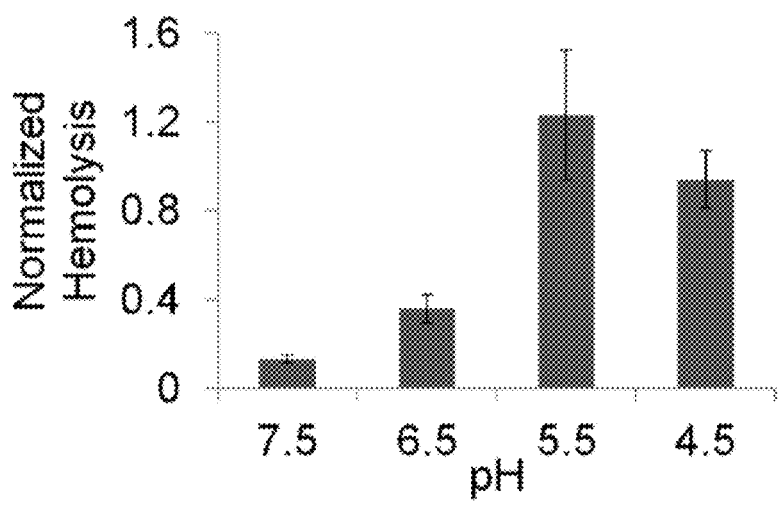
Figure 21E:

To corroborate particle disassembly, pH-dependent p5RHH release from p5RHH/siRNA nanoparticles was quantified after dialysis through a 10K dialysis membrane. These assays reveal that approximately 40% of p5RHH remained free after particle assembly, and a strong release of p5RHH occurred at pH ≤5.5 (FIG. 21C). This pH dependence matches the pH dependence seen for siRNA dye binding, confirming that pH does indeed trigger nanoparticle disassembly and subsequent release of both p5RHH and siRNA.

Figure 22A:
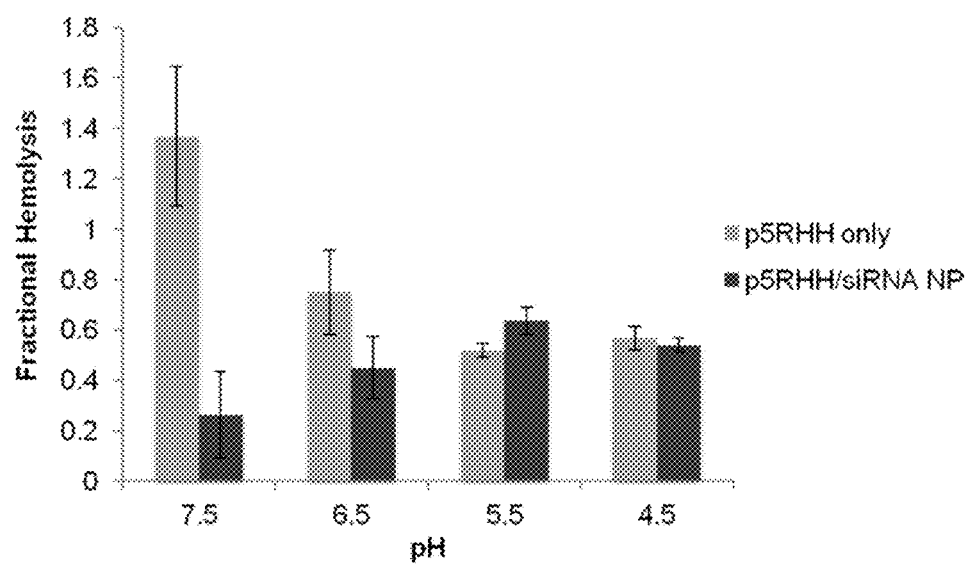
FIG. 22A-B depicts two graphs of 5RHH mediated transfection. (A) Normalized hemolysis shows a pH-dependent decrease in free p5RHH's ability to disrupt RBC. In contrast, p5RHH/siRNA nanoparticles show an increase in RBC disruption with decreased pH, recovering the same lytic capacity of free p5RHH at pH 5.5. Results are reported as fractional hemolysis normalized to maximum lysis by 100 µM p5RHH at pH 7.5 recorded in separate experiments. (B) RBC hemolysis normalized to maximal hemolysis by 0.1% Triton-X indicates that p5RHH lyses RBC with an $IC_{50}$ between 200-400 µM.
Figure 22B:
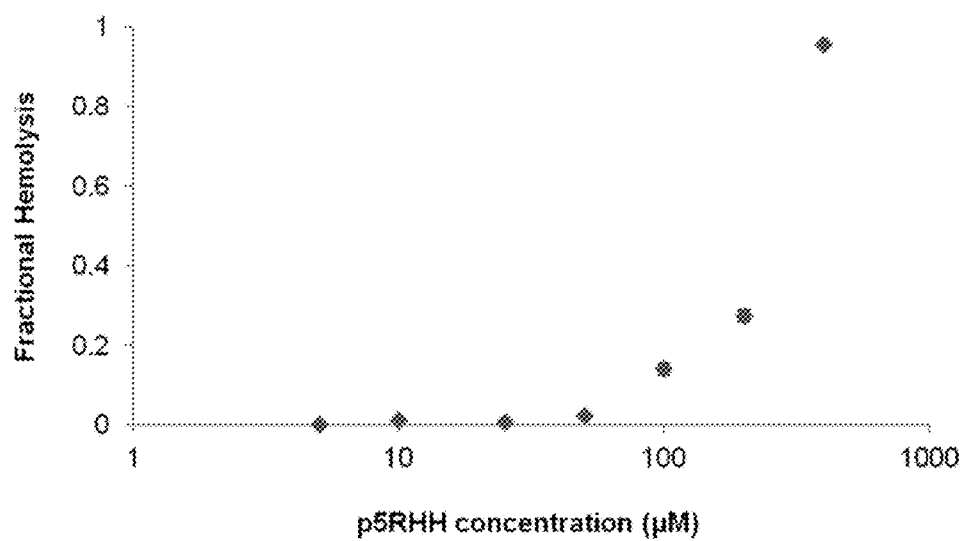

The lytic capacity of liberated p5RHH can be quantified in vitro with red blood cell (RBC) hemolysis assays. When incubated at decreasing pH, the ability of p5RHH/siRNA nanoparticles to lyse RBC is enhanced, due to the release of free p5RHH at pH ≤5.5 (FIG. 21O). These assays were performed at 4° C. to decrease the rate of auto-hemolysis observed at higher temperatures. RBC hemolysis indicates that free p5RHH is capable of lysing membrane-bound structures and could potentially disrupt endosomal membranes in intact cells (FIG. 22).

Figure 21F:
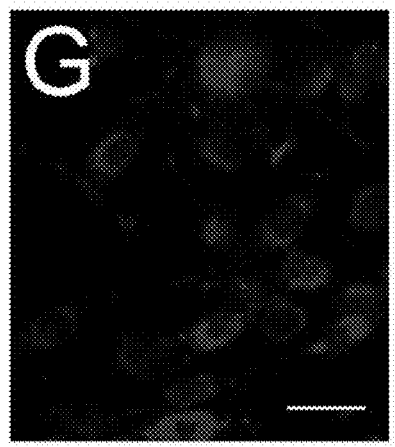
Figure 21G:
Figure 21H:
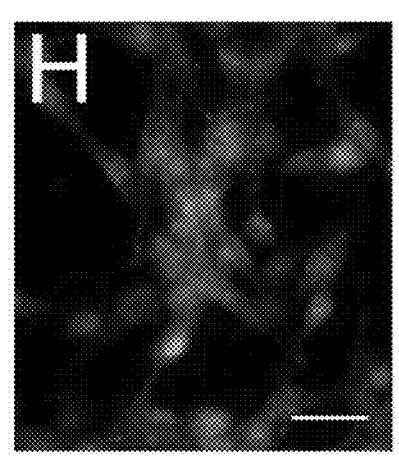
Figure 21I:
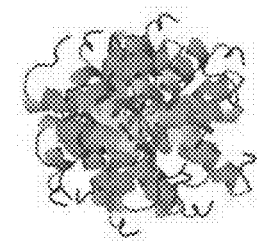
Figure 21J:
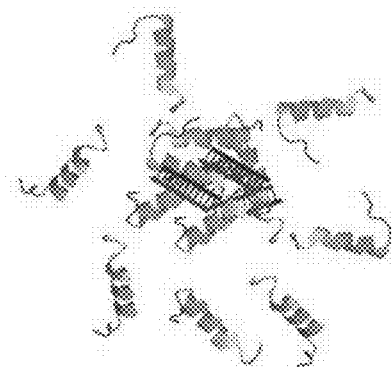
Figure 21K:
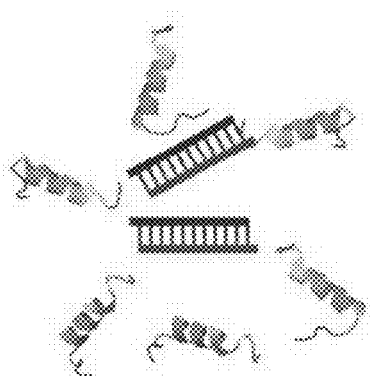

Endosomal disruption in living cells was observed by acridine orange staining. Cells were first loaded with acridine orange (10 μM, 15 minutes), which fluoresces red at low pH in the endosome but green at cytoplasmic pH. Endosomal disruption can be visualized by an increase in cytoplasmic green fluorescence in the presence of 100 μM chloroquine (FIG. 21F). Similarly, cells transfected with p5RHH/siRNA also released acridine orange from cytoplasmic endosomal vesicles, confirming efficient endosomal disruption, whereas cells transfected with p5RWR/siRNA nanoparticles did not exhibit endosomal disruption (FIG. 21H, G). These results highlight the importance of nanoparticle disassembly and release of membrane-active peptide measured in vitro for endosomal disruption in a cellular context (FIG. 21I-K) While p5RHH/siRNA nanoparticles are pH-responsive and release p5RHH for endosomal disruption, p5RWR/siRNA nanoparticles do not disassemble and do not alter endosomal integrity.

One potential mechanism for the pH-responsive properties of p5RHH/siRNA nanoparticles appears to be protonation of histidine residues. With a pKa of 6, histidine likely provides the critical trigger for particle disassembly because increased siRNA dye binding and p5RHH release are recorded at pH<pKa of histidine. Traditionally, protonation of histidine has often been used as a trigger for siRNA delivery in the context of the proton sponge effect, in which the buffering capacity of histidine-containing polymers leads to the accumulation of Cl⁻ counterions and ultimately osmotic rupture of the endosome. In comparison to methods relying on endosomal buffering for osmotic rupture, the presence of only two histidine residues in the present peptide suggests that these proposed modifications to melittin likely do not yield adequate buffering capacity to achieve the proton-sponge effect for endosomal escape. As an example, it has been shown that TAT must be augmented by at least ten histidine residues for successful nucleic acid release into the cytoplasm. While it cannot be completely ruled out that some contribution exists of the proton-sponge effect to the endosomolysis by p5RHH observed for acridine orange release, the need for only two histidine residues is an indication that pH triggers particle disassembly and subsequent release of the membrane lytic peptide. Osmotic rupture likely plays only a minor role, if any.

Example 13

Successful Knockdown of GFP in B16 GFP Cells by siRNA Nanoparticle

Figure 23A:
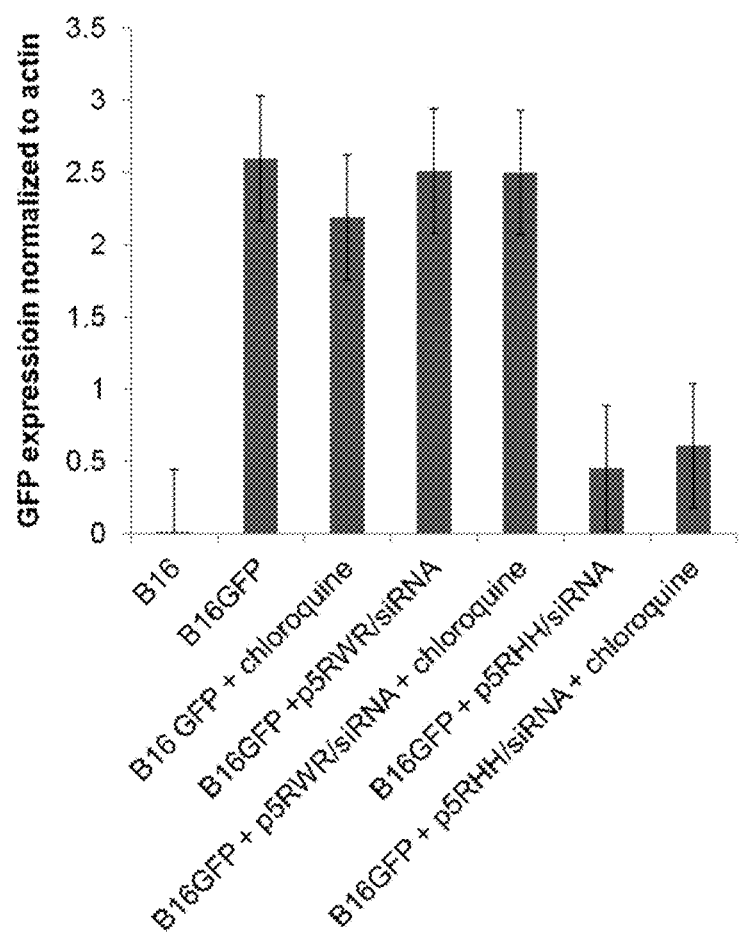
FIG. 23A-F depicts graphs and microscopy images comparing p5RHH and p5RWR mediated transfection. (A) Knockdown of GFP in B16 GFP cells reveals that only p5RHH can successfully deliver GFP siRNA to the cytoplasm, whereas p5RWR cannot, even with endosomal escape induced by chloroquine. (B) FACS reveals both p5RWR and p5RHH deliver similar amounts of alexa 488-labeled siRNA. Untreated control (red square); 50 nM a488 siRNA/p5RWR (beige square); 50 nM a88 siRNA/p5RWR+chloroquine (blue square); 50 nM a488 siRNA/p5RHH (green square); 50 nM a88 siRNA/p5RHH+chloroquine (turquoise square). Confocal microscopy (scale bar 10 µm) reveals that p5RWR (C) delivers siRNA by remains in punctate vesicles whereas p5RHH achieves cytoplasmic distribution (D). Simultaneous incubation with chloroquine is required to release siRNA to the cytoplasm when transfected by p5RWR (E) but has no effect on p5RHH-mediated transfection (F).
Figure 23B:
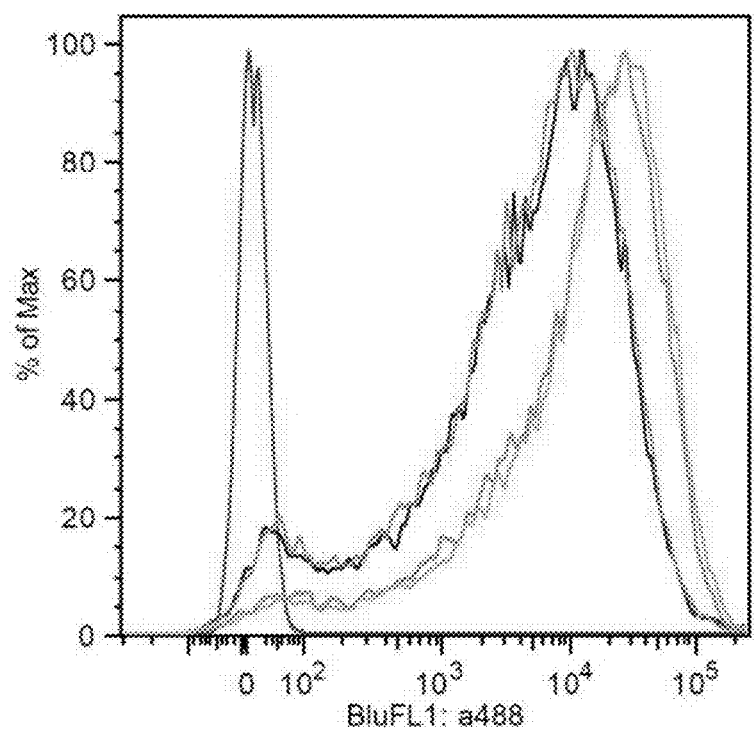
Figures 23C, 23D:
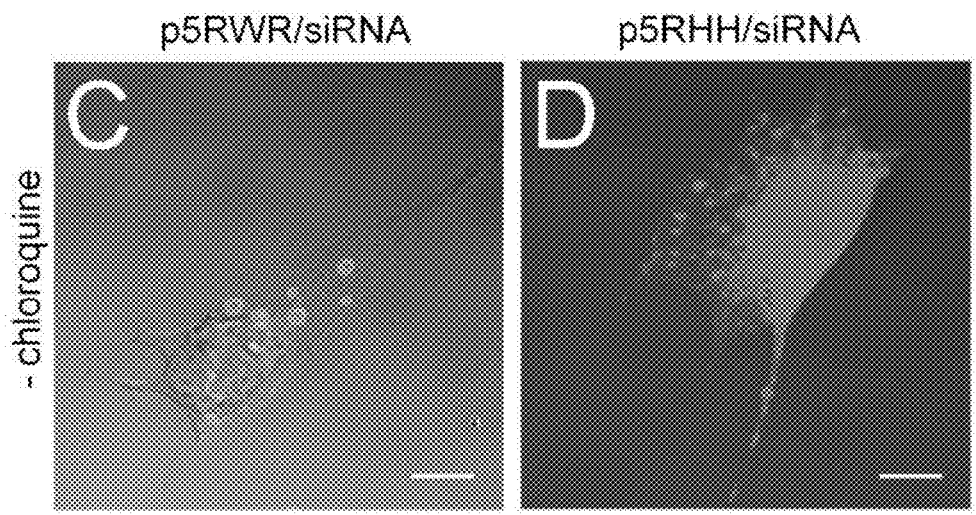

When examining the ability of p5RHH to deliver GFP siRNA to B16-GFP cells, a strong decrease in GFP expression at 50 nM siRNA is observed by western blotting 24 hours after transfection (FIG. 23A). Moreover, transfection of cells in the presence of 50 μM chloroquine, a known endosomolytic agent, does not improve knockdown. The lack of additional knockdown by chloroquine verifies that p5RHH itself is able to fully and efficiently release siRNA from the endosomal compartment, a finding that is visualized by confocal microscopy (FIG. 23D, F).

Figures 23E, 23F:
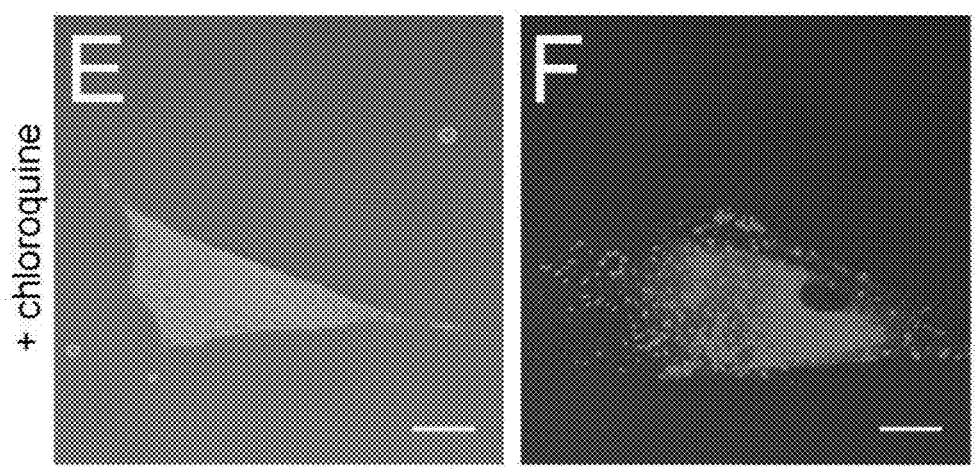

Despite nearly equal uptake of p5RWR/siRNA nanoparticles (FIG. 23B), p5RWR is unable to induce GFP knockdown even in the presence of chloroquine (FIG. 23A). Confocal microscopy reveals a high degree of endosomal entrapment, suggesting p5RWR/siRNA nanoparticles do not reach the cytoplasm (FIG. 23C), unless treated with chloroquine (FIG. 23E). The fact that GFP knockdown remains impaired despite endosomal release by chloroquine (FIG. 23A) indicates that siRNA accessibility to the RNA-induced silencing complex is impaired, reflecting the poor siRNA release from p5RWR-based nanoparticles observed by TOPRO3 binding and gel mobility shift assays in vitro (FIG. 21A, B).

These data highlight that the ability of p5RHH/siRNA nanoparticles to disassemble in response to low pH is crucial for siRNA delivery to the cytoplasm. Specifically, nanoparticle disassembly with siRNA release from the vector and concurrent endosomolysis by p5RHH is a coordinated, event yielding access of free siRNA to the cytoplasmic compartment. The essential role of coordinated siRNA release and endosomal escape in successful siRNA transfection is well known. For example, premature siRNA release in the endosome allows siRNA degradation by endosomal hydrolases. On the other hand, peptides which bind too strongly to siRNA are also hypothesized to prevent successful RNAi. Consequently, siRNA release from p5RHH/siRNA nanoparticles must be concurrent with endosomal escape for maximal mRNA degradation.

Example 14

Highly Efficient In Vivo Transfection of siRNAs Targeting NFκB Pathways in Model of Adult T-Cell Leukemia/Lymphoma (ATLL)

Figure 24A:
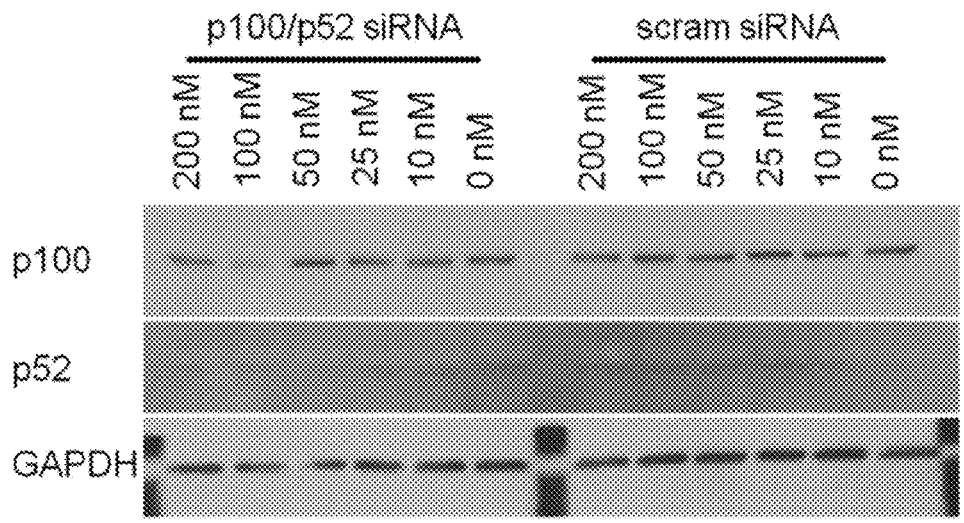
Figure 24B:
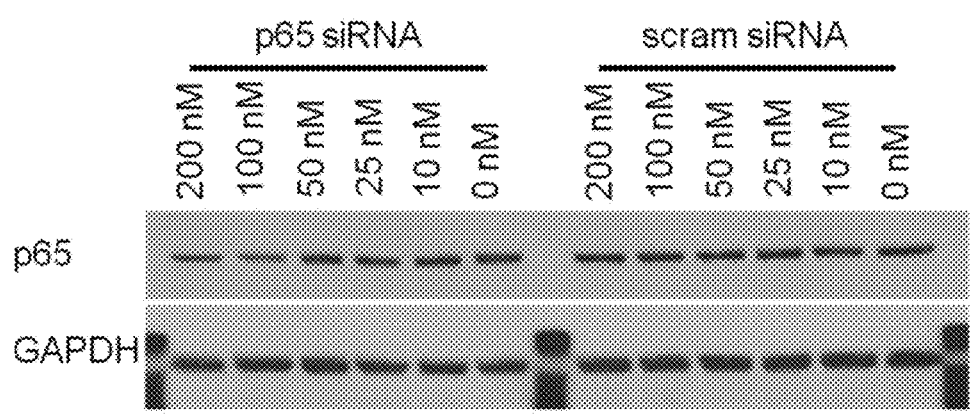
Figure 24C:
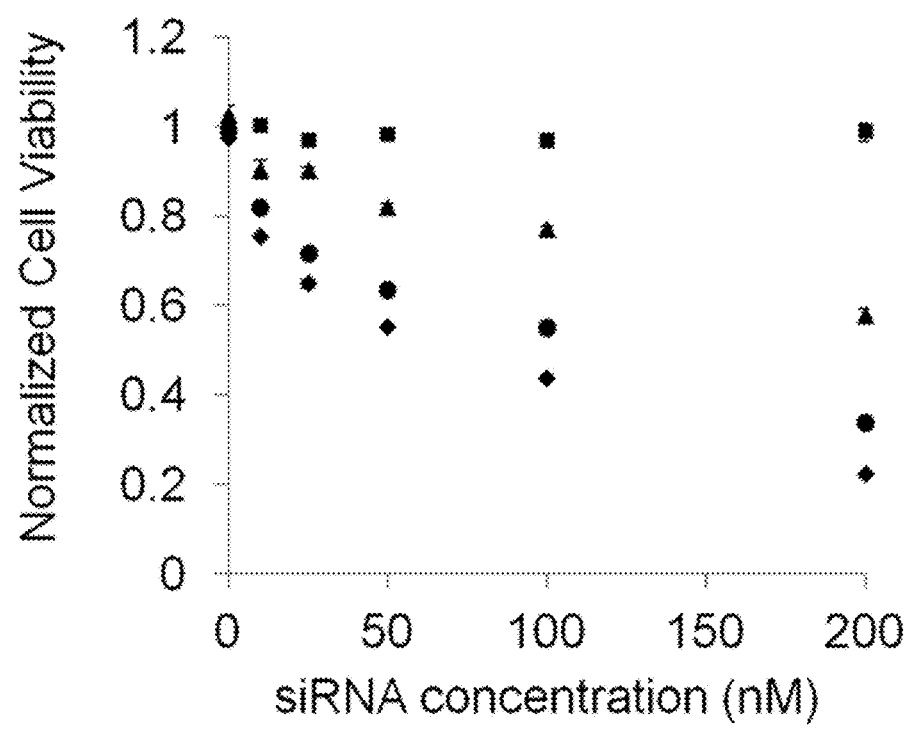
Figure 24F:
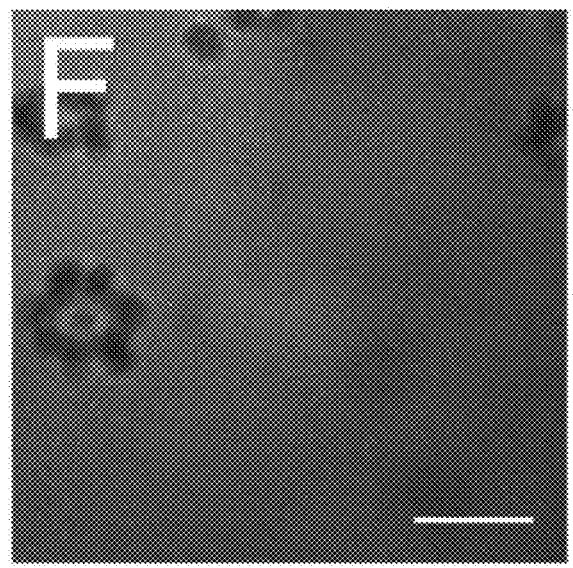
Figure 24G:
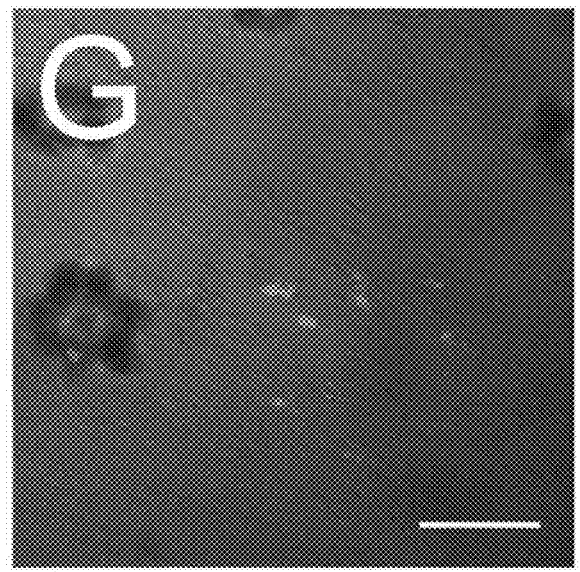
Figure 25:
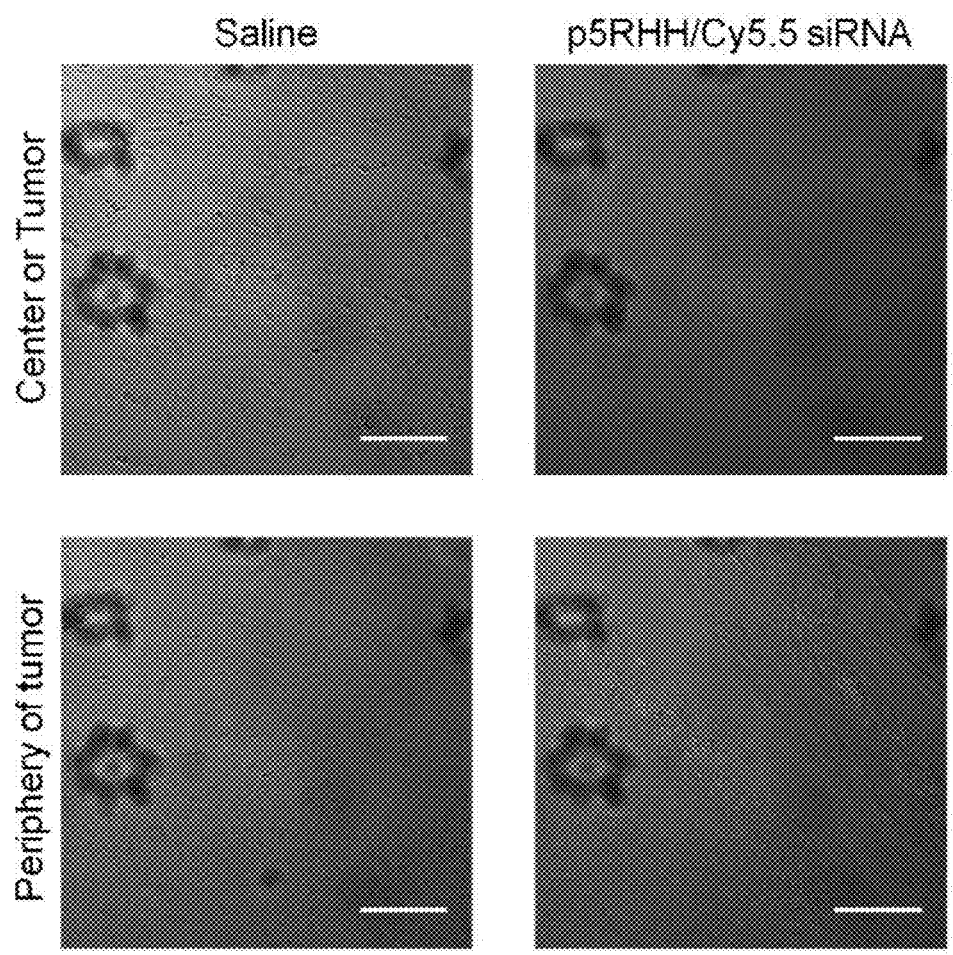
FIG. 25 depicts confocal microscopy images showing that tumors from mice injected with p5RHH/Cy5.5 siRNA nanoparticles exhibit Cy5.5 siRNA accumulation in the periphery, whereas limited Cy5.5 siRNA is found in the center of the tumor. (Scale Bar 50 µm).

The therapeutic potential of albumin-coated p5RHH/siRNA nanoparticles was demonstrated by the highly efficient transfection of siRNAs targeting both the canonical and non-canonical NFκB pathways in F8 cells, a murine model of HTLV-1 induced ATLL. The transcription factor NFκB was chosen as a therapeutic target due to its central role in ATLL, where it promotes resistance to chemotherapy by driving the expression of anti-apoptotic proteins. While small molecule proteasome inhibitors and inhibitors of the IKK complex can decrease NFκB activation in some ATLL disease models, questions regarding their specificity and ability to inactivate NFκB in vivo highlight the need for more specific therapeutics. The potential synergy provided by direct inhibition of both canonical and non-canonical NFκB pathways via siRNA may be the key to successful blockade of NFκB signaling required for therapeutic success.

siRNAs were chosen to target the p65 subunit of the canonical pathway and p100/p52 subunit of the non-canonical pathway. Western blotting performed 24 hours after transfection revealed a dose-dependent decrease in the expression of both proteins that was not seen when cells were transfected with a scrambled siRNA control (FIG. 24A, B). Alamar blue assays (FIG. 24C) 48 hours after transfection demonstrate that knockdown of these pathways in vitro is therapeutically relevant as a strong decrease in cell viability is recorded with both p65 and p100/p52 siRNAs. Moreover, it is clear that blockade of the non-canonical NFκB pathway with p100/p52 siRNA ($IC_{50}$~100 nM) is superior to blockade of the canonical pathway ($IC_{50}$~200 nM) in this cell line. The non-canonical pathway is hypothesized to play a more prominent role in promoting anti-apoptotic protein expression than does the canonical pathway, labeling it as the more desirable target for modulating the proliferation of ATLL cells. Data presented herein, utilizing p5RHH-mediated siRNA delivery, not only confirm this hypothesis, but also reveal a synergistic response when targeting both the canonical and non-canonical NFκB pathways with a single p5RHH/siRNA formulation simultaneously packaging both p65 and p100/p52 siRNAs. Use of this dual-targeted p5RHH/siRNA formulation improves NFκB blockade-mediated cell death, with an $IC_{50}$ ~50 nM. It is important to note that despite the ability to lyse RBC in vitro and endosomal membranes in vivo, transfection with scrambled siRNA does not result in any toxicity of F8 cells. Work by the inventors has shown that N-terminal truncation of melittin decreases its lytic capacity by 2 orders of magnitude (unpublished observation), and while it appears that p5RHH is able to lyse endosomes at high concentration, p5RHH is safe after endosomal release and dilution in the cytoplasm. Given the safety of p5RHH in tissue culture, pilot experiments were conducted to examine tumor localization of p5RHH/siRNA nanoparticles when delivered in vivo. IVIS imaging and confocal microscopy reveal tumor delivery of Cy5.5 labeled scrambled siRNA (FIG. 24D-G and FIG. 27) when introduced by tail-vein injection into mice carrying spontaneous ATLL tumors at a dose of 1 mg/kg. Tumors from mice injected with p5RHH/Cy5.5 siRNA nanoparticles exhibit Cy5.5 siRNA accumulation in the periphery, whereas limited Cy5.5 siRNA is found in the center of the tumor (FIG. 25).

Prior attempts to target NFκB expression itself have focused on the use of naked antisense DNA oligonucleotides or lentiviral shRNA expression, which have limited therapeutic potential. The use of antisense oligonucleotides is inefficient, requiring an order of magnitude more oligonucleotide in vitro than the siRNA formulation presented herein. On the other hand, viral vectors for shRNA expression present myriad challenges for human trials ranging from induction of cancer to toxicity associated with saturation effects. Due to the ability to simultaneously target both NFκB pathways, it is believed that the current siRNA approach shows that the use of p5RHH for highly efficient, low toxicity transfection of NFκB targeted siRNA reflects a synergistic strategy for the treatment of ATLL or other disease processes that are driven by NFκB induction.

Conclusion for Examples 1-14

Figure 26:
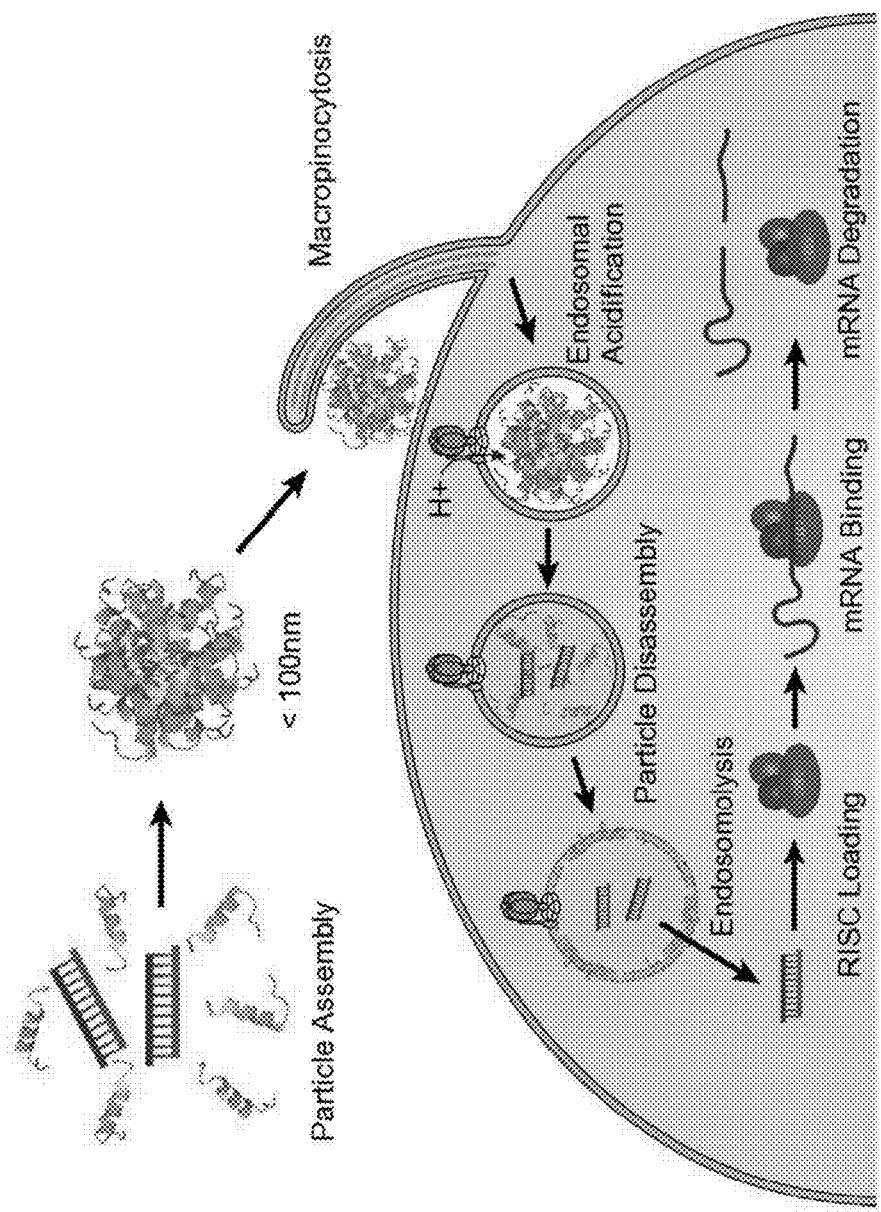
FIG. 26 depicts a schematic of siRNA delivery into the cytoplasm using p5RHH/siRNA particles, showing entry into a cell and release of siRNA from the endosome and peptide/siRNA particle into the cytoplasm.
Figures 27A, 27B:
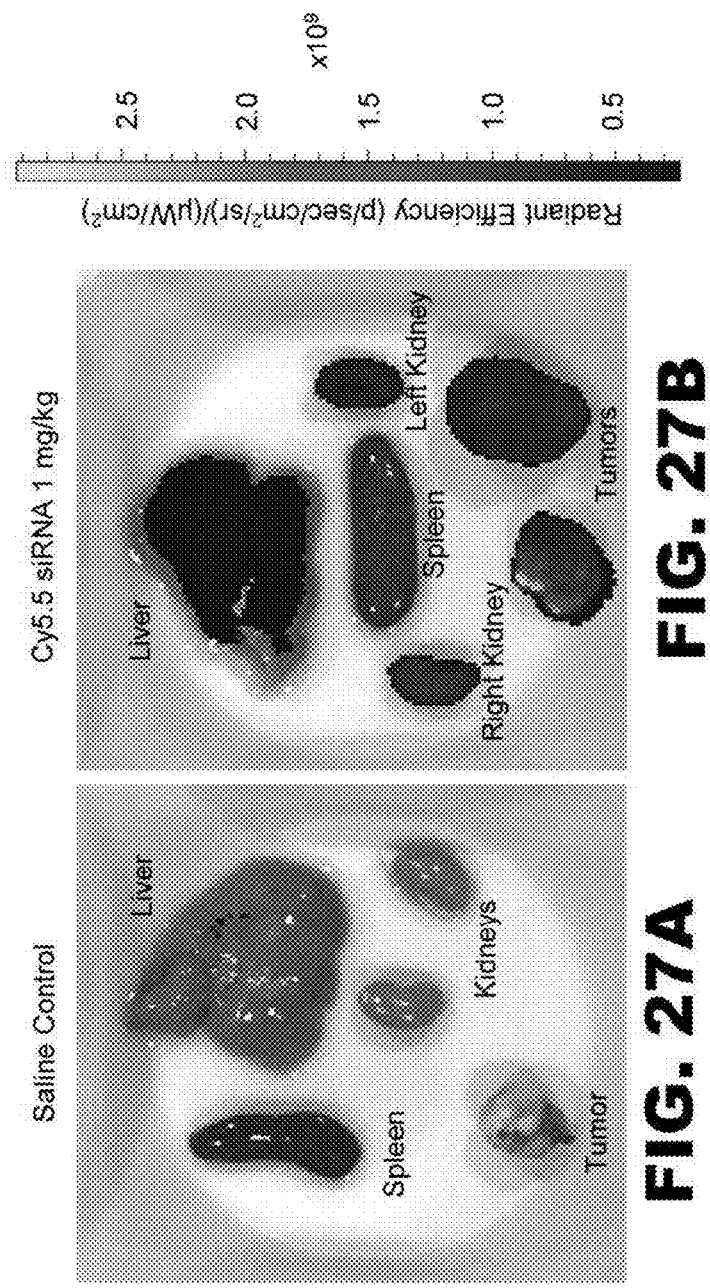
FIG. 27A-B depicts IVIS images of organs and tumors from an animal administered a saline control (A), and an animal administered p5RHH/siRNA with Cy5.5-labeled NFκB siRNA (B).

In summary, membrane-lytic peptides can be recruited as endosomal escape agents to promote the cytoplasmic delivery of siRNA by preventing the siRNA entrapment associated with alternative PTD-mediated transfection. An albumin-stabilized p5RHH/siRNA formulation with a final size of ~55 nm is reported. These nanoparticles are endocytosed by fluid phase uptake via macropinocytosis. Subsequent endosomal acidification provides a trigger for pH-mediated particle disassembly with concurrent siRNA release and endosomal escape brought on by release of free p5RHH (FIG. 26). When utilized for the simultaneous transfection of p65 and p100/p52 siRNAs in a model of ATLL, p5RHH mediates a synergistic decrease in cell viability suggesting the potential of further in vivo studies. The unique ability of p5RHH/siRNA nanoparticles to efficiently coordinate peptide and siRNA release with endosomal portends potential for the use of p5RHH-mediated transfection in a variety of disease substrates. Furthermore, analysis of p5RHH's mechanism of action provides insight that may guide the further development of future peptide vectors for siRNA transfection.

Materials and Methods for Examples 9-14

Preparation of Peptide/siRNA Nanoparticles and Analysis

Melittin derivatives p5RHH (VLTTGLPALISWIRRRHRRHC; SEQ ID NO: 1) and p5RWR (VLTTGLPALISWIKRKRQQRWRRRR; SEQ ID NO: 55) were synthesized by Genscript (Piscataway, N.J.), dissolved at 10 mM in RNAse/DNAse free water (Sigma, St. Louis, Mo.) and stored in 4 µl aliquots at −80° C. before use. p5RHH/siRNA transfection complexes were prepared by diluting p5RHH 1:200 in Phosphate Buffered Saline (PBS, Gibco), vortexing for 30 seconds, followed by addition of siRNA (stock concentration of 10 µM in 1×siRNA buffer (Thermo Scientific, Waltham, Mass.)) to achieve a peptide to siRNA ratio of 100 to 1, and incubated for 40 minutes at 37° C. with shaking in an Eppendorf Thermomixer R. For animal experiments, peptide and siRNA were incubated at a 10 fold higher concentration for 10 minutes on ice. Wet-mode atomic force microscopy was performed by ARC Technologies (White Bear Lake, Minn.).

Cell Culture

B16-F10 (ATCC, Manassas, Va.) cell lines were maintained under standard cell culture conditions (37° C. and 5% CO2 in a humidified incubator) in DMEM (Gibco, Carlsbad, Calif.) supplemented with 10% fetal bovine serum (Gibco). F8 cells were cultured in RPMI (Gibco) supplemented with 10% fetal bovine serum in accordance with previous publications.

Uptake Inhibition by Flow Cytometry

B16-F10 cells were incubated with alexa 488-labeled siRNA packaged with p5RHH (25 nM), FITC-Transferrin (5 µg/ml, Life Technologies) or 70 kDa FITC-Dextran (100 µg/ml, Sigma) in the presence or absence of endocytosis inhibitors for 40 minutes. After incubation, cells were washed 3× in PBS trypsinized and resuspended in FACS buffer (HBSS with 0.2% FBS and 0.5 mM EDTA) for flow cytometry analysis. Inhibitors were used as follows: EIPA (80 µM, Sigma), filipin (100 µg/ml, Sigma), and PAO (10 µM Sigma).

Confocal Microscopy

B16-F10 cells were cultured on glass coverslips overnight before incubation with p5RHH nanoparticles and appropriate uptake markers for 40 minutes or 24 hours. p5RHH/Cy-3 siRNA nanoparticles were added at a final siRNA concentration of 200 nM in the presence of either 70 kDa FITC-Dextran (10 mg/ml) or FITC-Transferrin (25 µg/ml). After the incubation, cells were washed on ice 3× in PBS for 10 minutes and fixed in 4% paraformaldehyde before mounting on glass slides (Vectashield Mounting Medium with DAPI, Vector Labs, Burlingame, Calif.). Cells were imaged on a Zeiss Meta 510 (Thornwood, N.Y.).

Analysis of GFP Knockdown

B16 GFP cells were plated at 150,000 cells/well in 6 well plates and transfected 12 hours later at a final concentration of 50 nM siRNA in 1 mL of 10% DMEM in the presence or absence of 1 µM bafilomycin A1 (1 mM stock in DMSO, Sigma). 24 hours after B16-GFP cells were transfected with p5RHH/siRNA nanoparticles containing GFP specific or scrambled siRNA, cells were trypsinzed and resuspended in FACS buffer (0.2% FBS and 0.5 mM EDTA) for analysis of GFP fluorescence. eGFP siRNA (Sense: 5'-GACGUAAACGGCCACAAGUUC-3; SEQ ID NO: 84') was purchased from Sigma. Scrambled siRNA was purchased from Qiagen (Valencia, Calif.).

siRNA Dye Accessibility at Low pH

Preformed p5RHH/siRNA nanoparticles were incubated in Hank's Balanced Salt Solution (HBSS, Gibco) at the indicated pH for 30 minutes in the presence of TOPRO3 (Life Technologies) diluted 1 to 1000. TOPRO3 fluorescence is measured in a 96-well plate with excitation at 642 nm and emission at 661 nm. Fluorescence values are then normalized to siRNA only controls and presented as the average of 3 separate experiments.

pH Dependent Gel Mobility Assays p5RHH/siRNA nanoparticles are incubated in HBSS at the indicated pH for 30 minutes before resolution on a 20% TBE-PAGE gel. siRNA is visualized by staining with SYBR GOLD in 1×TBE (IBIScientific) diluted 1 to 10000 for 15 minutes.

Acridine Orange Staining for Lysosomal Disruption

B16F10 cells plated on coverslips are loaded with acridine orange at 10 µM for 15 minutes and washed for 3× in PBS before incubation in the presence of p5RHH/siRNA nanoparticles in 10% DMEM at a final siRNA concentration of 100 nM for 12 hours. Alternatively, cells were exposed to chloroquine (Sigma) at 100 µM for 15 minutes prior to imaging. Live cells were visualized by fluorescence microscopy on an Olympus BX610 (Tokyo, Japan).

RBC Hemolysis

Rabbit red blood cells (RBC) were isolated from whole blood by centrifugation and washed in PBS 3× before storage at 4° C. Prior to hemolysis studies, RBC were washed 3× in pH appropriate HBSS and diluted 1 to 5000. RBCs in pH-specific buffer were then incubated with p5RHH/siRNA nanoparticles for 12 hours. The RBC remnants were pelleted by centrifugation and the hemoglobin content of the supernatant was measured by UV absorbance at 550 nm. Absorbance values were then normalized against maximum lysis by p5RHH only controls and presented as the average of 3 separate experiments.

Analysis of NFκB Knockdown in F8 Cells

F8 cells were plated in 6 well plates at 200,000 cells/well and transfected at varying siRNA concentrations in a final volume of 1 mL with the designated siRNA. siGENOME mouse NFκB (p65) siRNA 5 and siGENOME mouse NFκB 2 (p100/p50) siRNA 1 were purchased from Dharmacon (Lafayette, Colo.). Scrambled siRNA was purchased from Qiagen (Valencia, Calif.). 24 hours after transfection, F8 cells were pelleted at 1000 rpm in a Precision AKR-1000. Cell pellets were then resuspended in 100 µl RIPA buffer (10 mMTris-HCl (pH 7.5), 150 mMNaCl, 1.0% IgepalCA-630, 0.5% sodium deoxycholate, 0.1% sodium dodecyl sulfate, 1 mM EDTA, 5% glycerol) with 1 mM PMSF and Complete Protease Inhibitor Cocktail (Roche) and incubated on ice for 1 hour. Cell lysates were then centrifuged at 4° C. for 5 minutes and supernatants stored at −20° C. Lysates were resolved on NupageBis-Tris gels (Life Technologies) and transferred to 0.22 µm nitrocellulose before blocking in 5% bovine serum albumin (Sigma) in TBS-T. Primary antibodies used were rabbit anti-p65 (1:1000, Cell Signaling, Danvers, Mass.), rabbit anti-p100/p50 (1:1000, Cell Signaling). Secondary antibody: anti-Rabbit HRP (1:5000, Santa Cruz Biotechnology). Blots were developed using ECL Western Blotting Substrate (Pierce, Rockford, Ill.).

F8 Cell Viability Measurements

F8 cells were plated in 24-well plates 12 hours before transfection at 20,000 cells/well in 400 µl and cultured under standard cell culture conditions. p5RHH/siRNA nanoparticles were prepared and incubated with cells for 48 hours in a final volume of 600 µl before viability measurements using Alamar Blue (Life Technologies). Briefly, Alamar Blue was diluted 1 to 10 into cell culture media and incubated with cells for 2-4 hours. Fluorescence was measured on a fluorescent plate reader with excitation at 570 nm and emission at 585 nm (Varian Cary Eclipse, Agilent Technologies, Santa Clara, Calif.).

Animal Experiments

The experimental animal protocols were approved by the Animal Care Committee of the Washington University School of Medicine. Transgenic mice with spontaneous tumors were a gift from the Ratner lab. Mice with advanced tumors were selected for pilot experiments and injected with a single dose at 1 mg/kg 24 hours before sacrifice. Animals were perfused with saline, and tumors were excised for IVIS imaging and frozen sectioning.

Example 15 p5RHH Cytotoxicity

Figure 28A:
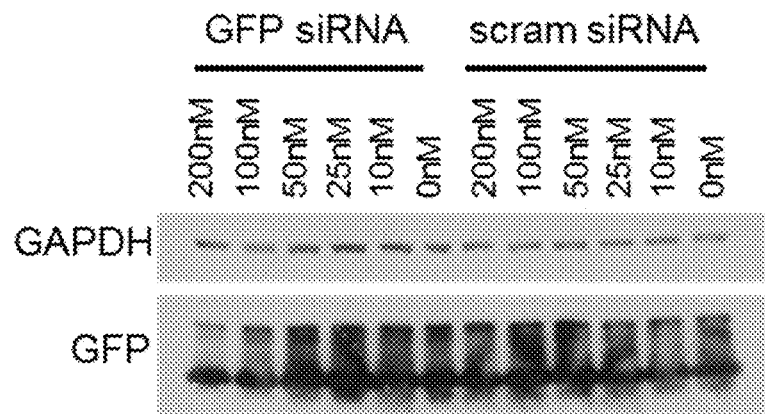
FIG. 28A-D depicts Northern blots (A, B) and graphs (C, D) showing cytotoxicity of p5RHH/siRNA (A, C) in comparison to Lipofectamine 2000 (B, D).
Figure 28B:
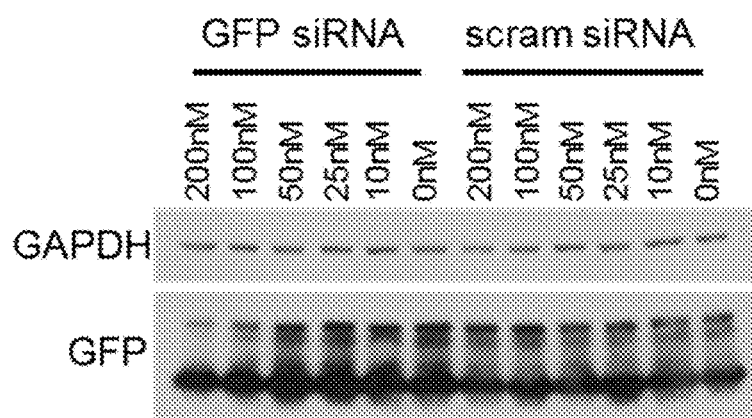
Figure 28C:
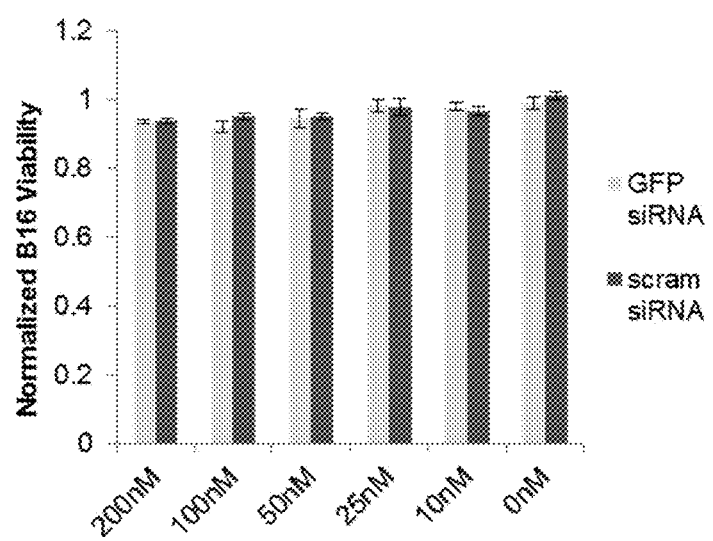
Figure 28D:
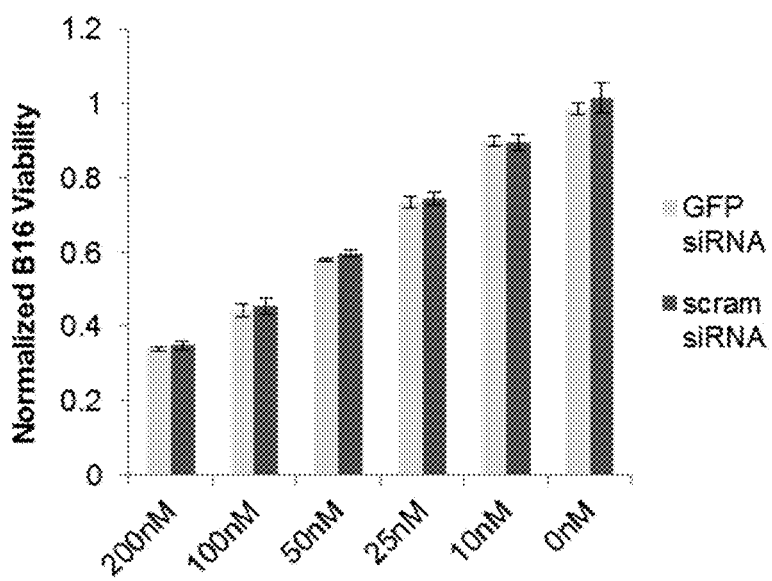

B16 GFP cells were transfected with increasing concentrations of p5RHH/siRNA nanoparticles containing GFP-specific or scrambled siRNA. For comparison, B16 GFP cells were also transfected with increasing concentrations of GFP specific or scrambled siRNA using lipofectamine 2000. RNA extracted from transfected cells was analyzed using Northern blot analysis, and normalized viability of transfected B16 cells was determined (FIG. 28). In contrast to transfections using Lipofectamine 2000 (FIG. 28B, D), p5RHH/siRNA was determined to be safe at all tested doses (FIG. 28A, C).

Example 16

Figure 29:
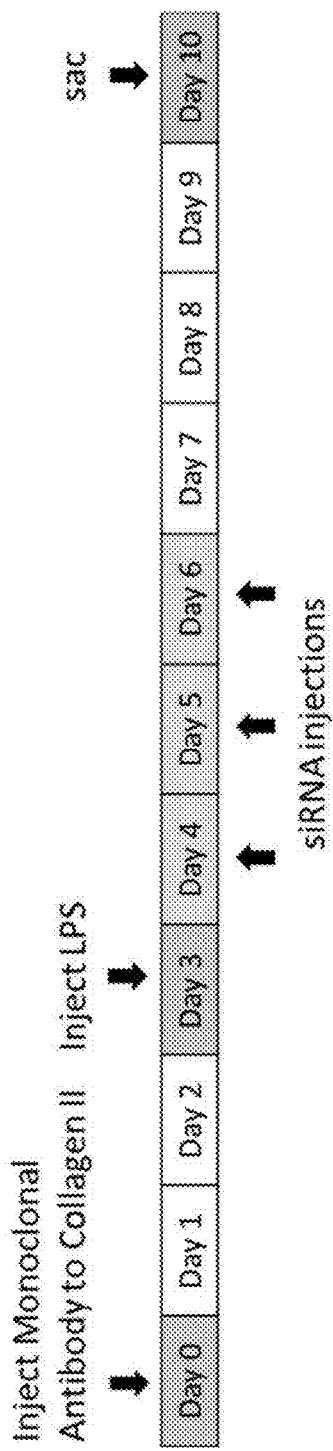
FIG. 29 depicts a schematic of collagen antibody-induced murine model and administration of siRNA.

NFκB Blockade Relieves Arthritic Symptoms in Collagen Antibody-Induced Arthritis The therapeutic potential of albumin-coated p5RHH/siRNA nanoparticles was demonstrated in a collagen antibody-induced murine model of arthritis. In short, the model comprises injection of a monoclonal antibody to collagen II, followed a few days later by injection of lipopolysaccharide to enhance the arthritic symptoms. Collagen antibody-induced murine model and the administration of siRNA is as described in FIG. 29.

siRNA targeting the p65 subunit of the canonical pathway was used. Scrambled siRNA was used as a control. siRNA was labeled with Cy5.5. The concentration of siRNA at each administration was 1 mg/kg of siRNA. Three mice were administered saline, three mice were administered scrambled siRNA, and 4 mice were administered p65 siRNA. Severity of arthritis was determined by rating ankle thickness, arthritic score, and body weight on days 0, 3, 4, 6, 8, and 10.

Figure 30A:
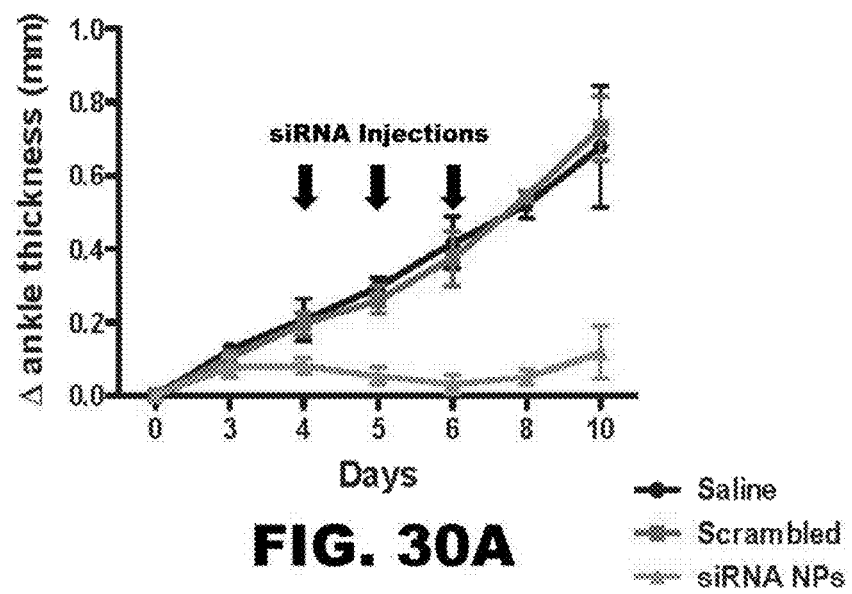
FIG. 30A-C depicts graphs and an IVIS image showing (A) ankle thickness (B) and arthritic score of animals administered saline, and animals transfected with p5RHH/siRNA with scrambled siRNA or siRNA targeting the p65 subunit of the canonical pathway. (C) IVIS image of animals administered saline or p5RHH/siRNA with siRNA targeting the p65 subunit of the canonical pathway.
Figure 30B:
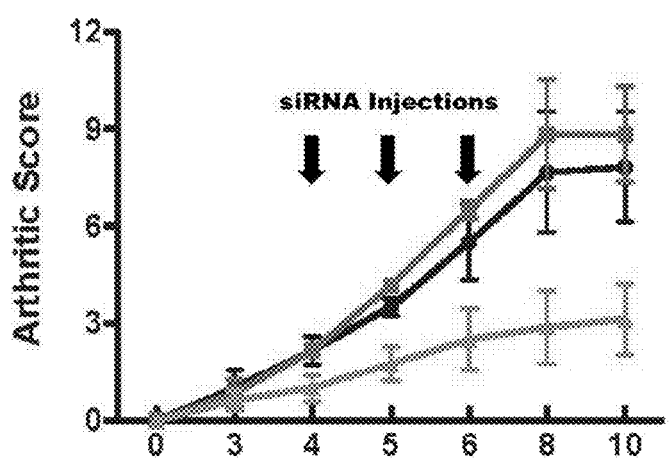
Figure 30C:
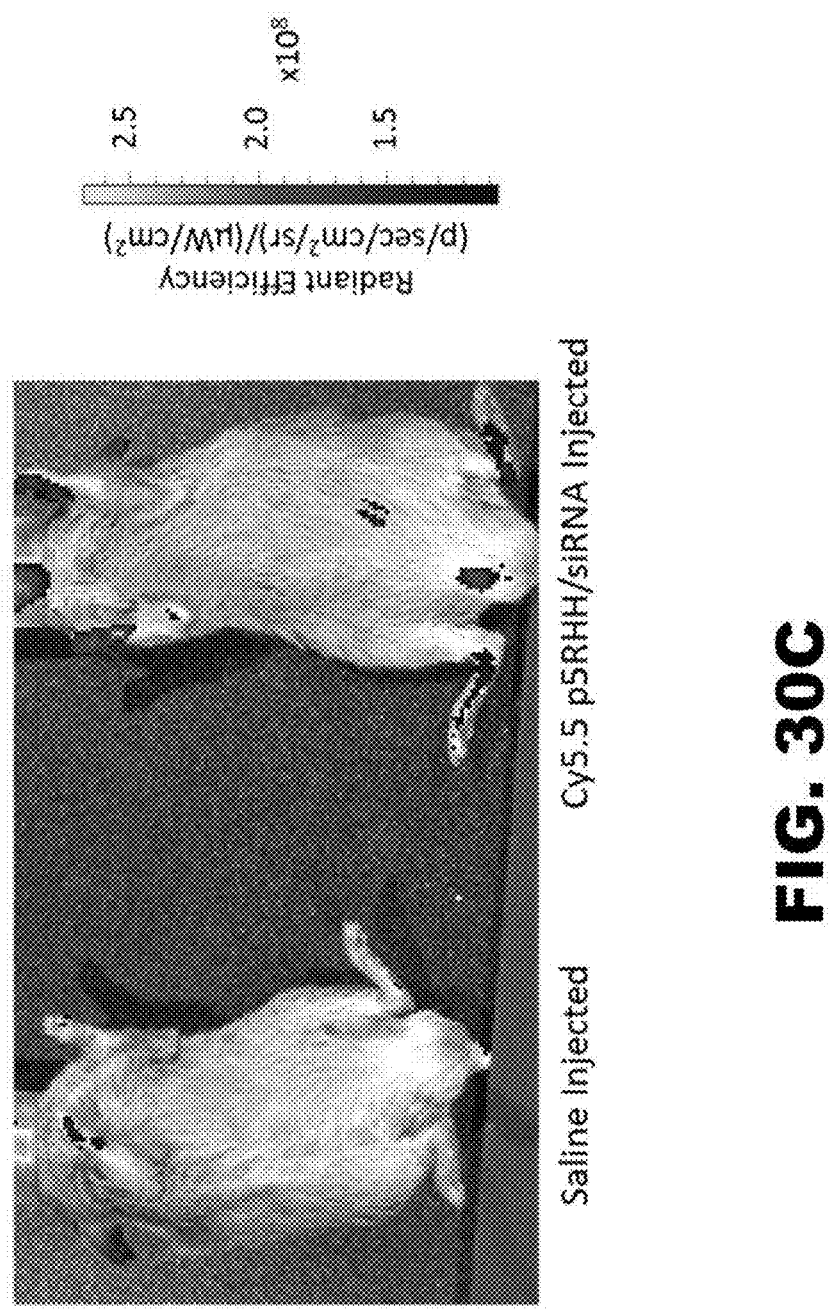

As shown in FIG. 30, NFκB blockade using p5RHH/siRNA particles with siRNA targeting the p65 subunit of the canonical pathway decrease collagen antibody-induced arthritis as measured by ankle thickness (FIG. 30A), and arthritic score (FIG. 30B). IVIS imaging shows that siRNA accumulated in arthritic paws of the animals (FIG. 30C).

In addition, ultrasonic molecular imaging was used to visualize efficacy of treating arthritis using p5RHH/siRNA with siRNA targeting the p65 subunit. Ultrasonic imaging measures changes in the physical composition (fibrosis, edema, inflammatory cells, etc.) and organization of tissues at subvoxel resolution for similar tissues undergoing treatment (Hughes et al., 2011 J Acoust Soc Am. 129:3756; Hughes 2011 IEEE Trans Ultrason Ferroelectr Freq Control. 58:2361-2369; Hughes et al., 2007 Ultrasound Med Biol. 33:1236-1243; Hughes et al., 2007 Journal of the Acoustical Society of America. 121:3542-3557; Hughes et al., 2013 J Acoust Soc Am. 133:283-300; Hughes et al., 2009 Journal of the Acoustical Society of America. 126:2350-2358)

Figure 31:
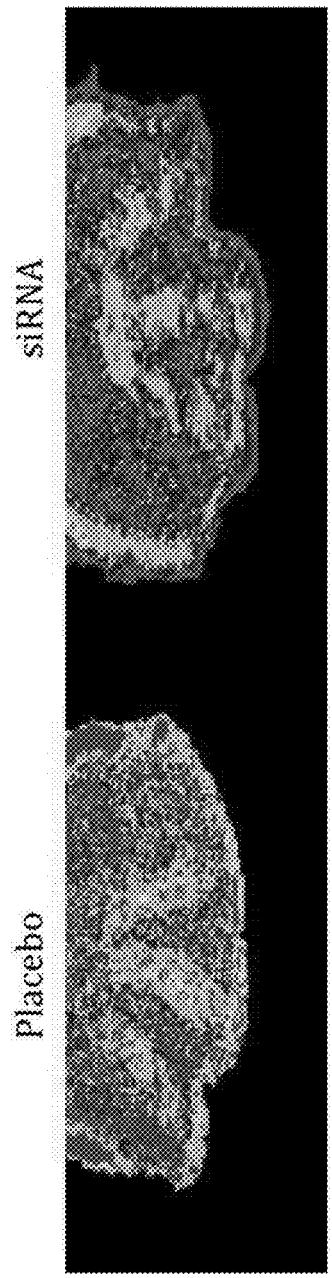
FIG. 31 depicts an image showing efficacy of arthritis therapy using p5RHH/siRNA targeting the p65 subunit of the canonical pathway using ultrasound entropy imaging.

Entropy imaging shows that three bones of the paw are visible (blue to red) 4 days after treatment with saline (placebo). While three of the bones of the paw are visible in animals 4 days after treatment with p5RHH/siRNA with siRNA targeting the p65 subunit, their pixel values are much closer to normal background (FIG. 31).

Example 17 siRNA Nanoparticles to Suppress the Inflammatory Response in Collagen Antibody Induced Arthritis The goal of this study is to demonstrate the ability of siRNA nanoparticles to suppress the inflammatory response in collagen antibody induced arthritis in mice. The NFκB pathway was targeted as a central check-point in inflammation by incorporating siRNA against p65 subunits, which are the main transcriptional regulators of the canonical NFκB pathway. Nanoparticles were prepared in the usual way and injected intravenously in three consecutive daily doses after establishment of joint swelling. Joint responses were measured over time, and a number of other tests performed to define safety of the material.

Arthritis Induction and Treatment: Arthritis was induced using the collagen antibody-induced arthritis model (CAIA) with Arthrogen-CIA arthrogenic monoclonal antibody 5-clone cocktail (Chondrex, Inc.). Six to eight week-old male DBA/1 J mice (Taconic) were injected i.p. with 1.5 mg of the 5-clone antibody cocktail on day 0 and 50 ug of LPS on day 3. Starting on day 4, when early arthritis was established in all mice, animals received daily serial i.v. injections of saline, nanoparticles with scrambled RNA sequence or p-65 siRNA (1 mg/kg i.v. by tail vein). Clinical manifestation of arthritis was assessed daily on a scale of 0-3 (0=no swelling or erythema, 1=slight swelling or erythema, 2=moderate erythema and swelling in multiple digits or entire paw, 3=pronounced erythema and swelling of entire paw, maximum score of 3×4 paws=12 per mouse). Change from baseline in paw thickness was determined daily by dial calipers and an average change in ankle thickness was determined for each mouse from the two hind paw measurements. Mice were also weighed every other day and the percentage of weight loss from baseline was calculated. On day 9, mice were sacrificed and their blood, paws, and organs harvested for analysis.

Cytokine Analysis: Paws were homogenized in 1 ml PBS and lysates were cleared by centrifugation. TNF-α, IL-6 and MCP-1 concentrations in paw lysates were measured by cytometric bead array using the mouse inflammatory kit (BD Bioscience) according to manufacturers' recommendations. IL-1β was measured by ELISA (R&D Systems) according to the manufacturers' recommendations.

Hematologic Parameters and Serum Chemistries: Day 10 blood was drawn from the inferior vena cava and sent for WBC/differentials and serum chemistries (hepatic and renal functions). The analysis was performed by the Washington University Department of Comparative Medicine.

Immune Responses to Nanoparticles: Total IgG and IgM were measured using a standard ELISA assay. Briefly, 96-well plate was coated with goat anti-mouse IgG (Southern Biotechnology Associates, Inc.) or goat anti-mouse IgM (Southern Biotechnology Associates, Inc.) capture antibody (1 ug/ml in PBS) and incubated at 4° C. overnight. After washing and blocking with 1% BSA in PBS, diluted mouse sera (1:40,00-1:400,00 dilutions) were added to wells and incubated at room temperature for 1 h. After washing, 100 ul of HRP-conjugated goat anti-mouse IgG (Southern Biotechnology Associates, Inc.) or goat anti-mouse IgM (Southern Biotechnology Associates, Inc.) antibody (1:3,000 dilution in 1% BSA in PBS) were added to the plate and incubated for 2 h at room temperature. After washing 100 μL of peroxide-chromogen solution (R&D Systems) was added to each well, and color development was read at 450 nm with a SpectraMax Plus reader (Molecular Devices, Sunnyvale, Calif., USA). Purified mouse IgG (Jackson ImmunoResearch Laboratories) and IgM (Rockland Immunochemicals) were used to establish the standard curves.

To measure IgM or IgG specific response to the p5RHH peptide or peptide:siRNA nanoparticles, Immunlon 4 HBX plates (Thermo Fisher Scientific Inc., Waltham, Mass.) were either incubated with 100 µl/well of P5RHH peptide or siRNA-P5RHH nanoparticles at P5RHH peptide concentration of 2 µM at 4° C. overnight. To determine the amount the materials coated on the surface the wells of the plate, unbound P5RHH peptide or siRNA-P5RHH nanoparticles were measured using a fluorescent spectrofluorometer (Varian Inc, Palo Alto, Calif.), since P5RHH has one tryptophan residue. Tryptophan fluorescence emission spectra (300 nm to 500 nm) were measured after excitation at 280 nm. Standard curves have been generated and the amounts of unbound materials were calculated against standard curves. For the peptide coated plate, coated peptide has the concentration of 2.21 µg/ml; For the siRNA-P5RHH nanoparticles (NP) coated plate, peptide concentration was 3.58 µg/ml. After washing and blocking with 1% BSA in PBS, diluted mouse sera (1:10-1:100 dilution) were added to wells and incubated for 1 h at room temperature followed by HRP-conjugated goat anti-mouse IgG (Southern Biotechnology Associates, Inc.) or goat anti-mouse IgM (Southern Biotechnology Associates, Inc.) antibody as above. Color development was performed using of peroxide-chromogen solution (R&D Systems) as above. Data are presented as direct absorbance (OD at 450 nm).

Off-Target Nanoparticle Uptake: Mice were injected i.v. with 200 ul of HBSS or Cy3-labeled peptide:scrambled RNA seq nanoparticles. After 30 mice were sacrificed and peripheral blood white cells and splenocytes obtained for analysis of cell-associated Cy3-labeled particles by flow cytometry. Cells were also stained with Ly6G (neutrophils) and Ly6C (monocytes) to look for specific colocalization.

Complement Activation: Mice were injected i.v. with 200 ul of peptide:siRNA nanoparticles. Blood was collected from the inferior vena cava at 30 min following NP injection directly into 10 mM EDTA tubes to prevent further ex vivo complement activation. Fresh plasma was prepared from collected blood for C3a ELISA. Briefly, plates were coated overnight at 4 □C with rat anti-mouse C3a (4 µg/mL) monoclonal antibody (BD Pharmingen). After being blocked with reagent diluent (1% BSA in PBS) for 1 h at RT, the plates were washed 3× with ELISA wash buffer (0.05% (v/v) Tween 20 in PBS) and incubated with samples (100 µL of same day, freshly obtained plasma diluted 1:100 in reagent diluent) for 1 h at RT. The plates were washed (3×), followed by incubation with biotinylated anti-mouse C3a (250 ng/mL) for 1 h at RT. After washing, the plates were incubated with streptavidin-peroxidase (400 ng/mL; Sigma) for 30 min, washed and 100 µL of peroxide-chromogen solution (R&D Systems) was added to each well, and color development was read at 450 nm with a SpectraMax Plus reader (Molecular Devices, Sunnyvale, Calif., USA). Mouse recombinant C3a (BD Pharmingen) was used to establish the standard curve.

Figure 32D:
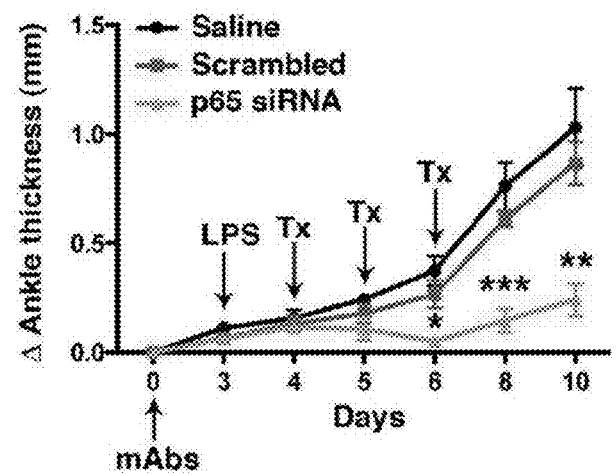
Figure 32E:
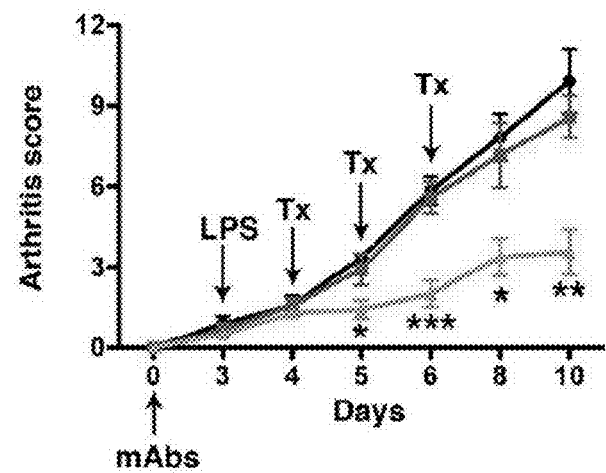
Figure 32F:
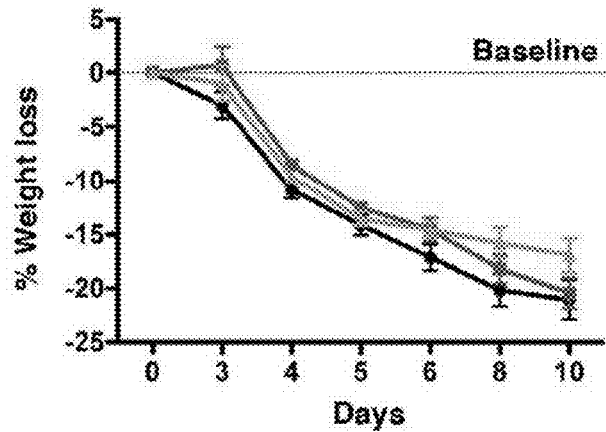
Figure 33A:
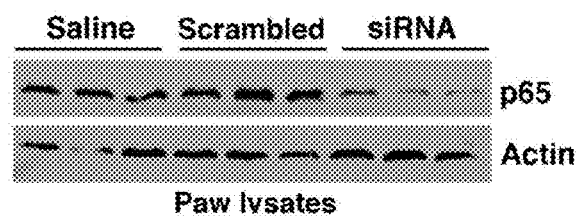
FIG. 33A-E depicts immunoblots and graphs showing p65-siRNA nanotherapy suppresses p65 expression and inflammation in CAIA. On day 10, mice were sacrificed and the paws were harvested, homogenized, and cleared lysates blotted for p65 expression (A). Lysates were also assayed for inflammatory cytokines [TNFα (B), IL-1β(C), IL-6 (D), MCP-1 (E)] by cytometric bead arrays and ELISA. P<0.01, *P<0.001
Figure 33B:
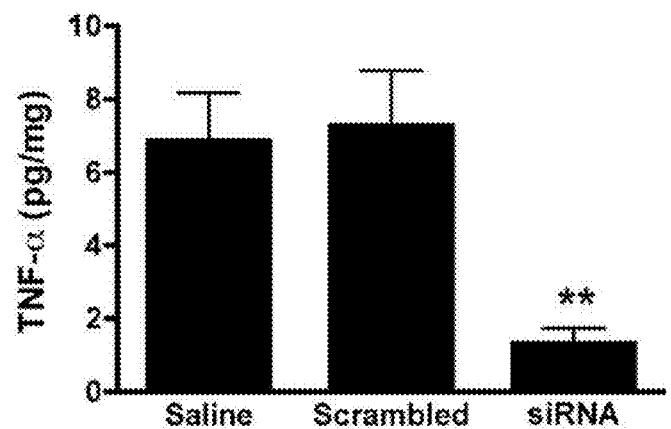
Figure 33C:
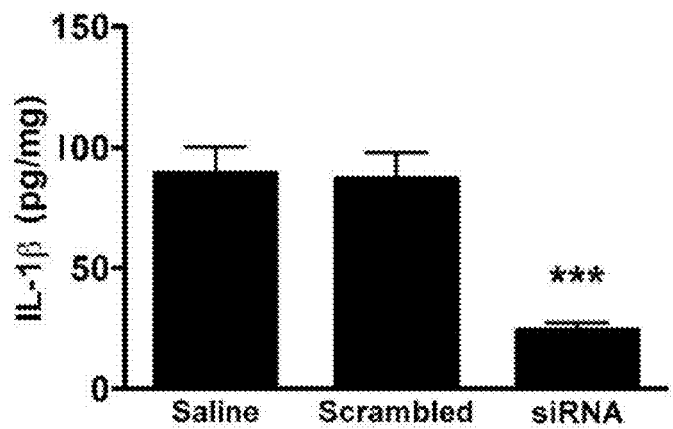
Figure 33D:
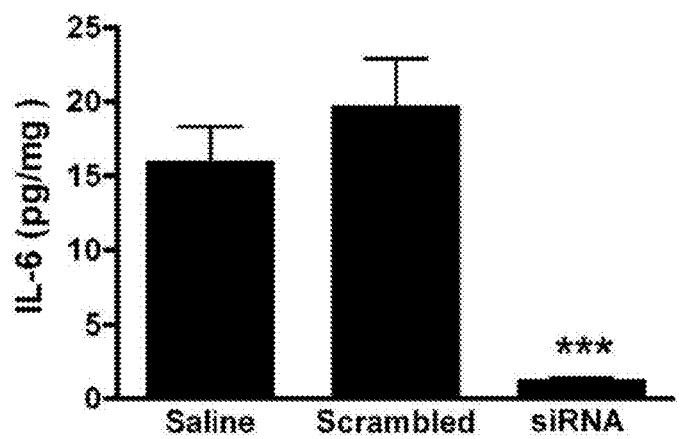
Figure 33E:
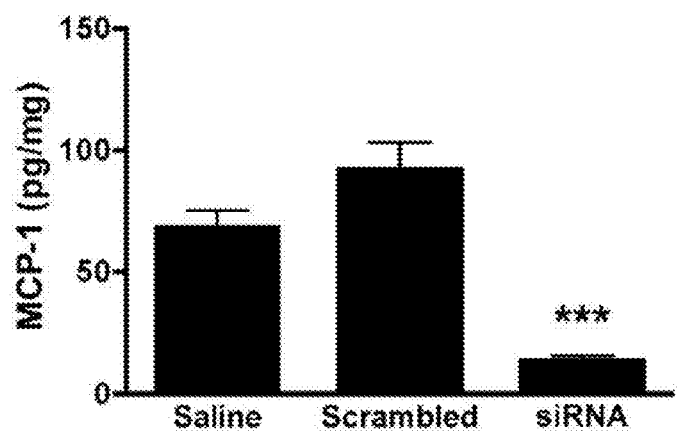
Figure 34A:
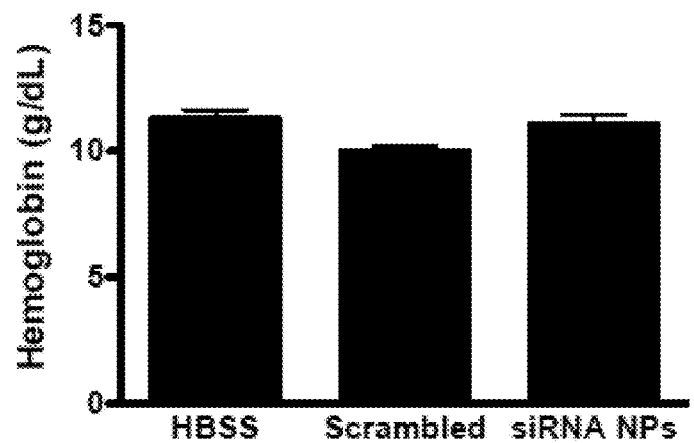
FIG. 34A-E depicts graphs showing hematologic parameters following nanoparticle administration. On day 10, mice were sacrificed and blood obtained for WBC and differentials. N=6-8 mice per treatment group. (A) hemoglobin; (B) HCT; (C) platelet; (D) WBC; and (E) WBC, segmented neutrophils, and lymphocytes.
Figure 34B:
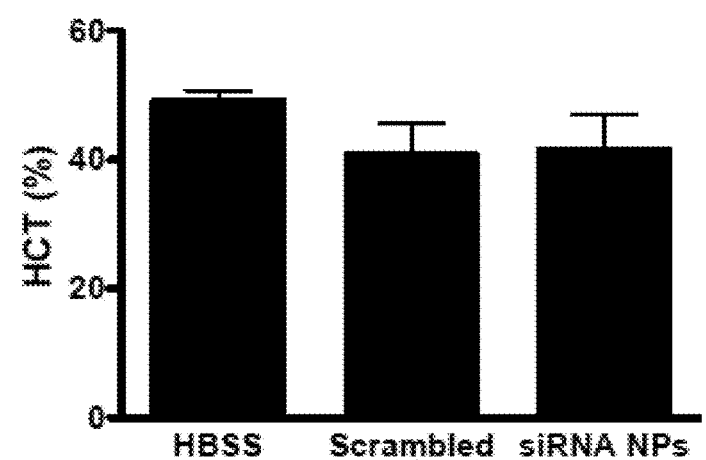
Figure 34C:
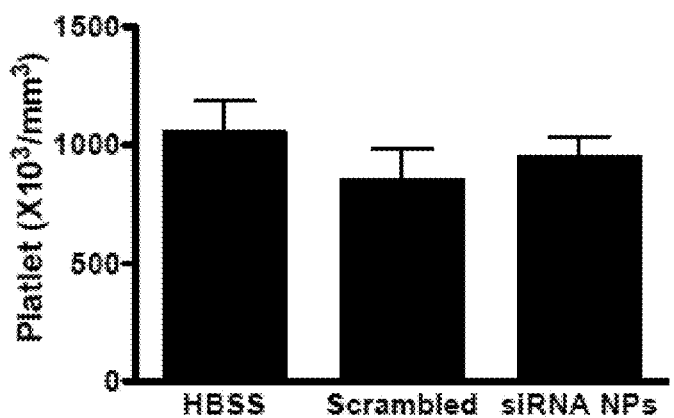
Figure 34D:
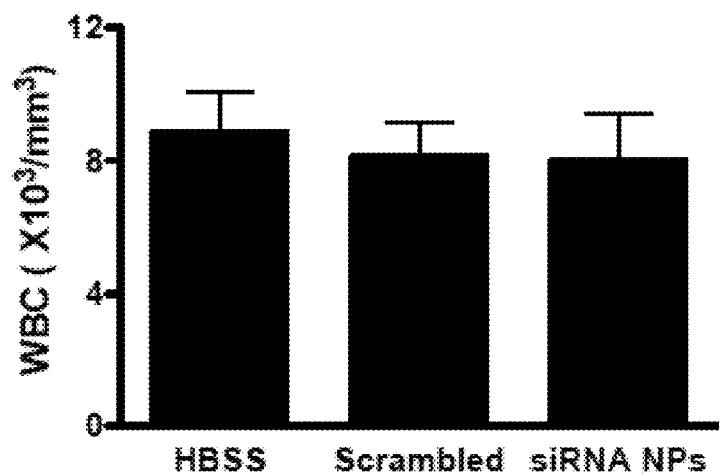
Figure 34E:
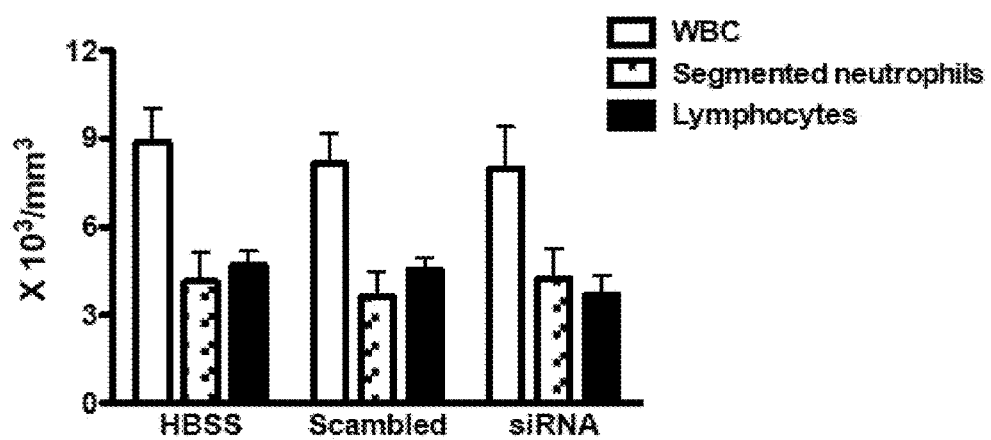
Figure 35A:
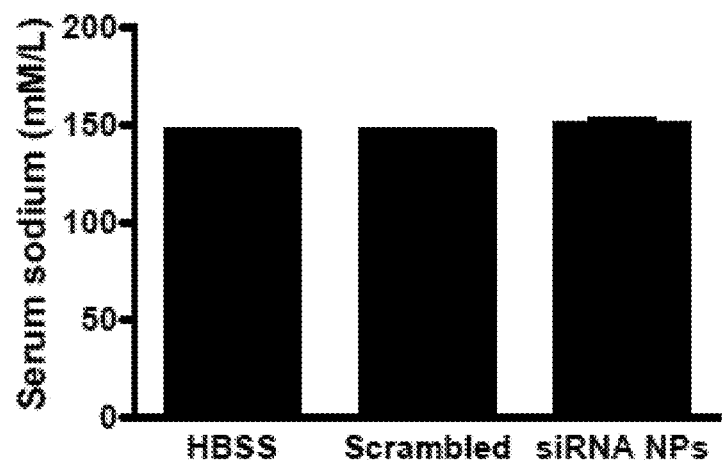
FIG. 35A-E depicts graphs showing renal function following nanoparticle administration. On day 10 mice were sacrificed and blood obtained for electrolyte and renal function analysis. (A) serum sodium; (B) serum chloride; (C) serum potassium; (D) BUN; (E) creatinine.
Figure 35B:
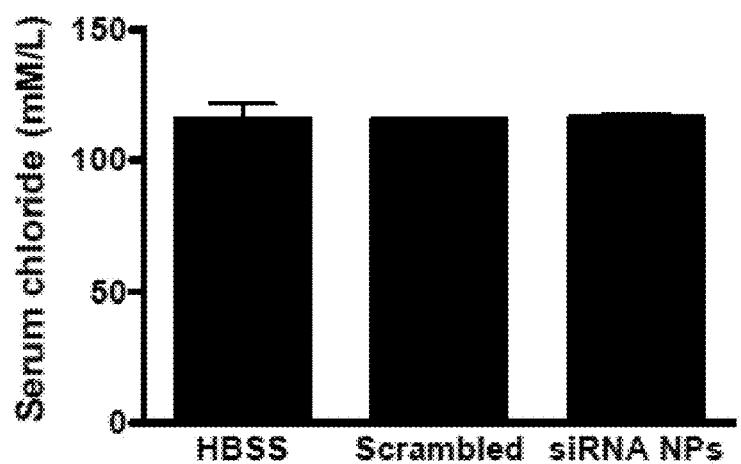
Figure 35C:
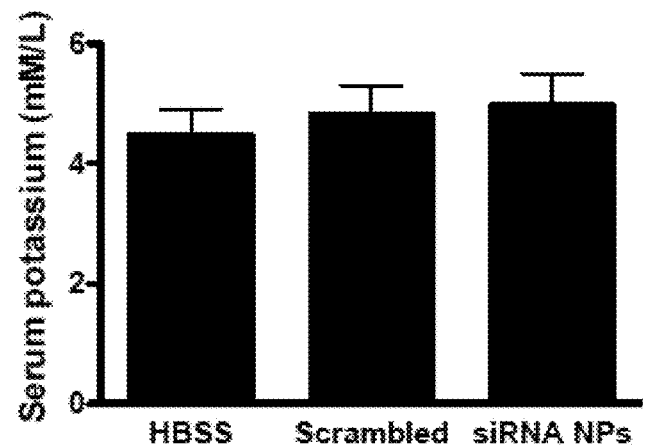
Figure 35D:
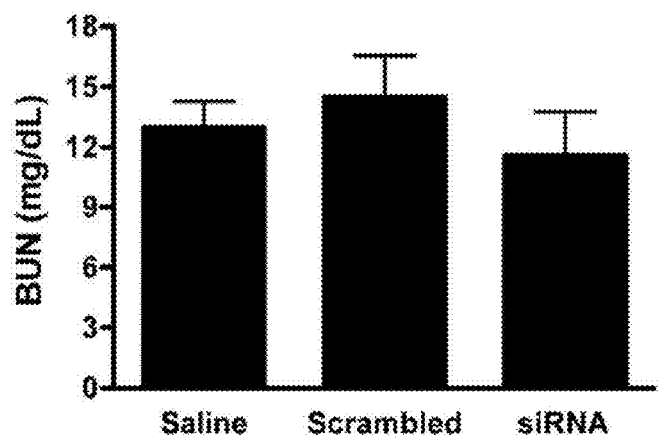
Figure 35E:
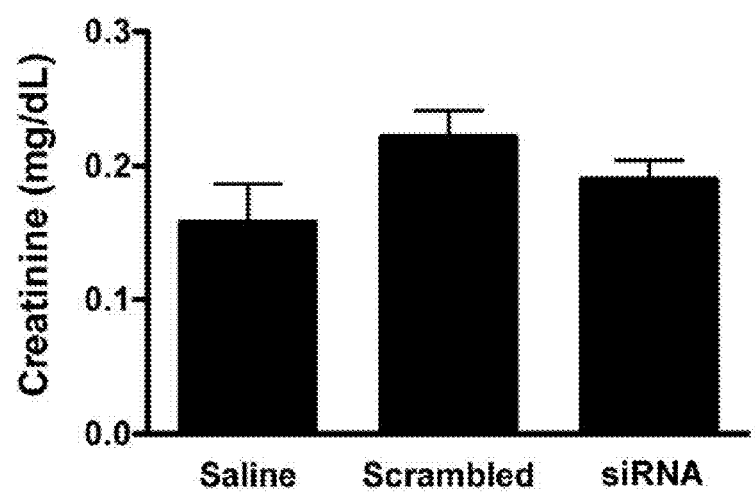

Results: Both ankle thickness and arthritis score are reduced early in the disease process by the active but not the scrambled siRNA (FIG. 32). Body weight did not differ among the groups. p65, the molecular target obtained from paw lysates, was reduced by the active siRNA (FIG. 33). Broad cytokine suppression was observed in paws, consistent with inhibiting the upstream NFkB checkpoint.

Figure 36A:
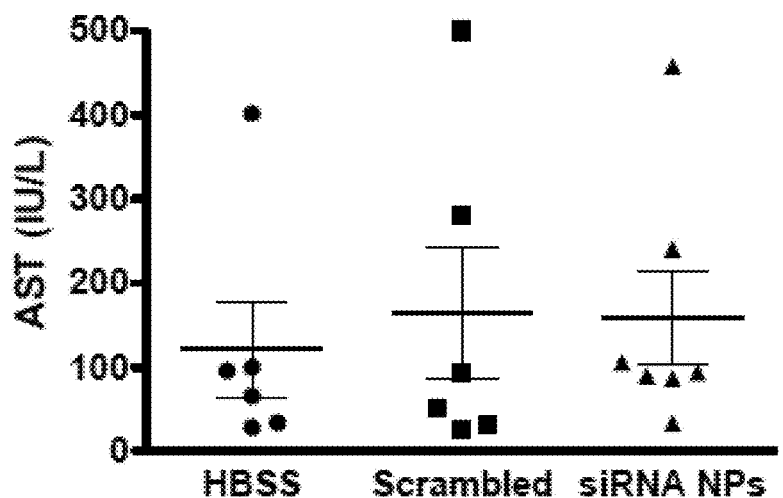
FIG. 36A-C depicts graphs showing hepatic function following nanoparticle administration. On day 10 mice were sacrificed and blood obtained for liver function tests. (A) AST; (B) ALT; (C) total bilirubin.
Figure 36B:
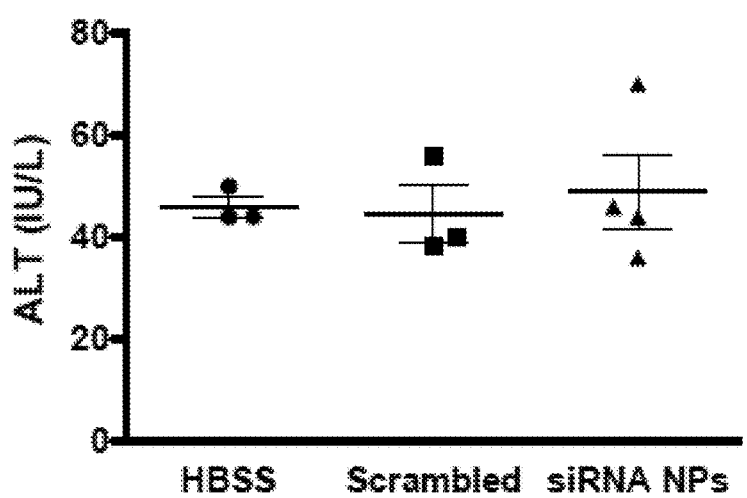
Figure 36C:
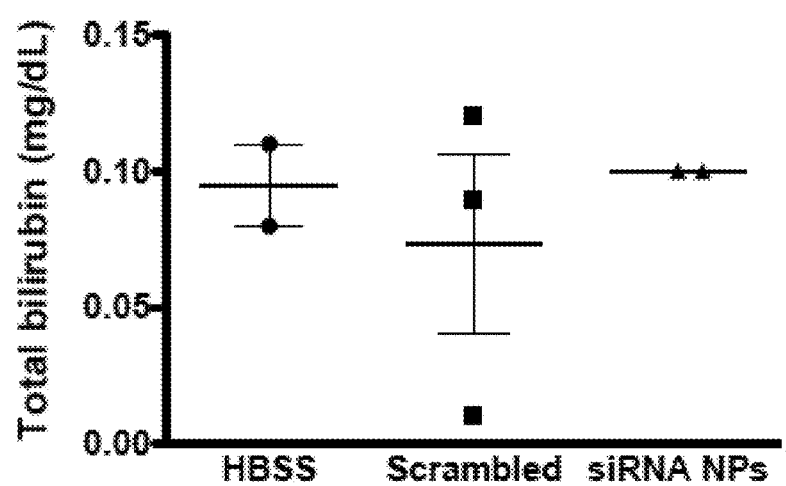
Figure 37:
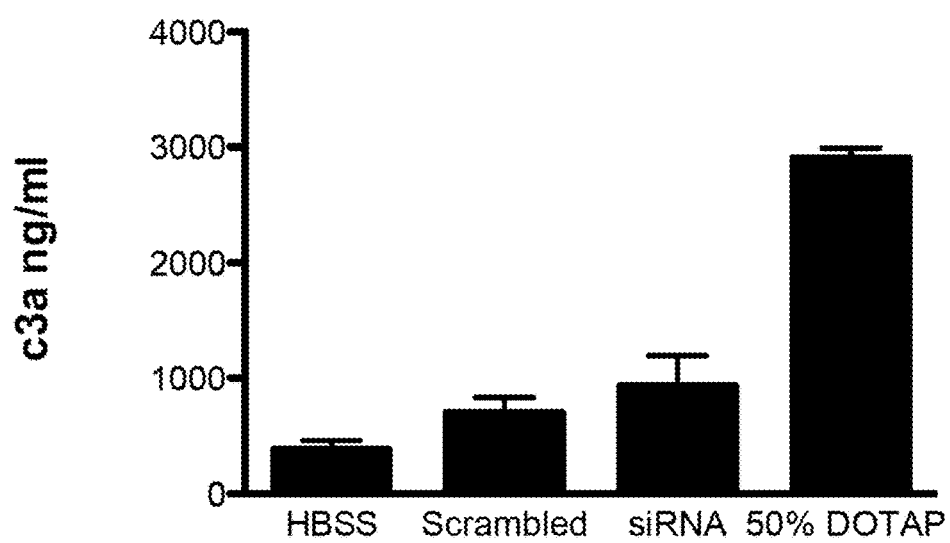
FIG. 37 depicts a graph showing complement activation following nanoparticle administration. Mice were injected i.v. with the indicated control (HBSS) or nanoparticles and plasma collected at 30 min for C3a generation, an indication of complement activation. 50 mol % DOTAP PFOB nanoparticles, which have been shown to strongly activated complement in vivo, served as positive control. There is no statistical significant difference between HBSS and the scrambled or p65-siRNA nanoparticle group.
Figure 38A:
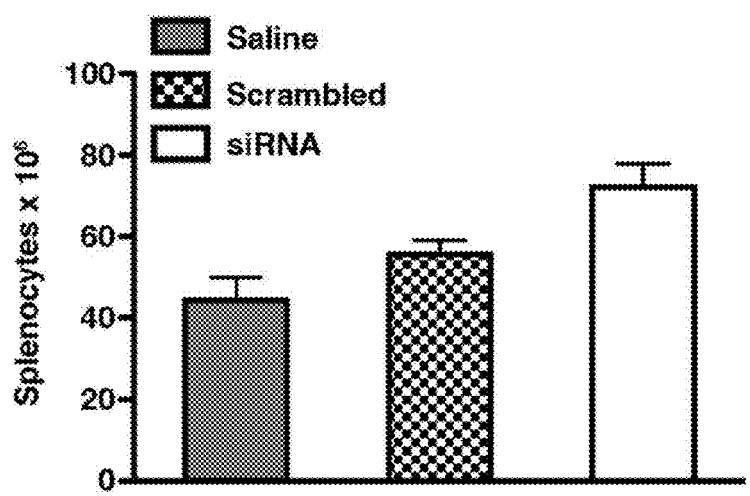
FIG. 38A-B depicts the off target effects of nanoparticles. Spleen was harvested on day 10 and splenocytes enumerated and graphed in (A). Subpopulations of splenocytes were analyzed by flow cytometry and graphed in (B).
Figure 38B:
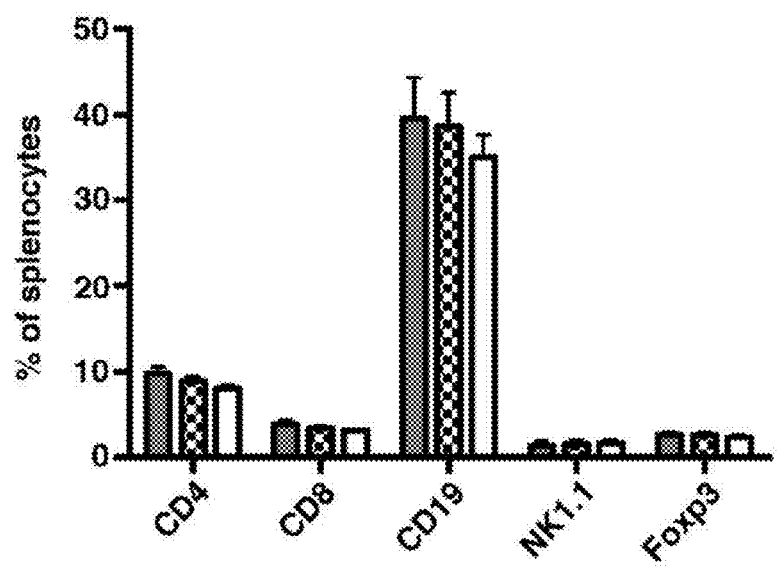
Figure 39A:
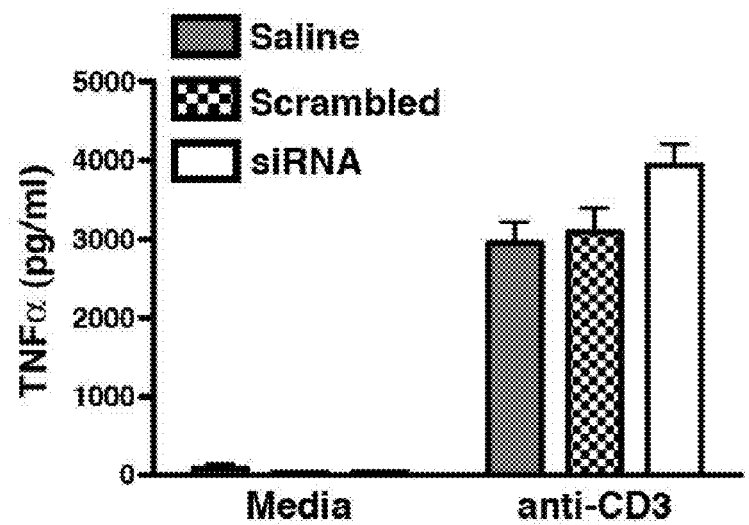
FIG. 39A-D depicts the off target effect of nanoparticles. CD4+ T cells were positively selected from splenocytes and stimulated with plate-bound anti-CD3 monoclonal antibody (5 ug/ml). At 72 h the culture supernatant was analyzed for cytokine secretion by cytometric bead array. (A) TNF-α; (B) IFN-gamma; (C) IL-6; (D) IL-10.
Figure 39B:
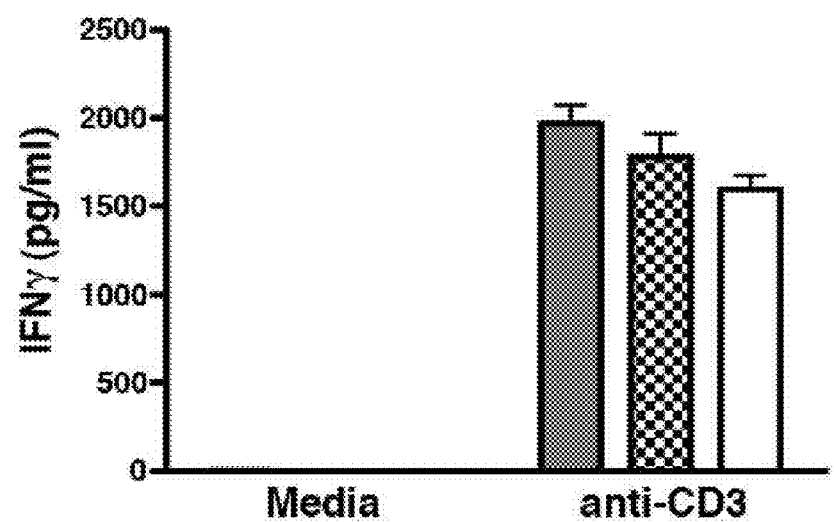
Figure 39C:
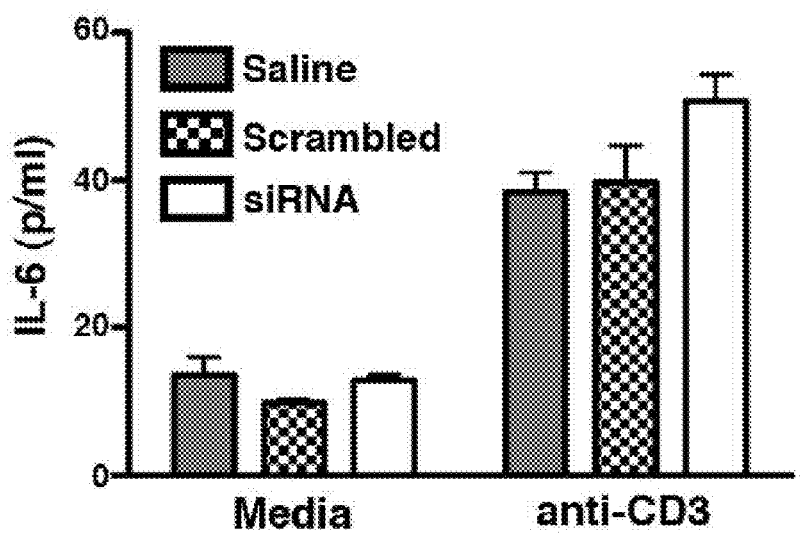
Figure 39D:
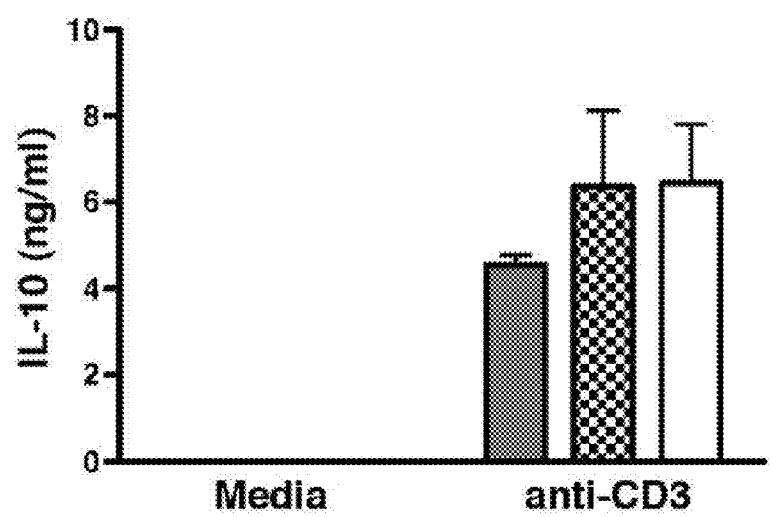

Blood tests performed on the final day of the experiment revealed no changes in RBC's, WBC's (including differential), or platelets (FIG. 34). Renal function tests revealed no changes in relevant serum chemistries or measures of kidney function (FIG. 35) and liver function tests also were unchanged (FIG. 36). Complement activation studies revealed no significant increases associated with nanoparticle therapy, indicating avoidance of innate immune activation (FIG. 37). Very slight elevation in splenocyte counts were observed with no alteration in the types of cells that were present, indicating minimal effects on immune responsiveness to the nanoparticles (FIG. 38).

Figure 40A:
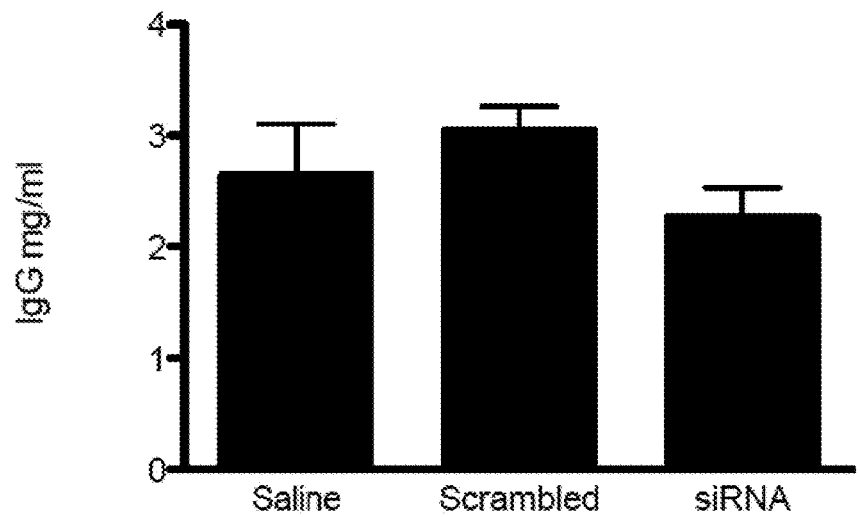
FIG. 40A-B depicts graphs showing the humoral response to siRNA nanoparticles. On day 10 mice were sacrificed and sera collected. Total IgG (A) and IgM (B) levels were measured by sandwich ELISA.
Figure 40B:
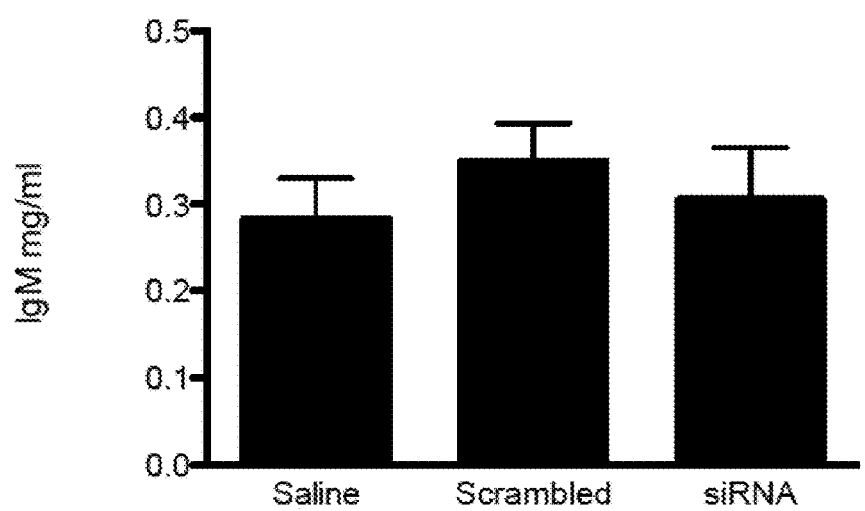
Figure 41A:
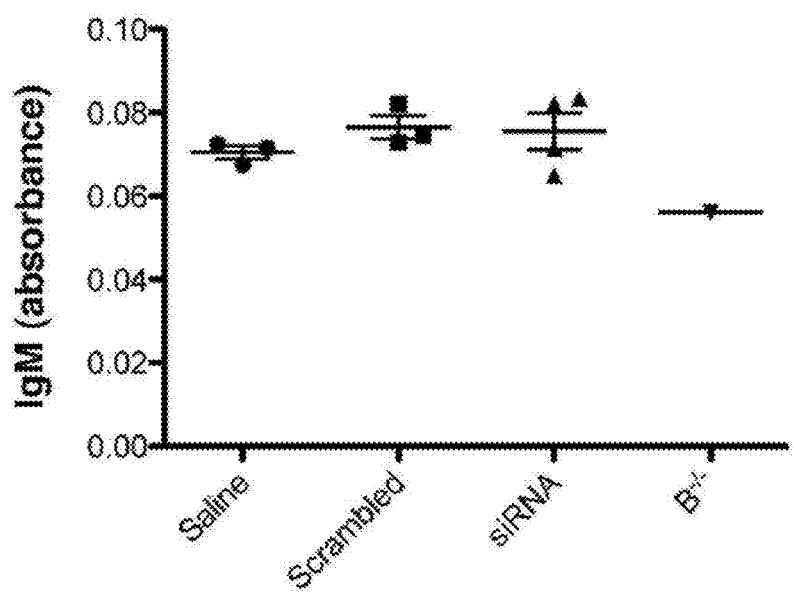
FIG. 41A-D depicts graphs showing the humoral response to nanoparticles. On day 10 mice were sacrificed and sera collected. IgM (A, C) and IgG (B, D) specific response to the peptide-nanoparticles (p5RHH, A-B) and the siRNA-nanoparticles (p5RHH:p65 siRNA, C-D) were assessed using modified sandwich ELISA assay.
Figure 41B:
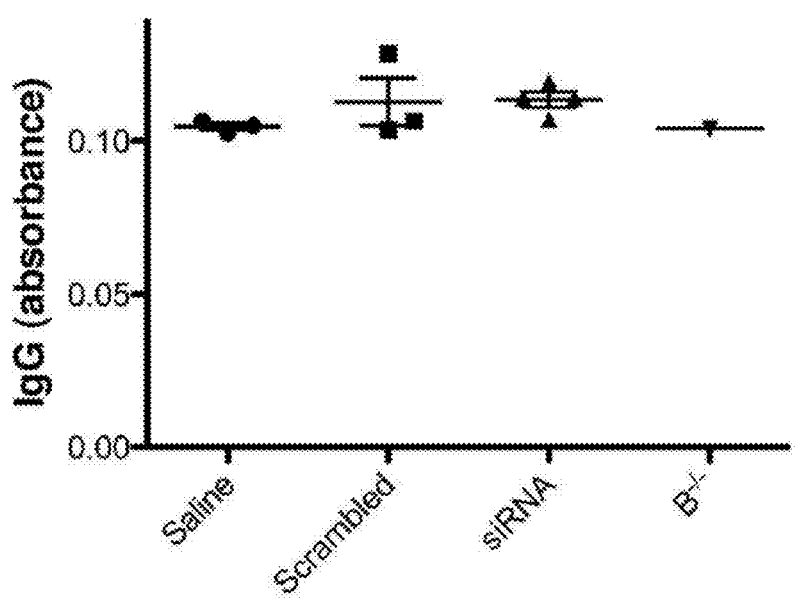
Figure 41C:
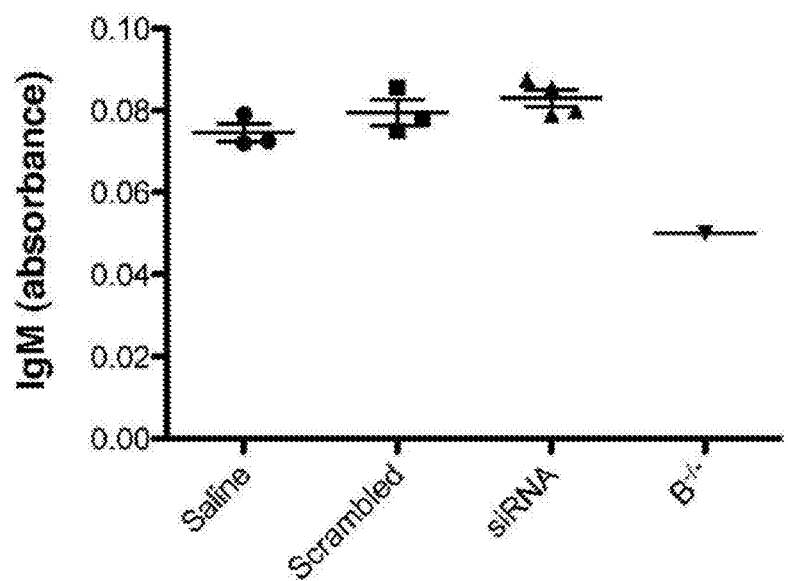
Figure 41D:
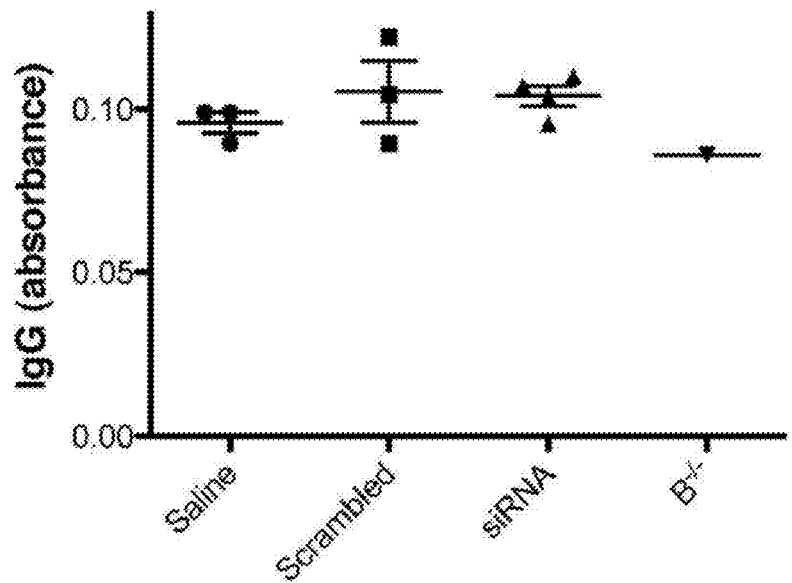
Figure 42A:
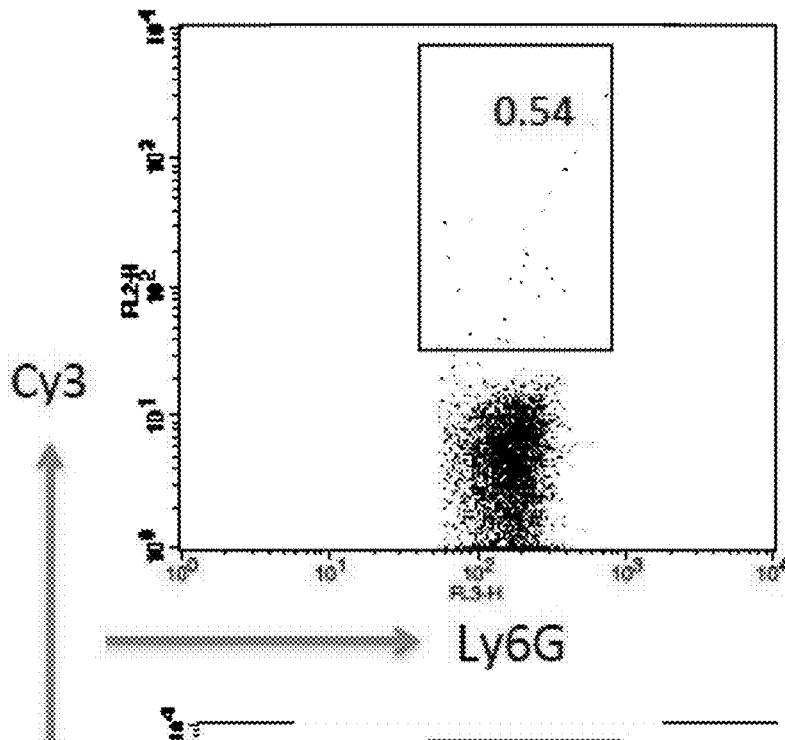
FIG. 42A-D depicts off target nanoparticle uptake in peripheral blood cells. Mice were injected with HBSS (B, D) or nanoparticle containing Cy3-labeled scrambled sequence (A, C). After 30 min mice were sacrificed and peripheral blood white cells were obtained and analyzed for cell-associated nanoparticles (Cy3+ cells) by flow cytometry. Cells were co-stained with Ly6G (neutrophils; A-B) and Ly6C (monocytes; C-D).
Figure 42B:
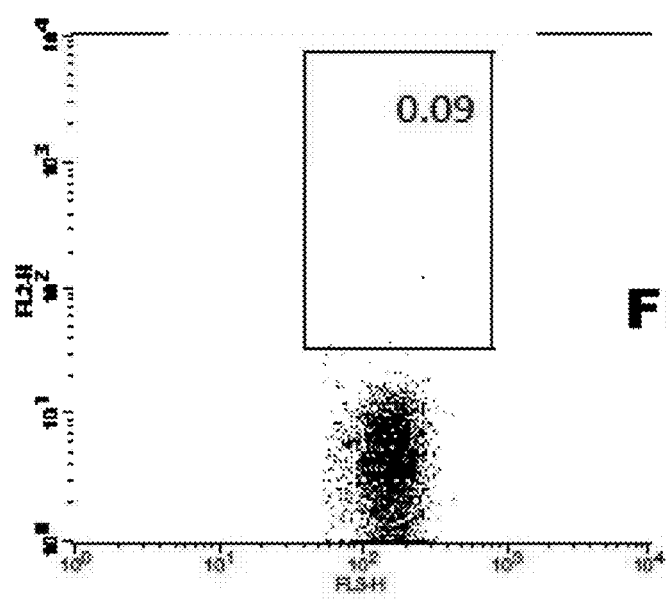
Figure 42C:
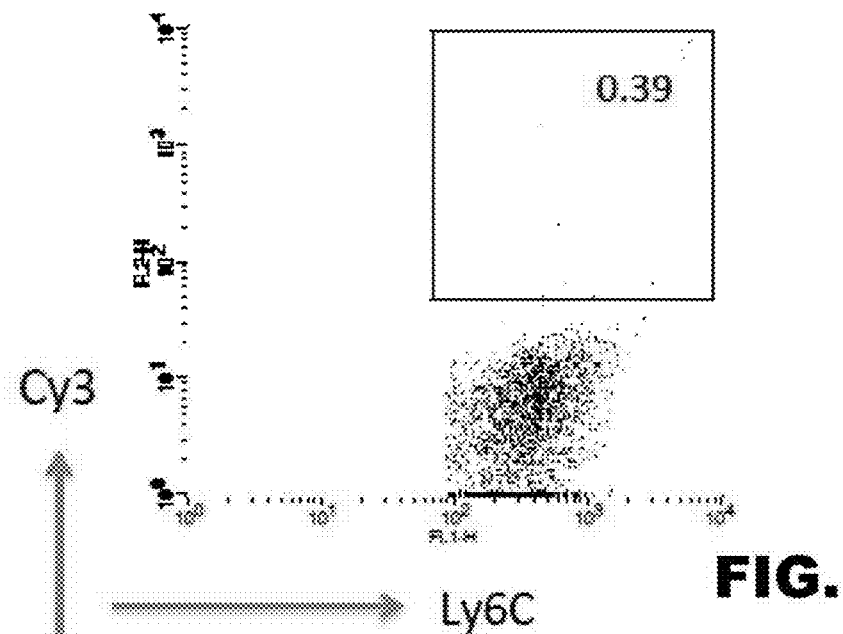
Figure 42D:
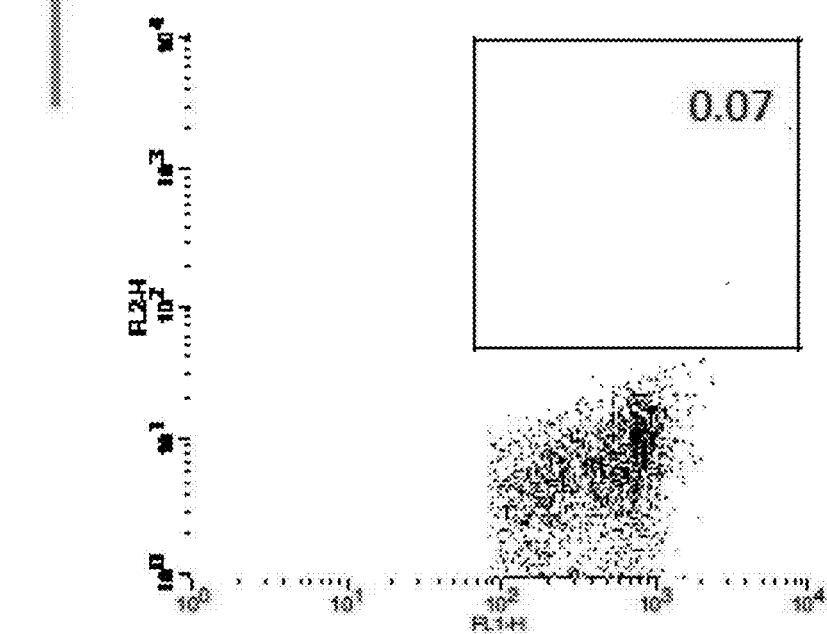

Native immune responsiveness to challenge with anti-CD3 antibody in CD4+ T cells from spleens was well preserved for important immune effectors, indicating that systemic immune responsiveness would be maintained, despite broad local inhibition of inflammation in the affected joints (FIG. 39). No short term induction of antibodies against the siRNA-nanoparticles was observed, indicating lack of stimulation of adaptive immunity and potential to avoid resistance to the agent after serial injections (FIG. 40). No immune responses were observed for either the naked siRNA or the fully formed siRNA particles, confirming lack of adaptive immune stimulation (FIG. 41).

Figure 43A:
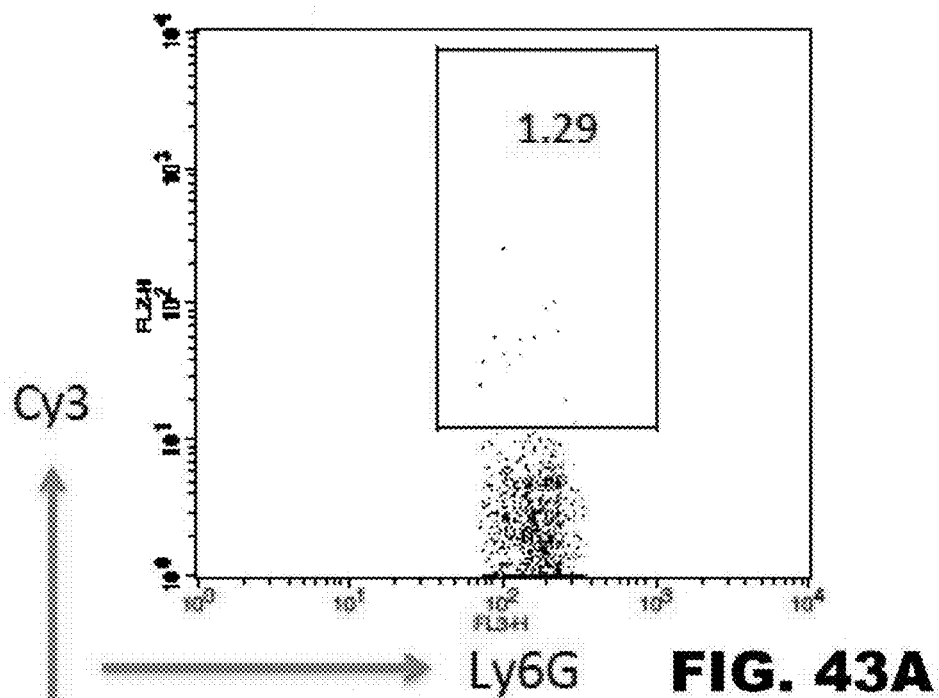
FIG. 43A-D depicts off target nanoparticle uptake in splenocytes. Mice were injected with HBSS (B, D) or nanoparticle containing Cy3-labeled scrambled sequence (A, C). After 30 min mice were sacrificed and splenocytes were obtained and analyzed for cell-associated nanoparticles (Cy3+ cells; y-axis) by flow cytometry. Cells were co-stained with Ly6G (neutrophils; A, B) and Ly6C (monocytes; C, D).
Figure 43B:
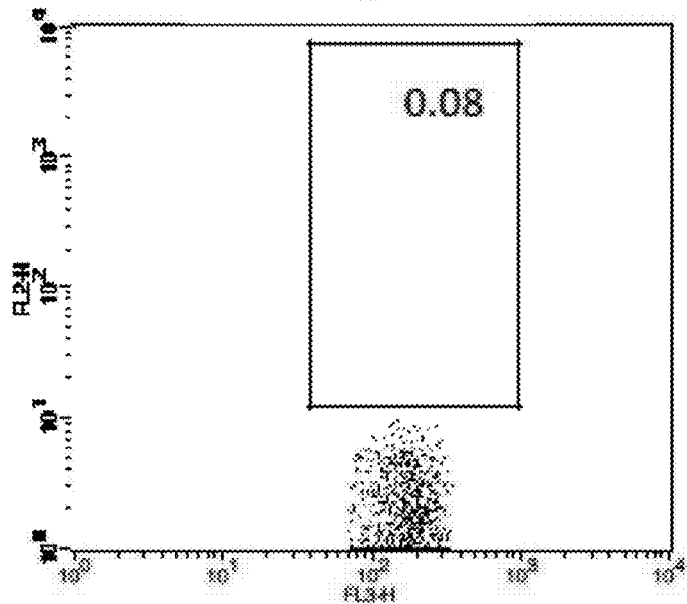
Figures 43C, 43D:
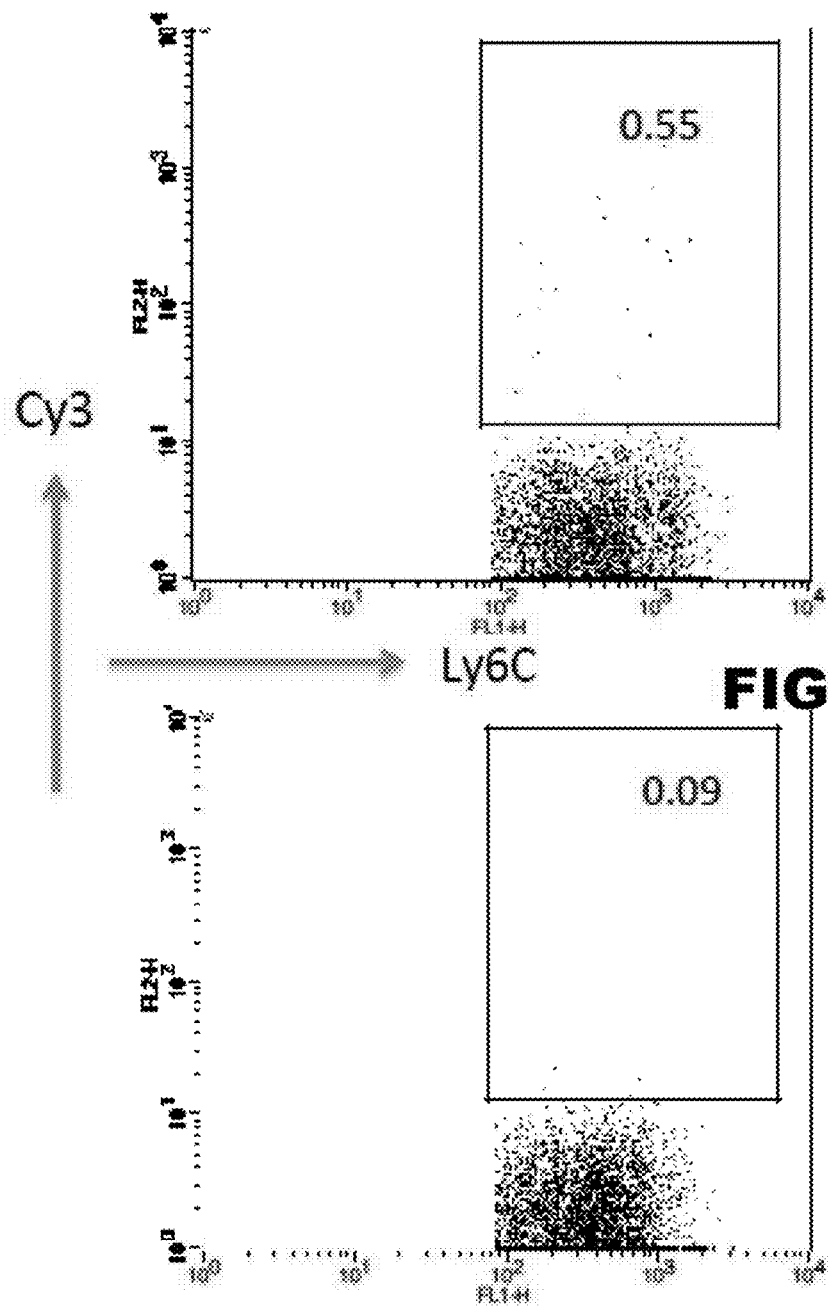

To rule out delivery of nanoparticle complexes to joints by white blood cells, lack of uptake of particles in the peripheral circulation by neutrophils and monocytes was confirmed by flow cytometry, showing only minimal signals from nanoparticles associated with these cell types, which are otherwise prominent components of the inflammatory process. This suggests that the likely target cell type already is resident in the joints themselves and not inhibited in the peripheral circulation before arriving in the joints (FIG. 42). In the spleen, it is also apparent that neutrophils and monocytes do not take up the particles to any significant extent, confirming that the nanoparticles avoid the spleen and will not stimulate an immune response, nor be transported to inflamed tissues by activated splenocytes (FIG. 43).

What is claimed is:

1. A pharmaceutical composition comprising a peptide-polynucleotide complex, the peptide-polynucleotide complex comprising a ratio of peptide:polynucleotide that is more than about 50:1 and less than about 200:1, wherein the peptide is (a) non-lytic, non-cytotoxic, and capable of affecting the release of a polynucleotide from an endosome of a cell, and (b) comprises an amino acid sequence with (i) at least 80% identity to an amino acid sequence chosen from SEQ ID NO: 1, SEQ ID NO: 57 or SEQ ID NO: 63, and (ii) two or more contiguous, basic amino acids (a cationic region) and one or more histidine residues located adjacent to the cationic region.

2. The composition of claim 1, wherein the ratio of peptide to oligonucleotide is about 50:1 to about 100:1.

3. The composition of claim 1, wherein the complex is a nanoparticle with a diameter of about 50 nm to about 200 nm.

4. The composition of claim 1, wherein the peptide comprises an amino acid sequence with at least 90% identity to an amino acid sequence chosen from SEQ ID NO: 1, SEQ ID NO: 57 or SEQ ID NO: 63.

5. The composition of claim 1, wherein the polynucleotide is a non-coding RNA capable of regulating or inhibiting the expression of a nucleic acid sequence.

6. The composition of claim 1, wherein the polynucleotide is a small interfering RNA (siRNA) or an microRNA (miRNA).

7. The composition of claim 1, wherein the complex is coated with albumin.

8. The composition of claim 1, wherein the polynucleotide of the complex disrupts at least one nucleic acid sequence encoding a protein selected from the group consisting of STAT3, JNK2, p65, and p100/52.

9. A method of delivering a polynucleotide to the cytoplasm of a cell, the method comprising contacting a cell with a peptide-polynucleotide complex, the peptide-polynucleotide complex comprising a ratio of peptide : polynucleotide that is more than about 50:1 and less than about 200:1, wherein the peptide is (a) non-lytic, non-cytotoxic, and capable of affecting the release of a polynucleotide from an endosome of a cell, and (b) comprises an amino acid sequence with (i) at least 80% identity to an amino acid sequence chosen from SEQ ID NO: 1, SEQ ID NO: 57 or SEQ ID NO: 63, and (ii) two or more contiguous, basic amino acids (a cationic region) and one or more histidine residues located adjacent to the cationic region.

10. The method of claim 9, wherein the polynucleotide is delivered to the cytoplasm of a cell in a subject in need thereof and the method comprises administering to the subject a therapeutically effective amount of a pharmaceutical composition comprising the peptide-polynucleotide complex.

11. The method of claim 9, wherein:
(a) the polynucleotide disrupts a nucleotide normally associated with the NFκB signaling pathway and the subject needs therapeutic treatment for a tumor;
(b) the polynucleotide disrupts a nucleotide normally associated with the NFκB signaling pathway and the subject needs therapeutic treatment for arthritis;
(c) the polynucleotide disrupts STAT3 expression in a cell and the subject needs therapeutic treatment to inhibit angiogenesis;
(d) the polynucleotide disrupts JNK2 expression in a cell and the subject need therapeutic treatment to inhibit foam cell formation; or
(e) the polynucleotide disrupts p65 expression in a cell and the subject need therapeutic treatment for arthritis.

12. A peptide comprising an amino acid sequence that has (a) at least 80% identity to an amino acid sequence chosen from SEQ ID NO: 1, SEQ ID NO: 57 or SEQ ID NO: 63, and (b) two or more contiguous, basic amino acids (a cationic region) and one or more histidine residues located adjacent to the cationic region, wherein a therapeutically effective amount of the peptide is non-lytic, non-cytotoxic, and capable of affecting the release of a polynucleotide from an endosome of a cell.

13. The peptide of claim 12, wherein the peptide comprises an amino acid sequence that has at least 90% identity to an amino acid sequence chosen from SEQ ID NO: 1, SEQ ID NO: 57 or SEQ ID NO: 63.

14. The peptide of claim 13, wherein the peptide comprises an amino acid sequence that has at least 95% identity to an amino acid sequence chosen from SEQ ID NO: 1, SEQ ID NO: 57 or SEQ ID NO: 63.

15. The peptide of claim 14, wherein the peptide comprises an amino acid sequence that has 100% identity to an amino acid sequence chosen from SEQ ID NO: 1, SEQ ID NO: 57 or SEQ ID NO: 63.

* * * * *

SEQUENCE LISTING

```
<160> NUMBER OF SEQ ID NOS: 68

<210> SEQ ID NO 1
<211> LENGTH: 21
<212> TYPE: PRT
<213> ORGANISM: Artificial Sequence
<220> FEATURE:
<223> OTHER INFORMATION: SYNTHESIZED

<400> SEQUENCE: 1
```

Val Leu Thr Thr Gly Leu Pro Ala Leu Ile Ser Trp Ile Arg Arg Arg
1               5                   10                  15

His Arg Arg His Cys
            20

<210> SEQ ID NO 2
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 2

Val Leu Thr Thr Gly Leu Pro Ala Leu Ile Ser Trp Ile Arg Arg Arg
1               5                   10                  15

His

<210> SEQ ID NO 3
<211> LENGTH: 18
<212> TYPE: PRT
<213> ORGANISM: Artificial Sequence
<220> FEATURE:
<223> OTHER INFORMATION: SYNTHESIZED

<400> SEQUENCE: 3

Val Leu Thr Thr Gly Leu Pro Ala Leu Ile Ser Trp Ile Arg Arg Arg
1               5                   10                  15

His Arg

<210> SEQ ID NO 4
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 4

Val Leu Thr Thr Gly Leu Pro Ala Leu Ile Ser Trp Ile Arg Arg Arg
1               5                   10                  15

His Arg Arg

<210> SEQ ID NO 5
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 5

Val Leu Thr Thr Gly Leu Pro Ala Leu Ile Ser Trp Ile Arg Arg Arg
1               5                   10                  15

His Arg Arg His
            20

<210> SEQ ID NO 6
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 6

Leu Thr Thr Gly Leu Pro Ala Leu Ile Ser Trp Ile Arg Arg Arg His
1               5                   10                  15

```
<210> SEQ ID NO 7
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 7

Leu Thr Thr Gly Leu Pro Ala Leu Ile Ser Trp Ile Arg Arg Arg His
1               5                   10                  15

Arg

<210> SEQ ID NO 8
<211> LENGTH: 18
<212> TYPE: PRT
<213> ORGANISM: Artificial Sequence
<220> FEATURE:
<223> OTHER INFORMATION: SYNTHESIZED

<400> SEQUENCE: 8

Leu Thr Thr Gly Leu Pro Ala Leu Ile Ser Trp Ile Arg Arg Arg His
1               5                   10                  15

Arg Arg

<210> SEQ ID NO 9
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 9

Leu Thr Thr Gly Leu Pro Ala Leu Ile Ser Trp Ile Arg Arg Arg His
1               5                   10                  15

Arg Arg His

<210> SEQ ID NO 10
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 10

Leu Thr Thr Gly Leu Pro Ala Leu Ile Ser Trp Ile Arg Arg Arg His
1               5                   10                  15

Arg Arg His Cys
            20

<210> SEQ ID NO 11
<211> LENGTH: 15
<212> TYPE: PRT
<213> ORGANISM: Artificial Sequence
<220> FEATURE:
<223> OTHER INFORMATION: SYNTHESIZED

<400> SEQUENCE: 11

Thr Thr Gly Leu Pro Ala Leu Ile Ser Trp Ile Arg Arg Arg His
1               5                   10                  15

<210> SEQ ID NO 12
<211> LENGTH: 16
<212> TYPE: PRT
```

```
<213> ORGANISM: Artificial Sequence
<220> FEATURE:
<223> OTHER INFORMATION: SYNTHESIZED

<400> SEQUENCE: 12

Thr Thr Gly Leu Pro Ala Leu Ile Ser Trp Ile Arg Arg Arg His Arg
1               5                   10                  15

<210> SEQ ID NO 13
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 13

Thr Thr Gly Leu Pro Ala Leu Ile Ser Trp Ile Arg Arg Arg His Arg
1               5                   10                  15

Arg

<210> SEQ ID NO 14
<211> LENGTH: 18
<212> TYPE: PRT
<213> ORGANISM: Artificial Sequence
<220> FEATURE:
<223> OTHER INFORMATION: SYNTHESIZED

<400> SEQUENCE: 14

Thr Thr Gly Leu Pro Ala Leu Ile Ser Trp Ile Arg Arg Arg His Arg
1               5                   10                  15

Arg His

<210> SEQ ID NO 15
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 15

Thr Thr Gly Leu Pro Ala Leu Ile Ser Trp Ile Arg Arg Arg His Arg
1               5                   10                  15

Arg His Cys

<210> SEQ ID NO 16
<211> LENGTH: 14
<212> TYPE: PRT
<213> ORGANISM: Artificial Sequence
<220> FEATURE:
<223> OTHER INFORMATION: SYNTHESIZED

<400> SEQUENCE: 16

Thr Gly Leu Pro Ala Leu Ile Ser Trp Ile Arg Arg Arg His
1               5                   10

<210> SEQ ID NO 17
<211> LENGTH: 15
<212> TYPE: PRT
<213> ORGANISM: Artificial Sequence
<220> FEATURE:
<223> OTHER INFORMATION: SYNTHESIZED

<400> SEQUENCE: 17

Thr Gly Leu Pro Ala Leu Ile Ser Trp Ile Arg Arg Arg His Arg
1               5                   10                  15
```

```
<210> SEQ ID NO 18
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 18

Thr Gly Leu Pro Ala Leu Ile Ser Trp Ile Arg Arg Arg His Arg Arg
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 19

Thr Gly Leu Pro Ala Leu Ile Ser Trp Ile Arg Arg Arg His Arg Arg
1               5                   10                  15

His

<210> SEQ ID NO 20
<211> LENGTH: 18
<212> TYPE: PRT
<213> ORGANISM: Artificial Sequence
<220> FEATURE:
<223> OTHER INFORMATION: SYNTHESIZED

<400> SEQUENCE: 20

Thr Gly Leu Pro Ala Leu Ile Ser Trp Ile Arg Arg Arg His Arg Arg
1               5                   10                  15

His Cys

<210> SEQ ID NO 21
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 21

Gly Leu Pro Ala Leu Ile Ser Trp Ile Arg Arg Arg His
1               5                   10

<210> SEQ ID NO 22
<211> LENGTH: 14
<212> TYPE: PRT
<213> ORGANISM: Artificial Sequence
<220> FEATURE:
<223> OTHER INFORMATION: SYNTHESIZED

<400> SEQUENCE: 22

Gly Leu Pro Ala Leu Ile Ser Trp Ile Arg Arg Arg His Arg
1               5                   10

<210> SEQ ID NO 23
<211> LENGTH: 15
<212> TYPE: PRT
<213> ORGANISM: Artificial Sequence
<220> FEATURE:
<223> OTHER INFORMATION: SYNTHESIZED

<400> SEQUENCE: 23
```

Gly Leu Pro Ala Leu Ile Ser Trp Ile Arg Arg Arg His Arg Arg
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: SYNTHESIZE

<400> SEQUENCE: 24

Gly Leu Pro Ala Leu Ile Ser Trp Ile Arg Arg Arg His Arg Arg His
1               5                   10                  15

<210> SEQ ID NO 25
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 25

Gly Leu Pro Ala Leu Ile Ser Trp Ile Arg Arg Arg His Arg Arg His
1               5                   10                  15

Cys

<210> SEQ ID NO 26
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 26

Leu Pro Ala Leu Ile Ser Trp Ile Arg Arg Arg His
1               5                   10

<210> SEQ ID NO 27
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 27

Leu Pro Ala Leu Ile Ser Trp Ile Arg Arg Arg His Arg
1               5                   10

<210> SEQ ID NO 28
<211> LENGTH: 14
<212> TYPE: PRT
<213> ORGANISM: Artificial Sequence
<220> FEATURE:
<223> OTHER INFORMATION: SYNTHESIZED

<400> SEQUENCE: 28

Leu Pro Ala Leu Ile Ser Trp Ile Arg Arg Arg His Arg Arg
1               5                   10

<210> SEQ ID NO 29
<211> LENGTH: 15
<212> TYPE: PRT
<213> ORGANISM: Artificial Sequence
<220> FEATURE:
<223> OTHER INFORMATION: SYNTHESIZED

```
<400> SEQUENCE: 29

Leu Pro Ala Leu Ile Ser Trp Ile Arg Arg Arg His Arg Arg His
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 30

Leu Pro Ala Leu Ile Ser Trp Ile Arg Arg Arg His Arg Arg His Cys
1               5                   10                  15

<210> SEQ ID NO 31
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 31

Pro Ala Leu Ile Ser Trp Ile Arg Arg Arg His
1               5                   10

<210> SEQ ID NO 32
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 32

Pro Ala Leu Ile Ser Trp Ile Arg Arg Arg His Arg
1               5                   10

<210> SEQ ID NO 33
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 33

Pro Ala Leu Ile Ser Trp Ile Arg Arg Arg His Arg Arg
1               5                   10

<210> SEQ ID NO 34
<211> LENGTH: 14
<212> TYPE: PRT
<213> ORGANISM: Artificial Sequence
<220> FEATURE:
<223> OTHER INFORMATION: SYNTHESIZED

<400> SEQUENCE: 34

Pro Ala Leu Ile Ser Trp Ile Arg Arg Arg His Arg Arg His
1               5                   10

<210> SEQ ID NO 35
<211> LENGTH: 15
<212> TYPE: PRT
<213> ORGANISM: Artificial Sequence
<220> FEATURE:
<223> OTHER INFORMATION: SYNTHESIZE

<400> SEQUENCE: 35
```

```
Pro Ala Leu Ile Ser Trp Ile Arg Arg His Arg His Cys
1               5                   10                  15
```

<210> SEQ ID NO 36
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 36

```
Ala Leu Ile Ser Trp Ile Arg Arg Arg His
1               5                   10
```

<210> SEQ ID NO 37
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 37

```
Ala Leu Ile Ser Trp Ile Arg Arg Arg His Arg
1               5                   10
```

<210> SEQ ID NO 38
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 38

```
Ala Leu Ile Ser Trp Ile Arg Arg Arg His Arg Arg
1               5                   10
```

<210> SEQ ID NO 39
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 39

```
Ala Leu Ile Ser Trp Ile Arg Arg Arg His Arg His
1               5                   10
```

<210> SEQ ID NO 40
<211> LENGTH: 14
<212> TYPE: PRT
<213> ORGANISM: Artificial Sequence
<220> FEATURE:
<223> OTHER INFORMATION: SYNTHESIZED

<400> SEQUENCE: 40

```
Ala Leu Ile Ser Trp Ile Arg Arg Arg His Arg His Cys
1               5                   10
```

<210> SEQ ID NO 41
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 41

Leu Ile Ser Trp Ile Arg Arg Arg His Arg
1               5                   10

<210> SEQ ID NO 42
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 42

Leu Ile Ser Trp Ile Arg Arg Arg His Arg Arg
1               5                   10

<210> SEQ ID NO 43
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 43

Leu Ile Ser Trp Ile Arg Arg Arg His Arg Arg His
1               5                   10

<210> SEQ ID NO 44
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 44

Leu Ile Ser Trp Ile Arg Arg Arg His Arg Arg His Cys
1               5                   10

<210> SEQ ID NO 45
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 45

Ile Ser Trp Ile Arg Arg Arg His Arg Arg
1               5                   10

<210> SEQ ID NO 46
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 46

Ile Ser Trp Ile Arg Arg Arg His Arg Arg His
1               5                   10

<210> SEQ ID NO 47
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 47

Ile Ser Trp Ile Arg Arg Arg His Arg Arg His Cys

```
<210> SEQ ID NO 48
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 48

Ser Trp Ile Arg Arg Arg His Arg Arg His
1               5                   10

<210> SEQ ID NO 49
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 49

Ser Trp Ile Arg Arg Arg His Arg Arg His Cys
1               5                   10

<210> SEQ ID NO 50
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 50

Trp Ile Arg Arg Arg His Arg Arg His Cys
1               5                   10

<210> SEQ ID NO 51
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 51
ggaguacccu gaagcuaua                                                19

<210> SEQ ID NO 52
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 52
gaaagaagac agagccuau                                                19

<210> SEQ ID NO 53
<211> LENGTH: 26
<212> TYPE: PRT
<213> ORGANISM: Apis cerana

<400> SEQUENCE: 53

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

<210> SEQ ID NO 54
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 54

Val Leu Thr Thr Gly Leu Pro Ala Leu Ile Ser Trp Ile Lys Arg Lys
1               5                   10                  15

Arg Gln Gln Cys
            20

<210> SEQ ID NO 55
<211> LENGTH: 25
<212> TYPE: PRT
<213> ORGANISM: Artificial Sequence
<220> FEATURE:
<223> OTHER INFORMATION: SYNTHESIZED

<400> SEQUENCE: 55

Val Leu Thr Thr Gly Leu Pro Ala Leu Ile Ser Trp Ile Lys Arg Lys
1               5                   10                  15

Arg Gln Gln Arg Trp Arg Arg Arg Arg
            20                  25

<210> SEQ ID NO 56
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 56
gacguaaacg gccacaaguu c                                         21

<210> SEQ ID NO 57
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 57

Val Leu Thr Thr Gly Leu Pro Ala Leu Ile Ser Trp Ile Arg Arg Arg
1               5                   10                  15

His Arg Arg Cys
            20

<210> SEQ ID NO 58
<211> LENGTH: 15
<212> TYPE: PRT
<213> ORGANISM: Artificial Sequence
<220> FEATURE:
<223> OTHER INFORMATION: SYNTHESIZED

<400> SEQUENCE: 58

Val Leu Thr Thr Gly Leu Pro Ala Leu Ile Ser Trp Ile Arg Arg
1               5                   10                  15

<210> SEQ ID NO 59
<211> LENGTH: 16
<212> TYPE: PRT
<213> ORGANISM: Artificial Sequence
<220> FEATURE:

<223> OTHER INFORMATION: SYNTHESIZED

<400> SEQUENCE: 59

Val Leu Thr Thr Gly Leu Pro Ala Leu Ile Ser Trp Ile Arg Arg Arg
1               5                   10                  15

<210> SEQ ID NO 60
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 60

Val Leu Thr Thr Gly Leu Pro Ala Leu Ile Ser Trp Ile Arg Arg Arg
1               5                   10                  15

His

<210> SEQ ID NO 61
<211> LENGTH: 18
<212> TYPE: PRT
<213> ORGANISM: Artificial Sequence
<220> FEATURE:
<223> OTHER INFORMATION: SYNTHESIZED

<400> SEQUENCE: 61

Val Leu Thr Thr Gly Leu Pro Ala Leu Ile Ser Trp Ile Arg Arg Arg
1               5                   10                  15

His Arg

<210> SEQ ID NO 62
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 62

Val Leu Thr Thr Gly Leu Pro Ala Leu Ile Ser Trp Ile Arg Arg Arg
1               5                   10                  15

His Arg Arg

<210> SEQ ID NO 63
<211> LENGTH: 23
<212> TYPE: PRT
<213> ORGANISM: Artificial Sequence
<220> FEATURE:
<223> OTHER INFORMATION: SYNTHESIZED

<400> SEQUENCE: 63

Val Leu Lys Val Leu Thr Thr Leu Ala Pro Ala Leu Ile Ser Trp Ile
1               5                   10                  15

Arg Arg Arg His Arg Arg Cys
            20

<210> SEQ ID NO 64
<211> LENGTH: 18
<212> TYPE: PRT
<213> ORGANISM: Artificial Sequence
<220> FEATURE:
<223> OTHER INFORMATION: SYNTHESIZED

<400> SEQUENCE: 64

Val Leu Lys Val Leu Thr Thr Leu Ala Pro Ala Leu Ile Ser Trp Ile

```
1               5                   10                  15
Arg Arg

<210> SEQ ID NO 65
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 65

Val Leu Lys Val Leu Thr Thr Leu Ala Pro Ala Leu Ile Ser Trp Ile
1               5                   10                  15

Arg Arg Arg

<210> SEQ ID NO 66
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 66

Val Leu Lys Val Leu Thr Thr Leu Ala Pro Ala Leu Ile Ser Trp Ile
1               5                   10                  15

Arg Arg Arg His
            20

<210> SEQ ID NO 67
<211> LENGTH: 21
<212> TYPE: PRT
<213> ORGANISM: Artificial Sequence
<220> FEATURE:
<223> OTHER INFORMATION: SYNTHESIZED

<400> SEQUENCE: 67

Val Leu Lys Val Leu Thr Thr Leu Ala Pro Ala Leu Ile Ser Trp Ile
1               5                   10                  15

Arg Arg Arg His Arg
            20

<210> SEQ ID NO 68
<211> LENGTH: 22
<212> TYPE: PRT
<213> ORGANISM: Artificial Sequence
<220> FEATURE:
<223> OTHER INFORMATION: SYNTHESIZED

<400> SEQUENCE: 68

Val Leu Lys Val Leu Thr Thr Leu Ala Pro Ala Leu Ile Ser Trp Ile
1               5                   10                  15

Arg Arg Arg His Arg Arg
            20
```